United States Patent [19]

Bacus

[11] 4,199,748

[45] Apr. 22, 1980

[54] AUTOMATED METHOD AND APPARATUS FOR CLASSIFICATION OF CELLS WITH APPLICATION TO THE DIAGNOSIS OF ANEMIA

[75] Inventor: James W. Bacus, Hinsdale, Ill.

[73] Assignee: Rush-Presbyterian-St. Luke's Medical Center, Chicago, Ill.

[21] Appl. No.: 875,126

[22] Filed: Feb. 3, 1978

Related U.S. Application Data

[63] Continuation-in-part of Ser. No. 825,673, Aug. 18, 1977, Pat. No. 4,097,845, which is a continuation-in-part of Ser. No. 737,531, Nov. 1, 1976, abandoned.

[51] Int. Cl.$^2$ .............................................. G06K 9/00
[52] U.S. Cl. ..................... 340/146.3 CA; 235/92 PC; 356/39; 364/416; 364/515
[58] Field of Search ................. 356/39, 102, 125, 244; 235/92 PC; 364/416, 515; 340/146.3 AC, 146.3 CA; 128/2 G

[56] References Cited

U.S. PATENT DOCUMENTS

| | | | |
|---|---|---|---|
| 3,315,229 | 4/1967 | Smithline | 235/92 PC |
| 3,733,136 | 5/1973 | Porath-Furedi | 356/39 |
| 3,851,156 | 11/1974 | Green | 356/39 |
| 3,916,205 | 10/1975 | Kleinerman | 356/39 |
| 3,963,350 | 6/1976 | Watanabe et al. | 356/39 |
| 4,097,845 | 6/1978 | Bacus | 340/146.3 CA |

OTHER PUBLICATIONS

Cooke-Yarborough et al., "The Automatic Counting of Red Blood Cells", *British Journal of Applied Physics*, Supp. #3, 1954, pp. 147–156.

Ward et al., "Coherent Optical Rec. & Counting of Red Blood Cells", *IEEE Trans. on Biomedical Eng.*, vol. BME-21, No. 1, Jan. 1974, pp. 12–20.

*Primary Examiner*—Leo H. Boudreau
*Attorney, Agent, or Firm*—Fitch, Even & Tabin

[57] ABSTRACT

A method and apparatus are disclosed for measuring characteristics of cells, such as red blood cells, and for analyzing parameters of the cell characteristics to define a patient's blood. These parameters may be compared for resemblance to predetermined reference characteristic values for a blood cell pathological condition such as a specific kind of anemia or for a normal blood. A report may be generated showing such resemblance to an anemia or to a normal blood. A report may be generated showing parameters of a multivariate dispersion of distribution for a subpopulation of biconcave cells, an indication of skewness of the distribution of the cells with regard to shape variations in central pallor size; the proportion of abnormal kinds of cells found, and closeness of blood to several specific anemias. To expedite the system, a plurality of microprocessors are employed with one microprocessor controlling the imaging means and the summing of measured characteristics while one or more additional microprocessors are measureing characteristics and analyzing the digitized image signals. An improved method of measuring central pallor size is provided.

99 Claims, 29 Drawing Figures

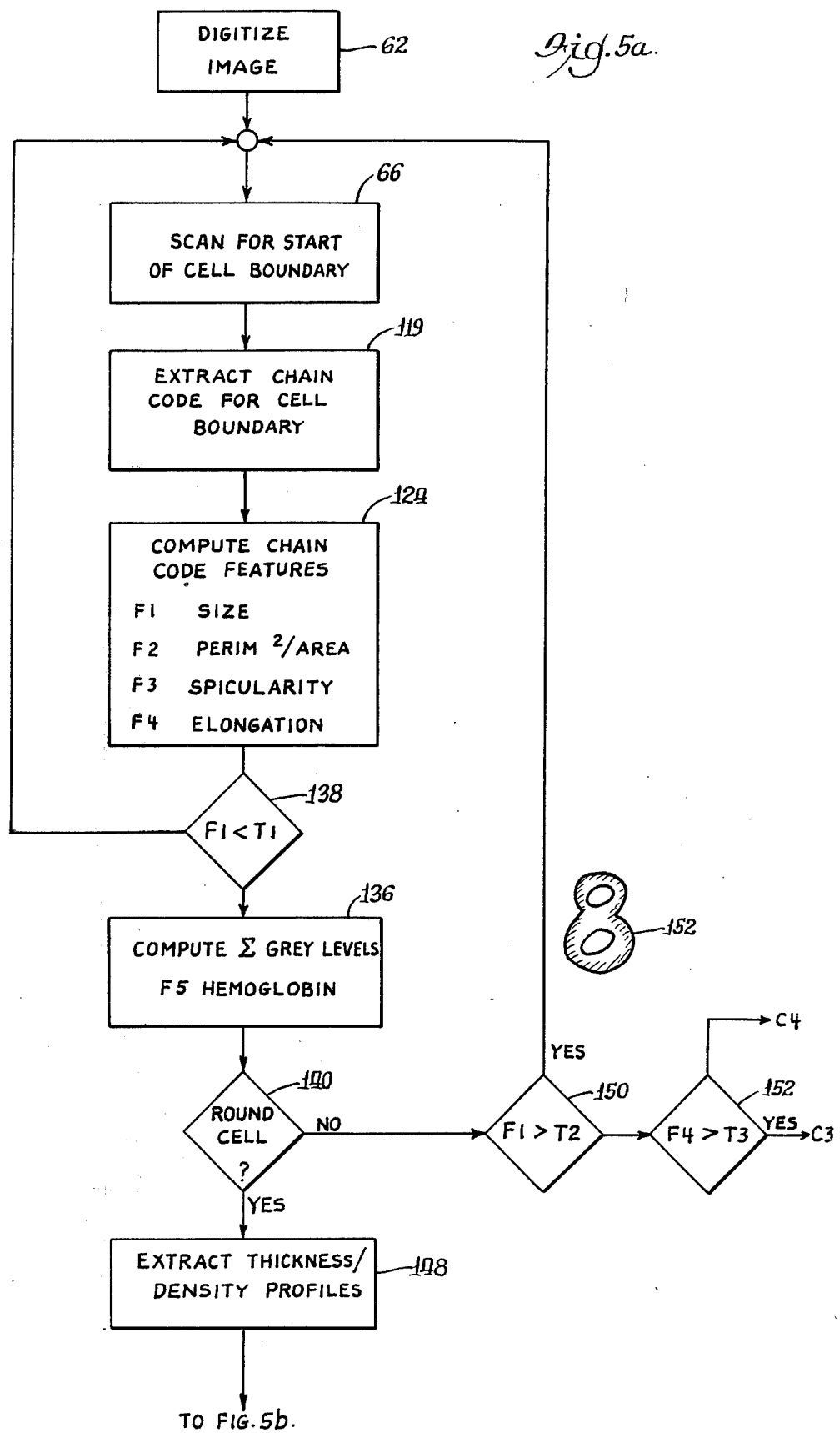

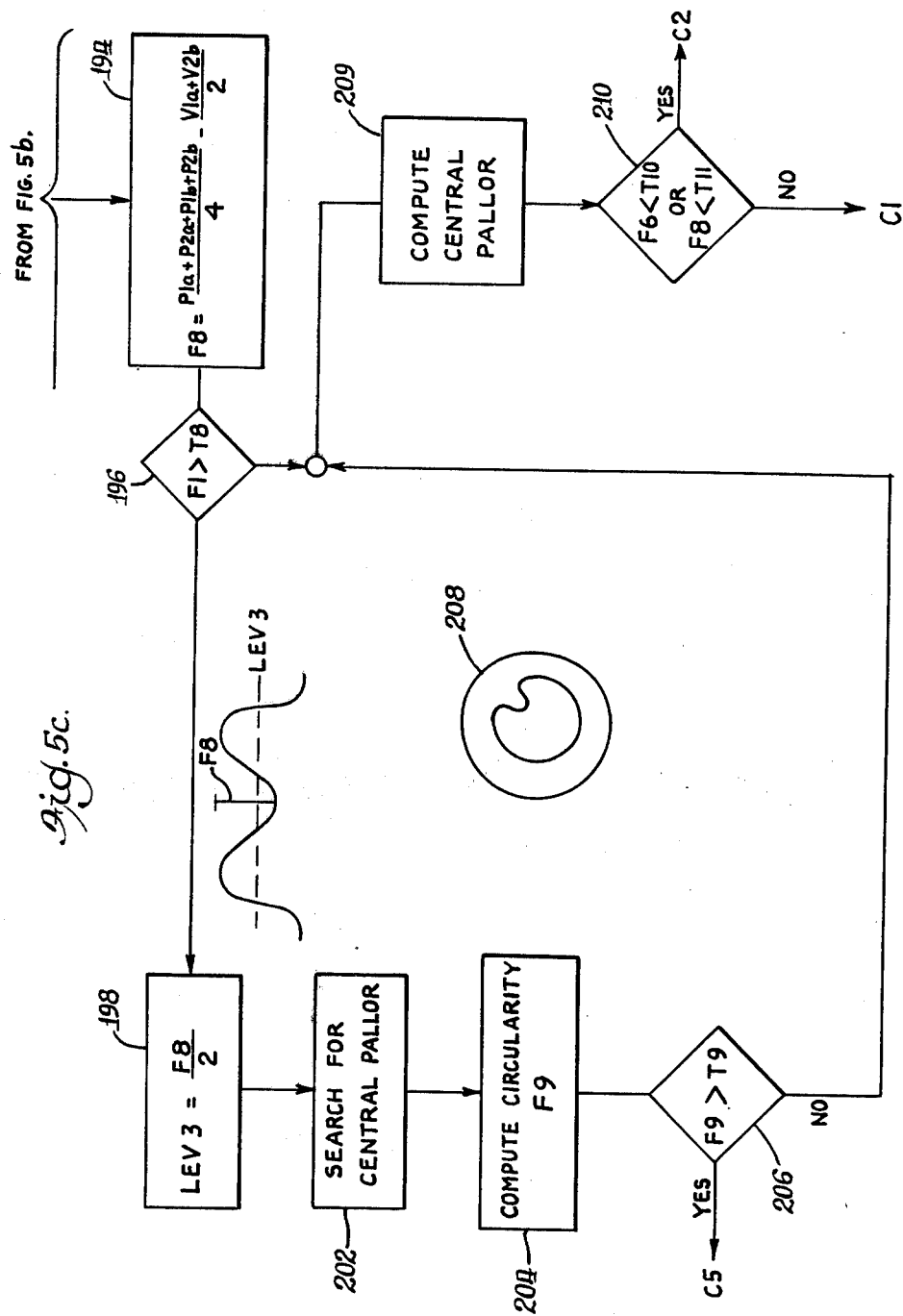

Fig. 9a.
BICONCAVE 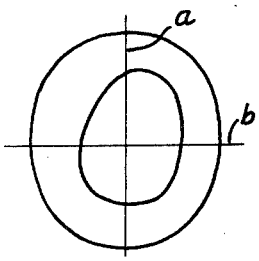 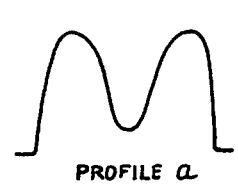 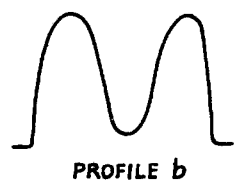
PROFILE a     PROFILE b
Fig. 9b.
TARGET 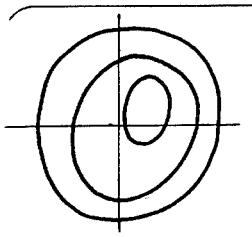 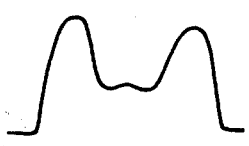 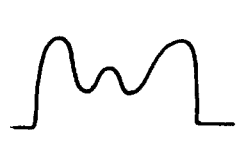
PROFILE a     PROFILE b
Fig. 9c.
SPHEROCYTE 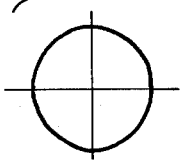 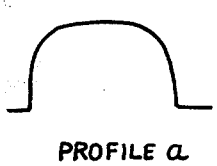 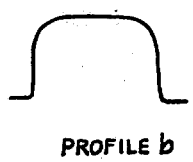
PROFILE a     PROFILE b
Fig. 10.
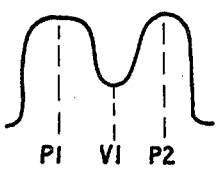 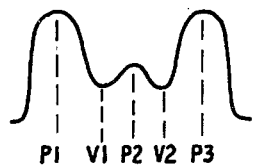 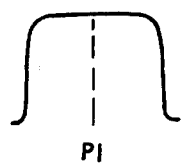
Fig. 10a.     Fig. 10b.     Fig. 10c.

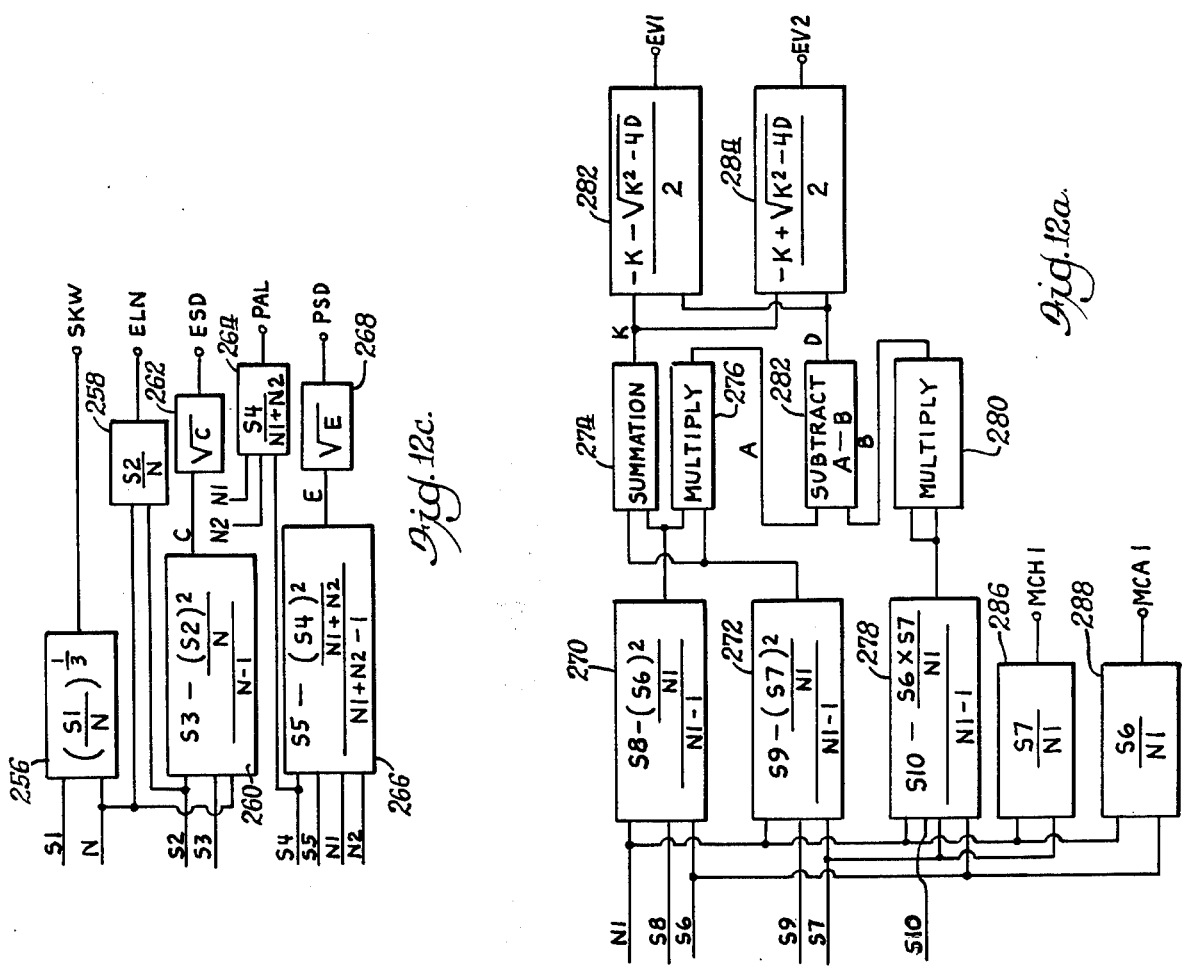
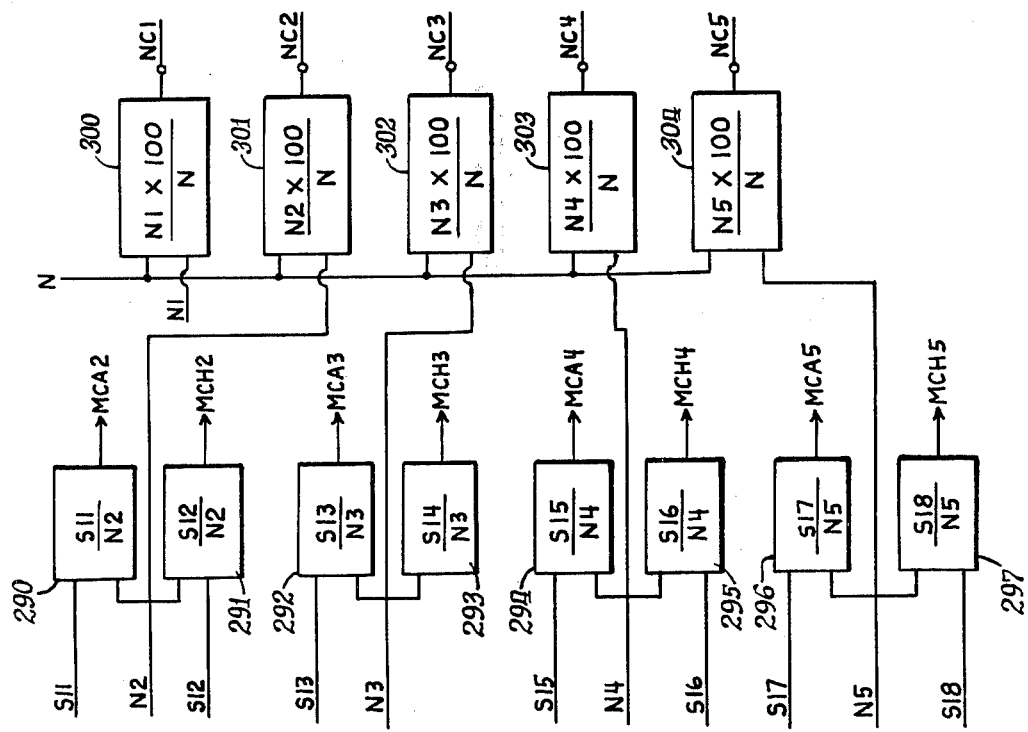

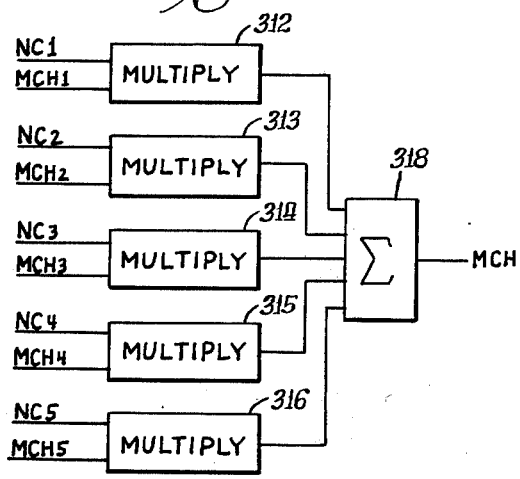
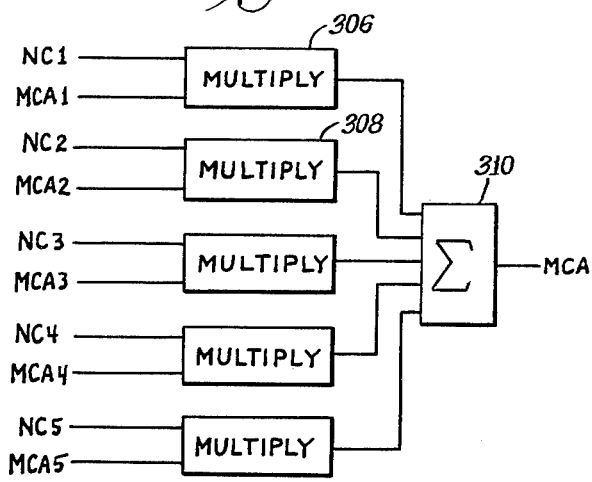
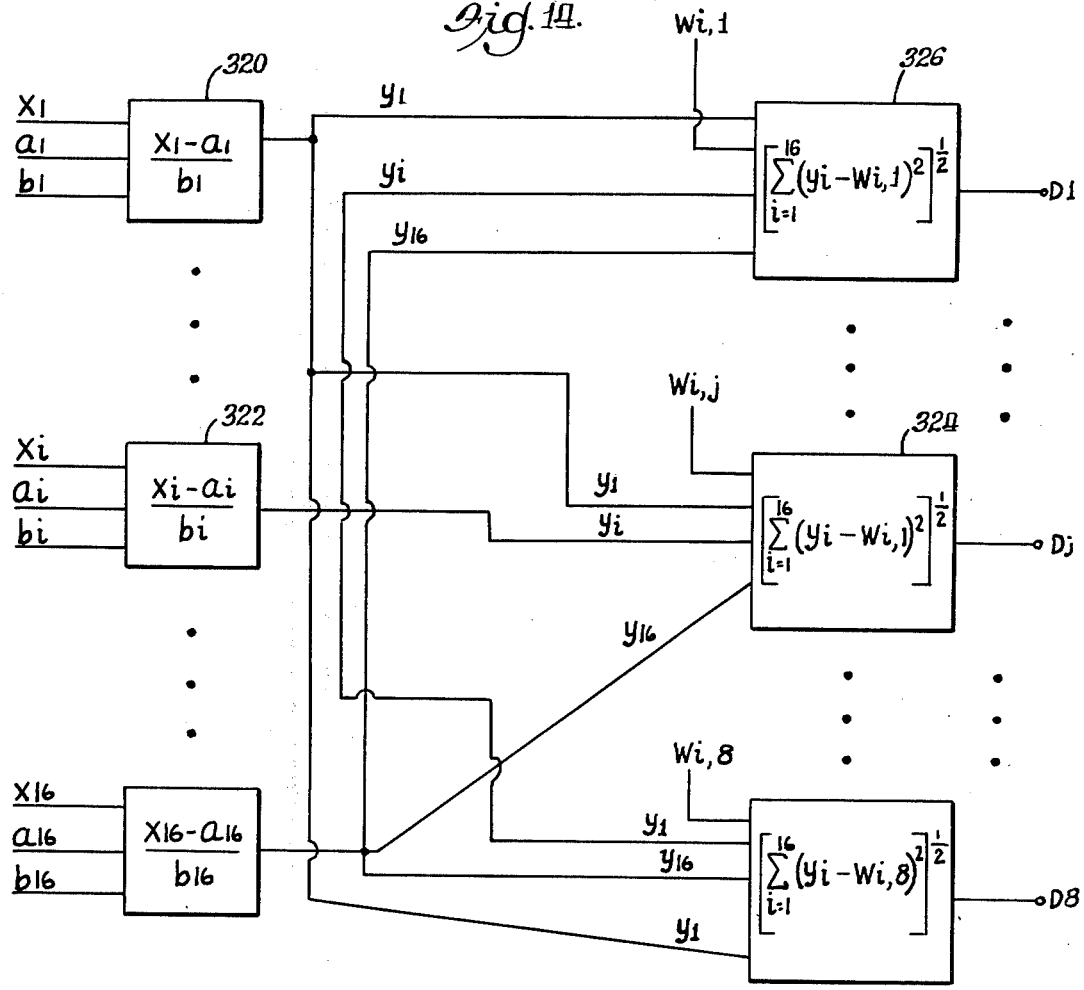

POPULATION DISTRIBUTIONS OF RED CELL SHAPE

NORMAL
SICKLE CELL ANEMIA

POPULATION DISTRIBUTIONS OF RED CELL CENTRAL PALLOR

SPHEROCYTOSIS
NORMAL
IRON DEFICIENCY

AUTOMATED METHOD AND APPARATUS FOR CLASSIFICATION OF CELLS WITH APPLICATION TO THE DIAGNOSIS OF ANEMIA

This application is a continuation in part application of Ser. No. 825,673, filed Aug. 18, 1977 (now U.S. Pat. No. 4,097,845) which is a continuation in part of application Ser. No. 737,531, filed Nov. 1, 1976 and entitled "Method of and an Apparatus for Automatic Classification of Red Blood Cells", now abandoned.

This invention relates to an apparatus for automatically analyzing blood, and through the accumulation of measured properties from individual cells, of thereby classifying the blood specimen according to its close resemblance to the normal or to various pathological conditions. More particularly it is concerned with automatically classifying red blood cells and by accumulating measurements relative to each cell generating characteristic values, which by automated means identify the given blood specimen as typical of either normal or of the pathological condition of a specific type of red cell disorder or anemic condition.

According to present medical practice, the diagnosis of a particular one of more than a dozen major types of anemia uses three broad categories of information; (1) mean descriptors of cell number, size and hemoglobin content, (2) subjective microscopic visual evaluation of the stained blood cells by a trained hemotologist, and (3) specific biochemical or other tests to pinpoint the precise cause of the anemia.

With conventional equipment, the most common of the first category of red cell sample descriptors are; (1) the red cell count, or the number of red cells per unit volume of blood, (2) the hemoglobin content, or amount of hemoglobin per unit volume of blood, (3) the packed cell volume, or the percentage of blood occupied by red cells, (4) a mean cell size parameter, usually taken as the mean cell volume, which is derived by dividing the packed cell volume by the red cell count, (5) a mean cell hemoglobin parameter, which is derived by dividing the total blood hemoglobin content by the red cell count, and (6) the mean cell hemoglobin concentration, which is derived by dividing the total cell hemoglobin by the packed cell volume.

In the second category, a subjective visual evaluation of the stained blood specimen relates to the tedious and time consuming process by a hemotologist of examining a blood film under the microscope and identifying characteristic abnormal cells, such as large cells, or macrocytes, small cells such as microcytes, target cells, elongated cells such as sickle cells, and giving estimates of size variation e.g. anisocytosis +1, +2, or +3, or a subjective evaluation of population shape changes, such as poikilocytosis +1, +2, or +3.

Today, in addition to the overall mean red cell parameters, and the visual descriptions, certain biochemical and other sophisticated tests are often performed to further clarify the pathology of the anemia. These include; iron kinetics tests, serum iron level tests, hemoglobin electrophoresis, folic acid level tests, vitamin B12 tests, and the extraction of a bone marrow sample for evaluation of maturation changes and stainable iron levels. These are very time consuming and expensive, and as to the extraction of a bone marrow sample, very painful.

In accordance with the above, one aspect of the present invention replaces the tedious visual examination with an automatic classification of the normal and abnormal red blood cells into sub-populations and extracts meaningful red blood cells parameters for the separate sub-populations. These and other parameters are used for the automatic classification of the blood specimen with respect to the categories of anemia. An example of automatic classification of red blood cells into sub-populations is fully disclosed in my co-pending continuation-in-part application, Ser. No. 825,673, Filed Aug. 18, 1977. As noted there, one difficulty encountered in separating the normal and abnormal cells into meaningful and widely recognized sub-populations on an automated basis is that of accurately segregating the cells by their morphology and color, particularly where their respective areas or sizes and shapes overlap and their respective principal distinguishing feature is the configuration of their respective central pallors (or a lack of central pallor). Central pallor is the thin, disc-shaped central area of red blood cells which may be circular and particularly pronounced for some cells. For instance, target cells and normocytes may have substantially the same size area and shape, but differ in a central pallor configuration. Thus, to distinguish between these cells, and subsequently to distinguish between anemias, the automated analysis should be able to examine and classify cells on the basis of their interior configuration, as well as their exterior configurations.

Other cells, such as spiculed red blood cells, may have the same general size, area and interior configurations of normocytes or the like, but are distinguished principally by their indented spiculed perimeters. Likewise, adding to the difficulty of classifying abnormal cells such as sickle cells from other elongated cells is that they may have similar peripheral measurements, sizes, and areas, but differ principally from one another in the presence of pointed projections, or spicules. Still other abnormal cells may be separately categorized from other morphologically similar cells only by their hemoglobin content, measured in terms of color or density. Therefore, it may be desirable to distinguish the hypochromic cells from those that are normochromic.

It has been further discovered that the classification of the red cells into subpopulations is not always discerning enough with regard to automatic anemia classification, but that further statistical descriptions of these subpopulations are often required. For example, different anemia bloods may have the same percentage of round biconcave cells but show considerable variation in the dispersion of the cells with regard to size, hemoglobin content and central pallor. Other anemias may result in blood with the same percentage of elongated or spiculed cells, but differ significantly with regard to measures of mean size, hemoglobin, or with regard to the total population skewness relative to a shape measure.

As will be explained in greater detail hereinafter, the present invention is described in connection with a microscopic slide, digital image and pattern recognition system. However, the invention is not to be construed as limited to such a system, as the feature analysis of the sample to classify the blood and to test the blood for abnormalities may be performed using other techniques, such as a coherent optical analysis technique disclosed in U.S. Pat. No. 3,947,123; or a liquid flow process technique such as disclosed in U.S. Pat. Nos. 3,819,270 and 3,822,095. To be commercially feasible, the digital image and pattern recognition process for the blood cells should operate on a real time basis and with sufficient speed and accuracy that it will perform as well as the now commercially accepted leukocyte differential counting systems, such as for example, the LARC manufactured by Corning Glass Works of Corning, N.Y., and generally disclosed in U.S. Pat. No. 3,883,852.

The Coulter Counter, manufactured by Coulter Electronics, Hialiah, Fla., provides results which are helpful in diagnosing anemia in that it provides a red blood cell count and mean red blood cells parameters characterizing the entire population of cells; more specifically, the Wintrobe indices of mean cells volume, mean cell hemoglobin and mean cell hemoglobin concentration along with the number of red cells per cubic millimeter. However, no differentiation between abnormal or normal red blood cells is achieved with the Coulter Counter. Furthermore, the hemoglobin content for individual cells is not determined and measures of dispersion and skewness are not performed. Finally, no automatic categorization or quantitative direct association with known anemias or other pathologies is automatically included as part of the analysis.

Heretofore, some offline experimental work has been performed on image processing of erythrocytes. One of these works, "*Bentley, S. A. and S. M. Lewis,* The Use of an Image Analyzing Computer for the Quantification of Red Cell Morphological Characteristics, Brit. J. Haemat. 29:81, 1975", describes an offline analysis of dried and stained red blood cells of a total cell population measuring three red blood cells parameters by an image analysis technique. This analysis is similar to the Coulter Counter analysis in that the parameters measured were from the total population of cells being analyzed, and were analogous to the Wintrobe Indices. The drying of the red cells introduced artifacts, and there was a lack of central pallor, or internal red cell analysis to provide a highly refined classification. Moreover, there was not disclosed the capability for differentiating between and classifying normal red blood cells from abnormal red blood cells. Likewise, there was no capability disclosed for the automatic classification of the red blood cells with respect to categories of anemias.

Measurements of normal erythrocytes without differentiation of any abnormal erythrocytes by image processing has been disclosed by J. W. Green and reported in a paper entitled "*Green, J. E.,* 'Computer Methods For Erythrocytes Analysis', Proceedings of Symposium of Feature Extraction and Selection and pattern recognition, IEE Catalog No. 70C 51C pp. 100, Argonne, Ill., 1970". A similar type of paper reporting measurements on the red cells and how to measure their features without any classification thereof was disclosed in a paper entitled "Eden, N., 'Image Processing Techniques in Relation to Studies of Red Cell Shape', edited by M. Bessis, R. Weed and Leblond, Springer-Verlag. New York, pp. 141, 1973".

In U.S. Pat. No. 3,851,156 Green provides a technique for scene segmentation of stained red and white blood cells through the use of a color algebra technique. In so doing features of perimeter, size and color are generated for red blood cells. These are measured on the total population of cells and no classification into subpopulations is performed. Further, a precise central pallor analysis is not considered, and means are not provided to acquire sub-population statistical measures, such as the bivariate dispersion of the hemoglobin and size, nor is it indicated that they are important to achieve an anemia categorization, or a profile of similarity measures to prototype anemias.

In short, none of the aforementioned systems have the ability to analyze cells by their features, particularly the inner features of cell pallor, to quickly classify the blood sample or report it as similar.

With the method and apparatus disclosed in my above-identified co-pending patent application, a quantitative analysis of abnormal subpopulations of cells has been performed on a scale heretofore not possible. Because this equipment and techniques enable analysis of cells more quickly and accurately than can the human eye or other existing equipment, it has been possible to gain a better quantitative understanding of abnormal red blood cell subpopulations for different anemias and the relationship of the abnormal red blood cell subpopulations to normal cell subpopulations. It has now been found that a red blood cell sample of blood contains significantly more information concerning the type of anemia present than heretofore known or thought.

Thus, with the present invention, it has been possible to quantify and identify blood from patients with anemia by variables or measures of characteristic values of subpopulations, such as size, hemoglobin content, percentages of cells, and other parameters such as measures of dispersion and skewness for certain single and combined parameters over different subpopulations as well as the population of cells as a whole. These measured properties of the subpopulation of cells and the population as a whole provide a robust description of a patient's blood sample.

Also, with the present invention, it is now possible to compare these red blood cells descriptors relative to characteristic values for the red blood cells in a standard normal blood sample and to those typically found in each of a plurality of recognized kinds of anemia. It is also possible to generate an indice of the relative closeness of the blood sample to one or more standard anemias so that the clinician is given a powerful quantitative relationship to aid in his diagnosis. Additionally, by testing the patient's blood at different times, particularly after successive treatments, one can generate a series of indices of the patient's blood relative to each type of anemia. Thus, it is possible to determine a patient's progress to see if his blood is deteriorating or is progressing towards a more normal blood. With expanded and accepted usage of the present invention, it is thought that some of the other time consuming, painful and/or expensive tests, above discussed, and now commonly used in the diagnosis of anemia, may be eliminated. Therefore, and as will be explained in greater detail hereinafter, a real time analysis of the red blood cell sample and to determine its make-up and a comparison to standard types of anemia is feasible.

To this end, the present invention uses multiple logic systems operating simultaneously and in a controlled relationship one with another to divide and perform tasks therebetween. Thus, the ability to analyze hundreds of red blood cells and to extract their various features and then to define the parameters for the subpopulations for comparison with anemia standards can be accomplished by the division of the functions and tasks between these simultaneously cooperating logic systems, all as will be explained in greater detail hereinafter.

A general object of the invention is to provide a new and improved, as contrasted to the prior art, system for the automatic analysis and classification of cells.

An object of the invention is to provide a method and apparatus for automatically classifying the blood and its relationship to recognized categories of anemias.

Another object of the invention is to provide an improved method and apparatus for automatically testing blood for abnormalities.

These and other objects of the invention will become apparent from the following detailed description and the accompanying drawings in which.

Figure 5B:
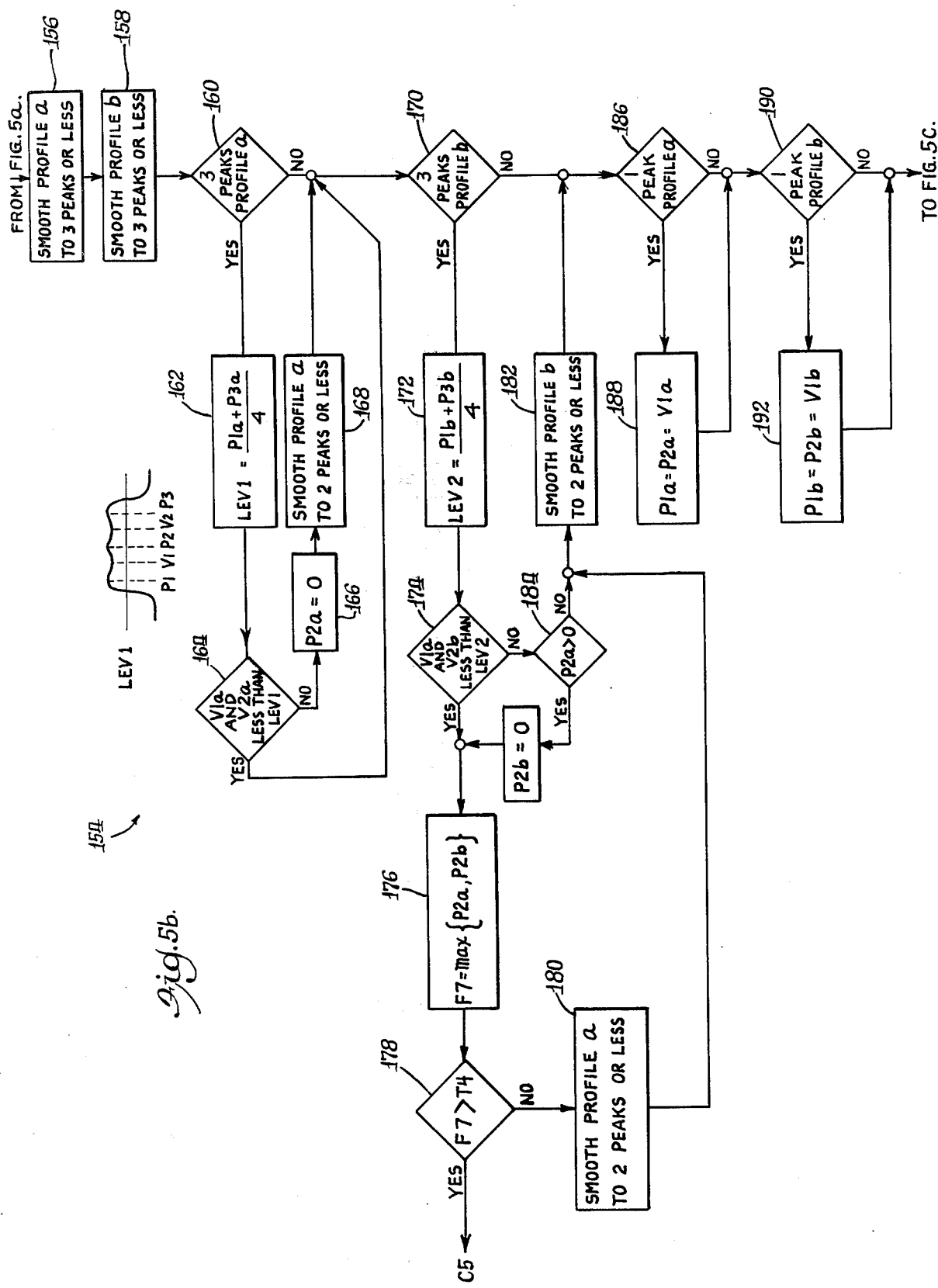

FIGS. 5a, 5b, and 5c are flow charts of the preferred classification technique for classifying the blood cells into mutually exclusive subpopulations.

Figure 6:
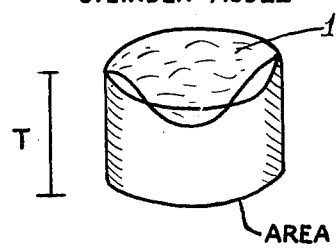

FIG. 6 is a diagrammatic view of a model for red blood cell central pallor measurement.

Figure 7:
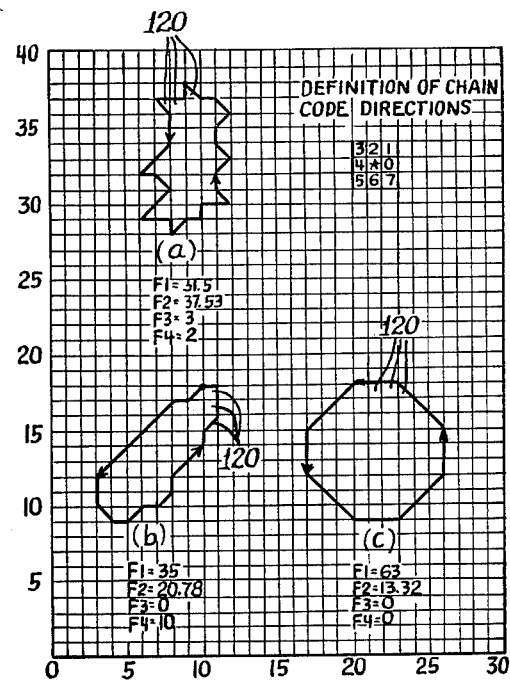
Figure 8:
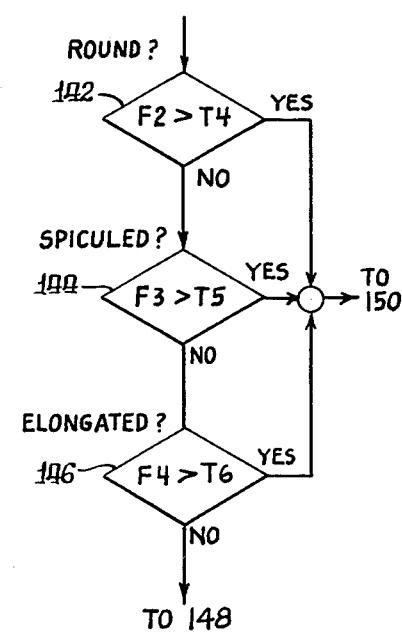
Figure 11:
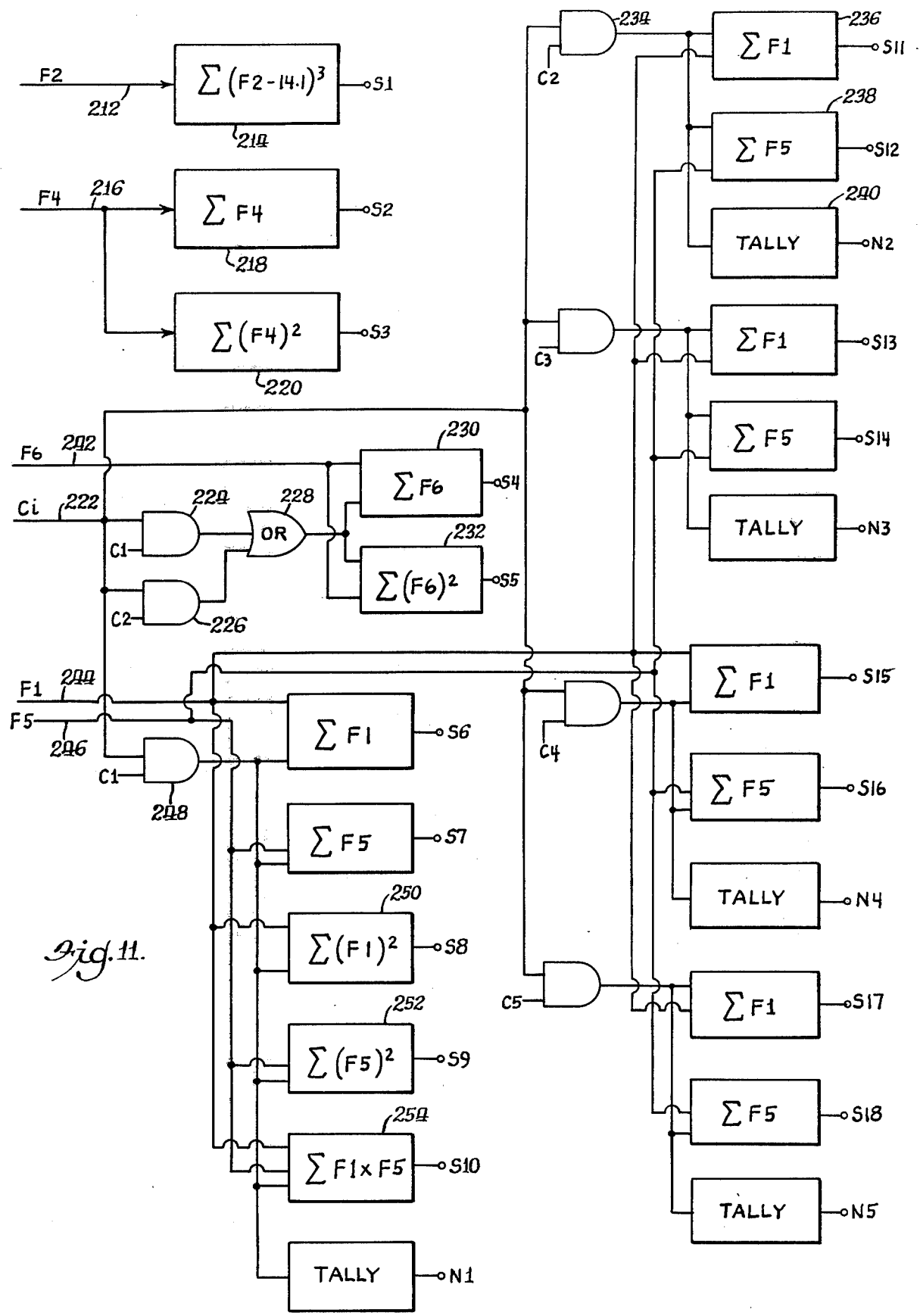

FIG. 7 illustrates a chain code description and analysis method for three diagramatic red blood cell outlines;

FIG. 8 is a block diagram of the preferred process for determining whether a cell is round;

FIG. 9a, 9b and 9c are graphs illustrating thickness/density profile measurements for three different, typically appearing cell types, measured in two orthogonal directions. These profiles are used to measure the cell central pallor features and target cell features. FIG. 9a illustrating a "flat" cell having little or no central pallor development;

FIGS. 10a, 10b, and 10c are graphs illustrating the profiles of the cells of FIGS. 9a, 9b and 9c with the peaks and valleys of each profile labelled;

FIG. 11 is a schematic of the preferred process for accomulating red blood cell subpopulation parameters;

FIG. 12a, 12b, 12c, 12d and 12e are schematics illustrating the preferred process of computing the subpopulation characteristics from the accumulated values from a plurality of cells;

FIGS. 13a, 13b, 13c and 13d are graphs of bivariate distributions of red blood cells subpopulations exhibiting normal and anemic characteristics;

FIG. 14 is a schematic block diagram of the preferred process for generating a similarity, or n-space distance, measure between a given sset of measurement values describing a blood and a stored set of characteristic values, prototypic of various anemic conditions, or the normal blood.

FIG. 15a is a graph of population distributions of the cell circularity shape measure, illustrating the differences in skewness of these distributions, over all subpopulations, for normal blood compared to that of sickle cell anemia.

Figure 16:
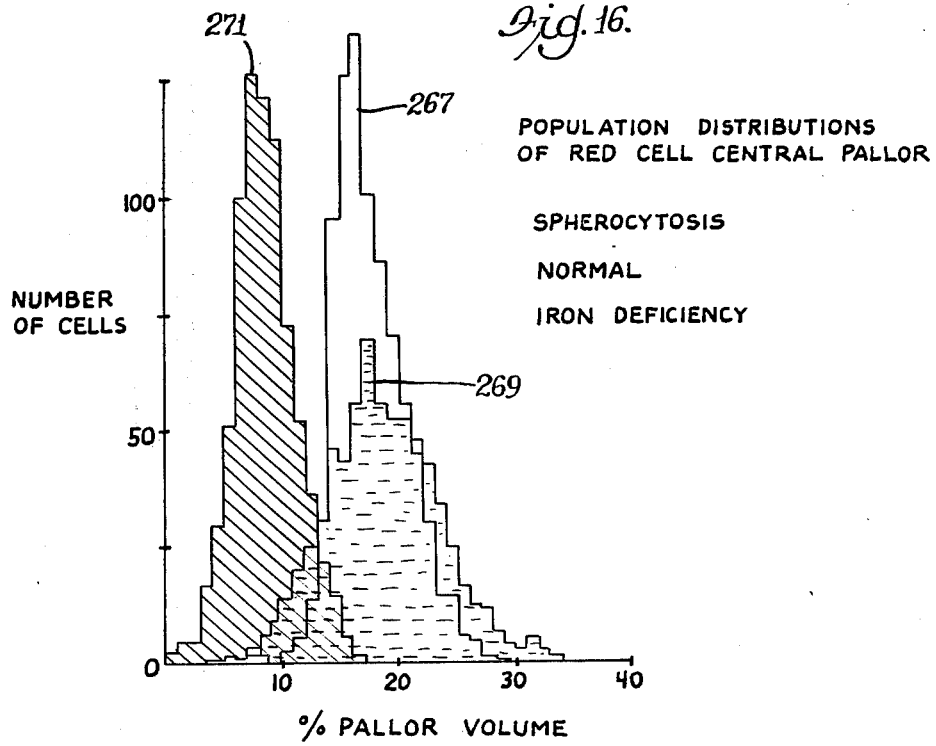

FIG. 16 is a graph of population distributions of individual cell central pallor measurements, for the 2 subpopulating, biconcave and spherocyte, illustrating the differences in mean values and dispersion for bloods of spherocytosis, normal and iron deficiency anemia.

As shown in the drawings for purposes of illustration, the invention is embodied in a method and apparatus for automatically classifying red blood cells and for analyzing the relationship of the patient's blood sample to at least one recognized category of anemia or to a normal blood, or to a red blood cell disorder other than an anemia. More specifically, individual red blood cells are automatically examined and classified into different cell subpopulations such as, for example, a spherocytic cell subpopulation, an elongated cell subpopulation, an irregular shape cell subpopulation, a target cell subpopulation and a generally round and biconcave cell subpopulation, and then a plurality of characteristic values are generated for the patient's subpopulations and population of cells as a whole for comparison with reference characteristic values which define a recognized anemia. By way of example, the selected characteristic values, which identify a given anemia, have been found and are given hereinafter for the following anemias: iron deficiency, chronic disease, B-thalassemia, megaloblastic, hemoglobin SS, hemoglobin SC and spherocytic; and likewise, reference characteristic values defining a normal blood, i.e, substantially all normocytic cells or the like, has been developed and will be given hereinafter.

Figure 15:
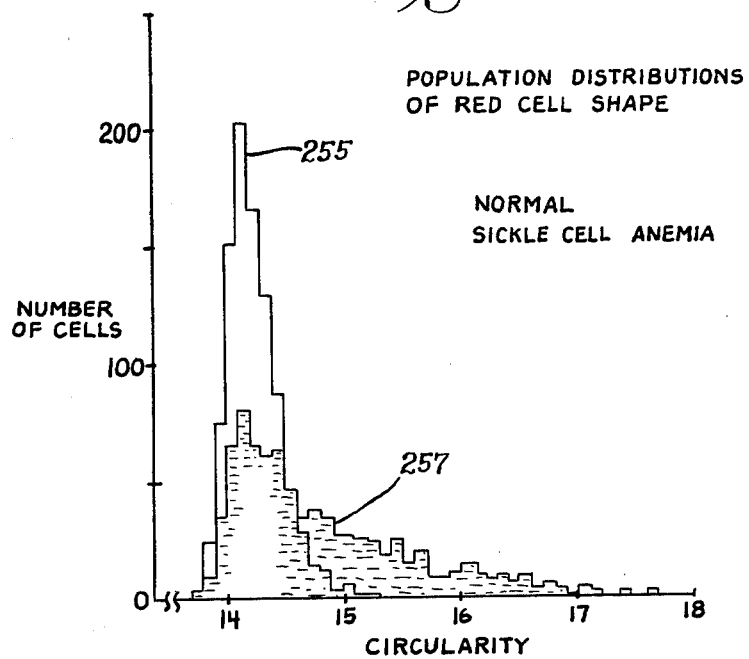

Also, as will be explained in greater detail hereinafter, a population or subpopulation dispersion measure of the red blood cells in a patient's blood relative to characteristics such as, for example, hemoglobin, mean cell size (or area) shape, and central pallor, may be reported to the clinician. For example, broadly speaking, the bivariate red cell distribution of size and hemoglobin content for each cell is generally in the form of an elliptically shaped profile, as best seen in FIGS. 13a-13d and having axii at 45° and 135°. The length and width as measures of the bivariate dispersion, and the location of the profile by measures of the means values, may be reported to provide the clinician with an impression of the patient's total cell make up. Similarly, measures of central tendency dispersion and skewness of pallor and shape are provided to further quantify the total cell make up on the total cell population, or on subpopulations, as illustrated in FIGS. 15 and 16.

Figure 13A:
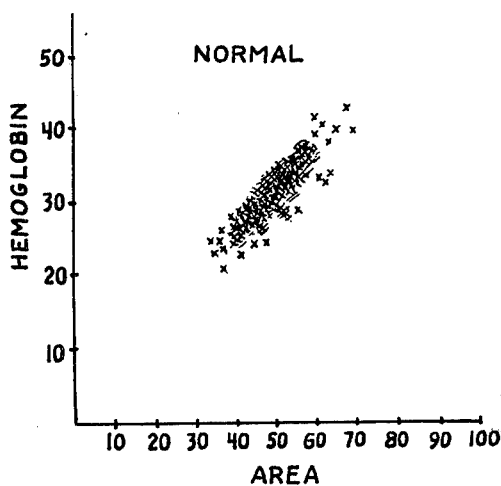
Figure 13B:
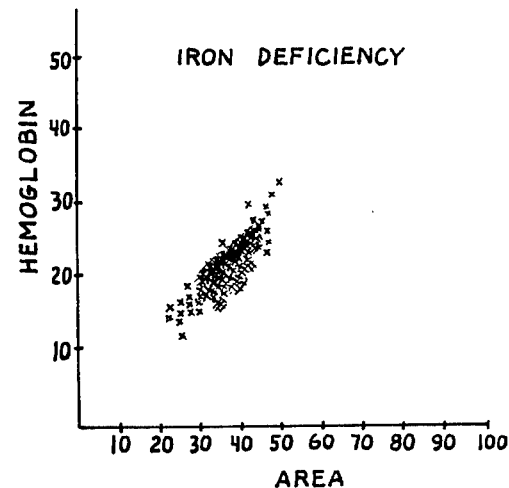
Figure 13C:
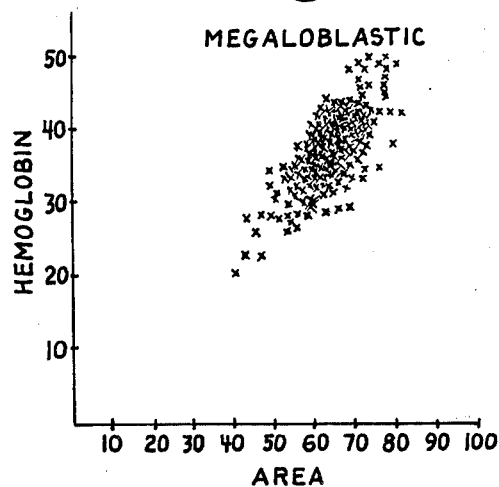
Figure 13D:
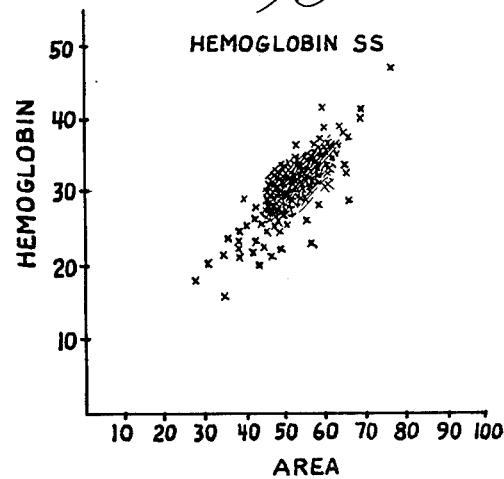

The patient, who has anemia generally is experiencing difficulty in either manufacturing new normocytic red blood cells or his existing red blood cells are being destroyed at an abnormal rate or by an abnormal process. Red blood cells typically have a life of about 120 days and their generation, growth and death is a continuous process. An anemic disorder generally manifests itself in blood cells having unusual sizes or shapes relative to a normal red blood sample, which predominantly contains round normocytic red blood cells, or in blood cells having hemoglobin characteristics differing from the hemoglobin characteristics for normal blood cells. Thus, since the currently existing cells, for example in a normal patient who has just developed an underlying disease process leading to anemia, have a life span of 120 days, new cells with differing characteristics will tend to produce a wider dispersion of population measurements, as in FIG. 13c compared to FIG. 13a, when sampled and examined by the precise measurement techniques described herein. Such information provides the clinician with a knowledge of the presence of any previously visually estimated anisocytosis, i.e. a large measure of cell variations in size, and also as well the variations in hemoglobin content. The mean cell hemoglobin and mean cell size information locate the central tendency of the cell distributions in FIGS. 13a-13d.

In the embodiment of the invention described herein, each of the specified anemias is identified by 16 stored parameters or properties. The patient's body is analyzed on an individual cell basis with each cell being classified into a subpopulation and then parameters such as mean cell size, mean cell hemoglobin and the percentage of cells in the subpopulation of the total cell population are generated to give subpopulation results. Also, a plurality of other measured properties or parameters of the patient's blood are generated from the subpopulation parameters, to total sixteen parameters to define a set of reference characteristic values, i.e. an n-space location, and a calculation is made of the closeness of the patient's blood location relative to the eight reference character values or n-space locations for the seven anemias and the normal blood. A report of the closeness of the patient's blood sample relative to these standard anemias provides the clinician with a statement as to what type of anemia, if any, the patient has, or how similar it is to a known type. Then, after the patient's treatment, the clinician is able to make later analyses and achieve new quantified results showing whether the patient is progressing towards a more normal blood or is deteriorating.

To achieve the analysis of the individual cells and the classification of same into subpopulations and the comparison of the blood subpopulations variables to those defining a specific anemia on a real time basis, the preferred equipment employs first and second logic systems which operate simultaneously and in a controlled manner so as to proportion the work and efforts therebetween. Also, as will be explained in greater detail, the present apparatus and method include a number of powerful and novel techniques and means of and for cell classifying and analyzing which result in an efficient and less expensive method and apparatus for doing the red blood cell analysis. For instance, the present invention recognizes that a normal blood sample generally will have a very high percentage of round cells with identifiable central pallor which can be grouped into a common subpopulation called a "biconcave" cell subpopulation and that seven different anemias can be identified when using only four other subpopulations with this biconcave subpopulation. It is to be understood, however, that the present invention is not limited to any subpopulations described or defined herein, as the particular names and make up of subpopulations may be varied and still fall within the purview of the invention herein claimed.

Figure 1:
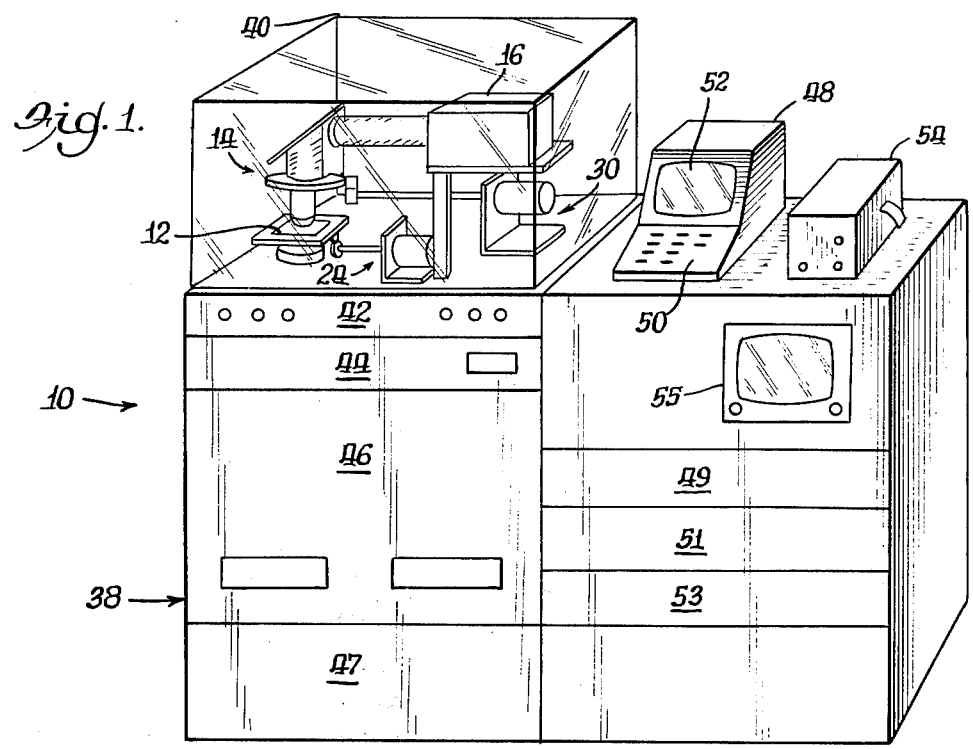
FIG. 1 is a perspective view of an apparatus for practicing the method of blood analysis and embodying normal features of the invention.
Figure 2:
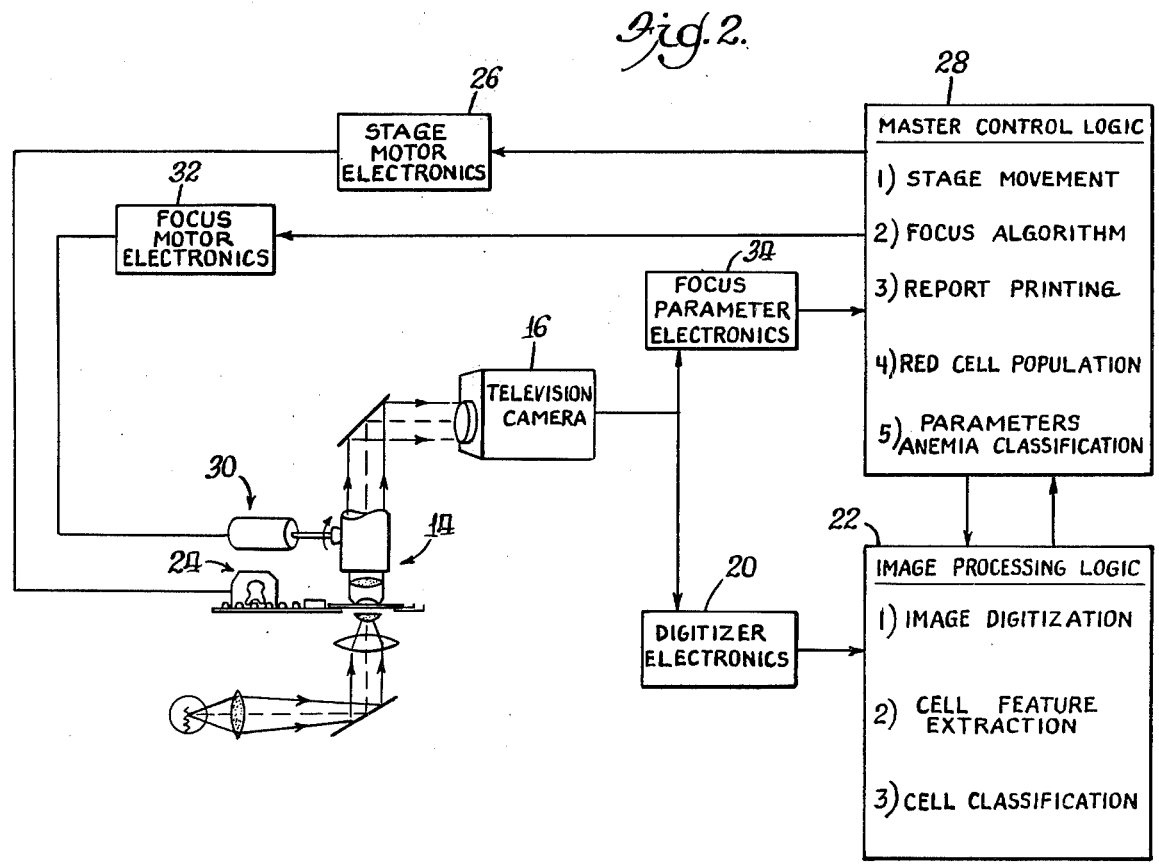
FIG. 2 is a block diagram showing the operation of the apparatus illustrated in FIG. 1.

As shown in FIGS. 1 and 2 of the drawings, for purposes of illustration, the invention is embodied in an apparatus 10 which comprises a microscopic digital image processing and pattern recognition system which analyzes a mono layer of red blood cells on a microscope slide 12 with the cells being spaced from each other to ease the automated classification thereof. Suitable high resolution microscope optics 14 form an optical image for each red blood cell on a vidicon television camera tube or other detector 16 which converts the scanned electronic charged distribution of the optical image point by point into a numerical or digitized image representing the optical transmission of the points in each image. The output of the vidicon camera is applied to digitizer electronics 20 which includes an analog to digital converter which is connected to an image processing logic 22 which controls the digitizer electronics 20 and receives and stores the digitized cell images into a memory store. The image processing logic 22 operates on the digitized cell images in a manner that will be hereinafter described which includes cell feature extraction and cell classification.

A suitable stage motor means 24 is provided and controlled by stage motor electronics 26 which are in turn controlled by a master control logic 28. The stage motor 24 is provided to shift the slide 12 in order to iteratively process different image areas of the blood specimen on the slide. To control the focus of the microscope, a focus control motor means 30 is connected to the microscope and is operated by focus motor electronics 32 which are also controlled by the master control logic 28 by means of the focus parameter electronics 34. Focus control of slides for image analysis is well known in the art, e.g. U.S. Pat. No. 3,967,110.

The apparatus 10 shown in FIG. 1 includes a housing 38 having a cover 40 enclosing the microscope optics 14 and the television vidicon 16. An upper section 42 of the housing 38 houses the control switches of the apparatus the next lower section 44 houses the master control logic 28 with the next two lower portions 46 and 47 of the housing containing the memory store for the image processing logic 22 and master control logic 20 and the motor electronics 26 and 32. A terminal 48 is connected to the master control logic 28 and has a keyboard 50 for input of identifying information about the specimen or for other instructions. A monitoring screen 52 provides a visual display of the final report, and preferably a written printout is also made by a printer means 54 to afford a permanent record. A TV monitor 55 provides desired pictorial displays. The TV camera electronics are housed in a section 49 below the monitor. The next lower section 51 houses the analog to digital converter with the first section 53 housing the image processing logic 22. The results of the red cell analysis may also be transmitted for storage in a medical computer data bank.

In accordance with the present invention, red blood cells may be examined such that normal cells are distinguished from abnormal cells and classified by the apparatus 10 into subpopulations automatically in a detailed fashion heretofore not possible by a manual/visual examination of cells. Also, each of the red blood cells being examined may be classified into mutually exclusive subpopulations and reported out so that the presence of a minor number of abnormal cells is not overlooked or forgotten and so that accurate parameters about a given subpopulation may also be provided. For the first time, the individual red blood cells may be examined individually for the hemoglobin contents. Thus, a report may be made not only of the kind of cells found in the subpopulation but also of their number of their hemoglobin characteristcs. Advantageously, the individual red blood cells may be analyzed and classified with less subjectivity into a large number of mutually exclusive subpopulation (Table I) such as biconcave (round cells with central pallor), elongated cells, targets, and irregular cells (cells not fitting into any of the above classifications).

The preferred hemoglobin characteristic gathered from the analysis of the hemoglobin contents of the individual cells within a given subpopulation and reported out is the mean cell hemoglobin (MCH) for a given subpopulation of cells, such as shown in Table I. In addition to the hemoglobin parameters, the individual cells are counted for each subpopulation to provide their respective percentages of the total population; and likewise mean cell area (MCA) for each subpopulation may also be reported as shown in Table I. It has been found to be helpful in detecting abnormalities in blood samples to determine multivariate distributions of the red blood cells in particular subpopulations of a sample with respect to a plurality of quantifiable features. In this regard a bivariate distribution is shown in FIG. 13a as a distribution of round biconcave cells, with respect to a preferred quantifiable feature cell area on one axis and the cell hemoglobin content on the other axis.

By means of a measurement and analysis procedure to be described, parameters are reported which describe this distribution with regard to its central disposition, or mean values over the plurality of variables, and its variability, spread, or dispersion. The mean cell area and mean cell hemoglobin describe the center of the distribution and are reported as shown in Table I. Two other statistical parameters EV1 and EV2 are reported in Table I and describe the variance of the dispersion of the distribution in the orthogonal directions of its major and minor elliptical spread. EV1 and EV2 stand for eigenvalue 1 and eigenvalue 2, respectively, and describe the dispersion or spread of the distribution. If the points of the distribution are through of as defining an ellipse, then EV1 and EV2 can be thought of as relating to the length and breath of the ellipse. Advantages derived from reporting parameters relating to a distribution of a particular subpopulation will be more fully described hereinafter.

Other parameters reported in Table I include the mean pallor volume (PAL) for the biconcave and spherocyte cells as we-1 as the standard deviation for the distribution of the biconcave and spherocyte cells with respect to central pallor volume. The pallor volume standard deviation (PSD) is a parameter which describes the variance of the distribution of this measure over these subpopulations of cells. Another parameter reported is the skewness (SKW) which measures the skewness of the distribution of all the cells with respect to the quantifiable feature (perimeter of the cell) 2 area of the cell.

This data has been unavailable prior to this invention from any commerical instrument, or in any other fashion, such as from special research instrumentation. The closest analogous instrument is the Coulter counter (Coulter Company, Hialeah, FL) which is unable to classify red blood cells into subpopulations and which reports the mean cell size and mean cell hemoglobin for the entire population of red blood cells. As seen in Table I, the present invention is also capable of reporting the total population, or average mean cell hemoglobin as well as the average mean cell area (which is related to the mean cell size) in addition to the other parameters suggested. In that table these are denoted in the line with AVERAGE parameters.

Thus, as indicated above, herein, the invention will be described as having the ability to classify red blood cells into the several mutually exclusive subpopulations set forth in Table I. The subpopulations listed are the preferred subpopulations for classifying blood with respect to recognized categories of anemias but there may be other subpopulations defined. The mean cell area (MCA) is reported in microns$^2$ with the mean cell hemoglobin (MCH) reported in picograms (pg).

The several subpopulations described and their associated parameters hereinafter are:

TABLE I

| 96.8 BICONCAVE | | MCA | MCH |
|---|---|---|---|
| MCA 50 | 0.5% Spherocytes | 47 | 30 |
| MCH 31 | 0.2% Elongated | 5 | 2 |
| EV1 42 | 2.3% Irregular | 38 | 23 |

TABLE I-continued

| EV2 2 | 0.2% Targets | 57 | 34 |
|---|---|---|---|
| AVERAGE 50 MCA | 31 MCH | 17 PAL  3 PSD | 8 SKW |
| 0.9 Normal | | 4.2 Megaloblastic | |
| 4.2 Iron Deficient | | 6.2 Hemoglobin SS | |
| 2.5 Chronic Disease | | 4.8 Hemoglobin SC | |
| 3.8 B-Thalassemia | | 4.9 Spherocytic | |

In accordance with another aspect of the present invention, samples of blood may be analyzed and thereby classified by "similarity" or "distance" measures being reported at to compare said sample to recognized categories of anemic or normal bloods. In the preferred embodiment, 24 parameters are measured for the subpopulations of the sample of blood taken from the patient. Of these, 16 are used for the tested sample of blood define a point in this 16-space. Consequently, the typical parameter values for a particular anemia also define a point in the 16 parameter space. In accordance with the present invention, the distance, from the point representing the values for the sample blood taken from the patient, to each of the points representing the typical parameter values for each of the categories of anemia, may be determined. Thus, a physician would be able to determine which of the categories of anemia the sample of blood taken from the patient most closely resembles and could make a diagnosis from that information. Alternatively, simple decision logic could point out the most probable diagnosis. The normalized distance of the parameter values for a sample of blood is shown for a normal category of blood as well as the recognized categories of anemia in Table I. As seen in Table I, this particular sample of blood is closest to normal since 0.9 is less than any other distance reported and therefore the blood most closely resembles normal blood.

Figure 3:
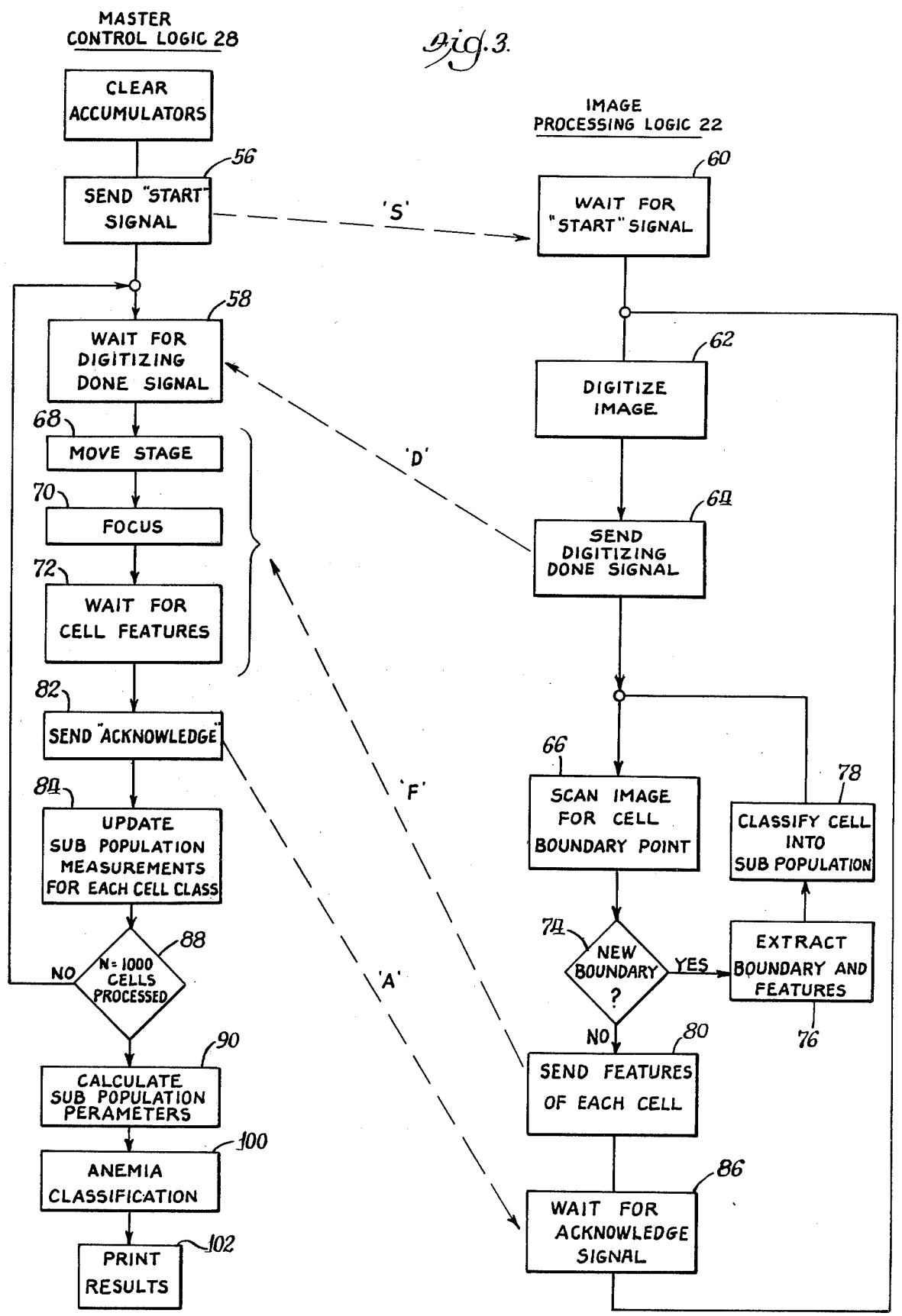
FIG. 3 is a block diagram of the preferred process for analyzing and classifying blood cells.

With reference now to another aspect of the present invention, a multiple parallel logic architecture has been found to provide the rapid processing necessary for efficient analyzing of cells on a slide. Thus, in the preferred embodiment, there is provided a first processing means, the master control logic 28, and a second processing means, the image processing logic 22 as shown in FIG. 3. The analysis of the cells on a slide requires a sequence of operations to be performed, and since one operation often requires the results of a previous operation, there are provided synchronizing means for synchronizing the processors so that the results necessary to perform a particular operation are available when that operation is begun.

FIG. 3 illustrates the specific interrelationships between the master control logic 28 and the image processing logic 22. Because of this multiple parallel logic or architecture, the master control logic may proceed with one task or operation while the image processing logic is proceeding with another operation.

As seen in FIG. 3, the operations carried out by the master control logic 28 are listed in the lefthand column with the operations of the image processing logic 22 in the righthand column. The master control logic, after clearing its associated accumulators, proceeds to operation 56 in which a start signal is sent to the image processing logic and thereafter continues to operation 58. The image processing logic meanwhile is waiting for the start signal (operation 60) from the master control logic. Upon receipt of the start signal, the image processing logic 22 proceeds to operation 62 which includes digitizing the image produced by the vidicon camera 16 (FIG. 2). Upon completion of the digitizing, the image processing logic sends a "digitizing done" signal (operation 64) to the master control logic indicating the completion of the digitizing process and proceeds to operation 66. The master control logic operation 58 is currently waiting for the "digitizing done" signal and upon its receipt, proceeds to move the stage (operation 60) on which the slide rests so that a new field of cells may be imaged since the previous field has already been digitized by the image processing logic 22. The optics 14, FIG. 2, are providing an imaging means of the cells on the slide. The stage motor drive 24, and the focus motor drive 30, and their associated electronics, are controlled by the master control logic 28. After moving the stage so that a new field may be imaged, the master control logic proceeds to operation 70 wherein the field is focused and then proceeds to operation 72.

After transmitting the "digitizing done" signal, the image processing logic scans the digitized image for a cell boundary point (operation 66). If a cell boundary point is found (operation 74), the image processing logic extracts the cells boundary and features (operation 76) and classifies the cell as to its proper subpopulation (operation 78).

The image processing logic then returns to operation 66 and continues scanning the image for another cell boundary point. The scanning, feature extraction, and cell classification operations will be describe in more detail below. If the logic section 74 determines that a new boundary point has not been located, then the image processing logic proceeds to operation 80 wherein the features of each cell located as well as each cell's subpopulation classification is transmitted to the master control logic which will be in the process of executing operations 68, 70, or 72. The transmittal of the information is on an interrupt basis, i.e., should the master control logic be in the process of controlling the imaging means (operations 68 or 70), the master control logic will interrupt these operations and store the information received from the image processing logic before proceeding with moving the stage and focusing the microscope. However, if these operations have already been completed then the master control logic proceeds to operation 72 wherein the master control logic waits for the data to be transmitted from the image processing logic. In response to the receipt of the data, the master control logic will transmit an acknowledge signal (operation 82) to the image processing logic and then proceeds to operation 84 wherein the subpopulation data for each subpopulation is updated, as will be more fully explained below.

Upon receipt of the acknowledge signal, the image processing logic proceeds to digitize the image of the new field that has been moved into view by the master control logic. The master control logic, upon completing the update of the subpopulation data, determines at logic section 88 whether N, the total number of cells processed, is equal to one thousand. If 1000 cells have not been processed, the master control logic returns to operation 58 and waits for the "digitizing done" signal from the image processing logic, otherwise the master control logic calculates the subpopulation parameters (operation 90), proceeds with an anemia classification (operation 100), and prints the results (operation 102), as will also be more fully explained below.

Thus, because of the dual processor architecture, the master control logic is free to control the imaging means wherein a new field is brought into view to be imaged while the image processing logic is proceeding with the digitizing and analyzing of the image from the previous field. Similarly, while the master control logic is accumulating the data extracted from the image by the image processing logic, the image processing logic may simultaneously digitize and analyze a new image provided by the new field which had been brought into view by the master control logic. It should be noted that although for purposes of illustration, only one image processing logic is described as associated with the master control logic, it is capable of utilizing information from several image processing logics operating in parallel and independently on different images.

The present invention is directed to the optimization of the time of analysis as well as the number of features used in the classification logic so that the amount of storage and classifying techniques may be reduced substantially along with equipment requirements therefor. With an optimization of analysis time for classification, there is a danger that the reliability and accuracy of the classification are compromised. Despite this, a relatively foolproof feature set and classification logic has been invented for a large number of subpopulations such as those shown in Table 1. The preferred classification features are size, hemoglobin content, spicularity, roundness, elongation, central peak height (if present) from cross-sectional cell scans, and central pallor. By suitable combinations and analyses of such features, it is possible to differentiate from normal blood and to identify biconcave round cells, spherocytes, target cells, irregular shaped cells, and elongated cells.

In the preferred method and apparatus, the cell classifications are achieved by an image processing and pattern recognation with great accuracy and reliability by rendering white blood cells and other artifacts substantially invisible to the optics 14 by using a light having an optical wavelength of about 415 Nanometers. At this optical wavelength, the red blood cells are relatively contrast enhanced to the ultraviolet sensitive Vidicon camera without staining, while the white blood cells and other formed elements are substantially invisible. The staining of the red blood cells prior to being analyzed by a microscopic image processing technique has been found to be a time-consuming process, as well as undesirable in that the staining may introduce a number of stained artifacts which detract from the accuracy of the analysis. Furthermore, many of the stains are not stoichiometric in the representation of hemoglobin concentration according to density, thus distorting the quantization of the hemoglobin content of the cell on a per-cell basis. A particular manner of vapor fixing of cells before they dry without staining thereof to prevent the formation of artifacts by distortion of the central pallor is disclosed in my co-pending application entitled "Method and Apparatus for the Preparation of Blood Samples for Automated Analysis", filed Dec. 21, 1977, and hereby incorporated by reference as fully reproduced herein. Thus, by rapidly preparing the specimens in a monolayer and fixing with a formaldehyde vapor prior to the drying of red blood cells, as disclosed in the afore-mentioned co-pending patent application, and by not employing a time consuming staining to contrast enhance the cells, as in white blood cell analysis, these specimens may be quickly prepared and analyzed accurately.

The location of the cell image and the identification and feature extraction has been greatly simplified as described below to locate and define the cells by a boundary procedure which defines the cell in the form of an octal chain code. The use of octal chain codes as an image processing technique is described in a paper by Freeman H., Computer Processing of line-drawing images, ACM Computing Surveys 6:57, 1974. As will be explained in greater detail, the octal chain code allows feature extraction as to: (1) cell size, (2) perimeter length and roundness shape measure, (3) irregular shape measure and (4) elongation shape measure. This is followed by extracting the summed density or hemoglobin feature, and then by extracting cross-sectional scans (thickness/density profiles) for central pallor measurement and target cell measurement. Finally, inner central pallor boundaries are determined and features analyzed for more precise target cell identification.

After having extracted these identifying features, the cells are then categorized by a classification means. The preferred classification means (FIGS. 5a, 5b and 5c) comprise either a digital logic system of electrical devices or a programmed microprocessor which uses Boolean logic to classify the red blood cells.

Referring now in greater detail to the specific features of the illustrated embodiment of the invention, the images of the cells are digitized (operation 62 of FIG. 3) in a manner known to the art, e.g., U.S. Pat. No. 3,883,852 as a television digitizing system. Magnified blood cell images are obtained by using microscope optics with ultraviolet illumination, arranged to provide a 0.23 micron pixel resolution in the image plane. A pixel is a picture element having a specific location in the digitized image stored in the memory analyzer.

Figure 4:
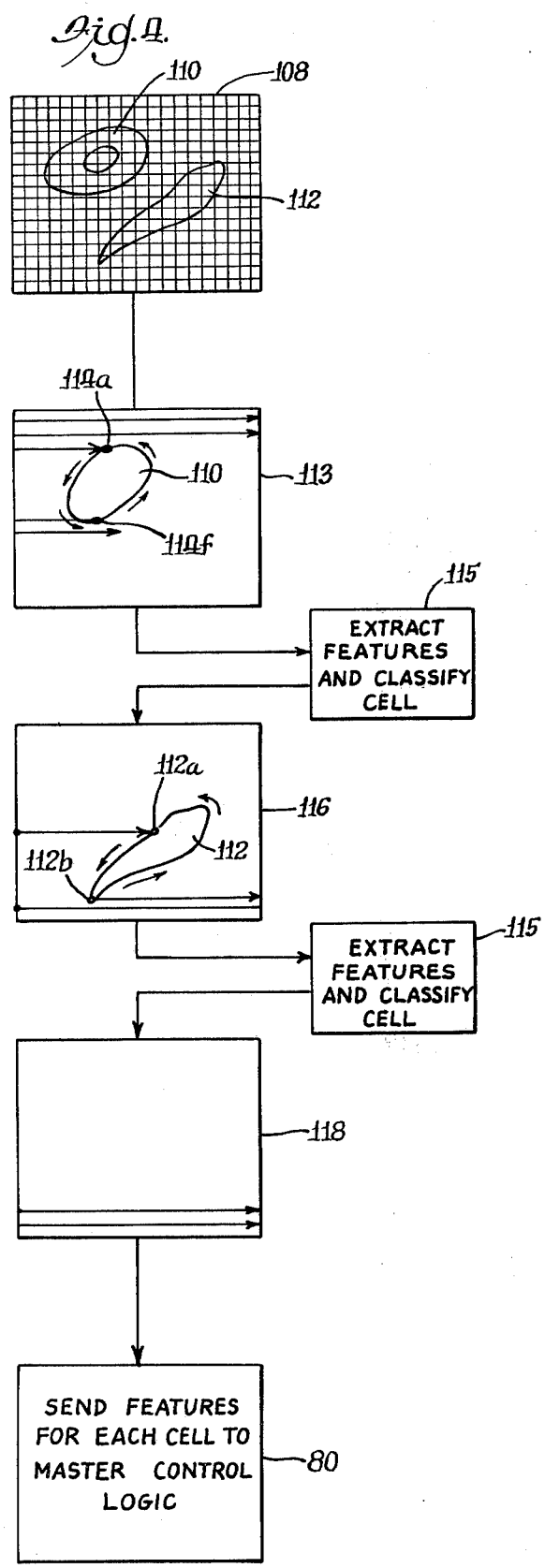
FIG. 4 illustrates a scanning technique for locating cells and determining the boundary point of cells in an image.

Referring now to FIG. 4 which illustrates in greater detail the operation 66 (FIG. 3) by the image processing logic. An original microscopic image which had been digitized is stored as represented by the image 108 for the purpose of further analysis. This analysis is carried out by the image processing logic and is represented by the blocks indicated at 115 which comprise the operations 76 and 78 (FIG. 3). In this preferred embodiment of the invention, individual cells 110 and 112 in a digitized image 108 are located by a technique in which a raster scan is made of the digitized image to locate objects above a critical threshold, such as illustrated for cell 110 in block 113. The boundary of the cell is traced by examining the neighboring pixel elements by a counterclockwise search, by techniques which are well known in the art, one such technique is disclosed in U.S. Pat. No. 3,315,229. During this counter-clockwise boundary tracing operation herein, the picture element at the "top" of the cell, pixel 114a, which is usually the pixel located first, and the one at the "bottom" of the cell, here pixel 114f, are stored for reference in the later analysis. The analysis process then proceeds to extract features and to classify the located cell into one of a plurality of subpopulations, as in block 115, and as described in detail later.

The raster scan of the digitized image is then continued from the bottom pixel 114f to hit the next digitized cell 112 by impacting a pixel 112a which is above the threshold as seen in block 116. After the boundary is traced and the features for this cell are extracted and the cell is classified, the raster scan continues from the bottom pixel 112b, and, as seen in block 118, no more cells are located in the image field. At this time, the image processing logic transmits the cell features and subpopulation classifications to the master control logic (operation 80) as shown in FIG. 4.

The initial image processing done by the image processing logic outlined in FIG. 3 is shown in greater detail in FIG. 5a. After the image has been digitized (operation 62), the image is scanned to locate a cell (operation 66) and the boundary is traced as explained above.

During this boundary tracing operation octal chain codes are formed in an operation 119. The outer boundaries, defining a cell, is processed in the following manner. Each pixel element defining the boundary is stored in a list as a series of numbers indicating a line description of the cell. For instance, referring to FIG. 7, a digital image of cells as defined by their boundary pixels 120 are illustrated.

As is well known in the art, e.g., as described in "Bacus, J. W. and J. H. Weens, 'An Automated Method of Differential Red Blood Cell Classification with Application to the Diagnosis of Anemia,' Journal of Histochemistry and Cytochemistry, 25:7, 1977," a plurality of features F1–F4 can be computed from this chain code. The details of this computation are fully described in the aforementioned publication, which is hereby incorporated by reference as if fully reproduced herein.

The above features are combined with other features for use in the classification of the cells. In this regard, the following features are used herein:

TABLE 2

| Feature | Description | How Determined |
|---|---|---|
| F1 | Area size | Number of pixels enclosed by cell boundary |
| F2 | Shape (circularity) | (Number of perimeter pixels$^2$/area |
| F3 | Shape (spicularity) | Number of "spicules" on boundary |
| F4 | Shape (elongation) | Comparison of orthogonal boundary chain code orientations |
| F5 | grey levels | Sum of grey levels as a measure of Cell Hemoglobin |
| F6 | Pallor (volume) | The percentage volume of the central pallor |
| F7 | Central Peak | The height of the central peak of a 3 peaked profile of a cell |
| F8 | Pallor (depth) | For a 2 peaked profile, the difference of the valley from the peak heights |
| F9 | Pallor (circularity) | (Number of pallor boundary pixels)$^2$/area of pallor |

As indicated above, features F1–F4 are calculated in an operation 124 by the image processing logic as shown in FIG. 5a. Feature F1 relates to the area or size of the cell as determined by the number of picture elements or pixels that are enclosed by the cell boundary. Feature F2 is the (boundary perimeter)$^2$/area and is of assistance in classifying round and non-round objects. A round object would have a theoretical value of $4\pi$ and non-round objects have greater values.

In actual practice the value of the perimeter squared divided by the area for round digitized objects varies as a function of the number of pixels, and in addition always involves quantization error, such that in practice for quantized circles the value approximates 14.0, and is a better approximation to this reference number as the number of pixels, or size, of an object increases. For total cell areas above 500 pixels the quantization error is within ±0.2 units.

Features F3 and F4 relate to the spicularity and elongation shapes, respectively, F3 being a count of the number of spicules in a chain code boundary, and F4 measuring the non-roundness due to elongation of the boundary, as shown in FIG. 7. Feature F5 is the integrated optical density of the cell (operation 136). It is the sum of the grey levels within the enclosed boundaries of the cell. Feature F6, which is a measure of the pallor volume, assists in distinguishing cells with large pallors, such as hypochromic cells from normocytes. Feature F7 is equal to the larger of the two central peaks of two cross sectional orthogonal 3 peaked thickness/density profiles, either having a central peak, and is used to detect target cells. Feature F8, is a measure of the depth of the central pallor, as determined from two cross sectional, orthogonal, 2 peaked, thickness/density profiles. Feature F9 is a measure of the degree of roundness of the pallor itself, and is also used in distinguishing target cells.

The logic decisions for determining the various features that have been briefly described are carried out by the image processing logic using the logic flow chart shown in FIGS. 5a, 5b, and 5c. The logic decisions are made using the various features together with threshold values that are identified as T1 through T11. The thresholds T1–T11 are described in Table 5 and specific values are also provided. As shown therein, the thresholds are used by the logic with the various features in making logic decisions leading to the classification of the cell of interest in accordance with the flow chart shown in FIGS. 5a, 5b, and 5c. In this regard, FIGS. 5a, 5b, and 5c illustrate various decisions that are made on the basis of various features either exceeding or being less than certain threshold values as will be specifically described.

Referring to FIG. 5a, an object that is located is examined by logic section 138 to determine if it is sufficiently large to be a cell, rather than a noise or dirt artifact, and thus is to be further analyzed. If feature F1, which is the size or area of the object under consideration, is less than the threshold value T1 which may be a value of about 6 microns$^2$, then the object is not considered by the decision logic and another object will be located for analysis and classification. However, if the area of the cell is greater than the threshold value T1, feature F5 is computed in operation 136 wherein the hemoglobin content of the cell is determined. This is simply a summing of the grey levels inside the boundary of the chain coded cell and then dividing by a conversion factor 1290 or thereabout to convert the grey level measurements to picograms of hemoglobin per cell.

For this purpose the electronics generating the television signal and digitizing said signal should be adjusted to produce grey levels corresponding to the following optical density at 418 nanometers:

TABLE 3

| Optical Density | Grey Level |
| --- | --- |
| .134 | 17 |
| .294 | 35 |
| .403 | 52 |
| .505 | 43 |
| .605 | 57 |

Also, for calculation of hemoglobin and the area the optics and television electronics should be adjusted such that round objects of the following dimensions produce the given number of pixels.

TABLE 4

| Size $\mu^2$ | Pixels |
| --- | --- |
| 111 | 1850 |

TABLE 4-continued

| Size $\mu^2$ | Pixels |
| --- | --- |
| 93 | 1550 |
| 77 | 1283 |
| 58 | 967 |
| 34 | 567 |
| 23 | 383 |
| 17 | 283 |
| 4 | 67 |

The decision logic then operates to determine whether the cell is round or non-round. This is performed by a logic section indicated generally at 140. The logic section 140 is shown in FIG. 8 to include logic subsections 142, 144, and 146. The subsections 142, 144 and 146 are operable to jointly make the roundness determination with the features F2, F3 and F4 being examined with respect to thresholds T4, T5 and T6. If the cell has a small roundness value, a small spiculated value and a small elongated value, then it is considered to be round and is passed on to the next operation 148 (FIG. 5a) which is the first step in the target cell analysis and central pallor analysis. Similarly, if it is determined that the cell is not round, then logic subsection 150 (FIG. 5a) operates to determine if the size of the cell exceeds an upper boundary threshold T2, and if it does, the cell is not further analyzed and a new cell will be considered. The effect of the subsection 150 is to eliminate double cells such as that shown in the pictorial representation 152. It should be appreciated from the pictorial representation that such a double cell would not pass the roundness test, but it is also not a non-round cell of the type for cells of classes 3 and 4. Thus, it cannot be accurately classified and it is for this reason that the subsection 150 eliminates such cells from further consideration.

As previously mentioned, the roundness of the cell is determined by feature F2 which will have a value of 14.0 for a perfect circle and will increase as the shape of the cell departs from circular. Thus, the threshold value T4 is chosen to reflect reasonably good circularity and if the feature F2 exceeds the threshold T4, that is an indication that the shape is not circular, hence the logical flow to subsection 150 indicating that the object is not round. If feature F2 is not greater than threshold T2, it is one indication that the cell is round and if the decision from the subsections 144 and 146 also indicate adequate roundness, the logic flow then proceeds to logic subsection 148 (FIG. 5a).

In operation 148 thickness/density profiles are extracted from the cell image. These profiles are illustrated in FIGS. 9a–9c and 10a–10c. A thickness density profile is determined by the grey levels of the pixels along a particular direction across the cell image. As noted earlier, the grey level of a pixel is determined by the hemoglobin density at that point. It has been found that the grey level of the cell at a particular point is related to the hemoglobin density and the cell thickness at that point. Two such thickness/density profiles, profile a and profile b are shown in FIG. 9a for a biconcave cell determined in two orthoginal or transverse directions, a and b. Two profiles each are also illustrated in FIGS. 9b and 9c for a target cell and a spherocyte cell. As seen in FIG. 9b, one direction (direction a) practically missed the center area. Since these profiles are used to distinguish target cells (Features F7), two transverse directions are preferably analyzed. Thus for each cell, two cross-sectional profiles are determined wherein the profile relates to the thickness of the cell along the points of the cross-sections.

A profile for each cell of FIG. 9 is discussed more fully in connection with FIGS. 10a–10c. As seen in FIG. 10a, the profile has two "peaks," P1 and P2, and one "valley," V1. P1 and P2 are relative maxima of the profile of the cell with respect to the cell thickness and thus determine the two relative maximum thickness density points along the profile. V1 determines the relative minimum point of thickness density. Similarly, the target cells have three relative maximums P1 P2 and P3 with two relative minima, V1 and V2 as shown in FIG. 10b. The spherocyte has one peak P1 and no valleys (FIG. 10c). These profiles are utilized in a target cell analysis and a central pallor analysis as will be more fully explained hereinafter.

After the image processing logic extracts the thickness/density profiles for the cell, it proceeds to the target cell analysis performed by the logic section, referred to generally at 156 of FIG. 5b. The first step of the target cell analysis is to smooth the two profiles, profile a and profile b, as shown in operations 156 and 158, which is performed by the image processing logic before proceeding to a logic subsection 160. The logic subsection 160 determines whether a profile has three peaks and if so forwards it to an operation 162 which determines half the average of the two non-center peaks, P1 and P3, or "LEV1." A logic subsection 164 determines whether the two valleys, V1a and V2a are less than LEV1 and if so then the cell located might be a target cell and the image processing logic proceeds to examine profile b. If not, then the valleys are not deep enough to be a target cell so the center peak, P2a, is set to zero in an operation 166 and profile a is smoothed to two peaks or less in an operation 168.

After profile a is examined, profile b is examined for three peaks in a logic subsection 170. If the logic subsection determines that profile b has three peaks, it is forwarded to an operation 172 and logic subsection 174 wherein the two valleys, V2a and V2b are compared to LEV2 which is half the average of the two non-center peaks P1b and P3b as for profile a. If the two valleys are less than LEV2, then it is forwarded to operation 176 wherein the feature, F7, is determined as to which is the larger of the two center peaks, P2a and P2b, of the profiles a and b. Features F7 is compared to a threshold T7 in a logic subsection 178, and if larger, the cell is classified as a target cell (C5). In other words, if the larger of the two center peaks is larger than a certain threshold, then the cell is determined to be a target cell. If not, then the center peaks of the profiles are probably due to "noise" in the image video and digitizing and not due to a center area of a target cell. In that case, both profiles are smoothed to two peaks or less in operations 180 and 182. However, if the logic subsection 174 determined that the valleys of profile b were not less than LEV2, then the profile b is forward to a logic subsection 184 which checks whether the center peak of profile a had been set to zero. If not, then profile a may have detected a target cell and thus P2b is set to zero and subsection 176 determines the maximum value for F7 as described.

If the center peak, P2a had been set to zero, then neither profile has passed the tests at logic subsection 164 and 174 respectively. Thus the cell is probably not a target cell and profile b is also smoothed to two peaks or less at operation 182. However, some target cells might not be detected in this analysis, therefore, other tests are performed on the cell as will be explained later.

After the center peaks of profiles a and b have been examined as explained above, a logic subsection 186 determines whether profile a has only one peak. If so, the variables P1a, P2a and V1a are set equal to each other in an operation 188. In either case, the image processing logic then examines profile b to determine whether it has only one peak, at the logic subsection 190. If profile b has only one peak then the variables P1b, P2b, and V1b are set equal to each other in an operation 192.

Continuing with FIG. 5c therein, a feature F8, which is the average value of the 2 valleys subtracted from the average value of the four peaks of the two profiles of the cell is determined by subsection 194. Then the cell feature F1 is examined to determine whether the size of the cell is larger than a threshold T8 at a logic subsection 196.

If the cell is large, i.e., F1 is greater than T8, it is possible that the cell is a target cell despite the previous target cell analysis and therefore another target cell analysis will be performed beginning in operation 198. Therein, a variable LEV3, is set equal to one-half the value of feature F8 (operation 198).

Next, a search for the central pallor of the cell is initiated by searching a direction along the line from the top pixel of the cell through the center of the cell looking for a threshold condition, i.e., hitting a pixel which is below the threshold LEV3, before the center is reached. The chain code is then formed for the central pallor boundary (operation 202). The pallor circularity feature F9 is then computed in an operation 204. F9 is calculated as the number of pallor boundary pixels squared divided by the area of the central pallor. F9 is then compared to a threshold value T9 at a logic subsection 206 to determine the circularity of the central pallor. This operation is necessary since the two profiles from the previous target cell analysis may have missed the central area as shown for the cell 208. Thus, if circularity feature F9 is greater than the threshold T9, then the cell is a target cell otherwise, the cell is forwarded to the operation 209 wherein a feature relating to the size of the central pallor of the cell is computed.

The central pallor feature is defined as the percentage volume of a cylinder, with the height and area of the cell under consideration, not occupied by hemoglobin. This is illustrated in FIG. 6, where T represents the cell height or thickness, and 132 indicates the indented central pallor region. The cell area is known from previous analysis on that cell, i.e., F1. Also, feature F5 is the sum of the grey levels for pixels enclosed by the chain code defining the boundary of the cell. As noted above, the hemoglobin density is related to the thickness of the cell and in this manner, the hemoglobin feature F5 defines a volume which is related to the thickness or volume of the cell. The cylinder height, or thickness (T), is derived by using the average value of the peaks of the two thickness/density profiles of the cell, as:

$$T = \frac{P1a + P2a + P1b + P2b}{4}$$

Thus, the volume of the central pallor may be calculated as: T times the area of the cell (F1) minus the hemoglobin content. Finally, the percentage pallor volume F6 is:

$$F6 = \frac{(T \times F1 - F5)}{T \times f1} \times 100\%$$

After this feature has been computed, the image processing logic proceeds to a logic subsection 210 wherein the cell is distinguished between biconcave cells (C1) and spherocyte cells (C2) as it has already been determined that the cell is not an elongated cell (C3), an irregular cell (C4) or a target cell (C5). The logic subsection 210 compares the percentage pallor volume feature F6 to a threshold value T10 and the pallor depth feature F8 to a threshold T11 and if either feature is less than its associated threshold then the cell is deemed a spherocyte cell (C2), otherwise it is a biconcave cell (C1).

Referring back to FIG. 3, the feature extraction operation 76 and the cell subpopulation classification operation 78 have been completed for the cell that had been located in the image scan. The image processing logic will then continue scanning the image for another cell (operation 66) and if no other cells are found then the features for those cells located as well as the cells' subpopulation classifications will be sent to the master control logic in the operation 80.

While the determination of the various features and decisions contained in the logic diagram of FIGS. 5a, 5b and 5c is carried out utilizing the threshold values contained in Table 6, it should be understood that the threshold values are based upon empirical and statistical analysis and can be varied somewhat without appreciably effecting the eventual classification of the cells. It should also be appreciated that the threshold values are believed to be optimum values which have been fixed to maximize the accuracy of the classification.

Table 5

| Threshold | Value | Description |
|---|---|---|
| T1 | $6\mu^2$ | Size threshold for artifact |
| T2 | $54\mu^2$ | Size threshold for double cells |
| T3 | 25 | Elongation threshold |
| T4 | 16 | Cell circularity threshold |
| T5 | 7 | Spiculed threshold |
| T6 | 25 | Elongation threshold |
| T7 | 5 grey levels | Target center peak heigh threshold |
| T8 | $47\mu^2$ | Size threshold for target cells |
| T9 | 20 | Pallor circularity threshold |
| T10 | 11% | Pallor volume threshold |
| T11 | 8 grey levels | Depth of pallor threshold |

Upon completion of the feature extraction and cell classification analyses for the cells located in the image, these features are transmitted to the master control logic as illustrated in FIG. 3. After acknowledging the receipt of the data (operation 82), the master control logic proceeds to update subpopulation measurements for each cell class located in the image just analyzed (operation 84). A diagram illustrating the updating operation in greater detail is shown in FIG. 11. A plurality of accumulators are provided to produce a running total of a plurality of measurements for the cell subpopulations or classes. Each accumulation is a function of one or more cell features, such as the cell feature value itself or the value squared, for example. The cell feature values F1, F2, F4, F5 and F6 for a particular cell are provided as inputs to the accumulaters together with the cell classification $C_i$ to which the cell features pertain. After the measurements for the cell have been accumulated, then the other cells in the image are similarly processed to further accumulate the measurements based on all of the cell's features.

Thus, the feature F2 (cell circularity feature) is provided at a line 212 to an accumulator 214. The accumulator 214 produces a running total S1, i.e., accumulates the measurement $(F2-14.1)^3$ for all the cells located by the image processing in logic wherein F2 is the cell circularity feature (Table 4), This measurement is used in a later calculation which provides a parameter describing the skewness of the distribution of all the red blood cells located, with respect to the circularity feature of the cells.

Also accumulated is the elongation feature F4 which is provided at a line 216 to accumulators 218 and 220. The accumulator 218 sums the total (S2) of the feature F4 for all the cells which is used to calculate the average elongation for the cells. The accumulator 220 provides a sum or running total (S3) of the elongation feature F4 squared, i.e., $(F4)^2$, which is used to calculate a parameter describing dispersion, or variation of the distribution of the red blood cells with respect to the mean of the elongation feature F4.

Not all feature measurements are accumulated for each subpopulation. For example, the feature F6 (pallor volume) is only accumulated for the biconcave cells (subpopulation C1) and the spherocyte cells (subpopulation C2). Therefore, in addition to the features for a particular cell, the subpopulation classification for the particular cell to which the features pertain is provided which is shown as $C_i$ at line 222. A plurality of logic utilize the input $C_i$ to discriminate among the cell subpopulations. Thus, the cell classification $C_i$ is provided to the inputs of a logic AND gate 224 and an AND gate 226 with subpopulation C1 constant (i.e. a 1) provided to the other input of the AND gate 224 and subpopulation C2 constant (1.e., a 2) provided to the other input of AND gate 226. The output of these AND gates are provided to an OR gate 228 which may enable the accumulators 230 and 232. The accumulator 230 provides a summation of the feature F6 (central pallor volume) as indicated by input lines 242, but only when enabled by the logic OR gate 228. Similarly, the accumulator 232 accumulates the sum of the feature $(F6)^2$ but only when enabled. Thus, the gates 224, 226, and 228 permit the accumulators 230 and 232 to accumulate the measurements derived from the feature F6 only when the feature had been extracted from a C1 or C2 biconcave or spherocyte class cell. The output of the accumulator 232 is provided at S5 which is used to compute the dispersion parameter of the distribution of spherocyte and biconcave cells with respect to the mean volume of the central pallor of the cells. The output of the accumulator 230 is provided at S4 which is also used to calculate the dispersion parameter and also to calculate the mean or average central pallor volume for the spherocyte and biconcave cells.

Similarly, a logic AND gate 234 enables accumulators 236, 238 and 240 when $C_i$ at line 222 is equal to a 2, i.e., the cell features appearing on the feature lines 244, and 246 were extracted from a class C2 (spherocyte) cell. The accumulator 236 accumulates the feature F1 (cell area) which is provided at S11, which will be used to calculate the mean cell area parameter for the cells in the C2 classification. The accumulator 238 provides at S12 the accumulated total of feature F5 (cell hemoglobin content) which is used to calculate the mean cell hemoglobin content for the class C2. The accumulator 240 provides a total of the number of cells in the C2 class, i.e., N2 equals the number of spherocyte cells located by the image processing logic.

In a similar manner the total cell area for the elongated (C3), the irregular (C4) and target (C5) cells are provided at S13, S15 and S17, respectively. The total of all cells hemoglobin content for the elongated, irregular, and target cells are provided at S14, S16 and S18, respectively. The total number of cells in each of the above subpopulations is provided at N3, N4 and N5.

Likewise, the total of all of the cells areas for the biconcave subpopulation is provided at S6, the total of all the cells hemoglobin contents is provided at S7, and the total number of biconcave cells is provided at N1. For additional accumulated measurements on the biconcave subpopulation, additional logic gates permit accumulators to discriminate among the class cells. Thus, an AND gate 248 enables accumulators 250, 252, and 254 when the features appearing at the lines 244 and 246 have been extracted from a C1, i.e., a biconcave cell. The accumulator 250 provides the accumulated sum of the measurement $(F1)^2$ at S8. The accumulator 252 similarly provides the accumulated total of the measurement $(F5)^2$ at S9. Finally, the accumulator 254 provides the accumulated sum of the product of the feature F1 times the feature F5 (F1 × F5). The accumulated S9 and S10 are used to calculated parameters descriptive of the dispersion, or variation of the bivariate distribution which will be further explained hereinafter.

Thus the features for each cell examined by the image processing logic provide the inputs to the logic described in FIG. 11 for up-dating or accumulating measurements based upon the cell features with the particular measurements up-dated for each cell depending upon the subpopulation classification to which that particular cell belongs. The measurements up-dated by the logic of FIG. 11 provide an intermediate step for the calculation of parameters which are descriptive of each subpopulation classification as well as parameters which are descriptive of multivariate distributions of cell subpopulations with respect to different cell features.

Referring back to FIG. 3, it is seen that at logic subsection 88 the determination is made whether a preset total of N cells have been processed. If not, the master control logic returns to operation 58 wherein it waits for the "digitizing done" signal indicating that the image processing logic has completed digitizing the next field. If N cells have been processed, e.g., N=one thousand, then the accumulated measurements which had been updated as illustrated in FIG. 11 for those N cells are used to calculate the parameters descriptive of the subpopulations (operation 90) which is illustrated in greater detail in FIGS. 12a through 12e.

The output S1 of the accumulator 214 (FIG. 11) is used in the calculation of a dispersion parameter which describes the skewness of a distribution. Herein, a distribution of all the cells with respect to the elongation feature (F4). Skewness is calculated as:

$$SKW = \left[ \frac{\sum_{k=1}^{N} (F2_k - 14.1)^3}{N} \right]^{\frac{1}{3}}$$

Thus a logic subsection 256 having inputs S2 and N produces the skewness parameter:

$$SKW = \left( \frac{S1}{N} \right)^{\frac{1}{3}}$$

The calculation of the skewness parameter is quite helpful in describing a population of cells. For example, a distribution of normal cells is shown in FIG. 15, generally at 255. The distribution is with respect to Feature F2 (circularity). Also shown is a distribution of sickle cell anemia cells, generally at 257. As can be seen there, the distribution of sickle cells is greatly skewed toward the right, indicating a great number of elongated cells. Note, however, that the mode of both distributions is identical. Thus, the skewness parameter is a valuable comparison tool for indicating anemias.

A logic subsection 258 having inputs S2 (the sum of the elongation measurements for the cells) and N (the total number of cells) produces the mean cell elongation parameter (ELN).

The general formula for the dispersion in the form of the standard deviation of a distribution with respect to a variable X is given by:

$$\text{Std. Dev.} = \left[ \frac{\sum_{k=1}^{N} x_k^2 - \frac{\left( \sum_{k=1}^{N} x_k \right)^2}{N}}{N-1} \right]^{\frac{1}{2}}$$

A logic subsection 260 produces the standard deviation of the elongation distribution of cells with respect to the elongation features. The logic subsection 260 has an input S2 equal to $$\sum_{k=1}^{N} F4_k$$

(FIG. 11) and an input S3 equal to $$\sum_{k=1}^{N} (F4_k)^2$$

and produces the elongation standard deviation (ESD) after the square root of the output has been taken by a logic subsection 262.

A parameter for the mean central pallor volume (PAL) of the bioconcave and spherocyte cells is provided by a logic subsection 264 having inputs N1 (the number of biconcave cells), N2 (the number of spherocyte cells) and S4 (the accumulated sum of the volumes of the central pallors of those subclassifications). A parameter of the distribution of the biconcave and spherocyte cells with respect to the central pallor volume, herein, the central pallor volume standard deviation (PSD) is provided by a logic subsection 266 having inputs S4 and S5 and a logic subsection 266 to finally produce the parameter PSD in a manner similar to that of the parameter ESD.

A distribution of three different populations of cells, normal, spherocytic, and iron deficient, with respect to the features F6, the percentage volume of central pallor is shown in FIG. 16. It is important to note that the distribution of normal cells at 267 has the same mean value (PAL) as the distribution of iron deficient cells at 269, yet they have a different variation or standard deviation (PSD) in central pallor volume. On the other hand the distribution of normal cells has the same standard deviation as the distribution of spherocyte cells at 271 but a different mean value. Thus both parameters have been found advantageous in the classification of blood with respect to anemias.

Two other parameters, EV1 and EV2, are computed utilizing the accumulated sums S6-S10 and N1 and which are descriptive of the amount of dispersions of a bivariate distribution of the biconcave cells. The two variables of the bivariate distribution are the cell size and the cell hemoglobin content. Four such distributions are illustrated in FIGS. 13a-13d wherein the cell area defines the abscissa axis and the cell hemoglobin content defines the ordinate axis. Each "X" represents a biconcave cell with its location within the graph defining the cell's area and hemoglobin content. Thus, as can be seen in the four Figures, the cells are distributed mainly on a 45° line passing through the origin. The mean cell area (MCA) and the mean cell hemoglobin (MCH) define the center of each distribution. The values, EV1 and EV2, define the dispersion or the amount of spread of the distribution in 2 principal independent axes. In particular, EV1 describes the amount of spread of the cluster or distribution along the direction at essentially 45°, or along the line of major dispersion of the ellipse with EV2 describing the dispersion in a direction which is orthogonal or transverse, that is 90°, relative to the dispersion of EV1.

Referring to FIG. 12a, a logic diagram is shown for the computation of the parameters EV1 and EV2. The general formula for computing the variance of a distribution with respect to a variable is similar to that given for the standard deviation. The variance of the distribution with respect to cell area is provided by a logic section 270 which has inputs N (the number of biconcave cells) S8 (the summation of $(F1)^2$ for each biconcave cell), and S6 (the summation of F1 for each biconcave cell). The variance of the distribution with respect to hemoglobin content is provided by a logic section 272 which has inputs N1, S9 (the summation of $(F5)^2$), and S7 (the summation of (F5)). A logic section 274 provides the sum, K, of the output of the logic sections 270 and 272 and a logic section 276 provides the product, A, of the output of the logic sections 270 and 272.

The co-variance of the distribution with respect to both the cell area and the cell hemoglobin content is provided by a logic section 278 having inputs N1, S7, S6 and S10 (the summation of the product F1 times F5 for each biconcave cell). A logic section 280 squares the output of the logic section 278 to produce an output, B. A logic section 282 subtracts the output A of the logic section 276 from the output B of the logic section 280 to provide an output D. K and D are coefficients of a quadratic equation wherein a logic section 282 produces the first solution, EV1, to the quadratic equation, and the logic section 284 produces the second solution, EV2, to the equation.

A logic section 286 produces the mean cell hemoglobin parameter for the biconcave cells by dividing the total hemoglobin content S7 for all the biconcave cells by the number (N1) of the biconcave cells. The mean cell area (MCA) of the biconcave cells is produced by a logic section 288 which divides the total cell area (S6) of the biconcave cells by the total number (N1) of the biconcave cells.

In a similar manner, as shown in FIG. 12b, the mean cell area and mean cell hemoglobin parameters are computed for the remaining four classes or subpopulations, i.e., the spherocytes, elongated, irregular, and target cells by eight logic sections 290-297. The number of cells in each subpopulation, N1-N5 are each transformed into a percentage of the total number of cells by five logic subsections 300-304, in FIG. 12b. For example, the percentage of biconcave cells (NC1) is provided by logic subsection 300 which divides the number of biconcave cells (N1) by a total number of cells located by the image processing means (N) and multiplies by 100.

Finally, in the preferred embodiment, two other parameters are calculated which describe the entire population of cells analyzed as illustrated in FIGS. 12d and 12e. First, a mean cell area parameter (MCA) is calculated as a weighted average by multiplying the percentage of a subpopulation (i.e. Ni-NC5 being first divided by 100) by the mean cell area for that subpopulation for each subpopulation and adding the products to produce the weighted average. For example, the percentage of biconcave cells (NC1) is multiplied by the mean cell area (MCA1) for the biconcave subpopulation by means of a logic section 306 and the percentage of the spherocyte cells (NC2) is multiplied by the mean cell area of the spherocyte cells (MCA2) by means of a logic section 308 and so on for the other subpopulations and adding these five products by means of a summation logic section 310 to produce the mean cell area (MCA) for the entire population. A weighted average of the hemoglobin content for the entire population (MCH) is produced in a similar manner by a plurality of "multiply" logic sections 312-316 and a summation logic section 318.

In the above manner, 24 parameters descriptive of the various subpopulations of red blood cells and the entire population of red cells as a whole may be calculated, 22 of which are listed in Table I. They are the percentage of the entire population for each subpopulation, the mean cell area (MCA) and the mean cell hemoglobin (MCH) for each subpopulation, the MCA and MCH for the entire population, the mean central pallor volume (PAL) of the distribution of biconcave and spherocyte cells, the standard deviation (PSD) of the central pallor volume distribution, and the skewness (SKW) of the circularity distribution of the entire population. Two parameters, the mean of the elongation distribution (ELN) and the standard deviation of the elongation distribution (ESD) are calculated but in the preferred embodiment are not reported, as in Table I. The parameters in Table I show values calculated for a sample of blood taken from a patient. Similarly, a sample of blood may be taken from another that is known to exhibit one of the known categories of anemia such as iron deficiency for example and the sixteen parameters may be calculated for the known anemic sample. Subsequently, the parameters calculated from the analysis of the sample of blood taken from the patient may be compared to the parameters of an iron deficient anemic sample to determine if the sample from the patient resembles iron deficient blood. Likewise parameters may be calculated for a plurality of known anemic samples of blood wherein the parameters of the patient's sample may be compared and in this manner the patient's blood may be classified with respect to those recognized categories of anemic blood. Referring to Table I, it is seen that the sample, from which the parameters of Table I were calculated, has been compared to eight types of blood which are normal, iron deficient, chronic disease, B- thalassemia, megaloblastic, hemoglobin SS, hemoglobin SC, and spherocytic. A specific classification technique to produce a similarity measure for the sample blood taken from the patient which is compared to recognized categories of anemia and normal blood is shown in FIG. 14. Sixteen of the 24 parameters can be thought of as defining a sixteen variable space or sixteen-space. Values for the sixteen different parameters would define a vector having sixteen components, one for each parameter. Thus, when a sample of blood taken from a patient is analyzed, the sixteen parameters calculated therefrom would define a vector Y having sixteen components ($y_1 \ldots y_i \ldots y_{16}$). Similarly, analysis of samples from the eight previously mentioned types of blood, normal and anemic, would define eight vectors, $W_{i,1}$ to $W_{i,18}$. Each component of the vector for a category of anemic or normal blood is determined by obtaining blood with prior knowledge of the anemic condition and measuring mean parameters over a plurality of such bloods for the sixteen parameters for that particular category. The vector Y representing the parameter values calculated for the sample of blood taken from the patient may be compared to the vectors representing the mean of various categories of anemic and normal blood. The vector that the vector Y most closely resembles, i.e., is the closest to in the sixteen-space would determine the classification of the patient's blood.

The first step in the anemia classification logic of FIG. 14 is to normalize each parameter value to produce the sixteen components of the Y vector. Thus a parameter value $X_1$ which represents, the mean cell area of biconcave cells in the patient's blood sample is normalized by a logic subsection 320 to produce the first component of the Y vector, $Y_1$. The logic subsection 320 in normalizing the parameter value $X_1$ subtracts the mean value $a_1$ from $X_1$ and divides by the standard deviation $b_1$ of the distribution of X, with respect to the biconcave cells. The distribution for each of the sixteen parameters has been determined with the mean $a_i$ and the standard deviation $b_i$ for each of the sixteen parameters as set forth in a Table 6 below:

TABLE 6

| | $a_i$ (mean) | $b_i$ (standard deviation) | parameter |
|---|---|---|---|
| i = 1 | 46.677 | 7.103 | $MCA_1 = X_1$ |
| 2 | 26.531 | 5.775 | $MCH_1 = X_2$ |
| 3 | 54.115 | 28.972 | $EV1 = X_3$ |
| 4 | 3.594 | 2.120 | $EV2 = X_4$ |
| 5 | 20.271 | 3.821 | $PAL = X_5$ |
| 6 | 4.646 | 1.161 | $PSD = X_6$ |

TABLE 6-continued

| | $a_i$ (mean) | $b_i$ (standard deviation) | parameter |
|---|---|---|---|
| 7 | 76.934 | 18.331 | $NC1 = X_7$ |
| 8 | 4.167 | 8.193 | $NC2 = X_8$ |
| 9 | 3.038 | 5.600 | $NC3 = X_9$ |
| 10 | 7.459 | 7.954 | $NC4 = X_{10}$ |
| 11 | 8.402 | 10.828 | $NC5 = X_{11}$ |
| 12 | 46.490 | 6.609 | $MCA = X_{12}$ |
| 13 | 26.490 | 5.548 | $MCH = X_{13}$ |
| 14 | 6.893 | 3.059 | $ELN = X_{14}$ |
| 15 | 5.949 | 2.363 | $ESD = X_{15}$ |
| 16 | 12.218 | 4.879 | $SKW = X_{16}$ |

There are sixteen logic sections represented by a logic section 322 which normalizes the parameter $x_i$ to produce one of the sixteen components $y_i$ of the vector Y. The vector Y representing the sixteen parameter values for the sample of blood taken from the patient is compared to the eight vectors $W_{i,1}$ to $W_{i,8}$ representing the parameter values for each of the eight categories of blood to determine the proper classification for the patient's blood.

Accordingly there are provided eight logic sections represented by a logic section 324 having the sixteen components $y_1–y_{16}$ of the vector Y as inputs. In addition, each of these logic sections has the sixteen components of a vector representing the parameter values of one of the categories of blood. For example, the first logic section 326 compares the parameter values for the patient's blood with the parameter values for normal blood. In this connection, the vector $W_{i,1}$ represents the sixteen components of the vector for normal blood. The two vectors, Y and $W_{i,1}$ are compared by the logic section 326 wherein the standard distance formula is used to calculate the distance between the two vectors to produce a distance D1. Referring to Table 1, it is seen that the patient's blood parameter vector has a distance of 0.9 to the normal blood parameter vector. In a like manner, the patient's parameter vector is compared to the parameter vectors for the seven categories of anemia, as seen in Table 1. The patient's blood parameter vector has a distance of 4.2 to the iron deficient category of anemia, a distance of 2.5 to the chronic disease category, and so on.

The sixteen components of the parameter vector for each of the eight categories of anemic and normal blood are set forth in a Table 7 below:

TABLE 7

| | | j | | | | | | Spherocytic |
|---|---|---|---|---|---|---|---|---|
| $W_{i,j}$ | Normal j = 1 | Iron def. 2 | Chronic 3 | Thal. 4 | Mega. 5 | SS 6 | SC 7 | 8 |
| i = 1 | 0.029 | −0.594 | −0.198 | −0.518 | 1.675 | 0.761 | 0.588 | −0.715 |
| 2 | 0.580 | −1.037 | −0.061 | −0.936 | 1.664 | 0.442 | 0.304 | −0.577 |
| 3 | −0.639 | −0.402 | −0.544 | −0.599 | 0.908 | 1.394 | 0.854 | −0.315 |
| 4 | −0.835 | 0.277 | −0.237 | −0.427 | 1.067 | 1.606 | 0.192 | −0.280 |
| 5 | −0.009 | 0.690 | −0.285 | 0.731 | 0.004 | 0.125 | 0.228 | −2.060 |
| 6 | −1.317 | 0.462 | −0.321 | 0.144 | 0.305 | 1.095 | 0.921 | −0.556 |
| i  7 | 1.073 | 0.356 | 0.196 | 0.330 | −0.120 | −1.028 | −1.065 | −0.642 |
| 8 | −0.439 | −0.319 | 0.143 | −0.303 | −0.041 | −0.158 | −0.162 | 2.677 |
| 9 | −0.483 | −0.201 | −0.411 | −0.093 | −0.338 | 1.297 | −0.336 | −0.439 |
| 10 | −0.715 | 0.153 | 0.154 | 0.130 | −0.509 | 0.774 | −0.144 | −0.033 |
| 11 | −0.709 | −0.370 | −0.340 | −0.377 | 0.782 | 0.620 | 2.204 | −0.687 |
| 12 | 0.024 | −0.652 | −0.253 | −0.547 | 1.806 | 0.556 | 0.726 | −0.679 |
| 13 | 0.590 | −1.039 | −0.072 | −0.967 | 1.688 | 0.287 | 0.272 | −0.449 |
| 14 | −0.607 | 0.082 | −0.476 | 0.137 | −0.281 | 1.162 | −0.599 | −0.750 |
| 15 | −0.767 | 0.080 | −0.494 | 0.203 | −0.392 | 1.610 | −0.270 | −0.695 |
| 16 | −0.903 | 0.171 | −0.360 | 0.204 | −0.451 | 1.333 | −0.013 | −0.497 |

Referring back to FIG. 3, upon completion of the anemia classification (operation 10), the master control logic proceeds to print the results (operation 102) of the analysis and similarity comparison or classification. One example of a print-out by the preferred method and apparatus has already been given as Table 1. The print-out in Table 1 indicates that the sample of blood analyzed is closest to normal based on the features analyzed. Two more examples are given in Tables 8 and 9 respectively, with Table 8 indicating hemoglobin SS anemia and Table 9 indicating β thalassemia.

Two examples of results of red blood cell analysis with the present invention will be listed below in Tables 8 and 9.

TABLE 8

| 66.5% Biconcave | | | | MCA | MCH |
|---|---|---|---|---|---|
| MCA 51 | | 2.3% Spherocytes | | 48 | 30 |
| MCH 29 | | 7.4% Elongated | | 41 | 24 |
| EV1 72 | | 14.6% Irregular | | 42 | 25 |
| EV2 6 | | 9.2% Targets | | 58 | 32 |
| Average 49 MCA | 29 MCH | 18 PAL | 5 PSD | 17 SKW | |
| 5.2 Normal | | 4.2 Megaloblastic | | | |
| 3.8 Iron Deficient | | 1.6 Hemoglobin SS | | | |
| 4.0 Chronic Disease | | 3.8 Hemoglobin SC | | | |
| 3.9 B-Thalassemia | | 5.9 Spherocytic | | | |

TABLE 9

| 78.2% Biconcave | | | | MCA | MCH |
|---|---|---|---|---|---|
| MCA 37 | | 2.4% Spherocytes | | 31 | 19 |
| MCH 21 | | 1.0% Elongated | | 26 | 15 |
| EV1 36 | | 13.5% Irregular | | 33 | 19 |
| EV2 3 | | 4.9% Targets | | 39 | 21 |
| Average 36 MCA | 21 MCH | 17 PAL | 5 PSD | 12 SKW | |
| 4.2 Normal | | 6.5 Megaloblastic | | | |
| 1.7 Iron Deficient | | 5.7 Hemoglobin SS | | | |
| 2.5 Chronic Disease | | 4.9 Hemoglobin SC | | | |
| 1.8 B-Thalassemia | | 4.1 Spherocytic | | | |

From the foregoing, it will be seen that the present invention allows a new and improved analysis of red blood cells heretofore not possible (even with the system disclosed in the above-identified co-pending application) and the discovery that the red blood cell population carries sufficient information to diagnose many anemias without resort to other conventional tests. That is, subtle, slight and early changes in either cell production or destruction may now be discovered, such as at the incipiency of an anemia because of the ability to measure accurately the hemoglobin content in individual blood cells, the cell shape, the cell size variations in size of central pallor, as well as the count of individual cell sizes, and an understanding of the total red cell population in blood samples that was heretofore not possible. With the continual process of red blood cell production and destruction over a 120 day life span for each cell, the high percentage of old normal red blood cells would mask the smaller number of new red cells being produced at the incipiency of a particular anemia. For instance, a chronic disease anemia such as caused by an infection, cancer or tuberculosis, may cause the new red blood cells being produced to be smaller in size with larger, central pallors than is normal and with decreased hemoglobin content. Naturally, early detection of a chronic disease kind of anemia would be most helpful in the treatment of this particular anemia.

With the present invention and for the first time, a total spectrum or galaxy of cells (i.e., the red cell population) may be automatically analyzed on an individual cell basis and over a sufficient number of cells and with sufficient accuracy to detect a dispersion of distribution indicative of a particular kind of anemia. Take, for example, a blood sample from a person suffering from an iron deficiency anemia. Typically, in such an instance, the usual values of dispersion, e.g., EV1 will be increased from a normal blood value of about 30 to values such as 45 or higher, and likewise the usual value of dispersion for EV2 will be increased from about 2 for a normal blood to about 3 or 4 or higher for an anemia such as an iron deficiency anemia. These slightly higher values of dispersion of distribution indicate that the normal cell population is changed because of the addition of these additional cells having small size, a large central pallor, and low amounts of hemoglobin. Thus, the diagnostician will see that the normal closely packed cell population has been expanded by these new cells formed after the onset of the anemia. The other values, such as location of the central tendency of the population's dispersion of distribution, which location is defined by the MCA and MCH values, may also have shifted because of the new anemia cells present. It is to be understood that the parameters used herein, such as MCA, MCH, EV1, EV2, skewness, etc., along with the central pallor descriptors, have been experimentally found to be most powerful (at this time) in analysis of the anemias illustrated and described herein. With further investigation, it may be that other parameters and/or measures may be used to describe and define the red cell population but such changes will still be within the purview of the appended claims and this invention. By way of example, the covariance, or correlation coefficients could be used to describe the red cell population as well as other measures, which are used to define a distribution and dispersion, and which could be used in lieu of the terms used herein in detail to describe the population of red blood cells.

Further, the present invention has been described principally in connection with the variables of mean cell hemoglobin and mean cell size although other variables such as pallor size and mean cell area have been tried and could be used. The particular parameters used and the names thereof may also be changed from that described herein and still fall within the purview of the present invention and the claims hereinafter recited.

The present invention is not to be construed as being limited to the classifying of cells into mutually exclusive subpopulations prior to making analysis of the dispersion of distribution of the red blood cells. For instance, it is possible to measure the characteristics of each of the red blood cells as to size, shape, hemoglobin, central pallor, etc., and then to make a multivariant dispersion distribution analysis without having a separate analysis of the biconcave cells as described herein. The classifying of the cells into a biconcave subpopulation and into other well known subpopulations is done because it is thought to be helpful to the diagnostician. Also, the classifying and reporting of subpopulations of biconcave cells, spherocytes, elongated cells, target cells, and irregular cells may be eliminated. The latter has been included merely as an aid to the diagnostician. Moreover, the listing of a plurality of anemias could be eliminated with the analysis and report being made only for one or more specific anemias thought to be most likely for the patient, or only that the blood sample appears to be normal. On the other hand, in a screening process of large numbers of blood samples each from a different person, it may be more helpful to include other anemias in addition to the seven anemias listed herein. The invention is thought to provide a particularly powerful tool for the screening of blood samples as well as for verification of anemias where a visual examination or other tests leave the diagnostician to suspect the presence of an anemia.

Of the seven listed anemias, the hardest anemias to distinguish from each other are the iron deficiency, chronic disease and B-Thalassemia. The accuracy of the diagnosis of these three anemias from one another is thought to be about 80% accurate with the existing equipment described herein. It is thought that the other anemias listed herein can be diagnosed with almost 100% accuracy. Generally speaking, when it has been found that the closest anemia listed was one of the three anemias of iron deficiency, chronic disease, B-Thalassemia and that closest anemia was not verified that the actual verified anemia will then be the next closest one listed of these three anemias. For this reason and other reasons, it is preferred to quantify the closeness of several anemias so that, if the first anemia is not verified, then the second closer anemia can be next chosen and examined for verification.

It will be recognized by hematologists skilled in the art that the diagnosis of some anemias, such as iron deficiency or chronic disease anemia, are most difficult today with conventional equipment even with all the information of other tests available to the hematologist. The present invention should provide a very useful tool for verification of a particular anemia when the other conventional tests which have been used and need to be verified.

Although the term "anemia" has been used extensively in this description, it should be noted that the term has been used in the general sense and the present invention may be used in a detection of other red cell disorders or pathologies such as hereditary elliptocytosis, for example, or others.

Although there has been described herein the use of first and second microcomputers, it is to be understood that only one larger computer could be used or hard wired logic could be used. On the other hand, more than one additional microcomputer may be added with each simultaneously measuring characteristics of a different red blood cell and each classifying different red blood cells into subpopulations. Thus, it is considered that one or more additional microcomputer may be used than described herein to expedite the system.

The above-described description and drawings provide a clear understanding of the invention and an enabling disclosure to persons skilled in the art. A specific example of the preferred equipment practicing the invention herein described is as follows: In the preferred embodiment, the master control logic 28 and the image processing logic 22 which carry out the flow diagram of FIG. 3 comprise two microcomputers such as the Digital Equipment Corporation LSI/11 microprocessors. In this embodiment, the listings shown in Appendix 1 and Appendix 2 can be used for implementing the flow diagram of FIG. 3 of the master control logic and image processing logic, respectively, using the features described herein together with the threshold values and parameter descriptors that have been previously set forth. The listing is of the binary load module as would be loaded into the microcomputer from the RT11 operating system monitor furnished by Digital Equipment Corp., with the listings being produced by the standard DUMP program with the /W/N option.

```
                    AN AUTOMATED METHOD AND APPARATUS FOR
                    CLASSIFICATION OF CELLS WITH APPLICATION TO
                    THE DIAGNOSIS OF ANEMIA

BLOCK NUMBER  00000
         000/  000002 000000 000006 000000 000012 000000 000016 000000
         020/  000022 000000 000026 000000 000032 000000 000036 000000
         040/  000042 000000 000046 000000 000052 000000 000056 000000
         060/  000062 000000 000066 000000 000072 000000 000076 000000
         100/  000102 000000 000106 000000 000112 000000 000116 000000
         120/  000122 000000 000126 000000 000132 000000 000136 000000
         140/  000142 000000 000146 000000 000152 000000 000156 000000
         160/  000162 000000 000166 000000 000172 000000 000176 000000
         200/  000202 000000 000206 000000 000212 000000 000216 000000
         220/  000222 000000 000226 000000 000232 000000 000236 000000
         240/  000242 000000 000246 000000 000252 000000 000256 000000
         260/  000262 000000 000266 000000 000272 000000 000276 000000
         300/  000302 000000 000306 000000 000312 000000 000316 000000
         320/  000322 000000 000326 000000 000332 000000 000336 000000
         340/  000342 000000 000346 000000 000352 000000 000356 000000
         360/  176377 000000 000000 100007 000374 000000 000000 000000
         400/  000000 000000 000000 000000 000000 000000 000000 000000
         420/  000000 000000 000000 000000 000000 000000 000000 000000
         440/  000000 000000 000000 000000 000000 000000 000000 000000
         460/  000000 000000 000000 000000 000000 000000 000000 000000
         500/  000000 000000 000000 000000 000000 000000 000000 000000
         520/  000000 000000 000000 000000 000000 000000 000000 000000
         540/  000000 000000 000000 000000 000000 000000 000000 000000
         560/  000000 000000 000000 000000 000000 000000 000000 000000
         600/  000000 000000 000000 000000 000000 000000 000000 000000
         620/  000000 000000 000000 000000 000000 000000 000000 000000
         640/  000000 000000 000000 000000 000000 000000 000000 000000
         660/  000000 000000 000000 000000 000000 000000 000000 000000
         700/  000000 000000 000000 000000 000000 000000 000000 000000
         720/  000000 000000 000000 000000 000000 000000 000000 000000
         740/  000000 000000 000000 000000 000000 000000 000000 000000
         760/  000000 000000 000000 000000 000000 000000 000000 000000
```

```
                                                                          BLOCK
000/ 000002 000000 000006 000000 000012 000000 000016 000000 NUMBER
020/ 000022 000000 000026 000000 000032 000000 000036 000000
040/ 000042 000000 000046 000000 000052 000000 000056 000000
060/ 000062 000000 000066 000000 000072 000000 000076 000000
100/ 000102 000000 000106 000000 000112 000000 000116 000000
120/ 000122 000000 000126 000000 000132 000000 000136 000000
140/ 000142 000000 000146 000000 000152 000000 000156 000000
160/ 000162 000000 000166 000000 000172 000000 000176 000000
200/ 000202 000000 000206 000000 000212 000000 000216 000000
220/ 000222 000000 000226 000000 000232 000000 000236 000000
240/ 000242 000000 000246 000000 000252 000000 000256 000000
260/ 000262 000000 000266 000000 000272 000000 000276 000000
300/ 000302 000000 000306 000000 000312 000000 000316 000000
320/ 000322 000000 000326 000000 000332 000000 000336 000000
340/ 000342 000000 000346 000000 000352 000000 000356 000000
360/ 176377 000000 000000 100007 000374 000000 000000 000000
400/ 000000 000000 000000 000000 000000 000000 000000 000000
420/ 000000 000000 000000 000000 000000 000000 000000 000000
440/ 000000 000000 000000 000000 000000 000000 000000 000000
460/ 000000 000000 000000 000000 000000 000000 000000 000000
500/ 000000 000000 000000 000000 000000 000000 000000 000000
520/ 000000 000000 000000 000000 000000 000000 000000 000000
540/ 000000 000000 000000 000000 000000 000000 000000 000000
560/ 000000 000000 000000 000000 000000 000000 000000 000000
600/ 000000 000000 000000 000000 000000 000000 000000 000000
620/ 000000 000000 000000 000000 000000 000000 000000 000000
640/ 000000 000000 000000 000000 000000 000000 000000 000000
660/ 000000 000000 000000 000000 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000

BLOCK NUMBER 00001
000/ 012706 001000 004567 104152 004567 065430 000401 005652
020/ 004567 064670 000401 003366 022767 000001 002330 001416
040/ 022767 000002 002320 001401 000757 012700 000011 012701
060/ 003370 012702 003412 012122 077002 000436 004567 065344
100/ 000401 006310 004567 064740 000401 003412 012700 000004
120/ 012701 006260 012703 006270 012167 000006 004567 065304
140/ 000401 000000 012702 000002 012367 000006 004567 064670
160/ 000401 000000 077207 077020 016700 002230 016701 002226
200/ 070100 010167 002232 016700 002212 006200 010067 002214
220/ 016700 002202 006200 010067 002204 016700 002156 016701
240/ 002154 070100 010167 004260 004567 102742 000404 003412
260/ 005534 005535 005532 022767 000001 004236 001002 000167
300/ 004250 022767 000002 004222 001002 000167 004272 004567
320/ 065064 000402 004504 003442 005067 013276 005067 013274
340/ 005067 013272 016701 012640 012700 015060 005020 077102
360/ 016701 012624 012700 014700 005020 077102 016701 012610
400/ 012700 014734 005020 077102 016701 012574 012700 014770
420/ 005020 077102 016701 012560 012700 015024 005020 077102
440/ 005067 011622 005067 011620 005067 011626 005067 003026
460/ 005067 004042 005267 004036 026767 004032 002002 001054
500/ 005067 004022 004567 064770 000405 015712 003414 003416
520/ 003420 003422 012700 015712 066700 003774 020037 170002
540/ 001361 004567 077534 000404 005530 015712 004510 004512
560/ 004567 077602 000405 004510 004512 004502 005512 005524
600/ 005367 003706 004567 064434 000403 005512 007317 004500
620/ 004567 064620 000401 007253 005267 011432 004567 064404
640/ 000403 013266 006713 004500 005002 004567 064622 000405
660/ 015712 003424 003426 003430 003432 005202 010267 012724
700/ 004567 064340 000403 014624 006734 004500 004567 064524
720/ 000401 006676 012700 015712 066700 001504 020037 170002
740/ 001344 016703 001532 005004 005267 002532 020367 002526
760/ 001067 005067 002520 004567 077310 000404 003440 015712
```

BLOCK NUMBER 00002
```
000/  004510 004512 004567 077356 000405 004510 004512 004502
020/  005512 005524 016701 003462 005301 016700 001440 060300
040/  020100 003401 005204 006303 160300 020100 002001 005204
060/  010167 012540 004567 064154 000403 014624 007173 004500
100/  004567 064340 000401 007125 005704 001412 004567 064324
120/  000401 007204 000000 006203 005303 010367 002350 000644
140/  004567 101712 000404 003412 005536 005542 005532 022767
160/  000001 003346 001002 000167 003360 022767 000002 003332
200/  001002 000167 003402 012767 003502 002106 012767 004324
220/  002222 012767 000001 011056 000167 005350 004567 101616
240/  000404 003412 005537 005535 005532 022767 000001 003252
260/  001002 000167 003264 022767 000002 003236 001002 000167
300/  003306 026727 002014 003502 001003 005067 002130 000406
320/  016700 001776 162700 003502 010067 002112 004567 102562
340/  000402 004502 004446 005767 002074 001405 004567 102542
360/  000402 004446 003502 016700 001020 004567 102574 000402
400/  005550 005532 005767 003122 001023 142767 000200 003130
420/  126767 003124 003117 001417 126767 003114 003111 001431
440/  126767 003104 003100 001002 000167 000442 000167 003072
460/  077034 000167 003122 004567 101664 000404 015712 003424
500/  003426 005532 005767 003022 001402 000167 004612 000167
520/  000374 004567 063660 000402 004476 004450 016700 000674
540/  010067 000304 010067 000304 162700 000002 010067 000074
560/  016700 000652 162700 000002 010067 000140 012702 004450
600/  012267 001642 016703 000624 016704 000622 012201 005301
620/  006301 006301 006301 062701 004324 012100 005300 010067
640/  000132 010067 000162 162100 005400 020027 000000 003415
660/  010067 011740 004567 063354 000403 014624 007001 004500
700/  004567 063540 000401 006753 000000 012100 005300 010067
720/  000064 010067 000076 162100 005400 020027 000000 003415
740/  010067 011660 004567 063274 000403 014624 007066 004500
760/  004567 063460 000401 007040 000000 022703 000000 002402
```

BLOCK NUMBER 00003
```
000/  010367 000024 022704 000000 002402 010467 000006 016701
020/  000402 070127 000000 062701 000000 062701 015712 012700
040/  055714 112120 077302 012703 000000 062701 000000 077407
060/  004567 101272 000404 055714 003434 003436 005532 005767
100/  002430 001402 000167 004220 005367 001332 001233 016700
120/  000270 004567 102044 000402 005550 005532 005767 002372
140/  001015 142767 000200 002400 126767 002374 002362 001417
160/  126767 002364 002353 001405 000167 002356 077026 000167
200/  002406 004567 063236 000401 006632 000167 176246 004567
220/  063222 000401 006654 000167 007234 004567 100620 000404
240/  003412 005543 005544 005532 022767 000001 002254 001002
260/  000167 002266 022767 000002 002240 001002 000167 002310
300/  020227 003502 001003 005067 001134 000406 016722 007762
320/  162702 003502 010267 001116 004567 101566 000402 004502
340/  004446 005767 001100 001405 004567 101546 000402 004446
360/  003502 000167 175662 017000 023420 000200 000060 000276
400/  000315 000200 000200 000276 000067 040265 002201 000534
420/  026000 124000 133605 157012 173777 161055 154377 001777
440/  173404 151035 154377 103777 173400 145012 173777 146055
460/  142377 001777 173407 137035 141377 145377 000001 000054
500/  000012 000207 005267 177670 026767 177676 177662 002003
520/  016767 177654 177664 000207 005367 177644 026767 177650
540/  177636 003403 016767 177630 000456 005000 172000 117205
560/  103777 054000 000001 000054 102770 004567 002442 000404
600/  005067 000072 013567 000070 013567 000066 013567 000064
620/  004567 000516 000402 103074 103076 004567 000504 000402
640/  000703 022000 017000 040206 041206 140206 036025 014206
660/  073572 125011 001001 040001 041206 176606 006035 000000
700/  073400 177000 022404 000001 000054 103104 004567 002326
720/  000405 013500 070035 010067 000124 010167 000122 004567
740/  000406 000402 103246 103250 163501 005600 163500 010067
760/  000100 000414 026000 065000 073606 037020 073400 167011
```

```
BLOCK NUMBER 00004
000/  001000 125001 126206 140206 123025 014206 141172 001025
020/  030000 175024 101777 140176 121025 010206 073572 115011
040/  000001 000034 103220 000504 000402 103246 103250 016775
060/  000014 000000 000167 002230 041710 000000 000747 026000
100/  127000 073606 066011 002404 073401 121027 033400 116012
120/  073400 120011 001000 054001 055207 140207 052025 010207
140/  073572 107027 033400 104012 115000 000001 000054 103324
160/  004567 000210 000402 103534 103536 075000 016767 000172
200/  000164 016767 000162 000154 004567 000346 000402 103534
220/  103536 016775 000144 000611 026000 175000 001206 173400
240/  055035 056000 173400 051035 052000 140000 002345 010000
260/  073572 044027 033400 041012 073400 043011 001000 054001
300/  055207 134207 000001 000054 103440 162700 000004 075030
320/  012767 000012 000056 005067 000050 004567 000054 000402
340/  103530 103532 162700 000004 075020 004567 000222 000402
360/  000615 014000 043000 056207 057207 176607 010035 001000
400/  073400 163000 132403 100500 046004 000001 000054 103540
420/  004567 001672 000402 005775 000000 001003 005775 000002
440/  001460 005001 017502 000000 017503 000002 005702 100006
460/  005102 005103 062703 000576 026000 103000 000607 000026
500/  000001 000002 000036 114025 000400 100040 004000 113404
520/  000566 102000 141012 100065 175000 000003 004341 141001
540/  000065 037777 000001 000054 103654 001404 073227 177777
560/  005204 000771 060400 042702 000200 072027 000007 074002
600/  005701 001402 052702 100000 010275 000000 010375 000002
620/  000716 005000 151000 073607 062000 137003 000001 000054
640/  103726 004567 001504 000402 005775 000000 001003 005775
660/  000002 001440 005001 017502 000000 017503 000002 005702
700/  100003 042702 100000 005201 000500 026000 176000 100207
720/  140020 077505 001200 141100 100125 013400 174564 140377
740/  114345 100000 140566 002413 041003 041412 141412 000545
760/  041000 136413 076420 000001 000020 104042 000000 010375

BLOCK NUMBER 00005
000/  000002 000167 001416 000656 026000 026000 073610 167011
020/  002002 040001 000037 073400 001035 004000 073400 010011
040/  001002 104001 000210 073400 027011 001002 105001 103210
060/  173610 031413 000001 000054 104122 000062 001010 142767
100/  000200 000056 126775 000052 000004 001403 000406 077026
120/  000411 005075 000006 000167 001310 012775 000001 000006
140/  000451 012000 074000 073610 137000 176402 001025 003000
160/  073400 132000 066402 000000 000010 104210 000001 000746
200/  026000 106000 073610 107011 002002 040001 000037 073400
220/  157011 001001 165001 163210 173610 041013 004000 173402
240/  100305 037000 176400 035255 001000 055400 000001 000054
260/  104262 001403 000416 077021 000421 016567 000004 000010
300/  004567 000614 000402 104350 000000 005075 000006 000167
320/  001150 012775 000001 000006 000574 012000 154000 073610
340/  057000 176402 001025 003000 073400 052000 146402 000001
360/  000010 104350 000001 000606 026000 166000 073610 027011
400/  002002 073401 142023 073400 001237 012400 073401 002237
420/  010000 036401 003012 140000 172025 173611 053035 171167
440/  144000 037213 000001 000054 104422 001430 004567 000546
460/  000402 105006 105010 005767 000000 000757 005300 005367 000312
500/  000334 126720 000330 001001 000757 005300 005367 000312
520/  000452 026000 034000 165611 176402 004025 051106 042115
540/  043514 040520 052102 051516 073400 004567 060466 000401
560/  005564 000000 020040 020040 025040 045040 047125 020113
600/  051105 047522 006522 000012 004567 060630 000401 005622
620/  000000 020040 020040 025040 052040 046511 026505 052517
640/  020124 051105 047522 006522 000012 020040 020040 042504
660/  040506 046125 020124 047514 050117 052040 046511 020105
700/  020075 030061 030060 006460 020012 020040 042040 043105
720/  052501 052114 054040 054454 042040 046511 047105 044523
740/  047117 020123 043117 046040 053517 053440 047111 047504
760/  020127 020075 031061 026070 032040 006470 020012 020040
```

```
BLOCK NUMBER 00006
000/  042040 043105 052501 052114 046040 053517 053440 047111
020/  047504 020127 043117 051506 052105 020123 020075 034461
040/  026060 031040 032460 005015 020040 020040 042504 040506
060/  046125 020124 026130 020131 044504 042515 051516 047511
100/  051516 047440 020106 044520 052103 051125 020105 020075
120/  031061 026070 030440 034062 005015 020040 020040 042504
140/  040506 046125 020124 044520 052103 051125 020105 044527
160/  042116 053517 047440 043106 042523 051524 036440 030440
200/  030071 020054 032465 005015 020040 020040 043111 040440
220/  054516 041440 040510 043516 026105 052040 050131 020105
240/  027131 042440 051514 026105 047040 020056 037055 000040
260/  006340 006416 006475 006550 003414 003416 003420 003422
300/  003424 003426 003430 003432 020040 020040 042440 052116
320/  051105 046040 047517 020120 044524 042515 035040 000040
340/  020040 020040 042440 052116 051105 046040 053517 053440
360/  047111 047504 020127 044504 042515 051516 047511 051516
400/  024040 044443 020130 044443 024531 035040 000040 020040
420/  020040 042440 052116 051105 046040 053517 053440 047111
440/  047504 020127 043117 051506 052105 020123 021450 047511
460/  030506 021440 047511 031106 020051 020072 020000 020040
500/  020040 047105 042524 020122 044520 052103 051125 020105
520/  044504 042515 051516 047511 051516 024040 044443 020130
540/  044443 024531 035040 000040 020040 020040 042440 052116
560/  051105 050040 041511 052524 042522 053440 047111 047504
600/  020127 043117 051506 052105 020123 021450 043117 020061
620/  044443 043117 024462 035040 000040 020040 020040 043440
640/  051040 041505 044505 042526 006504 000012 020040 020040
660/  046040 051040 041505 044505 042526 006504 000012 020040
700/  020040 050040 041511 052524 042522 010440 062716 000002
720/  020346 044504 044507 044524 042532 020104 000000 001000
740/  000000 052040 046511 051505 005015 020000 020040 020040
760/  026530 044504 020115 043117 041440 046105 020114 051511

BLOCK NUMBER 00007
000/  000040 023000 005400 006401 020012 020040 020040 047503
020/  052116 047111 042525 041040 020131 050047 006447 000012
040/  020040 020040 054440 042055 046511 047440 020106 042503
060/  046114 044440 020123 046000 047000 000000 005015 020040
100/  020040 041440 047117 044524 052516 020105 054502 023440
120/  023520 005015 020000 020040 020040 044520 052103 051125
140/  020105 040502 045503 051107 052517 042116 043440 042522
160/  026531 042514 042526 020114 051511 000040 000212 000000
200/  006616 000012 020040 020040 025040 040440 045104 051525
220/  020124 044526 042504 027117 041440 047117 044524 052516
240/  020105 054502 023440 023520 005015 020000 020040 020040
260/  047514 020127 044527 042116 053517 041040 041501 043513
300/  047522 047125 020104 042514 042526 020114 051511 000040
320/  000000 000322 006400 000012 016700 176176 005001 006200
340/  103402 005201 000774 006301 016167 007370 000006 004567
360/  057062 000401 000000 000000 007376 007446 007522 020040
400/  020040 020052 044520 020103 051124 047101 046523 051511
420/  044523 047117 052040 046511 026505 052517 020124 051105
440/  047522 006522 000012 020040 020040 020052 044520 020103
460/  051124 047101 046523 051511 044523 047117 045040 047125
500/  020113 042515 051523 043501 020105 051105 047522 006522
520/  000012 020040 020040 020052 044520 020103 051124 047101
540/  046523 051511 044523 047117 044440 051516 043125 044506
560/  044503 047105 020124 050123 041501 020105 051105 047522
600/  006522 000012 016767 003476 003472 016767 173634 003470
620/  004567 056764 000405 015712 003440 013310 013304 005532
640/  022767 000001 175664 001002 000167 172360 005267 003410
660/  012700 013232 012701 000016 012720 177777 077103 012767
700/  177777 003374 012767 177777 004674 012767 177777 004670
720/  005067 003346 005067 003344 005067 003342 004567 056756
740/  000413 015712 003424 003426 013304 013310 013312 013314
760/  014134 013306 004500 005532 022767 000001 175534 001002
```

```
BLOCK NUMBER 00010
000/ 000167 005270 022767 000002 175520 001456 004567 071566
020/ 000420 013304 003424 003426 013314 014134 014136 014140
040/ 014142 014144 014154 014146 014150 014152 014156 013236
060/ 005532 022767 000001 175442 001002 000167 005262 022767
100/ 000000 004032 001421 022767 000000 004026 001415 016701
120/ 173302 005301 020167 004010 001407 016701 173270 005301
140/ 020167 004000 001401 000404 005367 003114 000167 177424
160/ 026767 003770 173300 002770 004567 073064 000405 014150
200/ 014146 014154 014160 013234 016701 003742 070127 000144
220/ 005000 071067 003732 010067 003006 005002 026767 002774
240/ 173202 002012 026767 002766 173174 002006 026767 002760
260/ 173166 002002 005202 000407 026767 003660 173172 002403
300/ 005267 002776 000721 004567 057276 000415 013304 003424
320/ 003426 015712 013314 014134 013310 013232 013242 013272
340/ 004500 014206 005532 022767 000001 175156 001002 000167
360/ 005054 016700 002644 070067 173104 160167 002644 005667
400/ 002670 160067 002664 022702 000001 001434 026767 002616
420/ 173024 002414 026767 002610 173016 002404 012704 000005
440/ 000167 001602 012704 000006 000167 001572 026767 002560
460/ 172766 002404 012704 000007 000167 001552 012704 000010
500/ 000167 001542 004567 070072 000415 015712 003424 003426
520/ 014136 014140 014212 014142 014144 014356 014522 014524
540/ 014526 014530 000433 005003 016700 003752 012701 014212
560/ 112102 042702 177400 060203 077005 016700 003732 012701
600/ 014356 112102 042702 177400 060203 077005 005002 016700
620/ 003704 066700 003702 071200 010267 002422 004567 070336
640/ 000402 014526 014212 004567 070112 000407 014526 014212
660/ 014626 014532 014556 014602 014606 004567 070300 000402
700/ 014530 014356 004567 070054 000407 014530 014356 014626
720/ 014544 014570 014604 014610 022767 000003 003644 001057
740/ 012700 014556 011001 066001 000010 006201 010102 166702
760/ 002326 006202 006202 160201 026001 000002 002023 026001

BLOCK NUMBER 00011
000/ 000006 002020 016002 000002 066002 000006 006202 166002
020/ 000004 005402 010267 002220 020267 172440 002402 000167
040/ 001036 000415 004567 067714 000407 014526 014212 004502
060/ 014532 014556 014602 014612 066767 003516 003510 022767
100/ 000003 003500 001060 012700 014570 011001 066001 000010
120/ 006201 010102 166702 002160 006202 006202 160201 026001
140/ 000002 002024 026001 000006 002021 016002 000002 066002
160/ 000006 006202 166002 000004 005402 010267 002052 020267
200/ 172272 002402 000167 000670 000167 000674 004567 067544
220/ 000407 014530 014356 004502 014544 014570 014604 014614
240/ 066767 003350 003342 022767 000001 003326 001006 012700
260/ 014556 011060 000004 011060 000002 022767 000001 003304
300/ 001006 012700 014570 011060 000004 011060 000002 012700
320/ 000002 016001 014556 066001 014570 006201 010167 003256
340/ 012700 000004 016702 003206 066002 014556 066702 003210
360/ 066002 014570 006202 006202 010267 003224 160102 010267
400/ 001650 016700 003212 166700 172064 010067 001640 010067
420/ 003200 004567 071460 000405 013232 014622 013242 013272
440/ 013260 026727 001604 000010 002406 026767 001602 172004
460/ 003402 000167 000106 026767 001540 171746 002004 012704
500/ 000004 000167 000540 004567 071260 000404 013232 013272
520/ 013242 013254 026767 001524 171730 002404 012704 000004
540/ 000167 000502 026767 001462 171704 002004 012704 000002
560/ 000167 000462 012704 000003 000167 000452 026767 001432
600/ 171670 002002 000167 000300 016700 001436 006200 066700
620/ 002774 010067 001462 004567 066652 000406 015712 014522
640/ 013310 014532 013304 005532 022767 000001 173654 001002
660/ 000167 003640 004567 055026 000413 015712 003424 003426
700/ 013304 013310 013312 013314 014134 013306 014206 005532
720/ 022767 000001 173604 001002 000167 003340 022767 000002
740/ 173570 001002 000167 003660 004567 067632 000420 013304
760/ 003424 003426 013314 014134 014162 014164 014166 014170
```

```
BLOCK NUMBER 00012
000/ 013244 014172 014174 014176 014200 014204 005532 022767
020/ 000001 173506 001002 000167 003326 005767 001206 001004
040/ 012767 000310 001200 000410 004567 071204 000405 014174
060/ 014172 013244 014202 013246 026767 001152 171356 002404
100/ 012704 000011 000167 000136 016700 001156 016701 001122
120/ 073027 177776 020167 171330 002024 026767 001074 171302
140/ 002004 012704 000012 000167 000074 026767 001054 171276
160/ 002004 012704 000013 000167 000054 012704 000014 000167
200/ 000044 026767 001024 171232 002004 012704 000015 000167
220/ 000024 026767 001004 171226 002404 012704 000016 000167
240/ 000004 012704 000001 016767 002334 001006 016767 002330
260/ 001002 010467 001012 020427 000001 001013 022767 177777
300/ 000754 001407 005267 002326 066767 000742 002316 005567
320/ 002310 005304 006304 005264 015060 066764 000674 015024
340/ 005564 014770 066764 000672 014734 005564 014700 066764
360/ 000710 014700 022767 177777 000662 001007 004567 070372
400/ 000404 013232 013272 013242 013254 016700 171704 012701
420/ 013232 012702 000024 012120 077202 010067 171664 016700
440/ 172002 012701 014136 012702 000004 012120 077202 010067
460/ 171762 000167 175116 004567 053752 000401 013146 005004
500/ 012702 003502 022704 000034 001002 000167 170514 005764
520/ 015060 001002 000167 000406 005704 001011 016700 002072
540/ 016701 002070 071067 002066 010064 015240 000402 005064
560/ 015240 016400 014770 016401 015024 071064 015060 010067
600/ 002060 005067 002052 004567 070730 000402 014660 014662
620/ 012700 014654 075020 004567 071076 000402 014660 014662
640/ 016764 002016 015114 016467 014700 002014 016467 014734
660/ 002010 004567 070654 000402 014670 014672 012700 014664
700/ 075030 011060 000004 016060 000002 000006 005010 016460
720/ 015060 000002 004567 070612 000402 014670 014672 075030
740/ 004567 070764 000402 014674 014676 016764 001720 015150
760/ 016700 001712 070027 000144 071064 015114 010064 015204

BLOCK NUMBER 00013
000/ 010403 006203 005203 012700 014640 010320 016420 015060
020/ 016420 015114 016420 015150 016420 015204 016420 015240
040/ 012701 000006 012700 014640 012022 077102 012701 000005
060/ 005704 001002 012701 000006 012700 014640 012067 001524
100/ 004567 053140 000403 014624 013220 004500 004567 053324
120/ 000401 013220 077115 004567 053312 000401 013227 062704
140/ 000002 000167 177336 005015 020040 041440 040514 051523
160/ 041440 046105 051514 020040 041515 020101 020040 041515
200/ 020110 046440 044103 020104 020040 041515 006524 000012
220/ 002424 002426 000543 006400 000012 000400 143004 000424
240/ 040006 000407 055010 002011 072040 144410 000440 142044
260/ 000424 012046 000405 013050 032005 000001 000034 000003
300/ 007030 012314 013134 013136 013140 000620 013144 013154
320/ 013146 013150 013152 000620 027000 002000 000400 146004
340/ 000424 056006 000426 057010 000426 060012 000426 061014
360/ 000426 062016 000426 066020 000426 063022 000426 064024
400/ 000426 065026 013426 000001 000056 000003 007054 013156
420/ 012236 004532 022767 000001 175442 001002 000167 005262
440/ 022767 000000 004032 001421 022767 000000 004026 001415
460/ 016701 173302 000530 011000 002000 000400 067004 000426
500/ 117006 000424 055010 035411 000001 000056 000003 007122
520/ 005301 020167 004010 001407 016701 173270 005301 020167
540/ 004000 001401 000404 005367 003114 000167 177424 026767
560/ 003770 173300 002770 000500 027000 001400 074000 073416
600/ 000011 002400 064001 063026 066026 070026 116026 140424
620/ 161035 053407 062160 000000 033412 155162 033407 003020
640/ 091006 173412 003455 000001 000040 000004 003004 062332
660/ 012072 005001 013150 006001 013146 007001 013154 010001
700/ 013160 011001 012234 000510 027000 001400 117000 176016
720/ 101005 005366 173404 173055 076005 003366 173404 170055
740/ 073005 001366 101004 003412 173401 130055 075007 001766
760/ 133405 177012 145005 000001 000040 000003 007304 000721
```

```
BLOCK NUMBER 00014
000/ 004567 000000 000415 012304 002424 002426 014712 012314
020/ 013134 012310 012232 000737 026000 002000 002000 044410
040/ 024571 000426 142014 000424 012016 000405 013020 000405
060/ 145022 000431 146024 000424 056026 000426 144030 000424
100/ 115032 053424 000001 000056 000003 007334 012242 012272
120/ 003500 013206 004532 022767 000001 175156 001002 000167
140/ 005054 016700 002644 070067 173104 160167 002644 005667
160/ 002670 000776 015000 002000 000400 121004 000424 135006
200/ 000424 040010 000407 177777 000016 055014 165011 000001
220/ 000056 000003 007402 160067 002664 022702 000001 001434
240/ 026767 002616 173024 002414 026767 002610 173016 002404
260/ 012704 000005 000167 001602 012704 000006 000635 027000
300/ 001400 024000 073417 075000 173403 070055 173005 002365
320/ 142005 003425 073400 065000 142003 004025 073400 061000
340/ 073403 000011 006400 145001 012031 005405 000001 000024
360/ 000004 021004 063136 035101 023001 014712 024001 002424
400/ 000466 016000 001400 047000 013017 057005 060026 105026
420/ 061026 062026 167026 051026 052027 053027 123427 000001
440/ 000056 000004 002001 002426 003001 013136 004001 013140
460/ 005001 013212 006001 013142 007001 013144 010001 013356
500/ 011001 013522 012001 013524 013001 013526 000545 027000
520/ 001400 061000 054017 015427 001401 140012 165035 140407
540/ 105025 041026 141224 000105 101777 002540 140176 155035
560/ 140407 167025 041026 141224 000105 145777 000001 000022
600/ 000004 002001 013530 010001 013212 021001 013356 000635
620/ 027000 001400 104000 000003 000012 001176 140012 142035
640/ 140007 141155 100007 133562 011020 073405 037165 141217
660/ 053001 105027 042621 020001 003400 053001 151027 000001
700/ 000036 000004 015004 074327 077141 017001 013526 020001
720/ 013212 022004 062716 004101 024001 013526 000412 020000
740/ 001400 127000 105017 113026 055027 067027 101027 103027
760/ 073427 000011 001000 054001 167027 073426 030011 000001

BLOCK NUMBER 00015
000/ 000054 000004 002001 013212 003001 013626 004001 013532
020/ 005001 013556 006001 013602 007001 013606 011004 074327
040/ 077141 013001 013530 014001 013356 000463 027000 001400
060/ 143000 000017 003400 054001 167027 113026 062027 074027
100/ 102027 104027 173427 001445 122027 027407 140002 067025
120/ 000427 000422 004154 100400 021414 000001 000054 000004
140/ 002004 062716 004101 004001 013530 005001 013356 006001
160/ 013626 007001 013544 010001 013570 011001 013604 012001
200/ 013610 020001 013556 000730 027000 001400 166000 041017
220/ 141020 153355 101004 101014 100414 000740 001054 011400
240/ 000404 003054 010000 001004 001020 003154 101000
260/ 001014 002354 155000 000001 000056 000003 004567 051144
300/ 000401 015314 005367 175760 000167 164720 020040 020040
320/ 025040 046440 051117 020105 044124 047101 032040 030060
340/ 041440 040510 047111 041440 042117 051505 005015 040400
360/ 004567 051060 000401 015400 005367 175674 000167 164634
400/ 020040 020040 025040 041440 040510 047111 041440 042117
420/ 020105 040526 052514 020105 020076 006467 000012 004567
440/ 051002 000401 015456 005367 175616 000167 164556 020040
460/ 020040 025040 046440 051117 020105 044124 047101 034440
500/ 041040 052517 042116 051101 020131 047520 047111 051524
520/ 005015 000000 004567 050714 000401 015544 005367 175530
540/ 000167 164470 020040 025040 050040 046101 047125
560/ 020122 047520 047111 020124 047516 020124 047105 047503
600/ 047125 042524 042522 020104 042502 047506 042522 053040
620/ 046101 042514 006531 000012 004567 050610 000401 015650
640/ 005367 175424 000167 164364 020040 020040 025040 050040
660/ 046101 047514 020122 051511 040440 051440 047111 046107
700/ 020105 047520 047111 006524 000012 017001 013614 000622
720/ 027000 001400 125000 153020 003006 140002 067025 030027
740/ 002022 030000 001022 173400 000445 142000 003006 140002
760/ 074025 030027 002022 030000 001022 140000 115025 000001
```

```
BLOCK NUMBER 00016
000/ 000016 000004 005001 013556 017001 013570 000657 027000
020/ 001400 150000 001020 000400 067034 000427 074154 100427
040/ 073414 127020 140006 002025 141000 103035 001006 067154
060/ 141027 104155 001006 074154 101027 003414 000001 000026
100/ 000004 004001 013556 006001 013570 017001 013556 023001
120/ 013570 000541 027000 001400 173000 101020 133414 112020
140/ 041006 133740 124020 140003 105035 140006 032355 033764
160/ 120020 033403 100020 073406 000011 002400 115001 111024
200/ 067427 000001 000024 000004 021004 023356 143300 023001
220/ 012232 024001 013622 000600 027000 001400 016000 121021
240/ 135024 130024 153424 102055 004003 003000 173405 101055
260/ 002003 001364 073407 043000 173400 060055 163003 002363
300/ 142004 002025 007400 000001 000022 000004 002001 012242
320/ 003001 012272 004001 012260 000614 027000 001400 041000
340/ 073421 060000 073401 000011 002000 115001 135024 121024
360/ 126024 173424 052055 154003 002363 142005 002025 073400
400/ 041000 173401 031055 166403 000001 000034 000004 005004
420/ 023356 143160 007001 012232 010001 012272 011001 012242
440/ 012001 012254 000515 027000 001400 064000 142021 002363
460/ 142004 001025 073400 031000 142001 001425 073400 025000
500/ 173401 015055 134003 001363 073404 140000 140000 017035
520/ 100003 160014 000001 000056 000003 010616 066700 002774
540/ 010067 001462 004567 000000 000406 014712 013522 012310
560/ 013552 012304 004532 022767 000001 173654 001002 000167
600/ 003640 000510 022000 002000 002000 115016 020567 000424
620/ 145022 000431 051024 000427 144026 000424 055030 000427
640/ 142032 000424 055034 015411 000001 000036 000003 010664
660/ 004567 000000 000413 014712 002424 002426 012304 012310
700/ 012312 012314 013134 000622 026000 002000 002000 000406
720/ 110424 000472 145012 000431 012014 000405 013016 000405
740/ 142020 000424 144022 000424 145024 000424 146026 000424
760/ 056030 055026 000001 000056 000003 010712 012306 013206

BLOCK NUMBER 00017
000/ 004532 022767 000001 173604 001002 000167 003340 022767
020/ 000002 173570 001002 000167 003660 004567 000000 000420
040/ 012304 000771 016000 002000 000400 143004 000424 103006
060/ 000426 055010 002011 072044 144410 000440 142050 061424
100/ 000001 000034 000003 010760 002424 002426 012314 013134
120/ 013162 013164 013166 013170 012244 013172 000745 027000
140/ 002000 000400 012004 000405 013006 000405 146010 000424
160/ 056012 000426 071014 000426 072016 000426 073020 000426
200/ 074022 000426 122024 000424 075026 043426 000001 000056
220/ 000003 011004 013174 013176 013200 013204 004532 022767
240/ 000001 173506 001002 000167 003326 005767 001206 001004
260/ 012767 000310 001200 000410 004567 000737 015000 002000
300/ 000400 076004 000426 077006 000426 100010 000426 102012
320/ 000426 055014 175411 000001 000056 000003 011052 000000
340/ 000405 013174 013172 012244 013202 012246 026767 001152
360/ 171356 002404 012704 000011 000167 000136 016700 001156
400/ 016701 001122 000661 020000 002000 002000 155004 035144
420/ 000424 076010 000426 075012 000426 122014 000424 101016
440/ 000426 123020 155024 000001 000056 000003 011120 073027
460/ 177776 020167 171330 002024 026767 001074 171302 002004
500/ 012704 000012 000167 000074 026767 001054 171276 002004
520/ 012704 000013 000707 027000 001400 073000 073422 026000
540/ 142000 006025 073400 022000 173400 012055 115002 002362
560/ 142004 006425 073400 012000 173400 022055 113002 002362
600/ 142005 050025 000001 000056 000003 011234 000016 000167
620/ 000004 012704 000001 016767 002334 001006 016767 002330
640/ 001002 010467 001012 020427 000001 001013 022767 177777
660/ 000754 000454 027000 001400 141000 003422 133403 153012
700/ 173404 161155 147001 073404 144013 142004 142012 132014
720/ 030012 172030 136155 012001 072030 174013 172027 135155
740/ 063001 000001 000022 000004 015001 014060 020001 014024
760/ 022001 013770 000405 027000 001400 164000 156022 072027
```

```
BLOCK NUMBER 00020
000/ 140013 172027 144155 140001 173427 177445 131377 003401
020/ 073402 000011 002000 115001 135024 121024 126024 140024
040/ 142035 124763 000001 000050 000004 002001 013734 004001
060/ 013700 007001 013700 015004 023356 143160 017001 012232
100/ 020001 012272 021001 012242 022001 012254 000463 027000
120/ 001400 007000 140423 115025 141024 012025 050000 101024
140/ 033576 132020 140363 001035 140764 057025 141026 002025
160/ 050000 101024 033576 171020 073763 166400 000001 000016
200/ 000004 003001 012232 015001 013136 000651 027000 001400
220/ 032000 047023 073772 000011 000400 063001 002024 141012
240/ 041025 142005 016045 001000 073402 046000 172341 030013
260/ 001030 073402 003000 142001 141013 000001 000030 000004
300/ 004003 026476 123521 006001 012146 011001 002502 020001
320/ 014060 000452 027000 001400 055000 004423 140002 035035
340/ 140404 034035 033404 033162 032004 120020 001030 032001
360/ 120012 000030 174035 000427 012035 032030 030162 033430
400/ 117020 000001 000032 000004 012001 014240 015001 014240
420/ 017001 013770 021001 014024 023001 014060 000525 027000
440/ 001400 100000 030023 033404 025012 073404 000011 001000
460/ 130001 131027 140027 126025 010027 073572 000011 001000
500/ 130001 131027 172027 007035 046004 144430 000001 000052
520/ 000004 006004 035204 023557 010001 013660 011001 013662
540/ 013001 013654 016004 023557 035204 020001 013660 021001
560/ 013662 024001 014114 000412 027000 001400 123000 033423
600/ 140035 006027 033404 156035 004027 073404 000011 001000
620/ 134001 135027 140027 132025 014027 030172 002022 030000
640/ 001034 003000 114000 000001 000040 000004 003001 013700
660/ 006001 013734 011004 035204 023557 013001 013670 014001
700/ 013672 016001 013664 000733 027000 001400 146000 004023
720/ 030012 030035 001030 073400 000011 001000 134001 135027
740/ 014027 073572 000011 001000 136001 137027 172027 150035
760/ 043003 140030 022435 000001 000052 000004 004001 014060

BLOCK NUMBER 00021
000/ 007004 035204 023557 011001 013670 012001 013672 015004
020/ 023557 035204 017001 013674 020001 013676 023001 014150
040/ 000521 027000 001400 171000 145023 013403 062160 032000
060/ 046162 032030 102020 001430 101421 101414 140012 120025
100/ 150027 010020 030035 010030 046035 010030 064035 154030
120/ 000001 000036 000004 006001 014114 010001 014204 015001
140/ 013640 020001 014060 022001 014114 024001 014150 000522
160/ 027000 001400 014000 010024 102035 010030 120035 140430
200/ 003025 140000 120025 011027 041024 140576 002425 142000
220/ 001013 140402 003025 140000 120025 033427 042424 000001
240/ 000026 000004 003001 014204 005001 014240 011001 013640
260/ 023001 013640 000727 027000 001400 037000 052024 073403
300/ 000011 001400 112001 110027 040024 073407 000011 000400
320/ 110001 046424 073576 000011 000400 113401 142024 001145
340/ 073400 045400 000001 000054 000004 004004 035204 004473
360/ 006001 013624 007001 012220 010001 003500 012004 026476
400/ 123521 014001 012220 017004 026476 123521 021001 012227
420/ 000563 027000 001400 062000 157024 006776 020012 020400
440/ 046103 051501 020123 042503 046114 020123 046440 040503
460/ 020040 046440 044103 020040 041515 042110 020040 172440
500/ 000001 000016 000003 012212 041515 006524 000012 000525
520/ 005000 002000 004000 113000 037424 000001 000014 000003
540/ 012226 006400 000012 000457 005000 002000 004000 145000
560/ 005424 000001 000012 000003 012312 000620 000603 005000
600/ 002000 004000 103000 046426 000001 000014 000003 013206
620/ 177777 000016 000510 005000 002000 004000 113000 036027
640/ 000001 000014 000003 013626 000003 000012 000466 005000
660/ 002000 004000 126000 023027 000001 000014 000003 013654
700/ 037165 141217 000451 005000 002000 004000 132000 017027
720/ 000001 000014 000003 013664 042621 020000 000457 005000
740/ 002000 004000 136000 032430 000001 000056 000003 014274
760/ 003567 000000 000401 014314 005367 175760 000167 164720
```

```
BLOCK NUMBER 00022
000/ 020040 020040 025040 046440 051117 020105 044124 047101
020/ 032040 030060 041440 000771 010000 002000 002000 037006
040/ 050455 000647 146012 107430 000001 000025 000003 014342
060/ 040510 047111 041440 042117 051505 005015 024000 000001
100/ 000012 000004 000010 014360 000741 027000 001400 170000
120/ 073430 000011 000400 000001 173431 136012 073773 116000
140/ 020351 020040 020040 020052 044103 044501 020116 047503
160/ 042504 053040 046101 113525 000001 000020 000004 003004
200/ 026476 123521 005001 014400 000532 027000 001400 013000
220/ 042431 037040 033440 005015 073400 000011 000400 027001
240/ 173431 107012 073773 067000 020351 020040 020040 020052
260/ 047515 042522 052040 112110 000001 000020 000004 007004
300/ 026476 123521 011001 014454 000434 017400 001400 036000
320/ 040431 020116 020071 047502 047125 040504 054522 050040
340/ 044517 052116 006523 000012 000410 005000 002000 004000
360/ 052000 076031 000001 000056 000003 014524 004567 000000
400/ 000401 014544 005367 175530 000167 164470 020040 020040
420/ 025040 050040 046101 047514 020122 047520 047111 020124
440/ 047516 000533 010000 002000 002000 037006 050455 000647
460/ 062012 173031 000001 000056 000003 014572 020124 047105
500/ 047503 047125 042524 042522 020104 042502 047506 042522
520/ 053040 046101 042514 006531 000012 004567 000000 000401
540/ 014650 000561 010000 002000 002000 037044 050455 000647
560/ 124050 073031 000001 000056 000003 014640 005367 175424
600/ 000167 164364 020040 020040 025040 050040 046101 047514
620/ 020122 051511 040440 051440 047111 046107 020105 047520
640/ 047111 000651 006000 001400 143000 052031 005015 123000
660/ 000001 000006 000006 000363 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000

BLOCK NUMBER 00023
000/ 000001 000054 001000 012706 001000 004567 104152 004567
020/ 065430 000401 005652 004567 064670 000401 003366 022767
040/ 000001 002330 001416 022767 000002 002320 000455 026010
060/ 025000 000402 167403 140001 044425 140400 174025 141006
100/ 005025 051007 001024 017176 073401 162011 000552 144001
120/ 073414 160011 000551 005001 114007 000001 000054 001114
140/ 012700 000004 012701 006260 012703 006270 012167 000006
160/ 004567 065304 000401 000000 012702 000002 012367 000006
200/ 004567 064670 000401 000660 026000 071000 000002 103400
220/ 010176 140176 114035 140404 113035 040004 073560 115020
240/ 140004 105035 100004 033414 106020 140004 101035 100004
260/ 033414 001020 000001 000054 001230 002204 016700 002156
300/ 016701 002154 070100 010167 004260 004567 102742 000404
320/ 003412 005534 005535 005532 022767 000001 004236 001002
340/ 000455 026000 137000 073402 124000 173410 001045 111000
360/ 001010 073402 135000 073410 032011 001152 042001 021011
400/ 033407 137012 033426 136012 135012 023426 000001
420/ 000054 001344 016701 012640 012700 015060 005020 077102
440/ 016701 012624 012700 014700 005020 077102 016701 012610
460/ 012700 014734 005020 077102 016701 000525 026000 005000
500/ 076003 140025 174025 010031 041012 140576 070035 140025
520/ 012025 010032 041012 033576 111012 033423 110012 033423
540/ 113012 033423 013012 022006 000001 000455 001460 005067
560/ 004042 005267 004036 026767 004032 002002 001054 005067
600/ 004022 004567 064770 000405 015712 003414 003416 003420
620/ 003422 012700 000600 025000 053000 145003 140033 176155
640/ 017407 001040 170760 073402 056011 002177 054001 145013
660/ 041033 045011 073411 101011 002577 044001 045011 146011
700/ 000001 000052 001572 004550 005512 005524 005367 003706
720/ 004567 064434 000403 005512 007317 004500 004567 064620
740/ 000401 007253 005267 011432 004567 000545 020000 117000
760/ 002003 001551 133001 145426 040015 001011 073412 111011
```

```
BLOCK NUMBER 00024
000/ 002551 145001 012033 013007 014007 013407 000001 000054
020/ 001670 003432 005202 010267 012724 004567 064340 000403
040/ 014624 006734 004500 004567 064524 000401 006676 012700
060/ 015712 066700 001504 020037 000631 026000 157000 001003
100/ 162360 141402 055035 002003 133412 055012 173405 053040
120/ 033405 033402 050012 073405 144011 002176 020001 145007
140/ 044033 045011 171411 000001 000054 002004 004567 077356
160/ 000405 004510 004512 004502 005512 005524 016701 003462
200/ 005301 016700 001440 060300 020100 003401 005204 006303
220/ 160300 000717 026000 025000 040004 000440 102004 073412
240/ 060020 073425 066011 001550 112001 075431 040016 073411
260/ 160011 000550 052401 142016 005013 073403 152011 015150
300/ 000001 000054 002120 000401 007204 000000 006203 005303
320/ 010367 002350 000644 004567 101712 000404 003412 005536
340/ 005542 005532 022767 000001 003346 001002 000714 026000
360/ 073000 073404 170000 173406 001045 155000 001006 073402
400/ 001000 173407 041025 043007 173404 152025 111010 173404
420/ 000425 027000 073422 164000 113412 000001 000054 002234
440/ 004567 101616 000404 003412 005537 005535 005532 022767
460/ 000001 003252 001002 000167 003264 022767 000002 003236
500/ 001002 000167 003306 000512 026000 141000 153404 006055
520/ 041004 001407 033402 054012 003004 140001 177035 140003
540/ 041345 033407 045020 073404 071011 001205 041001 023011
560/ 173411 130013 000001 000054 002350 002074 001405 004567
600/ 102542 000402 004446 003502 016700 001020 004567 102574
620/ 000402 005550 005532 005767 003122 001023 142767 000200
640/ 000707 026000 007000 054005 173406 052255 047406 007406
660/ 173403 046255 044406 014406 173403 042255 040006 001006
700/ 073402 021000 073401 035000 016006 073576 001000 000001
720/ 000054 002464 003122 004567 101664 000404 015712 003424
740/ 003426 005532 005767 003022 001402 000167 004612 000167
760/ 000374 004567 063660 000402 004476 000607 026000 055000

BLOCK NUMBER 00025
000/ 024005 140011 136035 033401 142020 033400 142020 140000
020/ 001345 033400 036020 140000 125035 140001 001345 033400
040/ 060020 141000 024025 105411 000001 000054 002600 012267
060/ 001642 016703 000624 016704 000622 012201 005301 006301
100/ 006301 006301 062701 004324 012100 005300 010067 000132
120/ 010067 000162 000664 026000 123000 040005 000344 013413
140/ 000040 006400 033407 160020 073423 166011 001546 112001
160/ 000431 040016 073411 060011 000547 165401 000015 040000
200/ 002024 000001 000054 002714 005300 010067 000064 010067
220/ 000076 162100 005400 020027 000000 003415 010067 011660
240/ 004567 063274 000403 014624 007066 004500 004567 000524
260/ 026000 171000 030005 000547 020001 000016 141400 000045
300/ 001000 173405 012020 142000 000045 001000 033405 003021
320/ 140400 001035 053401 000160 140400 177545 000001 000054
340/ 003030 000000 062701 015712 012700 055714 112120 077302
360/ 012703 000000 062701 000000 077407 004567 101272 000404
400/ 055714 003434 003436 005532 000561 026000 037000 173406
420/ 014013 001005 073403 110000 173410 155012 115402 140002
440/ 134035 073400 022011 001204 064001 055013 173413 175013
460/ 006404 173402 077705 000001 000054 003144 000200 002400
500/ 126767 002374 002362 001417 126767 002364 002353 001405
520/ 000167 002356 077026 000167 002406 004567 063236 000401
540/ 006632 000771 026000 105000 073406 123000 073774 111011
560/ 000546 126001 073415 116000 073416 110011 002201 005001
600/ 061407 062013 055013 173413 000445 126000 001004 016002
620/ 000001 000054 003260 000167 002266 022767 000002 002240
640/ 001002 000167 002310 020227 003502 001003 005067 001134
660/ 000406 016722 007762 162702 003502 010267 000621 023000
700/ 153000 047006 073402 073011 001203 041001 023011 173411
720/ 040013 002402 073403 063011 001203 023001 041011 073407
740/ 171000 061773 000001 000030 003370 023420 000200 000060
760/ 000276 000315 000200 000200 000276 000067 000602 004000
```

BLOCK NUMBER 00026
000/ 040000 005007 123000 000001 000016 004476 000026 000001
020/ 000002 000036 000563 004000 044000 000011 122401 000001
040/ 000022 005534 051106 042115 043514 040520 052102 051516
060/ 000402 026000 065000 073413 133011 000541 072001 000013
100/ 020000 020040 020040 020052 052512 045516 042440 051122
120/ 051117 005015 073400 114011 000541 111001 045413 000001
140/ 000054 005620 000000 020040 020040 025040 052040 046511
160/ 026505 052517 020124 051105 047522 006522 000012 020040
200/ 020040 042504 040506 046125 020124 000624 026000 133000
220/ 046013 047517 020120 044524 042515 036440 030440 030060
240/ 030060 005015 020040 020040 042504 040506 046125 020124
260/ 026130 020131 044504 104115 000001 000054 005734 047105
300/ 044523 047117 020123 043117 046040 053517 053440 047111
320/ 047504 020127 020075 031061 026070 032040 006470 020012
340/ 020040 042040 000543 026000 001000 042414 040506 046125
360/ 020124 047514 020127 044527 042116 053517 047440 043106
400/ 042523 051524 036440 030440 030071 020054 030062 006465
420/ 127412 000001 000054 006050 020040 020040 042504 040506
440/ 046125 020124 026130 020131 044504 042515 051516 047511
460/ 051516 047440 020106 044520 052103 051125 020105 000763
500/ 026000 047000 036414 030440 034062 020054 031061 006470
520/ 020012 020040 042040 043105 052501 052114 050040 041511
540/ 052524 042522 053440 047111 047504 145127 000001 000054
560/ 006164 047440 043106 042523 051524 036440 030440 030071
600/ 020054 032465 005015 020040 020040 043111 040440 054516
620/ 041440 040510 043516 026105 000454 026000 115000 020014
640/ 054524 042520 054440 020056 046105 042523 020054 027116
660/ 026440 020076 160000 007014 036415 064015 006015 007007
700/ 010007 011007 045007 000001 000054 006300 003424 003426
720/ 003430 003432 020040 020040 042440 052116 051105 046040
740/ 047517 020120 044524 042515 035040 000040 020040 020040
760/ 042440 000551 026000 163000 047014 042524 020122 047514

BLOCK NUMBER 00027
000/ 020127 044527 042116 053517 042040 046511 047105 044523
020/ 047117 020123 021450 054111 021440 054511 020051 010472
040/ 000001 000054 006414 000040 020040 042440 052116
060/ 051105 046040 053517 053440 047111 047504 020127 043117
100/ 051506 052105 020123 021450 047511 030506 000676 026000
120/ 031000 020015 044443 043117 024462 035040 000040 020040
140/ 020040 042440 052116 051105 050040 041511 052524 042522
160/ 042040 046511 047105 044523 146117 000001 000054 006530
200/ 051516 024040 044443 020130 024531 035040 000040
220/ 020040 020040 042440 052116 051105 050040 041511 052524
240/ 042522 053440 047111 000721 026000 077000 042015 053517
260/ 047440 043106 042523 051524 024040 047443 030506 021440
300/ 047511 031106 020051 020072 020000 020040 020040 020107
320/ 042522 016103 000001 000054 006644 044505 042526 006504
340/ 000012 020040 020040 046040 051040 041505 044505 042526
360/ 006504 000012 020040 020040 050040 041511 052524 042522
400/ 000570 003400 145000 020015 000401 010400 150400 020015
420/ 044504 044507 044524 042532 020104 000463 022400 161000
440/ 020015 044524 042515 006523 000012 020040 020040 054040
460/ 042055 046511 047440 020106 042503 046114 044440 020123
500/ 000542 026000 003400 006416 020012 020040 020040 047503
520/ 052116 047111 042525 041040 051050 050047 006447 000012
540/ 020040 020040 054440 042055 046511 047440 056506 000001
560/ 000017 007055 041440 046105 020114 051511 114440 000001
600/ 000054 007074 005015 020040 020040 041440 047117 044524
620/ 052516 020105 054502 023440 023520 005015 020000 020040
640/ 020040 044520 052103 051125 020105 000401 017400 061000
660/ 041016 041501 043513 047522 047125 020104 051107 054505
700/ 046055 053105 046105 044440 020123 000670 026000 100000
720/ 006416 000012 020040 020040 025040 040440 045104 051525
740/ 020124 044526 042504 027117 041440 047117 044524 052516
760/ 020105 054502 023440 156120 000001 000054 007247 006447

```
BLOCK NUMBER 00030
000/  000012 020040 020040 046040 053517 053440 047111 047504
020/  020127 040502 045503 051107 052517 042116 046040 053105
040/  046105 044440 000525 004000 146400 051416 124440 000001
060/  000053 007325 005015 140000 077035 000774 100012 001014
100/  100607 176012 140401 073414 174034 003016 073400 031011
120/  000536 000001 000000 177000 050416 000001 000054 007372
140/  007446 007522 020040 020040 020052 044520 020103 051124
160/  047101 046523 051511 044523 047117 052040 046511 026505
200/  052517 020124 051105 000632 026000 020000 051017 051117
220/  005015 020000 020040 025040 050040 041511 052040 040522
240/  051516 044515 051523 047511 020116 052512 045516 046440
260/  051505 075123 000001 000054 007506 043501 020105 051105
300/  047522 006522 000012 020040 020040 020052 044520 020103
320/  051124 047101 046523 051511 044523 047117 044440 051516
340/  000566 026000 066000 052417 043106 041511 042511 052116
360/  051440 040520 042503 042440 051122 051117 005015 173400
400/  037035 035007 173407 116035 034367 073407 067011 000001
420/  000054 007622 056764 000405 015712 003440 013310 013304
440/  005532 022767 000001 175664 001002 000167 172360 005267
460/  003410 012700 013232 012701 000016 000516 026000 134000
500/  150017 177425 041777 173576 177425 176377 173406 177425
520/  136377 173411 177425 134377 033411 163012 033406 162012
540/  033406 161012 073406 140411 000001 000032 007736 056756
560/  000413 015712 003424 003426 013304 013310 013312 013314
600/  014134 000626 026000 171000 143017 040026 055011 173413
620/  000445 056000 001373 073402 134000 173412 001045 050000
640/  027373 073403 073011 010163 142001 012026 013007 070407
660/  000001 000032 010030 013314 014134 014136 014140 014142
700/  014144 014154 014146 014150 014152 000577 026000 026000
720/  067020 117030 055026 173413 000445 021000 001373 073402
740/  131000 173412 000045 015000 010410 173403 000045 013000
760/  006410 140403 141035 052766 000001 000054 010122 005301

BLOCK NUMBER 00031
000/  020167 004010 001407 016701 173270 005301 020167 004000
020/  001401 000404 005367 003114 000167 177424 026767 003770
040/  173300 002770 000503 026000 074000 073420 032011 002566
060/  064001 063030 066030 070030 116030 140426 161035 053407
100/  062160 000000 033412 155162 033407 003020 001006 173412
120/  053055 000001 000054 010236 002774 173202 002012 026767
140/  002766 173174 002006 026767 002760 173166 002002 005202
160/  000407 026767 003660 173172 002403 005267 002776 000715
200/  017000 142000 150420 073401 137011 006536 142001 012026
220/  013007 145007 146033 056026 144030 115026 133026 000001
240/  000054 010334 013242 013272 004500 014206 005532 022767
260/  000001 175156 001002 000167 005054 016700 002644 070067
300/  173104 160167 002644 005667 002670 000767 026000 001000
320/  033421 132340 141005 000445 016000 173403 107055 012005
340/  006366 173405 104055 007005 002366 142005 002425 073400
360/  101000 142003 003025 120000 000001 000054 010450 000167
400/  001572 026767 002560 172766 002404 012704 000007 000167
420/  001552 012704 000010 000167 001542 004567 070072 000415
440/  015712 003424 000540 015000 047000 013021 057007 060030
460/  105030 061030 062030 167030 051030 052031 053031 113031
500/  000001 000054 010542 014530 000433 005003 016700 003752
520/  012701 014212 112102 042702 177400 060203 077005 016700
540/  003732 012701 014356 112102 042702 177400 000710 026000
560/  104000 101421 002540 001176 140012 142035 140007 141155
600/  100007 133562 011020 073405 157011 001160 053001 105031
620/  073430 045011 003560 053001 143431 000001 000036 010656
640/  014212 014626 014532 014556 014602 014606 004567 070300
660/  000402 014530 014356 004567 000763 026000 143000 026021
700/  003560 054001 167031 113030 062031 074031 102031 104031
720/  173431 001445 122000 027407 140002 067025 000431 000422
740/  004154 100400 075014 000001 000054 010754 010102 166702
760/  002326 006202 006202 160201 026001 000002 002023 026001
```

```
BLOCK NUMBER 00032
000/  000006 002020 016002 000002 066002 000006 006202 166002
020/  000004 000735 026000 011000 001022 133413 110020 133404
040/  020040 001365 073405 017000 006402 073401 146011 003557
060/  053001 105031 041030 055011 067031 101031 105031 054031
100/  000001 000054 011070 066767 003516 003510 022767 000003
120/  003500 001060 012700 014570 011001 066001 000010 006201
140/  010102 166702 002160 006202 006202 160201 000574 026000
160/  057000 000422 001054 012000 000404 003054 010400 001004
200/  001034 001000 003154 101000 001014 002354 001000 133413
220/  025020 133404 135040 001364 031005 000001 000054 011204
240/  000167 000670 000167 000674 004567 067544 000407 014530
260/  014356 004502 014544 014570 014604 014614 066767 003350
300/  003342 022767 000001 000425 026000 125000 153022 003006
320/  140002 067025 030031 002022 030000 001022 173400 000445
340/  142000 003006 140002 074025 030031 002022 030000 001022
360/  140000 114425 000001 000054 011320 000002 016001 014556
400/  066001 014570 006201 010167 003256 012700 000004 016702
420/  003206 066002 014556 066702 003210 066002 014570 006202
440/  000402 026000 173000 101022 133414 112020 041006 133740
460/  124020 140003 105035 140006 032355 033764 120020 033403
500/  100020 073406 030011 002563 115001 111026 145431 000001
520/  000054 011434 013242 013272 013260 026727 001604 000010
540/  002406 026767 001602 172004 003402 000167 000106 026767
560/  001540 171746 002004 012704 000004 000414 026000 041000
600/  073423 060000 073401 130011 002162 115001 135026 121026
620/  126026 173426 052055 154003 002363 142005 002025 073400
640/  041001 173401 031055 143003 000001 000054 011550 171704
660/  002004 012704 000002 000167 000462 012704 000003 000167
700/  000452 026767 001432 171670 002002 000167 000300 016700
720/  001436 006200 000743 026000 107000 140023 176155 033405
740/  031020 073403 125011 003155 145001 051033 144031 055026
760/  142031 055026 173413 000445 126000 001367 073402 120000

BLOCK NUMBER 00033
000/  024007 000001 000034 011664 004567 055026 000413 015712
020/  003424 003426 013304 013310 013312 013314 014134 000425
040/  026000 145000 143023 103026 055030 173413 000445 102000
060/  001367 073402 160000 173406 001045 074000 001367 073402
100/  130000 073407 115011 010157 142001 165426 000001 000032
120/  011760 003424 003426 013314 014134 014162 014164 014166
140/  014170 013244 014172 000724 026000 002000 076024 077030
160/  100030 102030 055030 173413 000445 043000 001367 073402
200/  153000 173406 103013 002002 173402 144025 100000 004002
220/  073401 154011 000001 000054 012052 071204 000405 014174
240/  014172 013244 014202 013246 026767 001152 171356 002404
260/  012704 000011 000167 000136 016700 001156 016701 001122
300/  000664 026000 050000 013424 177166 073777 154040 012362
320/  173404 036055 141002 002362 142004 005025 073400 036000
340/  173400 026055 137002 002362 142004 005425 145000 000001
360/  000054 012166 000167 000054 012704 000014 000167 000044
400/  026767 001024 171232 002004 012704 000015 000167 000024
420/  026767 001004 171226 002404 012704 000523 026000 116000
440/  007024 073400 002000 142000 000425 173400 156035 003004
460/  173402 154035 001004 033402 005021 013402 000441 005400
500/  173402 177445 166377 027401 000001 000054 012302 001407
520/  005267 002326 066767 000742 002316 005567 002310 005304
540/  006304 005264 015060 066764 000674 015024 005564 014770
560/  066764 000672 000523 026000 164000 156024 072031 140013
600/  172031 144155 140001 173431 177445 131377 003401 073402
620/  175011 002160 115001 135026 121026 126026 140026 142035
640/  032363 000001 000054 012416 012701 013232 012702 000024
660/  012120 077202 010067 171664 016700 172002 012701 014136
700/  012702 000004 012120 077202 010067 171762 000167 000754
720/  076000 032000 047025 073772 165011 000527 063001 002026
740/  141012 041025 142007 016045 001000 073402 046000 172361
760/  030013 001032 073402 003000 142001 077013 000001 000054
```

```
BLOCK NUMBER 00034
000/  012532 001011 016700 002072 016701 002070 071067 002066
020/  010064 015240 000402 005064 015240 016400 014770 016401
040/  015024 071064 015060 010067 000627 026000 100000 030025
060/  033404 025012 073404 154011 001161 130001 131031 140031
100/  126025 010031 073572 037011 001162 130001 131031 172031
120/  007035 046004 143432 000001 000054 012646 016467 014700
140/  002014 016467 014734 002010 004567 070654 000402 014670
160/  014672 012700 014664 075030 011060 000004 016060 000002
200/  000006 000564 026000 146000 004025 030012 030035 001032
220/  073400 105011 001161 134001 135031 014031 073572 172011
240/  001161 136001 137031 172031 150035 064003 140032 136035
260/  000001 000054 012762 001712 070027 000144 071064 015114
300/  010064 015204 010403 006203 005203 012700 014640 010320
320/  016420 015060 016420 015114 016420 015150 000717 026000
340/  014000 010026 102035 010032 120035 140432 003025 140000
360/  120025 011031 041024 140576 002425 142000 001013 140402
400/  003025 140000 120025 033431 040024 000001 000054 013076
420/  001524 004567 053140 000403 014624 013220 004500 004567
440/  053324 000401 013220 077115 004567 053312 000401 013227
460/  062704 000002 000167 000504 026000 062000 157026 006776
500/  020012 020040 046103 051501 020123 042503 046114 020123
520/  046440 040503 020040 046440 044103 020040 041515 042110
540/  020040 174040 000001 000014 013212 041515 006524 000012
560/  000530 005000 113000 000026 005015 031000 000001 000010
600/  013312 000620 000606 005000 103000 177430 007377 045400
620/  000001 000012 014626 000003 000012 000471 005000 126000
640/  072431 107476 026302 000001 000012 014664 042621 020000
660/  000462 026000 136000 073432 062011 000522 146001 173432
700/  170012 073773 150000 020351 020040 020040 020052 047515
720/  042522 052040 040510 020116 030064 020060 042103 000001
740/  000023 015342 040510 047111 041440 042117 051505 005015
760/  025400 000001 000054 015360 004567 051060 000401 015400

BLOCK NUMBER 00035
000/  005367 175674 000167 164634 020040 020040 025040 041440
020/  040510 047111 041440 042117 020105 040526 052514 000426
040/  026000 013000 042433 037040 033440 005015 073400 001011
060/  000522 027001 173433 107012 073773 067000 020351 020040
100/  020040 020052 047515 042522 052040 040510 000001 000035
120/  015474 047101 034440 041040 052517 042116 051101 020131
140/  047520 047111 051524 005015 005400 000001 000054 015524
160/  004567 050714 000401 015544 005367 175530 000167 164470
200/  020040 020040 025040 050040 046101 047514 020122 047520
220/  047111 020124 047516 000477 026000 075000 052033 042440
240/  041516 052517 052116 051105 042105 041040 043105 051117
260/  020105 040526 046114 054505 005015 073400 104011 000521
300/  124001 114433 000001 000054 015640 005367 175424 000167
320/  164364 020040 020040 025040 050040 046101 047514 020122
340/  051511 040440 051440 047111 046107 020105 047520 047111
360/  000654 005000 143000 052033 005015 124400 000001 000054
400/  065714 004567 017520 000401 105737 177560 100375 113701
420/  177562 042701 177600 022701 000015 001401 010102 105737
440/  177564 100375 110137 177566 000400 026000 171000 140553
460/  006445 166400 157402 072213 176777 157600 005225 073000
500/  141377 047045 005000 141003 054445 001400 036403 000012
520/  003400 176401 057025 000001 000026 066030 000001 000000
540/  000403 012775 000002 000000 000167 017424 000642 026000
560/  024000 073554 172011 000436 140401 114025 001154 157412
600/  070213 176777 140200 071227 140377 100105 157777 072213
620/  176777 017600 073220 013777 067040 000001 000054 066116
640/  000060 002410 020027 000071 003005 005202 162700 000060
660/  010021 000751 005702 001001 000746 020027 000015 001006
700/  105737 177564 100375 000630 025000 072000 157554 005225
720/  073000 140777 114025 041554 113424 000440 002400 141003
740/  153412 005160 041400 102144 176576 000020 073400 122000
760/  002436 000001 000054 066244 004567 017170 000403 012703
```

```
BLOCK NUMBER 00036
000/  000005 016502 000002 112712 000040 062702 000006 005004
020/  005775 000004 100004 112767 000001 000015 000403 000603
040/  026000 145000 173554 100225 002400 040000 000037 001000
060/  000001 102013 000412 000020 013412 005162 140400 030125
100/  061000 144220 141576 002025 145000 015245 000001 000034
120/  066360 000060 001003 112722 000040 077306 005704 001402
140/  112742 000055 000167 017066 000504 022000 003000 073555
160/  013011 001036 040001 000037 040400 001035 157400 104213
200/  176773 150600 105227 003373 073576 014000 065036 000001
220/  000042 066444 004567 016770 000401 011500 105710 001406
240/  105737 177564 100375 112037 177566 000770 000167 016774
260/  000773 026000 040000 073555 156011 002435 157401 101025
300/  040155 017400 041012 173400 040025 133000 073602 124025
320/  141202 002025 140400 102025 040155 000027 155413 000001
340/  000044 066546 110021 077204 016767 000030 101232 016767
360/  000020 101222 012767 000101 101204 000001 000167 016672
400/  000002 000501 026000 104000 073555 112011 002435 076401
420/  001057 003000 013400 041005 041423 001037 101400 073540
440/  002037 005000 042000 003037 142000 102012 013540 140245
460/  000001 000046 066656 000000 103407 160204 010475 000006
500/  005075 000010 000167 016574 020304 001364 012775 000001
520/  000010 000167 016556 000442 026000 147000 073555 047011
540/  005435 041001 040025 033427 035020 033400 133020 033400
560/  152020 033400 063020 140001 033412 117020 033400 136020
600/  033400 131420 000001 000054 066764 000340 005200 005200
620/  010067 000240 010067 000276 013501 005301 010167 000322
640/  013503 005303 060302 005000 010301 071027 000000 010003
660/  000526 026000 015000 040156 140420 073420 140027 073400
700/  164027 041400 073425 007025 033401 150012 073400 020025
720/  156401 003413 173600 101225 123400 173400 102425 000001
740/  000054 067100 000001 000372 000406 112767 000207 000231
760/  012767 000000 000354 012567 000336 005067 000330 012737

BLOCK NUMBER 00037
000/  000435 067436 012737 000431 067346 000773 026000 063000
020/  002156 133412 114020 173400 004025 132000 073400 010020
040/  001401 173401 004025 124000 007400 067235 177557 007401
060/  073235 177557 141001 130745 000001 000054 067214 000000
100/  005200 005301 000434 162702 000000 005301 000430 162702
120/  000000 005300 005301 000423 005302 005300 000420 062702
140/  000000 005300 000764 026000 131000 100556 005412 141001
160/  000145 100400 003412 141001 000145 100000 100412 001012
200/  101001 100012 140012 023413 140405 022413 140005 000045
220/  035400 000001 000054 067330 000442 022701 000000 002437
240/  121227 000000 000434 005204 042704 177770 110423 005304
260/  042704 177770 020167 000216 003402 010167 000210 000711
300/  026000 177000 113556 000012 113400 000040 012000 002003
320/  077235 153557 000012 131400 173402 000525 015000 005400
340/  102001 000412 102001 142012 174105 041777 000001 000054
360/  067444 005327 000000 001255 052767 000002 000002 012737
400/  000000 000000 016737 177706 000000 022727 000000 000001
420/  001411 005267 000076 016701 000705 026000 045000 035157
440/  053400 000160 100400 057412 000020 073400 161000 173433
460/  102025 137012 173777 102025 100012 173777 004025 135000
500/  154377 001401 105010 000001 000034 067560 010414 014424
520/  021035 007005 013016 017426 002437 003405 000407 001401
540/  002403 000713 026000 104000 073557 112011 006433 036401
560/  014012 173400 004425 135000 176401 001012 073400 001037
600/  152000 073400 001037 177000 136400 001012 073400 003437
620/  000001 000054 067656 000002 000330 017567 000002 000370
640/  005275 000002 017567 000002 000316 017567 000002 000356
660/  005375 000002 012767 000024 000250 012767 000672 026000
700/  152000 012157 151000 173400 012025 030000 173401 012025
720/  076000 073401 006037 050000 040001 000037 140000 040012
740/  003155 141000 124035 141401 106425 000001 000054 067772
760/  003720 005022 005303 001375 005775 000024 100004 112767
```

```
BLOCK NUMBER 00040
000/ 000203 000457 000403 112767 000206 000447 005775 000026
020/ 100004 016767 000602 000525 026000 020000 066160 001401
040/ 173401 074035 062001 141001 060035 073401 055021 040401
060/ 004035 042400 005037 101400 141420 001145 145000 000045
100/ 005000 030003 000001 000054 070106 011204 020023 001411
120/ 005304 001374 021227 000000 002402 000167 000444 010013
140/ 005212 005305 001454 112104 116417 070630 000777 005200
160/ 000534 026000 066000 144560 000245 173000 161403 140001
200/ 000345 141000 000345 141000 007055 001001 133603 004020
220/ 154401 140001 000345 172400 140001 000345 171400 000001
240/ 000054 070222 000762 005300 022705 000001 001717 122711
260/ 000004 001736 000713 062700 000000 062702 000000 000706
300/ 062700 000000 000772 062700 000000 000740 026000 134000
320/ 173560 142401 150035 041000 100421 140424 000045 022400
340/ 140403 000445 017400 140403 100012 002020 001412 033412
360/ 133024 101400 140412 016440 000000 000054 070336 003011
400/ 022067 000254 101005 014067 000246 010004 062700 000002
420/ 000764 022704 000000 001403 011214 016712 000222 005301
440/ 022701 000000 000414 026000 002000 001561 141003 001145
460/ 161000 142401 000145 153000 002001 033412 076012 033400
500/ 075012 033400 071012 142400 065035 040000 000421 140424
520/ 075045 000001 000054 070452 000000 001433 011002 012003
540/ 005203 005301 001403 121327 000000 000771 160203 112204
560/ 042704 177400 060467 000112 005567 000110 005267 000456
600/ 026000 050000 040161 141400 172412 140402 000045 000400
620/ 164003 142401 000145 160000 142401 022035 176400 023035
640/ 007000 176400 021035 010000 176400 073035 000001 000034
660/ 070566 000036 000022 000167 014676 016705 000012 012775
700/ 000001 000030 000167 014660 000447 014000 111000 000161
720/ 000000 000000 000000 007405 012422 021035 122045 072161
740/ 041571 000001 000054 100504 004567 004730 000406 005075
760/ 000012 017567 000004 000024 017501 000002 005301 016502

BLOCK NUMBER 00041
000/ 000006 061201 016203 000002 161203 122127 000000 000461
020/ 017000 065000 003201 142203 176576 000425 005000 073400
040/ 142000 040411 076743 004020 073400 135000 153411 000001
060/ 000054 100602 004567 004632 000415 017500 000014 067500
100/ 000016 006200 017501 000000 070100 010100 067500 000006
120/ 061500 010075 000022 016501 000012 000552 026000 124000
140/ 041201 004037 041000 003357 101000 136412 013020 010400
160/ 101224 040576 006037 076400 001160 040000 040420 003037
200/ 040400 004157 100400 120014 000001 000054 100716 060100
220/ 061500 010075 000024 016501 000020 017502 000016 167502
240/ 000014 005202 010275 000030 111021 067500 000002 077204
260/ 000167 004510 000467 026000 172000 073601 024011 003411
300/ 036401 006012 073400 066023 040000 140027 073412 063023
320/ 040400 073425 066027 031400 041407 041025 073425 016023
340/ 066000 000001 000054 101032 005035 012704 000001 122111
360/ 101005 005204 005300 001373 005304 005200 005767 000112
400/ 001431 005237 000000 010423 005012 114112 062702 000703
420/ 026000 040000 001202 100400 173412 032012 102000 140012
440/ 012412 044403 175644 173606 023013 003400 011403 005021
460/ 045012 141230 001145 100400 157412 110401 000001 000034
500/ 101146 005235 004567 000022 000402 000000 000000 162705
520/ 000016 000705 000167 004300 000402 026000 077000 073602
540/ 117011 001010 040401 040027 140425 001012 141222 000105
560/ 101777 001020 141222 000105 002377 000634 142000 000105
600/ 001777 101541 147414 000001 000044 101244 060203 006203
620/ 110320 005301 001361 111004 042704 177400 060403 006203
640/ 060304 006204 110410 000167 004172 000516 026000 141000
660/ 073602 055011 002010 040001 040427 041025 041427 011423
700/ 141012 176412 162402 041013 141027 041412 002025 042012
720/ 001324 000441 102203 113020 000001 000024 101350 006304
740/ 060304 005214 005300 001366 000167 004106 000560 026000
760/ 173000 073602 023011 002410 073401 046023 040000 140027
```

BLOCK NUMBER 00042
```
000/ 073412 043023 040400 041025 022027 041407 073425 015023
020/ 016400 142012 000425 044400 116044 000001 000054 101434
040/ 003005 005204 005300 001373 005304 005200 005702 001415
060/ 005237 000000 010423 005302 005204 005300 001416 022111
100/ 002373 005702 001402 000537 017000 041000 011603 166021
120/ 073401 010011 001000 000001 000000 142400 005345 152400
140/ 073401 161000 107007 000001 000054 101532 004567 003702
160/ 000402 013501 012500 005301 005002 010203 011002 066003
200/ 000002 006203 060203 006203 010320 005301 001366 006203
220/ 060310 000663 006000 100000 104203 073414 133000 024007
240/ 000001 000054 101606 004567 003626 000420 005075 000036
260/ 017501 000000 005301 005000 071075 000002 010167 000762
300/ 016767 000756 000756 016767 000752 000740 000405 026000
320/ 126000 033603 163020 173401 161035 161001 173401 157035
340/ 151001 033401 155012 033401 157012 033401 156012 033401
360/ 155012 033401 140012 000401 051412 000001 000054 101722
400/ 005002 017503 000010 117567 000006 000712 016500 000006
420/ 010567 000644 112004 020427 000010 002402 000167 000604
440/ 116417 102602 000777 000403 026000 174000 133603 117012
460/ 140401 107155 173401 123011 034001 133401 114012 140401
500/ 100155 141001 173412 113011 173401 147011 027001 133401
520/ 103012 124401 000001 000054 102036 004767 000704 000451
540/ 005267 000576 166701 000542 005202 004767 000614 004767
560/ 000660 000437 005267 000536 166701 000516 004767 000572
600/ 000557 026000 042000 014204 133401 054012 140401 040355
620/ 141001 173412 065011 173401 075011 007001 133401 043012
640/ 173401 070011 004401 133401 037012 140401 073555 000001
660/ 000054 102152 000442 005202 004767 000470 004767 000534
700/ 020327 000001 003003 116705 000450 000401 111005 160504
720/ 005704 100002 062704 000010 022704 000753 026000 110000
740/ 001204 004400 142003 001445 003000 141403 141412 001013
760/ 073403 041000 001777 133401 163012 173400 142401 155035
```

BLOCK NUMBER 00043
```
000/ 176400 156035 016000 171400 000001 000054 102266 016775
020/ 000330 000012 016775 000324 000014 016775 000320 000016
040/ 016775 000314 000020 006202 060201 010175 000022 016703
060/ 000300 066703 000727 026000 156000 143204 176400 012020
100/ 141400 136035 141400 136155 176400 013020 000400 001012
120/ 173412 127355 121000 173400 125355 122000 173400 114013
140/ 145000 000001 000054 102402 100004 005467 000222 012701
160/ 000002 005767 000222 100004 005467 000214 012702 000002
200/ 005067 000202 004567 001100 000402 102640 102642 000611
220/ 026000 024000 140205 116025 010205 073572 123011 001002
240/ 120001 121205 173605 057055 062000 011400 173403 053055
260/ 056000 003400 100405 076412 014020 020400 000001 000054
300/ 102516 016775 000110 000032 000416 062702 000002 010275
320/ 000030 016775 000100 000032 000406 012775 000000 000030
340/ 012775 000000 000032 000167 000437 016000 072000 143205
360/ 142405 010035 176400 000425 017000 174000 000001 010407
400/ 020026 030447 023466 000001 000012 102634 040265 002201
420/ 000532 026000 125000 133605 157012 173777 161055 154377
440/ 001777 173404 151035 154377 103777 173400 145012 173777
460/ 146055 142377 001777 173407 137035 141377 144377 000001
500/ 000054 102720 000207 005267 177670 026767 177676 177662
520/ 002003 016767 177654 177664 000207 005367 177644 026767
540/ 177650 177636 003403 016767 177630 000454 005000 173000
560/ 117205 103777 053000 000001 000054 102772 004567 002442
600/ 000404 005067 000072 013567 000070 013567 000066 013567
620/ 000064 004567 000516 000402 103076 103100 004567 000504
640/ 000402 000675 022000 020000 041206 042206 140206 037025
660/ 014206 073572 125011 001001 041001 042206 176606 006035
700/ 000000 073400 177000 014404 000001 000054 103106 004567
720/ 002326 000405 013500 070035 010067 000124 010167 000122
740/ 004567 000406 000402 103250 103252 163501 005600 163500
760/ 010067 000100 000406 026000 066000 073606 037020 073400
```

```
BLOCK NUMBER 00044
000/  167011 001000 126001 127206 140206 124025 014206 141172
020/  001025 030000 175024 101777 140176 122025 010206 073572
040/  110011 000001 000034 103222 000504 000402 103250 103252
060/  016775 000014 000000 000167 002230 041710 000000 000741
100/  026000 130000 073606 066011 002404 073401 121027 033400
120/  116012 073400 120011 001000 055001 056207 140207 053025
140/  010207 073572 107027 033400 104012 111000 000001 000054
160/  103326 004567 000210 000402 103536 103540 075000 016767
200/  000172 000164 016767 000162 000154 004567 000346 000402
220/  103536 103540 016775 000144 000577 026000 176000 001206
240/  173400 055035 056000 173400 051035 052000 140000 002345
260/  010000 073572 044027 033400 041012 073400 043011 001000
300/  055001 056207 131207 000001 000054 103442 162700 000000
320/  075030 012767 000012 000056 005067 000050 004567 000054
340/  000402 103532 103534 162700 000004 075020 004567 000222
360/  000402 000607 014000 044000 057207 060207 176607 010035
400/  001000 073400 163000 132403 100500 043004 000001 000054
420/  103542 004567 001672 000402 005775 000000 001003 005775
440/  000002 001460 005001 017502 000000 017503 000002 005702
460/  100006 005102 005103 062703 000574 026000 104000 000607
500/  041000 100413 002012 140012 114025 113400 100040 004000
520/  113404 000566 102000 141012 100065 175000 000003 004341
540/  141001 000065 036777 000001 000054 103656 001404 073227
560/  177777 005204 000771 060400 042702 000200 072027 000007
600/  074002 005701 001402 052702 100000 010275 000000 010375
620/  000002 000714 005000 152000 073607 062000 136003 000001
640/  000054 103730 004567 001504 000402 005775 000000 001003
660/  005775 000002 001440 005001 017502 000000 017503 000002
700/  005702 100003 042702 100000 005201 000476 026000 177000
720/  100207 140020 077505 001200 141100 100125 013400 174564
740/  140377 114345 100000 140566 002413 041003 041412 141412
760/  000545 041000 136413 075420 000001 000020 104044 000000

BLOCK NUMBER 00045
000/  010375 000002 000167 001416 000654 026000 027000 073610
020/  167011 002002 040001 000037 073400 001035 004000 073400
040/  010011 001002 105001 000210 073400 027011 001002 106001
060/  104210 173610 025413 000001 000054 104124 000062 001010
100/  142767 000200 000056 126775 000052 000004 001403 000406
120/  077026 000411 005075 000006 000167 001310 012775 000001
140/  000006 000447 012000 075000 073610 137000 176402 001025
160/  003000 073400 132000 065402 000001 000010 104212 000001
200/  000744 026000 107000 073610 107011 002002 040001 000037
220/  073400 157011 001001 166001 164210 173610 041013 004000
240/  173402 100305 037000 176400 035255 001000 052400 000001
260/  000054 104264 001403 000416 077021 000421 016567 000004
300/  000010 004567 000614 000402 104352 000000 005075 000006
320/  000167 001150 012775 000001 000006 000570 012000 155000
340/  073610 057000 176402 001025 003000 073400 052000 145402
360/  000001 000010 104352 000001 000604 026000 167000 073610
400/  027011 002002 073401 142023 073400 001237 012400 073401
420/  002237 010000 036401 003012 140000 173025 173611 052035
440/  171167 144000 036213 000001 000054 104424 001430 004567
460/  000546 000402 105010 105012 005767 000346 001010 142767
500/  000200 000334 126720 000330 001001 000757 005300 005367
520/  000312 000444 026000 035000 165611 176402 004025 003000
540/  073400 173000 173401 002425 135000 073400 001011 001001
560/  003001 010212 140212 175025 173611 134011 073400 105011
600/  000001 000054 104540 000436 000402 105010 105012 005767
620/  000236 001025 142767 000200 000224 126767 000220 000203
640/  001423 126767 000210 000174 001405 012775 000614 026000
660/  103000 001211 003000 073400 127000 176401 002025 003000
700/  073400 122000 176401 000425 003000 073400 115000 001001
720/  001412 141012 064735 141400 071335 000001 000054 104654
740/  000146 070302 010367 000130 004567 000232 000402 105014
760/  000000 005067 000114 016700 177766 005001 112001 060167
```

BLOCK NUMBER 00046
```
000/ 000100 005367 000072 000643 026000 151000 174611 173402
020/ 033235 027400 173400 000425 023000 073400 067011 001000
040/ 003001 004612 140212 177425 173611 022011 073400 043000
060/ 051001 056120 000001 000021 104770 000111 050122 043400
100/ 051105 042120 010000 000001 000011 105020 050124 062523
120/ 000001 000054 105026 105710 001417 004567 000142 000402
140/ 105010 105012 005767 177742 001010 142767 000200 177730
160/ 126720 177724 001010 000757 000207 005726 000421 016000
200/ 036000 176612 000425 003000 073400 173000 153000 176413
220/ 001025 003000 073400 165000 035400 000001 000046 105122
240/ 004567 000312 000402 017501 000000 016500 000002 105737
260/ 175614 100375 112037 175616 005301 001371 000167 000312
300/ 000500 026000 071000 173612 105227 123373 102400 173400
320/ 001025 010001 073400 116011 001000 157401 002025 140213
340/ 017400 141012 173400 105227 104373 033400 050412 000001
360/ 000054 105230 000176 012767 000005 000174 012767 023420
400/ 000164 042737 000100 175610 052737 000100 175610 022767
420/ 000001 000140 001420 005367 000134 000444 026000 137000
440/ 173612 000045 053000 173000 173402 000045 050000 010000
460/ 173403 010025 043047 173400 042012 166000 176401 040235
500/ 000000 036400 001012 142000 000001 000054 105344 012767
520/ 113767 177646 000167 000116 042737 000100 175610 012775
540/ 000001 000002 012767 113767 177620 000167 000070 042737
560/ 000100 175610 000646 012000 005000 173613 105227 007373
600/ 173400 000425 001000 001000 022000 000001 000054 105440
620/ 010446 010346 010246 010146 010046 010504 016605 000012
640/ 022524 001001 000114 000167 000020 000205 012600 012601
660/ 012602 012603 012604 000721 005000 043000 102613 102425
700/ 002400 000001 000030 105512 010546 005046 010616 062716
720/ 000002 012746 001777 000004 000777 000626 026000 000000
740/ 001000 000000 003000 000000 005000 000000 007000 000000
760/ 011000 000000 013000 000000 015000 000000 017000 000000
```

BLOCK NUMBER 00047
```
000/ 021000 000000 023000 005400 000001 000054 000046 000000
020/ 000052 000000 000056 000000 000062 000000 000066 000000
040/ 000072 000000 000076 000000 000102 000000 000106 000000
060/ 000112 000000 000643 026000 046000 047000 000000 051000
100/ 000000 053000 000000 055000 000000 057000 000000 061000
120/ 000000 063000 000000 065000 000000 067000 000000 071000
140/ 143400 000001 000054 000162 000000 000166 000000 000172
160/ 000000 000176 000000 000202 000000 000206 000000 000212
200/ 000000 000216 000000 000222 000000 000226 000000 000653
220/ 026000 114000 115000 000000 117000 000000 121000 000000
240/ 123000 000000 125000 000000 127000 000000 131000 000000
260/ 133000 000000 135000 000000 137000 101400 000001 000054
300/ 000276 000000 000302 000000 000306 000000 000312 000000
320/ 000316 000000 000322 000000 000326 000000 000332 000000
340/ 000336 000000 000342 000000 000663 021000 162000 163000
360/ 000000 165000 000000 167000 000000 171000 000000 173000
400/ 000000 175000 000000 177000 000000 055400 000001 000006
420/ 001000 000367 000000 000000 000000 000000 000000 000000
440/ 000000 000000 000000 000000 000000 000000 000000 000000
460/ 000000 000000 000000 000000 000000 000000 000000 000000
500/ 000000 000000 000000 000000 000000 000000 000000 000000
520/ 000000 000000 000000 000000 000000 000000 000000 000000
540/ 000000 000000 000000 000000 000000 000000 000000 000000
560/ 000000 000000 000000 000000 000000 000000 000000 000000
600/ 000000 000000 000000 000000 000000 000000 000000 000000
620/ 000000 000000 000000 000000 000000 000000 000000 000000
640/ 000000 000000 000000 000000 000000 000000 000000 000000
660/ 000000 000000 000000 000000 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000
```

```
BLOCK NUMBER 00050
000/  052122 030455 020061 044514 045516 020040 020040 030126
020/  026464 032060 020101 020040 046040 040517 020104 040515
040/  020120 005015 046123 053101 020105 046056 040504 020040
060/  020040 020040 020040 020040 020040 020040 032062 045055
100/  047101 033455 006470 005012 042523 052103 047511 020116
120/  042101 051104 020040 020040 044523 042532 020040 020040
140/  047105 051124 020131 020040 042101 051104 020040 020040
160/  047105 051124 020131 020040 042101 051104 020040 020040
200/  047105 051124 020131 020040 042101 051104 005015 005015
220/  020056 041101 027123 030011 030060 030060 004460 030060
240/  030061 030060 051411 052105 031460 004440 030060 030060
260/  030060 006411 004412 030060 030061 030060 030011 032066
300/  030467 004464 041122 030103 020063 030011 030460 030060
320/  004460 005015 030011 032466 030467 004464 030060 030460
340/  032063 042411 044103 047117 004531 033060 033465 032061
360/  006411 004412 033060 030066 030065 030011 030060 033461
400/  004464 047503 030103 020063 030011 033066 032460 004460
420/  005015 030011 033066 032062 004464 030060 030460 031064
440/  044411 052116 051501 004503 033060 031066 032064 006411
460/  004412 033060 032066 033060 030011 030060 031460 004466
500/  042507 040504 031460 030011 033066 030064 004466 005015
520/  030011 033066 032064 004464 030060 030060 032063 043411
540/  053111 030132 004463 033060 032066 032064 006411 004412
560/  033060 032466 030060 030011 030060 030461 004460 044504
600/  050107 041511 030011 033066 030065 004460 005015 030011
620/  033066 030466 004460 030060 030460 033060 051411 040503
640/  031516 004440 033060 033066 030061 006411 004412 033060
660/  033466 033061 030011 030060 033466 004462 044103 044501
700/  031516 030011 033066 030467 004466 005015 030011 033466
720/  030466 004460 030460 033060 032067 051411 044520 052503
740/  004463 033060 033067 030061 006411 004412 030061 032460
760/  032060 030011 030060 033460 004466 000000 000000 000000

BLOCK NUMBER 00051
000/  042523 041522 031510 030411 030060 030065 004464 005015
020/  030411 030060 030066 004462 030060 030460 031066 050011
040/  043117 046111 004463 030061 033060 031060 006411 004412
060/  030061 033460 032066 030011 030060 030462 004462 045520
100/  040526 031514 030411 030060 033067 004464 005015 030411
120/  030460 033461 004466 030060 030460 032060 051411 047515
140/  044124 004463 030061 030461 033067 006411 004412 030061
160/  031461 031060 030011 030060 033060 004464 044510 052123
200/  020061 030411 030460 030063 004462 005015 030411 030460
220/  033063 004466 030060 030460 032064 050011 053113 046101
240/  030061 031461 033066 006411 004412 030061 032461
260/  031063 030011 030060 032460 004464 046523 052117 030510
300/  030411 030460 031465 004462 005015 030411 030460 030066
320/  004466 030060 030461 032066 040411 042116 044505 004463
340/  030061 033061 033060 006411 004412 030061 033462 031067
360/  030011 030060 030461 004464 044506 030506 020060 030411
400/  031060 033467 004462 005015 030411 031460 030061 004466
420/  030060 030460 031065 043011 043111 031061 004440 030061
440/  030463 033060 006411 004412 030061 031063 030066 030011
460/  030060 033062 004462 042520 041522 051111 030411 031460
500/  033062 004460 005015 030411 031460 032065 004462 030060
520/  030460 033066 044411 052116 046106 004517 030061 032463
540/  031064 006411 004412 030061 033463 030063 030011 030060
560/  031061 004466 046106 044517 052116 030411 031460 031467
600/  004460 005015 030411 032060 032460 004466 030060 030460
620/  033463 051411 030127 020063 004440 030061 030064 033065
640/  006411 004412 030061 031064 033061 030011 030060 031461
660/  004467 051527 031460 020040 030411 032060 030462 004466
700/  005015 030411 032060 032463 004466 030060 032460 032064
720/  054011 044515 030124 004463 030060 031464 033065 006411
740/  004412 030061 030465 031062 030011 030060 032060 004460
760/  044507 030126 020063 000011 000000 000000 000000 000000
```

BLOCK NUMBER 00052
```
000/  030061 030465 031062 006411 004412 030061 030465 031066
020/  030011 030060 032462 004465 042522 030123 020063 030411
040/  032460 033061 004462 052107 030124 020063 030411 032460
060/  033461 004462 042507 030124 020063 030411 032460 030062
100/  004460 005015 030411 032460 032064 004460 030060 030060
120/  031065 051411 053101 042522 004507 030061 032065 030064
140/  051011 051505 042522 004507 030061 032065 032067 006411
160/  004412 030061 032465 031061 030011 030060 031060 004462
200/  040502 041504 046101 030411 032460 030465 004462 005015
220/  052012 040522 051516 042506 020122 042101 051104 051505
240/  020123 020075 030060 030061 030060 006411 044012 043511
260/  020110 044514 044515 020124 020075 030061 032465 032063
300/  000014 000000 000000 000000 000000 000000 000000 000000
320/  000000 000000 000000 000000 000000 000000 000000 000000
340/  000000 000000 000000 000000 000000 000000 000000 000000
360/  000000 000000 000000 000000 000000 000000 000000 000000
400/  000000 000000 000000 000000 000000 000000 000000 000000
420/  000000 000000 000000 000000 000000 000000 000000 000000
440/  000000 000000 000000 000000 000000 000000 000000 000000
460/  000000 000000 000000 000000 000000 000000 000000 000000
500/  000000 000000 000000 000000 000000 000000 000000 000000
520/  000000 000000 000000 000000 000000 000000 000000 000000
540/  000000 000000 000000 000000 000000 000000 000000 000000
560/  000000 000000 000000 000000 000000 000000 000000 000000
600/  000000 000000 000000 000000 000000 000000 000000 000000
620/  000000 000000 000000 000000 000000 000000 000000 000000
640/  000000 000000 000000 000000 000000 000000 000000 000000
660/  000000 000000 000000 000000 000000 000000 000000 000000
700/  000000 000000 000000 000000 000000 000000 000000 000000
720/  000000 000000 000000 000000 000000 000000 000000 000000
740/  000000 000000 000000 000000 000000 000000 000000 000000
760/  000000 000000 000000 000000 000000 000000 000000 000000
```

BLOCK NUMBER 00053
```
000/  000001 000056 000001 070323 140250 000000 000000 127401
020/  007624 000410 000000 004164 020311 002100 000000 012001
040/  035221 002100 000000 012433 140250 002100 000000 000440
060/  027000 000400 067400 065432 040145 000004 140000 004437
100/  040140 000004 167000 070046 040306 000004 167000 140046
120/  040306 000004 067400 102047 040072 000004 121400 000001
140/  000056 000001 026214 005421 002100 000000 026476 123521
160/  002100 000000 026476 140250 002100 000000 027364 140250
200/  002100 000000 031573 100730 002100 000000 000741 027000
220/  000400 102000 035472 040011 000004 102000 067472 040047
240/  000004 155000 035144 040024 000000 147000 037545 040010
260/  000004 147000 040545 040010 000004 122000 000001 000056
300/  000001 063136 035101 002100 000000 070533 140250 002100
320/  000000 073471 056250 002100 000000 073632 012041 002100
340/  000000 073634 140250 002100 000000 000624 027000 000400
360/  153400 060570 040176 000004 044400 024571 040026 000004
400/  073000 040172 040316 000000 153000 040222 040316 000004
420/  010400 150630 040201 000004 157000 000001 000036 000001
440/  000000 000000 000450 064714 070323 140250 002150 000000
460/  000000 000000 001450 000000 000500 003000 001000 173400
500/  000001 000016 000004 000007 000000 000000 000000 000746
520/  027000 001400 000000 143000 000025 073400 000011 073400
540/  000011 000400 125001 073411 000400 173001 173404
560/  000445 154000 007004 173403 001045 150000 143004 000001
600/  000044 000004 003001 000000 005004 070533 140250 007004
620/  026476 123521 011001 004652 013004 017700 060011 015001
640/  002366 000734 027000 001400 023000 000400 167403 140001
660/  004425 140400 174025 141004 005025 051005 001024 017176
700/  073401 000011 000400 144001 073412 000011 000400 005001
720/  032005 000001 000000 000042 000004 007001 002370 011001 002412
740/  016004 026476 123521 020001 005310 022004 012433 140250
760/  024001 002412 000476 027000 001400 046000 140000 002025
```

```
BLOCK NUMBER 00054
000/  140400 130025 141412 134025 073412 003024 073400 000011
020/  000400 000001 141000 001025 173400 003024 073400 000011
040/  000400 000001 000001 000032 000004 005001 005260 007001
060/  005270 013004 026476 123521 023004 012433 140250 000414
100/  027000 001400 071000 000000 103400 010176 140176 114035
120/  140404 113035 040004 073560 115020 140004 105035 100004
140/  033414 106020 140004 101035 100004 033414 177420 000001
160/  000056 000003 000230 002204 016700 002156 016701 002154
200/  070100 010167 004260 004567 000000 000404 002412 004534
220/  004535 004532 022767 000001 004236 001002 000631 016000
240/  002000 002000 153026 040222 000716 005032 000405 056034
260/  000411 056436 000411 055040 115011 000001 000056 000003
300/  000276 000167 004250 022767 000002 004222 001002 000167
320/  004272 004567 000000 000402 003504 002442 005067 013276
340/  005067 013274 005067 013272 000706 012000 002000 002000
360/  106026 010454 000413 042032 000407 021034 047405 000001
400/  000056 000003 000344 016701 012640 012700 014060 005020
420/  077102 016701 012624 012700 013700 005020 077102 016701
440/  012610 012700 013734 005020 077102 016701 000530 011000
460/  002000 000400 030012 000430 140026 000427 156042 111027
500/  000001 000056 000003 000412 012574 012700 013770 005020
520/  077102 016701 012560 012700 014024 005020 077102 005067
540/  011622 005067 011620 005067 011626 005067 003026 000445
560/  007000 002000 000400 174010 000427 012024 112030 000001
600/  000056 000003 000460 005067 004042 005267 004036 026767
620/  004032 002002 001054 005067 004022 004567 000000 000405
640/  014712 002414 002416 002420 002422 012700 000750 020000
660/  002000 002000 067432 065432 000545 145036 000431 006040
700/  000405 007042 000405 010044 000405 011046 101005 000001
720/  000054 000003 000526 014712 066700 003774 020037 170002
740/  001361 004567 000000 000404 004530 014712 003510 003512
760/  004567 000000 000405 003510 003512 000663 027000 002000

BLOCK NUMBER 00055
000/  000400 145004 002031 075422 154063 000601 054026 000411
020/  145030 000431 044032 000407 045034 002007 147040 037545
040/  000410 044044 000407 045046 171007 000001 000054 000003
060/  000572 003502 004512 004524 005367 003706 004567 000000
100/  000403 004512 006317 003500 004567 000000 000401 006253
120/  005267 011432 004567 000756 027000 002000 000400 041004
140/  000407 045006 000411 052010 002011 102020 035472 000411
160/  045024 000411 147426 000414 040030 002007 037034 050455
200/  000647 125440 112014 000001 000042 000003 000636 000000
220/  000403 012266 005713 003500 005002 004567 000000 000405
240/  014712 002424 002426 002430 000612 027000 002000 002000
260/  102004 035472 000411 133010 000424 145412 000413 040014
300/  002007 067422 065432 000545 145026 000431 012030 000405
320/  013032 000405 014034 130005 000001 000056 000003 000670
340/  002432 005202 010267 012724 004567 000000 000403 013624
360/  005734 003500 004567 000000 000401 005676 012700 014712
400/  066700 001504 020037 025000 002000 000400 015004
420/  002005 102016 035472 000411 112022 000427 156024 000413
440/  040026 002007 037032 050455 000647 137036 000413 145042
460/  011031 000001 000056 000003 000736 170002 001344 016703
500/  001532 005004 005267 002532 020367 002526 001067 005067
520/  002520 004567 000000 000404 002440 014712 003510 003512
540/  000476 016000 002000 002000 075436 154063 000601 020042
560/  000405 145044 000431 044046 000407 045050 073007 000001
600/  000056 000003 001004 004567 000000 000405 003510 003512
620/  003502 004512 004524 016701 003462 005301 016700 001440
640/  060300 020100 003401 005204 006303 160300 000502 020000
660/  002000 002000 147006 037545 000410 044012 000407 045014
700/  000407 041016 000407 045020 000411 052022 071411 000001
720/  000056 000003 001052 020100 002001 005204 010167 012540
740/  004567 000000 000403 013624 006173 003500 004567 000000
760/  000401 006125 005704 001412 004567 000000 000567 024000
```

BLOCK NUMBER 00056
000/ 002000 002000 102020 035472 000411 112024 000427 075426
020/ 000414 040030 002007 037034 050455 000647 052440 002014
040/ 037050 050455 065647 000001 000056 000003 001120 000401
060/ 006204 000000 006203 005303 010367 002350 000644 004567
100/ 000000 000404 002412 004536 004542 004532 022767 000001
120/ 003346 001002 000440 020000 002000 000400 102006 002014
140/ 073026 040172 000716 005032 000405 057034 000411 061036
160/ 000411 055040 070011 000001 000056 000003 001166 000167
200/ 003360 022767 000002 003332 001002 000167 003402 012767
220/ 002502 002106 012767 003324 002222 012767 000001 011056
240/ 000167 005350 000630 007000 002000 000400 041026 000405
260/ 152034 114006 000001 000056 000003 001234 004567 000000
300/ 000404 002412 004537 004535 004532 022767 000001 003252
320/ 001002 000167 003264 022767 000002 003236 001002 000167
340/ 003306 000540 016000 002000 002000 073006 040172 000716
360/ 005012 000405 057414 000411 056416 000411 055020 057411
400/ 000001 000056 000003 001302 026727 002014 002502 001003
420/ 005067 002130 000406 016700 001776 162700 002502 010067
440/ 002112 004567 000000 000402 003502 003446 005767 000654
460/ 016000 002000 000400 041010 000405 041030 002005 037040
500/ 124055 000700 041044 000407 023046 073007 000001 000056
520/ 000003 001350 002074 001405 004567 000000 000402 003446
540/ 002502 016700 001020 004567 000000 000402 004550 004532
560/ 005767 003122 001023 142767 000200 000664 021000 002000
600/ 002000 037012 124055 000700 023016 000407 041020 002005
620/ 172030 124056 000700 064034 000411 055036 127011 000001
640/ 000056 000003 001416 003130 126767 003124 003117 001417
660/ 126767 003114 003111 001431 126767 003104 003100 001002
700/ 000167 000442 000167 003072 077034 000167 000777 027000
720/ 001400 032000 051003 073406 000011 002000 145001 012031
740/ 013005 055005 173411 011013 001006 073403 105000 073411
760/ 176000 073400 000011 001000 037001 156007 000001 000046

BLOCK NUMBER 00057
000/ 000004 004004 114021 100721 006001 014712 007001 002424
020/ 010001 002426 011001 004532 022004 026214 005421 024001
040/ 003476 000652 027000 001400 055000 024003 140007 136035
060/ 033401 142020 033400 142020 140000 001345 033400 036020
100/ 140000 125035 140001 001345 033400 060020 141000 024025
120/ 106007 000001 000016 000004 002001 003450 024001 003450
140/ 000541 027000 001400 100000 133403 121024 141403 112035
160/ 142001 111035 100401 140424 140412 140414 140414 140414
200/ 152145 040006 140024 033412 055020 033400 071020 131400
220/ 000001 000012 000004 016001 003324 000772 027000 001400
240/ 123000 040003 000344 013413 000040 006400 033407 160020
260/ 073423 000011 001400 112001 000427 040014 073407 000011
300/ 000400 165401 000013 040000 021024 000001 000042 000004
320/ 012004 035204 004473 014001 013624 015001 006001 016001
340/ 003500 020004 026476 123521 022001 005753 000715 027000
360/ 001400 146000 140003 033412 032020 033400 037020 040000
400/ 000344 013413 000040 006400 033407 130020 073423 000011
420/ 001400 112001 033027 040014 073407 074411 000001 000030
440/ 000004 017004 035204 004473 021001 013624 022001 006066
460/ 023001 003500 000434 027000 001400 171000 000003 000400
500/ 020001 000014 141400 000045 001000 173405 012020 142000
520/ 000045 001000 033405 003021 140400 001035 053401 000160
540/ 140400 112545 000001 000020 000004 002004 026476 123521
560/ 004001 006040 000513 027000 001400 014000 000004 140400
600/ 145145 140031 146025 050131 141224 141576 000025 140400
620/ 000145 003400 073577 000011 002000 146001 016131 017005
640/ 055005 133011 000001 000044 000004 004001 014712 006001
660/ 054714 017004 114021 100721 021001 054714 022001 002434
700/ 023001 002436 024001 004532 000470 027000 001400 037020
720/ 173404 014013 001005 073403 110000 173410 155012 115402
740/ 140002 134035 073400 000011 001000 064001 055011 173411
760/ 175013 006404 173402 024305 000001 000024 000004 015004

```
BLOCK NUMBER 00060
000/ 027364 140250 017001 004550 020001 004532 000453 027000
020/ 001400 062000 100004 000000 173405 176255 171004 007404
040/ 173403 172255 165404 002404 073403 167000 013004 073576
060/ 003000 073405 000011 000400 115001 176013 000001 000020
100/ 000004 022004 026476 123521 024001 005632 000622 027000
120/ 001400 105000 073404 123000 073774 000011 000400 126001
140/ 073413 116000 073416 000011 002000 005001 061405 062011
160/ 055011 173411 000445 126000 001004 026002 000001 000046
200/ 000004 005004 026476 123521 007001 005654 013004 075166
220/ 147100 015001 002412 016001 004543 017001 004544 020001
240/ 004532 000703 027000 001400 130000 073404 133000 173404
260/ 001045 120000 001004 073402 144000 113404 041040 001405
300/ 033402 056012 003002 151001 171035 141017 041345 133405
320/ 111020 000001 000016 000004 013001 002502 023001 002502
340/ 000441 024000 001400 153000 047004 073402 000011 001000
360/ 041001 023007 173407 040013 002402 073403 000011 001000
400/ 023001 041007 073405 131000 045373 000001 000046 000004
420/ 004004 026476 140250 006001 003502 007001 003446 014004
440/ 026476 140250 016001 003446 017001 002502 000010 002370
460/ 000701 015000 001400 174000 010004 100047 030000 137000
500/ 146400 100000 100000 137000 033402 077400 000001 000012
520/ 000004 000010 002500 000644 005000 001400 040000 005005
540/ 121400 000001 000012 000004 000010 003476 000644 010000
560/ 001400 037000 013007 000400 001000 017000 070000 000001
600/ 000012 000004 000010 003510 000632 005000 001400 044000
620/ 000007 121001 000001 000012 000004 000010 004534 000604
640/ 012000 001400 056000 043011 046522 046104 050107 041101
660/ 047124 177523 000001 000012 000004 000010 004552 000566
700/ 027000 001400 065000 073411 000011 000400 072001 000011
720/ 020000 020040 020040 020052 052512 045516 042440 051122
740/ 051117 005015 073400 000011 000400 111001 056011 000001
760/ 000032 000004 003004 026476 123521 005001 004564 022004

BLOCK NUMBER 00061
000/ 026476 123521 024001 004622 000635 027000 001400 110000
020/ 000011 020000 020040 020040 020052 044524 042515 047455
040/ 052125 042440 051122 051117 005015 020000 020040 042040
060/ 043105 052501 052114 110440 000001 000056 000003 004666
100/ 047514 050117 052040 046511 020105 020075 030061 030060
120/ 006460 020012 020040 042040 043105 052501 052114 054040
140/ 054454 042040 046511 000605 027000 001400 156000 042411
160/ 051516 047511 051516 047440 020106 047514 020127 044527
200/ 042116 053517 036440 030440 034062 020054 034064 005015
220/ 020040 020040 060104 000001 000056 000003 005002 043105
240/ 052501 052114 046040 053517 053440 047111 047504 020127
260/ 043117 051506 052105 020123 020075 034461 026060 031040
300/ 032460 005015 000654 027000 001400 024000 020012 020040
320/ 042040 043105 052501 052114 054040 054454 042040 046511
340/ 047105 044523 047117 020123 043117 050040 041511 052524
360/ 042522 170040 000001 000056 000003 005116 020075 031061
400/ 026070 030440 034062 005015 020040 020040 042504 040506
420/ 046125 020124 044520 052103 051125 020105 044527 042116
440/ 053517 000707 027000 001400 072000 020012 043117 051506
460/ 052105 020123 020075 034461 026060 032440 006465 020012
500/ 020040 044440 020106 047101 020131 044103 047101 042507
520/ 024454 000001 000056 000003 005232 052040 050131 020105
540/ 027131 042440 051514 026105 047040 020056 037055 000040
560/ 005340 005416 005475 005550 002414 002416 002420 002422
600/ 000527 023000 002000 000400 160032 000412 007034 000413
620/ 036436 000413 064040 000413 006042 000405 007044 000405
640/ 010046 000405 011050 133405 000001 000056 000003 005300
660/ 002424 002426 002430 002432 020040 020040 042440 052116
700/ 051105 046040 047517 020120 044524 042515 035040 000040
720/ 020040 020040 042440 000556 013000 002000 000400 012004
740/ 000405 013006 000405 014010 000405 015012 052405 000001
760/ 000056 000003 005346 052116 051105 046040 053517 053440
```

```
BLOCK NUMBER 00062
000/  047111 047504 020127 044504 042515 051516 047511 051516
020/  024040 044443 020130 044443 024531 035040 000416 027000
040/  001400 006000 020013 020000 020040 020040 047105 042524
060/  020122 047514 020127 044527 042116 053517 047440 043106
100/  042523 051524 024040 044443 043117 135461 000001 000056
120/  000003 005462 021440 047511 031106 020051 020072 020060
140/  020040 020040 047105 042524 020122 044520 052103 051125
160/  020105 044504 042515 051516 047511 000711 027000 001400
200/  054000 047013 020123 021450 054111 021440 054511 020051
220/  020072 020000 020040 020040 047105 042524 020122 044520
240/  052103 051125 020105 044527 147116 000001 000056 000003
260/  005576 047504 020127 043117 051506 052105 020123 021450
300/  043117 020061 044443 043117 024462 035040 000040 020040
320/  020040 043440 051040 041505 000431 027000 001400 122000
340/  042413 053111 042105 005015 020000 020040 020040 020114
360/  042522 042503 053111 042105 005015 020000 020040 020040
400/  044520 052103 051125 072505 000001 000011 000003 005712
420/  177040 000001 000012 000004 000010 005721 000415 011400
440/  001400 150400 020013 044504 044507 044524 042532 020104
460/  000460 005000 002000 004000 161000 176013 000001 000047
500/  000003 005742 052040 046511 051505 005015 020000 020040
520/  020040 026530 044504 020115 043117 041440 046105 020114
540/  051511 057440 000001 000012 000004 000010 006007 000726
560/  027000 001400 003400 006414 020012 020040 020040 047503
600/  052116 047111 042525 041040 020131 050047 006447 000012
620/  020040 020040 054440 042055 046511 047440 055106 000001
640/  000021 000003 006055 041440 046105 020114 051511 113040
660/  000001 000012 000004 000010 006074 000641 027000 001400
700/  036000 006414 020012 020040 020040 047503 052116 047111
720/  042525 041040 020131 050047 006447 000012 020040 020040
740/  050040 041511 052524 042522 177040 000001 000041 000003
760/  006142 040502 045503 051107 052517 042116 043440 042522

BLOCK NUMBER 00063
000/  026531 042514 042526 020114 051511 132440 000001 000012
020/  000004 000010 006201 000534 027000 001400 100400 006414
040/  000012 020040 020040 025040 040440 045104 051525 020124
060/  044526 042504 027117 041440 047117 044524 052516 020105
100/  054502 023440 154520 000001 000056 000003 006247 006447
120/  000012 020040 020040 046040 053517 053440 047111 047504
140/  020127 040502 045503 051107 052517 042116 046040 053105
160/  046105 044440 000522 005000 001400 146400 051414 123040
200/  000001 000012 000004 000010 006325 000410 026400 001400
220/  152400 006414 000012 016700 176176 005001 006200 103402
240/  005201 000774 006301 016167 006370 000006 004567 000000
260/  000401 000000 000000 006376 000742 012000 002000 000400
300/  174031 002014 037037 050455 000647 177047 010414 000001
320/  000056 000003 006372 006446 006522 020040 020040 020052
340/  044520 020103 051124 047101 046523 051511 044523 047117
360/  052040 046511 026505 052517 020124 051105 000633 007000
400/  002000 000400 023004 000415 051006 047415 000001 000056
420/  000003 006440 047522 006522 000012 020040 020040 020052
440/  044520 020103 051124 047101 046523 051511 044523 047117
460/  045040 047125 020113 042515 051523 000567 027000 001400
500/  043000 040415 042507 042440 051122 051117 005015 020000
520/  020040 025040 050040 041511 052040 040522 051516 044515
540/  051523 047511 020116 047111 071523 000001 000056 000003
560/  006554 043125 044506 044503 047105 020124 050123 041501
600/  020105 051105 047522 006522 000012 016767 003476 003472
620/  016767 173634 003470 004567 000553 027000 001400 111000
640/  000015 002400 145001 020031 144005 142024 055024 173411
660/  000445 132000 001373 073402 170000 133764 004012 140007
700/  115025 140424 007025 124000 000001 000044 000004 002004
720/  073471 056250 004001 014712 005001 002440 006001 012310
740/  007001 012304 010001 004532 022001 012232 000750 027000
760/  001400 134000 150015 177425 041777 173576 177425 176377
```

```
BLOCK NUMBER 00064
000/ 173406 177425 136377 173411 177425 134377 033411 163012
020/ 033406 162012 033406 161012 073406 137011 000001 000034
040/ 000003 006736 000000 000413 014712 002424 002426 012304
060/ 012310 012312 012314 013134 000756 026000 002000 002000
100/ 000404 110424 000472 145010 000431 012012 000405 013014
120/ 000405 142016 000424 144020 000424 145022 000424 146024
140/ 000424 056026 066026 000001 000056 000003 006762 012306
160/ 003500 004532 022767 000001 175534 001002 000167 005270
200/ 022767 000002 175520 001456 004567 000000 000420 012304
220/ 002424 002426 000543 022000 002000 000400 143004 000424
240/ 040006 000407 055010 002011 072040 144410 000440 142044
260/ 000424 012046 000405 013050 032005 000001 000034 000003
300/ 007030 012314 013134 013136 013140 013142 013144 013154
320/ 013146 013150 013152 000620 027000 002000 000400 146004
340/ 000424 056006 000426 057010 000426 060012 000426 061014
360/ 000426 062016 000426 066020 000426 063022 000426 064024
400/ 000426 065026 013426 000001 000056 000003 007054 013156
420/ 012236 004532 022767 000001 175442 001002 000167 005262
440/ 022767 000000 004032 001421 022767 000000 004026 001415
460/ 016701 173302 000530 011000 002000 000400 067004 000426
500/ 117006 000424 055010 035411 000001 000056 000003 007122
520/ 005301 020167 004010 001407 016701 173270 005301 020167
540/ 004000 001401 000404 005367 003114 000167 177424 026767
560/ 003770 173300 002770 000500 027000 001400 074000 073416
600/ 000011 002400 064001 063026 066026 070026 116026 140424
620/ 161035 053407 062160 000000 033412 155162 033407 003020
640/ 001006 173412 003455 000001 000040 000004 003004 062332
660/ 012072 005001 013150 006001 013146 007001 013154 010001
700/ 013160 011001 012234 000510 027000 001400 117000 176416
720/ 101005 005366 173404 173055 076005 003366 173404 170055
740/ 073005 001366 101004 003412 173401 130055 075007 001766
760/ 133405 177012 145005 000001 000040 000003 007304 000721

BLOCK NUMBER 00065
000/ 004567 000000 000415 012304 002424 002426 014712 012314
020/ 013134 012310 012232 000737 026000 002000 002000 044410
040/ 024571 000426 142014 000424 012016 000405 013020 000405
060/ 145022 000431 146024 000424 056026 000426 144030 000424
100/ 115032 053424 000001 000056 000003 007334 012242 012272
120/ 003500 013206 004532 022767 000001 175156 001002 000167
140/ 005054 016700 002644 070067 173104 160167 002644 005667
160/ 002670 000776 015000 002000 000400 121004 000424 135006
200/ 000424 040010 000407 103012 000426 055014 165011 000001
220/ 000056 000003 007402 160067 002664 022702 000001 001434
240/ 026767 002616 173024 002414 026767 002610 173016 002404
260/ 012704 000005 000167 001602 012704 000006 000635 027000
300/ 001400 024000 073417 075000 173403 070055 173005 002365
320/ 142005 003425 073400 065000 142003 004025 073400 061000
340/ 073403 000011 006400 145001 012031 005405 000001 000024
360/ 000004 021004 063136 035101 023001 014712 024001 002424
400/ 000466 016000 001400 047000 013017 057005 060026 105024
420/ 061026 062026 167026 051026 052027 053027 123427 000001
440/ 000056 000004 002001 002426 003001 013136 004001 013140
460/ 005001 013212 006001 013142 007001 013144 010001 013354
500/ 011001 013522 012001 013524 013001 013526 000545 027000
520/ 001400 061000 054017 015427 001401 140012 165035 140407
540/ 105025 041026 141224 000105 101777 002540 140176 155035
560/ 140407 167025 041026 141224 000105 145777 000001 000022
600/ 000004 002001 013530 010001 013212 021001 013356 000635
620/ 027000 001400 104000 101417 002540 001176 140012 142035
640/ 140007 141155 100007 133562 011020 073405 000011 001000
660/ 053001 105027 073426 000011 003400 053001 151027 000001
700/ 000036 000004 015004 074327 077141 017001 004567 017520
720/ 000401 105737 177560 100375 113701 177562 042701 177600
740/ 022701 000015 001401 010102 105737 177564 100375 110137
760/ 177566 022701 000015 001355 105737 177564 100375 112737
```

```
BLOCK NUMBER 00066
000/ 000012 177566 022702 000116 001412 022702 000131 001403
020/ 005075 000000 000407 012775 000001 000000 000403 012775
040/ 000002 000000 000167 017424 004567 017364 000401 012701
060/ 066230 005002 105737 177560 100375 113700 177562 042700
100/ 177600 105737 177564 100375 110037 177566 020027 000060
120/ 002410 020027 000071 003005 005202 162700 000060 010021
140/ 000751 005702 001001 000746 020027 000015 001006 105737
160/ 177564 100375 112737 000012 177566 012701 066230 012103
200/ 020227 000001 001405 005302 070327 000012 062103 077204
220/ 010375 000000 000167 017244 100414 000740 001054 011400
240/ 000404 003054 004567 017170 000403 012703 000005 016502
260/ 000002 112712 000040 062702 000006 005004 005775 000004
300/ 100004 112767 000001 000015 000403 112767 000200 000005
320/ 017500 000000 000402 005400 005204 010001 005000 071027
340/ 000012 052701 000060 110142 077310 012703 000004 122712
360/ 000060 001003 112722 000040 077306 005704 001402 112742
400/ 000055 000167 017066 004567 017026 000402 017500 000000
420/ 016501 000002 105737 175610 100375 113721 175612 077006
440/ 000167 017030 004567 016770 000401 011500 105710 001406
460/ 105737 177564 100375 112037 177566 000770 000167 016774
500/ 004567 016734 000405 012737 066602 000100 005037 000102
520/ 012767 000100 101266 012567 101250 012702 000004 012701
540/ 066604 013500 005400 110021 077204 016767 000030 101232
560/ 016767 000020 101222 012767 000101 101204 000001 000167
600/ 016672 000002 136000 073401 004567 016624 000405 027575
620/ 000002 000006 002427 011502 017503 000002 060203 017562
640/ 000004 000012 017504 000006 005304 060204 122427 000000
660/ 103407 160204 010475 000006 005075 000010 000167 016574
700/ 020304 001364 012775 000001 000010 000167 016556 004567
720/ 016516 000413 012502 013500 010067 000072 010067 000266
740/ 010067 000324 010067 000546 005300 010067 000236 010067
760/ 000274 010067 000340 005200 005200 010067 000240 010067

BLOCK NUMBER 00067
000/ 000276 013501 005301 010167 000322 013503 005303 060302
020/ 005000 010301 071027 000000 010003 010100 010301 013567
040/ 000300 013567 000350 012503 012567 000416 005067 000320
060/ 012567 000440 005735 100007 112767 000202 000247 012767
100/ 000001 000372 000406 112767 000207 000231 012767 000000
120/ 000354 012567 000336 005067 000330 012737 000435 067436
140/ 012737 000431 067346 005004 010267 000230 012767 000010
160/ 000264 010167 000420 000403 012767 000010 000250 116417
200/ 067556 000777 116417 067566 000777 162702 000000 005200
220/ 005301 000434 162702 000000 005301 000430 162702 000000
240/ 005300 005301 000423 005302 005300 000420 062702 000000
260/ 005300 005201 000413 062702 000000 005201 000407 062702
300/ 000000 005200 005201 000402 005202 005200 005700 002447
320/ 005701 002445 022700 000000 002442 022701 000000 002437
340/ 121227 000000 000434 005204 042704 177770 110423 005304
360/ 042704 177770 020167 000216 003402 010167 000210 005227
400/ 000000 020227 000000 001424 116404 067576 005327 000000
420/ 001263 052767 000001 000032 000413 005204 000401 005204
440/ 042704 177770 005327 000000 001255 052767 000002 000002
460/ 012737 000000 000000 016737 177706 000000 022727 000000
500/ 000001 001411 005267 000076 016701 000072 070127 000000
520/ 005201 010137 000000 000167 015742 012767 005204 177676
540/ 012767 005204 177600 012767 000010 177672 000730 004003
560/ 010414 014424 021035 007005 013016 017426 002437 003405
600/ 000407 001401 002403 002000 004567 015624 000415 005075
620/ 000030 012767 000011 000272 005375 000002 017567 000002
640/ 000324 017567 000002 000376 005275 000002 017567 000002
660/ 000330 017567 000002 000370 005275 000002 017567 000002
700/ 000316 017567 000002 000356 005375 000002 012767 000024
720/ 000250 012767 000024 000322 012767 000024 000460 012767
740/ 000024 000574 017567 000014 000520 017500 000000 005300
760/ 066500 000006 016702 000650 012703 003720 005022 005303
```

BLOCK NUMBER 00070
```
000/ 001375 005775 000024 100004 112767 000203 000457 000403
020/ 112767 000206 000447 005775 000026 100004 016767 000602
040/ 000554 000403 016767 000570 000544 016702 000540 010567
060/ 000532 016501 000010 017505 000012 062703 062703 000002
100/ 022712 000000 001412 011204 020023 001411 005304 001374
120/ 021227 000000 002402 000167 000444 010013 005212 005305
140/ 001454 112104 116417 070630 000777 005200 122711 000000
160/ 001766 000743 162700 000000 162702 000000 026702 000416
200/ 101402 010267 000410 000731 162700 000000 000765 162700
220/ 000000 000762 005300 022705 000001 001717 122711 000004
240/ 001736 000713 062700 000000 062702 000000 000706 062700
260/ 000000 000772 062700 000000 000767 016705 000320 010502
300/ 012201 022701 000000 001445 022701 000001 001437 005301
320/ 010200 005004 005003 012067 000266 005203 020301 003011
340/ 022067 000254 101005 014067 000246 010004 062700 000002
360/ 000764 022704 000000 001403 011214 016712 000222 005301
400/ 022701 000000 001403 062702 000002 000742 062705 000000
420/ 000726 005004 005067 000174 005067 000172 005067 000162
440/ 016705 000152 010500 012001 022701 000000 001433 011002
460/ 012003 005203 005301 001403 121327 000000 000771 160203
500/ 112204 042704 177400 060467 000112 005567 000110 005267
520/ 000100 005303 001365 022701 000000 001401 000750 062705
540/ 000000 000740 016705 000044 016775 000046 000016 016775
560/ 000042 000020 016775 000036 000022 000167 014676 016705
600/ 000012 012775 000001 000030 000167 014660 006411 043012
620/ 047514 000000 000000 000000 002400 011017 016425 022442
640/ 070644 074564 030061 004440 005015 041505 047510 054516
660/ 006411 042012 043511 044520 004503 005015 047503 030103
700/ 020063 006411 041412 040510 047111 004463 005015 047101
720/ 042504 031511 006411 005012 051124 047101 043123 051105
740/ 040440 042104 042522 051523 036440 030040 030460 030060
760/ 004460 005015 044510 044107 046040 046511 052111 036440
```

BLOCK NUMBER 00071
```
000/ 033060 033465 031061 000014 000000 000000 000000 000000
020/ 000000 000000 000000 000000 000000 000000 000000 000000
040/ 000000 000000 000000 000000 000000 000000 000000 000000
060/ 000000 000000 000000 000000 000000 000000 000000 000000
100/ 000000 000000 000000 000000 000000 000000 000000 000000
120/ 000000 000000 000000 000000 000000 000000 000000 000000
140/ 000000 000000 000000 000000 000000 000000 000000 000000
160/ 000000 000000 000000 000000 000000 000000 000000 000000
200/ 000000 000000 000000 000000 000000 000000 000000 000000
220/ 000000 000000 000000 000000 000000 000000 000000 000000
240/ 000000 000000 000000 000000 000000 000000 000000 000000
260/ 000000 000000 000000 000000 000000 000000 000000 000000
300/ 000000 000000 000000 000000 000000 000000 000000 000000
320/ 000000 000000 000000 000000 000000 000000 000000 000000
340/ 000000 000000 000000 000000 000000 000000 000000 000000
360/ 000000 000000 000000 000000 000000 000000 000000 000000
400/ 000000 000000 000000 000000 000000 000000 000000 000000
420/ 000000 000000 000000 000000 000000 000000 000000 000000
440/ 000000 000000 000000 000000 000000 000000 000000 000000
460/ 000000 000000 000000 000000 000000 000000 000000 000000
500/ 000000 000000 000000 000000 000000 000000 000000 000000
520/ 000000 000000 000000 000000 000000 000000 000000 000000
540/ 000000 000000 000000 000000 000000 000000 000000 000000
560/ 000000 000000 000000 000000 000000 000000 000000 000000
600/ 000000 000000 000000 000000 000000 000000 000000 000000
620/ 000000 000000 000000 000000 000000 000000 000000 000000
640/ 000000 000000 000000 000000 000000 000000 000000 000000
660/ 000000 000000 000000 000000 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000
```

```
BLOCK NUMBER 00072
000/  052122 030455 020061 044514 045516 020040 020040 030126
020/  026464 032060 020101 020040 046040 040517 020104 040515
040/  020120 005015 041122 030103 020063 046056 040504 020040
060/  020040 020040 020040 020040 020040 020040 032062 045055
100/  047101 033455 006470 005012 042523 052103 047511 020116
120/  042101 051104 020040 020040 044523 042532 020040 020040
140/  047105 051124 020131 020040 042101 051104 020040 020040
160/  047105 051124 020131 020040 042101 051104 020040 020040
200/  047105 051124 020131 020040 042101 051104 005015 005015
220/  020056 041101 027123 030011 030060 030060 004460 030060
240/  030061 030060 051411 052105 031460 004440 030060 030060
260/  030060 006411 004412 030060 030061 030060 030011 032066
300/  030467 004462 041122 030103 020063 030011 030460 030060
320/  004460 005015 030011 032466 030467 004462 030060 030460
340/  032063 042411 044103 047117 004531 033060 033465 031061
360/  006411 004412 033060 030066 033064 030011 030060 033461
400/  004464 047503 030103 020063 030011 033066 032060 004466
420/  005015 030011 033066 032062 004462 030060 030460 031064
440/  044411 052116 051501 004503 033060 031066 031064 006411
460/  004412 033060 032066 032060 030011 030060 031460 004466
500/  042507 040504 031460 030011 033066 030064 004464 005015
520/  030011 033066 032064 004462 030060 030060 032063 043411
540/  053111 030132 004463 033060 032066 031064 006411 004412
560/  033060 032066 033067 030011 030060 030461 004460 044504
600/  050107 041511 030011 033066 033464 004466 005015 030011
620/  033066 030066 004466 030060 030460 033060 051411 040503
640/  031516 004440 033060 033066 033060 006411 004412 033060
660/  033466 032061 030011 030060 033466 004462 044103 044501
700/  031516 030011 033066 030467 004464 005015 030011 033466
720/  030066 004466 030460 033060 032067 051411 044520 052503
740/  004463 033060 033067 033060 006411 004412 030061 032460
760/  031060 030011 030060 033460 004466 000000 000000 000000

BLOCK NUMBER 00073
000/  042523 041522 031510 030411 030060 030065 004462 005015
020/  030411 030060 030066 004460 030060 030460 031066 050011
040/  043117 046111 004463 030061 033060 030060 006411 004412
060/  030061 033460 031066 030011 030060 030462 004462 045520
100/  040526 031514 030411 030060 033067 004462 005015 030411
120/  030460 033461 004464 030060 030460 032060 051411 047515
140/  044124 004463 030061 030461 032067 006411 004412 030061
160/  031461 030060 030011 030060 033060 004464 044510 052123
200/  020061 030411 030460 030063 004460 005015 030411 030460
220/  033063 004464 030060 030460 032064 050011 053113 046101
240/  004461 030061 031461 032066 006411 004412 030061 032461
260/  030063 030011 030060 032460 004464 046523 052117 030510
300/  030411 030460 031465 004460 005015 030411 030460 030066
320/  004464 030060 030461 032066 040411 042116 044505 004463
340/  030061 033061 032060 006411 004412 030061 033462 030067
360/  030011 030060 030461 004464 044506 030506 020060 030411
400/  031060 033467 004460 005015 030411 031460 030061 004464
420/  030060 030460 031065 043011 043111 031061 004440 030061
440/  030463 032060 006411 004412 030061 031063 033065 030011
460/  030060 033062 004462 042520 041522 051111 030411 031460
500/  032462 004466 005015 030411 031460 032065 004460 030060
520/  030460 033066 044411 052116 046106 004517 030061 032463
540/  030064 006411 004412 030061 033463 033062 030011 030060
560/  031061 004466 046106 044517 052116 030411 031460 031067
600/  004466 005015 030411 032060 030462 004464 030060 030460
620/  033463 051411 030127 020063 004440 030061 030064 032065
640/  006411 004412 030061 031064 032061 030011 030060 031461
660/  004467 051527 031460 020040 030411 032060 030462 004464
700/  005015 030411 032060 032463 004464 030060 032460 032064
720/  054011 044515 030124 004463 030061 031464 032065 006411
740/  004412 030061 030465 030062 030011 030060 032060 004460
760/  044507 030126 020063 000011 000000 000000 000000 000000
```

```
BLOCK NUMBER 00074
000/  030061 030465 030062 006411 004412 030061 030465 030066
020/  030011 030060 032462 004465 042522 030123 020063 030411
040/  032460 033061 004460 052107 030124 020063 030411 032460
060/  033461 004460 042507 030124 020063 030411 032460 033461
100/  004466 005015 030411 032460 031464 004466 030060 030060
120/  031065 051411 053101 042522 004507 030061 032065 033063
140/  051011 051505 042522 004507 030061 032065 031067 006411
160/  004412 030061 032465 030061 030011 030060 031060 004462
200/  040502 041504 046101 030411 032460 030465 004460 005015
220/  052012 040522 051516 042506 020122 042101 051104 051505
240/  020123 020075 030060 030061 030060 006411 044012 043511
260/  020110 044514 044515 020124 020075 030061 032465 031063
300/  000014 000000 000000 000000 000000 000000 000000 000000
320/  000000 000000 000000 000000 000000 000000 000000 000000
340/  000000 000000 000000 000000 000000 000000 000000 000000
360/  000000 000000 000000 000000 000000 000000 000000 000000
400/  000000 000000 000000 000000 000000 000000 000000 000000
420/  000000 000000 000000 000000 000000 000000 000000 000000
440/  000000 000000 000000 000000 000000 000000 000000 000000
460/  000000 000000 000000 000000 000000 000000 000000 000000
500/  000000 000000 000000 000000 000000 000000 000000 000000
520/  000000 000000 000000 000000 000000 000000 000000 000000
540/  000000 000000 000000 000000 000000 000000 000000 000000
560/  000000 000000 000000 000000 000000 000000 000000 000000
600/  000000 000000 000000 000000 000000 000000 000000 000000
620/  000000 000000 000000 000000 000000 000000 000000 000000
640/  000000 000000 000000 000000 000000 000000 000000 000000
660/  000000 000000 000000 000000 000000 000000 000000 000000
700/  000000 000000 000000 000000 000000 000000 000000 000000
720/  000000 000000 000000 000000 000000 000000 000000 000000
740/  000000 000000 000000 000000 000000 000000 000000 000000
760/  000000 000000 000000 000000 000000 000000 000000 000000

BLOCK NUMBER 00075
000/  002551 145001 012033 013007 014007 013407 000001 000054
020/  001670 003432 005202 010267 012724 004567 064340 000403
040/  014624 006734 004500 004567 064524 000401 006676 012700
060/  015712 066700 001504 020037 000631 026000 157000 001003
100/  162360 141402 055035 002003 133412 055012 173405 053040
120/  033405 033402 050012 073405 144011 002176 020001 145007
140/  044033 045011 171411 000001 000054 002004 004567 077356
160/  000405 004510 004512 004502 005512 005524 016701 003462
200/  005301 016700 001440 060300 020100 003401 005204 006303
220/  160300 000717 026000 025000 040004 000440 102004 073412
240/  060020 073425 066011 001550 112001 075431 040016 073411
260/  160011 000550 052401 142016 005013 073403 152011 015150
300/  000001 000054 002120 000401 007204 000000 006203 005303
320/  010367 002350 000644 004567 101712 000404 003412 005536
340/  005542 005532 022767 000001 003346 001002 000714 026000
360/  073000 073404 170000 173406 001045 155000 001006 073402
400/  001000 173407 041025 043007 173404 152025 111010 173404
420/  000425 027000 073422 164000 113412 000001 000054 002234
440/  004567 101616 000404 003412 005537 005535 005532 022767
460/  000001 003252 001002 000167 003264 022767 000002 003236
500/  001002 000167 003306 000512 026000 141000 153404 006055
520/  041004 001407 033402 054012 003004 140001 177035 140003
540/  041345 033407 045020 073404 071011 001205 041001 023011
560/  173411 130013 002350 000001 000054 002074 001405 004567
600/  102542 000402 004446 003502 016700 001020 004567 102574
620/  000402 005550 005532 005767 003122 001023 142767 000200
640/  000707 026000 007000 054005 173406 052255 047406 007406
660/  173403 046255 044406 014406 173403 042255 040006 001006
700/  073402 021000 073401 035000 016006 073576 001000 000001
720/  000054 002464 003122 004567 101664 000404 015712 003424
740/  003426 005532 005767 003022 001402 000167 004612 000167
760/  000374 004567 063660 000402 004476 000607 026000 055000
```

```
BLOCK NUMBER 00076
000/ 024005 140011 136035 033401 142020 033400 142020 140000
020/ 001345 033400 036020 140000 125035 140001 001345 033400
040/ 060020 141000 024025 105411 000001 000054 002600 012267
060/ 001642 016703 000624 016704 000622 012201 005301 006301
100/ 006301 006301 062701 004324 012100 005300 010067 000132
120/ 010067 000162 000664 026000 123000 040005 000344 013413
140/ 000040 006400 033407 160020 073423 166011 001546 112001
160/ 000431 040016 073411 060011 000547 165401 000015 040000
200/ 002024 000001 000054 002714 005300 010067 000064 010067
220/ 000076 162100 005400 020027 000000 003415 010067 011660
240/ 004567 063274 000403 014624 007066 004500 004567 000524
260/ 026000 171000 030005 000547 020001 000016 141400 000045
300/ 001000 173405 012020 142000 000045 001000 033405 003021
320/ 140400 001035 053401 000160 140400 177545 000001 000054
340/ 003030 000000 062701 015712 012700 055714 112120 077302
360/ 012703 000000 062701 000000 077407 004567 101272 000404
400/ 055714 003434 003436 005532 000561 026000 037000 173406
420/ 014013 001005 073403 110000 173410 155012 115402 140002
440/ 134035 073400 022011 001204 064001 055013 173413 175013
460/ 006404 173402 077705 000001 000054 003144 000200 002400
500/ 126767 002374 002362 001417 126767 002364 002353 001405
520/ 000167 002356 077026 000167 002406 004567 063236 000401
540/ 006632 000771 026000 105000 073406 123000 073774 111011
560/ 000546 126001 073415 116000 073416 110011 002201 005001
600/ 061407 062013 055013 173413 000445 126000 001004 016002
620/ 000001 000054 003260 000167 002266 022767 000002 002240
640/ 001002 000167 002310 020227 003502 001003 005067 001134
660/ 000406 016722 007762 162702 003502 010267 000621 023000
700/ 153000 047006 073402 073011 001203 041001 023011 173411
720/ 040013 002402 073403 063011 001203 023001 041011 073407
740/ 131000 061773 000001 000030 003370 023420 000200 000060
760/ 000276 000315 000200 000200 000276 000067 000602 004000

BLOCK NUMBER 00077
000/ 040000 005007 123000 000001 000016 004476 000026 000001
020/ 000002 000036 000563 004000 044000 000011 122401 000001
040/ 000022 005534 051106 042115 043514 040520 052102 051516
060/ 000402 026000 065000 073413 133011 000541 072001 000013
100/ 020000 020040 020040 020052 052512 045516 042440 051122
120/ 051117 005015 073400 114011 000541 111001 045413 000001
140/ 000054 005620 000000 020040 020040 025040 052040 046511
160/ 026505 052517 020124 051105 047522 006522 000012 020040
200/ 020040 042504 040506 046125 020124 000624 026000 133000
220/ 046013 047517 020120 044524 042515 036440 030440 030060
240/ 030060 005015 020040 020040 042504 040506 046125 020124
260/ 026130 020131 044504 104115 000001 000054 005734 047105
300/ 044523 047117 020123 043117 046040 053517 053440 047111
320/ 047504 020127 020075 031061 026070 032040 006470 020012
340/ 020040 042040 000543 026000 001000 042414 040506 046125
360/ 020124 047514 020127 044527 042116 053517 047440 043106
400/ 042523 051524 036440 030440 030071 020054 030062 006465
420/ 127412 000001 000054 006050 020040 020040 042504 040506
440/ 046125 020124 026130 020131 044504 042515 051516 047511
460/ 051516 047440 020106 044520 052103 051125 020105 000763
500/ 026000 047000 036414 030440 034062 020054 031061 006470
520/ 020012 020040 042040 043105 052501 052114 050040 041511
540/ 053524 042522 053440 047111 047504 145127 000001 000054
560/ 006164 047440 043106 042523 051524 036440 030440 030071
600/ 020054 032465 005015 020040 020040 043111 040440 054516
620/ 041440 040510 043516 026105 000454 026000 115000 020014
640/ 054524 042520 054440 020056 046105 042523 020054 027116
660/ 026440 020076 160000 007014 036415 064015 006015 007007
700/ 010007 011007 045007 000001 000054 006300 003424 003426
720/ 003430 003432 020040 020040 042440 052116 051105 046040
740/ 047517 020120 044524 042515 035040 000040 020040 020040
760/ 042440 000551 026000 163000 047014 042524 020122 047514
```

```
BLOCK NUMBER 00100
000/  020127 044527 042116 053517 042040 046511 047105 044523
020/  047117 020123 021450 054111 021440 054511 020051 010472
040/  000001 000054 006414 000040 020040 020040 042440 052116
060/  051105 046040 053517 053440 047111 047504 020127 043117
100/  051506 052105 020123 021450 047511 030506 000676 026000
120/  031000 020015 044443 043117 024462 035040 000040 020040
140/  020040 042440 052116 051105 050040 041511 052524 042522
160/  042040 046511 047105 044523 146117 000001 000054 006530
200/  051516 024040 044443 020130 044443 024531 035040 000040
220/  020040 020040 042440 052116 051105 050040 041511 052524
240/  042522 053440 047111 000721 026000 077000 042015 053517
260/  047440 043106 042523 051524 024040 047443 030506 021440
300/  047511 031106 020051 020072 020000 020040 020040 020107
320/  042522 016103 000001 000054 006644 044505 042526 006504
340/  000012 020040 020040 046040 051040 041505 044505 042526
360/  006504 000012 020040 020040 050040 041511 052524 042522
400/  000570 003400 145000 020015 000401 010400 150400 020015
420/  044504 044507 044524 042532 020104 000463 022400 161000
440/  020015 044524 042515 006523 000012 020040 020040 054040
460/  042055 046511 047440 020106 042503 046114 044440 020123
500/  000542 026000 004567 004730 000406 005075 000012 017567
520/  000004 000024 017501 000002 005301 016502 000006 061201
540/  016203 000002 161203 122127 000000 101406 077304 012775
560/  000001 000012 000167 004704 161501 010175 000010 000167
600/  004672 004567 004632 000415 017500 000014 067500 000016
620/  006200 017501 000002 070100 010100 067500 000006 061500
640/  010075 000022 016501 000012 017502 000010 167502 000006
660/  005202 010275 000026 112021 077202 017501 000014 070175
700/  000002 010100 017501 000006 067501 000010 006201 060100
720/  061500 010075 000024 016501 000010 017502 000016 167502
740/  000014 005202 010275 000030 111011 067500 000002 077204
760/  000167 004510 004567 004450 000417 005075 000014 011567

BLOCK NUMBER 00101
000/  000154 013500 005300 011567 000146 012501 013567 000154
020/  003463 012503 012502 011567 000034 005035 012704 000001
040/  122111 101005 005204 005300 001373 005304 005200 005767
060/  000112 001431 005237 000000 010423 005012 114112 062702
100/  000002 005201 005367 000064 005204 005300 001425 122111
120/  103373 005767 000046 001407 010423 005012 114112 062702
140/  000002 005201 000737 005235 004567 000022 000402 000000
160/  000000 162705 000016 000705 000167 004300 046511 004567
200/  004236 000402 013501 012500 005301 111002 042702 177400
220/  010203 111002 042702 177400 116004 000001 042704 177400
240/  060403 006203 060203 006203 110320 005301 001361 111004
260/  042704 177400 060403 006203 060304 006204 110410 000167
300/  004172 004567 004132 000404 013500 012501 013502 011503
320/  005023 005302 001375 005745 013502 005302 012503 005004
340/  152104 020402 101401 010204 006304 060304 005214 005400
360/  001366 000167 004106 004567 004046 000405 011567 000114
400/  013500 005300 011567 000106 012501 013502 003444 012503
420/  011567 000032 005035 012704 000001 022111 003005 005204
440/  005300 001373 005304 005200 005767 001415 005237 000000
460/  010423 005302 005204 005300 001416 022111 002373 005702
500/  001402 010423 000754 004567 000020 000402 000000 000000
520/  162705 000012 000725 000167 003742 004567 003702 000402
540/  013501 012500 005301 005002 010203 011002 066003 000002
560/  006203 060203 006203 010320 005301 001366 006203 060310
600/  006210 000167 003666 004567 003626 000420 005075 000036
620/  017501 000000 005301 005000 071075 000002 010167 000762
640/  016767 000756 000756 016767 000752 000740 010067 000746
660/  016767 000742 000742 016767 000736 000722 005067 000732
700/  005067 000736 005067 000734 005067 000732 005067 000700
720/  005001 005002 017503 000010 117567 000006 000712 016500
740/  000006 010567 000644 112004 020427 000010 002402 000167
760/  000604 116417 102602 000777 005267 000636 066701 000614
```

```
BLOCK NUMBER 00102
000/  004767 000646 000470 005267 000630 066701 000600 005302
020/  004767 000626 004767 000716 000456 005267 000606 004767
040/  000704 000451 005267 000576 166701 000542 005202 004767
060/  000614 004767 000660 000437 005267 000536 166701 000516
100/  004767 000572 000430 005267 000530 166701 000500 005302
120/  004767 000552 004767 000572 000416 005267 000506 004767
140/  000560 000411 005267 000476 066701 000442 005202 004767
160/  000470 004767 000534 020327 000001 003003 116705 000450
200/  000401 111005 160504 005704 100002 062704 000010 022704
220/  000002 001411 022704 000003 001406 005303 005703 001402
240/  000167 177502 000403 005267 000346 000767 016705 000332
260/  016775 000334 000034 016775 000330 000012 016775 000324
300/  000014 016775 000320 000016 016775 000314 000020 006202
320/  060201 010175 000022 016703 000300 066703 000306 010375
340/  000024 016703 000274 066703 000274 010375 000026 005001
360/  005002 166767 000256 000242 166767 000252 000244 005767
400/  000230 100004 005467 000222 012701 000002 005767 000222
420/  100004 005467 000214 012702 000002 005067 000202 004567
440/  001100 000402 102640 102642 012700 102634 075020 004567
460/  001246 000402 102640 102642 026767 000136 000144 001423
500/  026767 000126 000134 002407 005201 010175 000030 016775
520/  000110 000032 000416 062702 000000 010275 000030 016775
540/  000100 000032 000406 012775 000000 000030 012775 000000
560/  000032 000167 002706 016705 000020 012775 000001 000036
600/  000770 003400 013021 023440 033061 001160 053001 105031
620/  073430 045011 003560 053001 143431 000001 040265 002201
640/  014212 014626 014532 014556 014602 005267 177736 026767
660/  177742 177730 002003 016767 177722 177730 000207 005367
700/  177712 026767 177714 177704 003403 016767 177676 177702
720/  000207 005267 177670 026767 177676 177662 002003 016767
740/  177654 177664 000207 005367 177644 026767 177650 177636
760/  003403 016767 177630 177636 000207 004567 002442 000404

BLOCK NUMBER 00103
000/  005067 000072 013567 000070 013567 000066 013567 000064
020/  004567 000516 000402 103076 103100 004567 000504 000402
040/  103102 103104 012700 103076 075030 004567 000652 000402
060/  103102 103104 016775 000014 000000 000167 002376 054031
100/  000001 000054 011070 004567 002326 000405 013500 070035
120/  010067 000124 010167 000122 004567 000406 000402 103250
140/  103252 163501 005600 163500 010067 000100 010167 000076
160/  004567 000356 000402 103254 103256 012700 103250 075030
200/  012702 000002 012060 177772 077203 012700 103244 075020
220/  004567 000504 000402 103250 103252 016775 000014 000000
240/  000167 002230 041710 000000 004567 067544 000407 014530
260/  004567 002154 000405 013567 000242 005067 000234 004567
300/  000240 000402 103532 103534 012700 103526 075020 013567
320/  000216 005067 000210 004567 000210 000402 103536 103540
340/  075000 016767 000172 000164 016767 000162 000154 004567
360/  000346 000402 103536 103540 016775 000144 000002 016767
400/  000132 000134 016767 000122 000124 162700 000004 075020
420/  013567 000110 005067 000102 004567 000106 000402 103532
440/  103534 162700 000004 075030 012767 000012 000056 005067
460/  000050 004567 000054 000402 103532 103534 162700 000004
500/  075020 004567 000222 000402 103536 103540 016775 000020
520/  000002 000167 001746 040265 002201 026727 001604 000010
540/  002406 004567 001672 000402 005775 000000 001003 005775
560/  000002 001460 005001 017502 000000 017503 000002 005702
600/  100006 005102 005103 062703 000001 005502 005201 005004
620/  012700 000230 020227 000200 002010 073227 000001 005204
640/  032702 000200 001772 160400 000410 032702 177400 001404
660/  073227 177777 005204 000771 060400 042702 000200 072027
700/  000007 074002 005701 001402 052702 100000 010275 000000
720/  010375 000002 000167 001544 004567 001504 000402 005775
740/  000000 001003 005775 000002 001440 005001 017502 000000
760/  017503 000002 005702 100003 042702 100000 005201 010200
```

```
BLOCK NUMBER 00104
000/  042700 100177 040002 052702 000200 072027 177771 162700
020/  000230 073200 005701 001405 005102 005103 062703 000001
040/  005502 010275 000000 010375 000002 000167 001416 004567
060/  001356 000404 017500 000000 016567 000002 000010 004567
100/  001020 000402 104212 000000 004567 001056 000402 104214
120/  104210 005767 000062 001010 142767 000200 000056 126775
140/  000052 000004 001403 000406 077026 000411 005075 000006
160/  000167 001310 012775 000001 000006 000167 001276 012775
200/  000002 000006 000167 001264 173402 000001 100000 004567
220/  001216 000404 017500 000000 004567 000736 000402 104354
240/  104350 005767 000102 001010 142767 000200 000076 126775
260/  000072 000002 001403 000416 077021 000421 016567 000004
300/  000010 004567 000614 000402 104352 000000 005075 000006
320/  000167 001150 012775 000001 000006 000167 001136 012775
340/  000002 000006 000167 001124 142004 000001 145000 004567
360/  001056 000404 011567 000304 117567 000002 000425 117547
400/  000004 000420 005075 000006 012700 104766 016767 073524
420/  000362 105710 001430 004567 000546 000402 105010 105012
440/  005767 000346 001010 142767 000200 000334 126720 000330
460/  001001 000757 005300 005367 000312 001353 012775 000010
500/  000006 000167 000766 012767 000005 000272 004567 000402
520/  000402 105006 105020 012700 104772 004767 000270 004567
540/  000436 000402 105010 105012 005767 000236 001025 142767
560/  000200 000224 126767 000220 000203 001423 126767 000210
600/  000174 001405 012775 000002 000006 000167 000656 012775
620/  000004 000006 000167 000644 012775 000001 000006 000167
640/  000632 005002 005003 156702 000151 156703 000146 070302
660/  010367 000130 004567 000232 000402 105014 000000 005067
700/  000114 016700 177766 005001 112001 060167 000100 005367
720/  000072 001371 116767 000066 000057 012767 000001 000046
740/  004567 000156 000402 105006 105011 012700 104777 004767
760/  000044 000167 000506 050122 000111 050122 043400 051105

BLOCK NUMBER 00105
000/  042120 001000 016700 002072 016701 002070 071067 002066
020/  050124 015123 000402 105710 001417 004567 000142 000402
040/  105010 105012 005767 177742 001010 142767 000200 177730
060/  126720 177724 001010 000757 000207 005726 012775 000001
100/  000006 000167 000366 005726 012775 000002 000006 000167
120/  000352 004567 000312 000402 017501 000000 016500 000002
140/  105737 175614 100375 112037 175616 005301 001371 000167
160/  000312 113767 175612 000246 000205 012767 000402 000020
200/  004567 000234 000402 012737 105404 000300 005037 000302
220/  113767 175612 000210 005067 000176 012767 000005 000174
240/  012767 023420 000164 042737 000100 175610 052737 000100
260/  175610 022767 000001 000140 001420 005367 000134 022767
300/  000000 000126 001366 022767 000000 000120 001420 012767
320/  023420 000106 005367 000104 000754 116775 000100 000000
340/  005075 000002 012767 113767 177646 000167 000116 042737
360/  000100 175610 012775 000001 000002 012767 113767 177620
400/  000167 000070 042737 000100 175610 113767 175612 000016
420/  012767 000001 000002 000002 014624 013220 004500 004567
440/  010446 010346 010246 010146 010046 016605 000012 000012
460/  022524 001001 000114 000167 000020 000205 012600 012601
500/  012602 012603 012604 012605 000205 010546 005046 010616
520/  062716 000002 012746 001777 000004 000777 041515 042110
540/  020040 174040 000001 000014 013212 041515 006524 000012
560/  000530 005000 113000 000026 005015 031000 000001 000010
600/  013312 000620 000606 005000 103000 177430 007377 045400
620/  000001 000012 014626 000003 000012 000471 005000 126000
640/  072431 107476 026302 000001 000012 014664 042621 020000
660/  000462 026000 136000 073432 062011 000522 146001 173432
700/  170012 073773 150000 020351 020040 020040 020052 047515
720/  042522 052040 040510 020116 030064 020060 042103 000001
740/  000023 015342 040510 047111 041440 042117 051505 005015
760/  025400 000001 000054 015360 004567 051060 000401 015400
```

BLOCK NUMBER 00106
```
000/ 013744 016300 000024 012601 001424 005716 100007 122627
020/ 000102 001364 112660 000020 005301 000766 121627 000103
040/ 001002 052710 000020 122627 000116 001366 052710 000010
060/ 000763 062706 000010 010601 062700 000006 062701 000036
100/ 012120 012120 012120 012110 016300 000024 062706 000116
120/ 004767 000124 001417 122711 000122 001002 052710 000500
140/ 122711 000117 001002 052710 000400 122711 000123 001002
160/ 052710 000004 004767 000060 001412 122711 000116 001002
200/ 052710 000010 122711 000103 001002 052710 000020 004767
220/ 000026 001405 105760 000020 001002 111160 000020 005063
240/ 000052 005063 000024 000207 105304 003404 012501 020127
260/ 177777 000207 005726 000763 012704 106372 012700 106374
300/ 104351 012700 106376 104351 012400 104351 016703 013426
320/ 005763 000146 001014 005263 000146 016304 000004 020463
340/ 000002 103005 112402 001773 004777 000034 000770 016300
360/ 000156 001401 000110 005200 104350 106374 000000 052123
400/ 050117 026440 020055 000600 123772 012446 063416 000134
420/ 012446 063416 113646 000134 013446 000770 013446 000771
440/ 012446 006316 062416 000134 012446 006316 062416 013646
460/ 000134 013446 000766 013446 000770 012446 006316 006316
500/ 062416 000134 012446 012600 006300 006300 062400 016046
520/ 000002 011046 000134 013446 000761 013400 000765 010546
540/ 016505 000002 011501 003003 001444 104715 000442 012746
560/ 000003 006201 062701 020100 005046 010146 005046 011546
600/ 005046 010146 012604 004437 106712 113326 106616 162716
620/ 000200 005366 000004 001410 016546 000002 011546 016646
640/ 000006 016646 000006 000756 012600 012601 005726 012605
660/ 000207 005000 005001 000773 013401 000401 012401 016146
700/ 000002 011146 000402 005046 012446 075036 000134 013400
720/ 011000 000404 013400 000402 012446 012600 070026 010146
740/ 103401 000134 005016 104701 000134 000240 013706 000042
760/ 016703 012762 016346 000150 016337 000152 000050 000403
```

BLOCK NUMBER 00107
```
000/ 013706 000042 011446 012737 107674 000034 005037 000036
020/ 012700 110406 104375 012700 107670 104375 013704 000054
040/ 013705 000050 010546 005725 013737 000042 000046 005046
060/ 012746 010000 010600 162706 000020 010666 000022 104375
100/ 023727 000000 000177 001413 032764 001000 000300 001007
120/ 005727 000000 001404 005716 001167 016404 000266 005744
140/ 010400 104354 013704 000050 020405 101552 162704 000172
160/ 010467 012562 010403 162704 000210 042704 000001 010446
200/ 012702 000007 001535 160204 010446 042704 000001 162704
220/ 000034 005302 001374 010446 162704 000070 010446 020405
240/ 101517 010302 062702 000172 005402 020204 101375 012663
260/ 000010 012663 000006 012663 000004 012663 000002 016663
300/ 000002 000166 016663 000004 000170 162704 000100 010463
320/ 000154 010463 000012 010401 012700 116776 012702 000040
340/ 012021 005302 001375 010563 000014 020405 101451 013700
360/ 000054 023727 000000 000177 001415 032760 001000 000300
400/ 001011 021627 000000 103406 013702 000042 062702 010000
420/ 020402 101426 062706 000024 012763 100000 000020 010363
440/ 000120 062763 000042 000120 012663 000152 012604 010463
460/ 000150 012737 106754 000040 052737 020000 000044 000134
500/ 012700 107547 104351 104350 012700 107520 104351 000607
520/ 042477 051122 032440 020071 051525 020122 047516 020124
540/ 047514 045503 042105 037400 051105 020122 031066 043040
560/ 051117 051124 047101 051440 040524 052122 043040 044501
600/ 000114 010046 032766 000001 000004 001402 104714 000407
620/ 032766 000010 000004 001402 104713 000401 104712 012700
640/ 107670 104375 012600 012666 000002 012666 000002 005066
660/ 000004 005066 000006 000002 014000 107602 010146 016601
700/ 000002 010046 010246 010346 014101 162701 104700 016703
720/ 012024 016302 000154 060102 105712 100433 001402 105212
740/ 104355 010246 012702 117076 112200 001405 120100 001403
760/ 105722 001376 000771 012703 110554 004767 000104 010200
```

```
BLOCK NUMBER 00110
000/ 104351 012703 110520 004767 000070 004767 000076 105736
020/ 100405 012603 012602 012600 012601 000002 016703 011706
040/ 016302 000016 001414 016263 000006 000016 016213 000004
060/ 012703 110513 004767 000012 004767 000020 000757 000167
100/ 176212 112300 001451 104341 103776 000773 012703 110530
120/ 004767 177756 016703 011616 016303 000016 001005 012746
140/ 035214 012700 130411 000402 012346 011300 004767 000130
160/ 012600 004767 000122 012703 110543 004767 177704 017700
200/ 011544 001005 112700 000077 104341 103776 000402 004767
220/ 000010 012700 110525 104351 000207 010046 005000 005200
240/ 162716 000012 002374 062716 000072 005300 001402 004767
260/ 177750 112600 104341 103776 000207 010003 005000 020303
300/ 101353 160203 005200 000773 012702 000050 004767 177752
320/ 010346 004767 177744 010346 012703 000003 116000 110443
340/ 104341 103776 005303 001730 012600 000770 104777 103776
360/ 022706 000500 103001 104775 013706 000042 012700 110412
400/ 104351 000167 175706 001400 110356 042477 051122 033040
420/ 020060 052123 041501 020113 053117 051105 046106 053517
440/ 042105 020000 041101 042103 043105 044107 045111 046113
460/ 047115 050117 051121 052123 053125 054127 055131 027044
500/ 030040 031061 032063 033065 034067 043071 047522 000115
520/ 047111 020040 006400 000012 051040 052517 044524 042516
540/ 021040 021000 020040 044514 042516 000040 005015 042477
560/ 051122 000040 010600 010446 010546 022020 012046 005720
600/ 011003 005010 004767 000150 004767 000244 001775 022702
620/ 000013 001405 022702 000015 001005 052716 040000 004767
640/ 000216 001405 162702 000020 020227 000011 101022 020027
660/ 006313 101403 005266 000016 000410 004767 000474 004767
700/ 000456 060205 005504 005501 005500 005716 100350 005216
720/ 000746 020227 177776 001421 162702 000024 006202 001425
740/ 005202 006002 062702 000006 001415 012703 111314 010346
760/ 005000 005001 005004 005005 000207 062716 100000 103765

BLOCK NUMBER 00111
000/ 105016 000715 005303 005266 000014 010046 010146 016600
020/ 000020 012702 100011 004767 173754 012602 012601 012600
040/ 103744 000415 112302 042702 177600 162702 000040 000207
060/ 005366 000016 100367 005726 016602 000010 005402 010003
100/ 050103 050403 050503 001502 111603 012746 000276 160302
120/ 066602 000020 002022 020227 177706 103025 005726 000705
140/ 005202 003040 004767 000320 000417 004767 000166 005216
160/ 020027 014630 101372 004767 000200 020227 000046 101356
200/ 005302 100365 005002 005003 032700 040000 001351 022703
220/ 050000 101002 062703 130000 006105 004767 000124 006303
240/ 005316 000762 004767 000074 032700 177000 001373 000316
260/ 001325 062600 103632 006116 006116 004767 000050 005505
300/ 005504 005501 005500 000100 103621 102620 005003 010602 062702
320/ 000020 010542 010442 005726 012605 012604 010142 010042
340/ 005403 000207 000241 006000 006001 006004 006005 000207
360/ 006305 006104 006101 006100 000207 010046 010146 010444
400/ 010546 004767 177752 004767 177746 062605 005504 005501
420/ 005500 062604 005501 005500 062601 005500 062600 000207
440/ 010046 010146 010446 010546 005001 012700 004000 005302
460/ 002754 004767 000002 000773 010103 010001 005000 071027
500/ 000012 010046 010100 010301 071027 000024 010046 010100
520/ 010401 071027 000050 010046 010104 071427 000120 010501
540/ 005000 071027 000012 010405 012604 010103 012601 006305
560/ 073427 000002 006101 060005 012600 072327 000014 000207
600/ 012702 042437 000407 005002 000405 012702 042431 000402
620/ 012702 042031 010603 005723 012300 012301 010446 010546
640/ 012304 012305 012643 012643 012643 010216 005046 006100
660/ 005616 005046 106202 103003 162766 000004 000020 005700
700/ 001004 006002 110266 000004 000466 000261 106000 010046
720/ 105016 041600 000316 004767 000424 012602 162702 000200
740/ 003007 004767 177424 004767 000404 005316 005202 003771
760/ 004767 177504 005216 004767 000364 005702 003371 001404
```

```
BLOCK NUMBER 00112
000/  004767 177340 005202 001374 016602 000016 106066 000004
020/  103401 061602 106066 000004 103002 021602 101402 066602
040/  000014 005702 100410 004767 177366 020027 010000 103403
060/  004767 177404 005216 016602 000014 106266 000004 103013
100/  021666 000016 101010 161666 000016 005002 005066 000014
120/  012766 000336 000004 160216 106266 000004 103402 006302
140/  061602 010203 003002 012703 000001 166603 000002 010246
160/  016602 000024 066603 000020 166603 000022 100143 004767
200/  000140 005766 000004 100002 112722 000055 005716 003471
220/  004767 177146 004767 177130 010003 042703 007777 040300
240/  000303 006203 006203 006203 006203 062703 000060 110322
260/  005316 003356 001450 005366 000020 100352 005726 012605
300/  005726 012603 106203 103004 106203 103050 004767 000022
320/  012600 012604 012605 062706 000010 006103 000110 112722
340/  000040 105203 100774 000207 004767 177004 005302 022700
360/  004000 101372 022700 010000 101366 004767 176746 005202
400/  000771 112722 000060 112722 000056 005716 001724 112722
420/  000060 005216 005366 000020 001370 000720 000303 110322
440/  012703 026453 005705 100002 005405 000303 110322 112712
460/  000057 105212 162705 000012 100374 062705 000072 110562
500/  000001 000706 005103 062706 000006 005726 001403 062766
520/  000004 000012 112722 000052 005366 000012 001373 000670
540/  012666 000002 012666 000002 005002 005202 012601 006116
560/  006101 006146 110103 105001 000301 162701 000201 002425
600/  001410 022701 000017 002417 000303 105003 156603 000003
620/  073201 005402 102406 003007 006026 103401 005402 010216
640/  000134 006026 103774 005746 104701 005002 000765 111600
660/  010016 000134 011646 011646 005066 000000 005066 000004
700/  005046 016601 000002 003002 001424 005401 006146 012702
720/  000220 105066 000004 006101 103402 005302 000774 110166
740/  000005 105001 150201 000301 006026 006001 106066 000003
760/  010116 000134 011600 005016 012446 000416 016600 000004

BLOCK NUMBER 00113
000/  016666 000002 000004 012616 000407 013401 000401 012401
020/  012600 016146 000002 011146 016046 000002 011046 075006
040/  012620 012610 000134 005002 012401 000402 012601 012601
060/  012600 016046 000002 011046 010246 010146 075016 012620
100/  012610 000134 013401 000401 012401 011600 016016 000002
120/  011046 016146 000002 011146 075016 012620 012610 000134
140/  013401 000401 012401 016146 000002 011146 000402 005046
160/  012446 075026 000134 005046 012446 000406 013401 000401
200/  012401 016146 000002 011146 012400 016046 000002 011046
220/  075006 012620 012610 000134 005003 012402 000402 012602
240/  012603 012400 016046 000002 011046 010346 010246 075016
260/  012620 012610 000134 013401 000401 012401 012400 016046
300/  000002 011046 016146 000002 011146 075016 012620 012610
320/  000134 005046 012446 075006 000134 013401 000401 012401
340/  016146 000002 011146 075006 000134 005046 012446 075016
360/  000134 013401 000401 012401 016146 000002 011146 075016
400/  000134 013400 011046 000403 013446 000401 012446 016601
420/  000002 006700 071026 010016 103002 104702 005016 000134
440/  016703 006302 010600 062700 000006 010063 000144 005763
460/  000024 001401 104732 012600 012663 000022 013602 010046
500/  004767 007160 010063 000024 032710 004000 004736 032710
520/  004000 001002 004767 007252 016363 000002 000032 016363
540/  000014 000130 000207 010004 032710 040000 001406 032710
560/  000002 001443 042710 000002 000436 005714 100036 032714
600/  001000 001423 016402 000016 010201 066402 000002 032710
620/  020000 001402 105022 000402 112722 000012 162701 000777
640/  001412 105022 005201 100775 000406 012702 000776 066402
660/  000002 052712 100000 004767 000632 000207 016703 006046
700/  005763 000024 001401 104732 004767 006750 010063 000024
720/  032710 004000 000207 122715 000003 001402 104720 000441
740/  024646 010600 112760 000021 000001 105010 010660 000002
760/  104375 022626 013700 000054 016000 000262 012703 177740
```

```
BLOCK NUMBER 00114
000/  010002 040302 062702 000110 006200 006200 110001 006201
020/  006201 006201 040301 000300 040300 022500 010035 010135
040/  010235 000207 012600 012601 012602 012603 000134 012600
060/  012601 000134 010446 016304 000024 016301 000032 010163
100/  000034 032764 000777 000016 001032 032714 000200 001423
120/  005263 000124 001406 112700 000012 104341 103776 005063
140/  000124 104340 103776 122700 000015 001020 104340 103776
160/  012700 000015 000413 004767 000532 005064 000016 016402
200/  000016 066402 000002 111200 005264 000016 042700 177600
220/  001730 022700 000012 001725 022700 000015 001404 110021
240/  020103 103717 104726 112711 000040 010163 000030 012604
260/  122741 000032 001002 000167 000602 000207 010546 010446
300/  016304 000024 016301 000032 105714 100002 010663 000124
320/  012700 000012 032714 000040 001426 112105 122705 000061
340/  001002 005720 000420 122705 000053 001417 122705 000044
360/  001005 005363 000034 005063 000124 000405 122705 000060
400/  001002 004767 000022 004767 000016 112100 020163 000034
420/  101772 012604 012605 000207 105714 100003 104341 103776
440/  000207 016402 000016 066402 000002 110012 005264 000016
460/  032764 000777 000016 001364 005064 000016 000167 000024
500/  044520 044514 114274 010546 012746 000001 010605 004714
520/  022626 000207 010046 016464 000026 000030 005264 000030
540/  026464 000026 000032 103403 016464 000026 000032 032714
560/  000100 001401 104743 004767 000234 012746 004636 012746
600/  104220 156416 000021 012746 114636 012746 000001 012746
620/  000400 016446 000002 016400 000026 000166 000010 103503
640/  122764 000001 000020 001003 004767 000152 000416 032714
660/  000001 001406 042714 000001 162764 001000 000002 000405
700/  052714 000001 062764 001000 000002 005264 000026 005002
720/  012600 000207 010046 005764 000030 001404 026464 000026
740/  000030 101052 004767 000056 012746 004636 012746 104200
760/  156416 000021 012746 115012 005046 012746 000400 016446

BLOCK NUMBER 00115
000/  000002 016400 000026 000166 000010 103415 005264 000026
020/  005002 012600 000207 012746 004636 012746 104240 156416
040/  000021 004716 103367 105737 000052 001406 005063 000160
060/  016304 000162 001011 104727 052714 010000 005063 000162
100/  016304 000160 001001 104730 000167 166600 005001 157301
120/  000022 005263 000022 000207 004767 000014 111000 000207
140/  112700 020040 110073 000034 016300 000034 020063 000030
160/  103002 005263 000034 000207 026363 000034 000106 103003
200/  016363 000106 000034 005063 000106 005763 000126 001006
220/  112700 000015 004767 177714 000173 000140 004773 000140
240/  005063 000126 005063 000124 000207 066301 000032 005301
260/  026363 000034 000106 101403 016363 000034 000106 010102
300/  016363 000106 000034 166301 000106 003031 010263 000034
320/  000571 016302 000040 010122 016322 000022 010263 000040
340/  000561 016302 000040 014200 005342 100770 010063 000022
360/  000551 110101 010163 000036 000545 004767 177532 005301
400/  100541 005773 000024 100371 004767 177524 000770 005773
420/  000022 100003 004767 177540 004773 000140 000522
440/  005763 000104 001427 000516 010102 000410 004767 177450
460/  110073 000022 005263 000022 005302 100504 005773 000024
500/  100365 004767 177406 010100 004767 177430 000765 016363
520/  000102 000022 005773 000024 100002 004767 177432 005763
540/  000104 001642 005763 000134 001036 016300 000162 001160
560/  104756 010663 000126 000446 005763 000104 001753 005773
600/  000024 100406 016302 000030 166302 000034 010273 000104
620/  004736 016703 004120 000426 005063 000126 005063 000036
640/  004734 016703 004100 005063 000106 005773 000024 100402
660/  004773 000140 016363 000120 000040 016363 000022 000102
700/  005063 000134 005002 004767 177202 110100 100402 005001
720/  000404 004767 177166 042700 177600 000170 116672 005202
740/  005202 005202 005202 005202 005202 005202 006302 110263
760/  000110 110063 000111 005263 000134 010163 000112 004767
```

```
BLOCK NUMBER 00116
000/ 177112 010163 000114 022702 000006 002004 004767 177074
020/ 010163 000116 005763 000104 001635 016300 000114 126327
040/ 000111 000050 002435 005702 001003 116300 000122 000430
060/ 022702 000006 002403 012700 000007 000422 122763 000010
100/ 000122 003011 012700 000031 012763 000020 000116 000410
120/ 010004 000167 165566 012700 000017 012763 000007 000116
140/ 016346 000034 016301 000030 161601 020001 003401 010100
160/ 005773 000024 100003 060063 000034 000442 005701 001435
200/ 005702 001771 010001 122773 000054 000034 001422 122773
220/ 000011 000034 001416 005263 000034 005301 001364 000420
240/ 004736 016703 003500 005363 000112 100614 116302 000110
260/ 000661 005263 000034 160100 001003 012716 115142 005200
300/ 010046 004767 000454 002004 016346 000116 016346 000036
320/ 016301 000122 005702 001415 120127 000003 002407 020227
340/ 000007 003007 016300 000162 001263 104755 020227 000007
360/ 003371 005773 000024 100034 016303 000104 005702 001473
400/ 122701 000001 001422 122701 000004 001002 005046 005046
420/ 042701 177400 160106 010600 006201 012320 005301 001375
440/ 004772 105376 103275 104706 000673 111301 010146 000770
460/ 004772 105416 016703 003256 103004 016300 000162 001210
500/ 104705 016300 000104 116301 000122 022701 000001 001421
520/ 022701 000004 001011 010602 022222 006112 012622 012612
540/ 005512 005516 102752 103751 006201 012620 005301 001375
560/ 000627 112610 000625 012602 012600 105001 000301 020201
600/ 003407 112720 000040 005302 000772 060203 160103 010102
620/ 112320 005302 003375 000604 005726 116301 000123 012602
640/ 016300 000104 012603 020201 002360 060100 160201 112740
660/ 000040 005301 001374 160200 000753 115664 115322 115342
700/ 115516 115562 115440 115752 115754 115746 115750
720/ 115736 115742 115744 115740 115450 115362 115570 115252
740/ 115402 115752 115754 115746 115750 115736 115742 115744
760/ 115740 001002 005266 000002 022702 000006 000207 077577

BLOCK NUMBER 00117
000/ 077577 076000 077777 077577 177574 076177 077577 077577
020/ 077577 077577 077577 077577 077577 077577 077577 077577
040/ 077577 077577 077577 077577 077577 077577 077577 077577
060/ 077577 077577 077577 077577 077577 077577 077577 030413
100/ 020061 046106 040517 044524 043516 052440 042116 051105
120/ 046106 053517 003000 020066 052517 050124 052125 041440
140/ 047117 042526 051522 047511 020116 051105 047522 000122
160/ 032004 041440 046517 052520 042524 020104 047507 047524
200/ 047440 052125 047440 020106 040522 043516 000105 030414
220/ 020062 046106 040517 044524 043516 055040 051105 020117
240/ 044504 044526 042504 001000 020062 047111 042524 042507
260/ 020122 042532 047522 042040 053111 042111 000105 031403
300/ 041440 046517 044520 042514 020122 042507 042516 040522
320/ 042524 020104 051105 047522 000122 030420 020066 051127
340/ 047117 020107 052516 041115 051105 047440 020106 051101
360/ 052507 042515 052116 000123 030415 020063 050523 052122
400/ 047440 020106 042516 040507 044524 042526 047040 046525
420/ 042502 000122 030401 044440 052116 043505 051105 047440
440/ 042526 043122 047514 000127 030412 020060 046106 040517
460/ 044524 043516 047440 042526 043122 047514 000127 032405
500/ 044440 050116 052125 041440 047117 042526 051522 047511
520/ 020116 051105 047522 000122 030416 020064 047125 042504
540/ 044506 042516 020104 054105 047520 042516 052116 040511
560/ 044524 047117 047440 042520 040522 044524 047117 007400
600/ 032461 046040 043517 047440 020106 042516 040507 044524
620/ 042526 047040 046525 042502 000122 033075 020061 046111
640/ 042514 040507 020114 042515 047515 054522 051040 043105
660/ 051105 047105 042503 012000 030462 044440 053116 046101
700/ 042111 046040 043517 041511 046101 052440 044516 020124
720/ 052516 041115 051105 012400 030462 047440 052125 047440
740/ 020106 053101 044501 040514 046102 020105 047514 044507
760/ 040503 020114 047125 052111 000123 031026 020062 047111
```

```
BLOCK NUMBER 00120
000/  052520  020124  042522  047503  042122  052040  047517  046040
020/  047117  000107  031027  020063  040510  042122  040527  042522
040/  044440  047457  042440  051122  051117  037400  031466  044440
060/  046114  043505  046101  044440  051516  051124  041525  044524
100/  047117  052040  040522  000120  031030  020064  052101  042524
120/  050115  020124  047524  051040  040505  027504  051127  052111
140/  020105  040520  052123  042440  042116  047440  020106  044506
160/  042514  014400  032462  040440  052124  046505  052120  052040
200/  020117  042522  042101  040440  052106  051105  053440  044522
220/  042524  015000  033062  051040  041505  051125  044523  042526
240/  044440  047457  047040  052117  040440  046114  053517  042105
260/  026400  032464  044440  041516  046517  040520  044524  046102
300/  020105  040526  044522  041101  042514  040440  042116  043040
320/  051117  040515  020124  054524  042520  000123  031033  020067
340/  052101  042524  050115  020124  047524  052440  042523  042040
360/  053105  041511  020105  047516  020124  047111  051440  051531
400/  042524  000115  031437  020061  047516  040440  040526  046111
420/  041101  042514  044440  047457  041440  040510  047116  046105
440/  016000  034062  047440  042520  020116  040506  046111  042105
460/  043040  051117  043040  046111  000105  031035  020071  047516
500/  051040  047517  020115  047506  020122  042504  044526  042503
520/  044040  047101  046104  051105  022000  033063  041040  042101
540/  043040  046111  020105  050123  041505  043111  041511  052101
560/  047511  020116  052123  044522  043516  026000  032064  031040
600/  042116  051040  041505  051117  020104  042522  052521  051505
620/  020124  047111  042440  041516  042117  027505  042504  047503
640/  042504  020000  031063  043040  052115  026504  047125  046506
660/  042124  051055  047101  047504  020115  027511  020117  047524
700/  051440  046501  020105  044506  042514  020400  031463  040440
720/  052124  046505  052120  052040  020117  042522  042101  050040
740/  051501  020124  047105  020104  043117  051040  041505  051117
760/  000104  031442  020064  047125  046506  042124  044440  047457

BLOCK NUMBER 00121
000/  052040  020117  052124  020131  051117  046040  052120  022400
020/  033463  051040  047101  047504  020115  041501  042503  051523
040/  051040  040505  027504  051127  052111  020105  042502  047506
060/  042522  042040  043105  047111  020105  044506  042514  023000
100/  034063  051040  047101  047504  020115  027511  020117  047516
120/  020124  046101  047514  042527  020104  047524  052040  054524
140/  047440  020122  050114  000124  031447  020071  042522  047503
160/  042122  046040  051101  042507  020122  044124  047101  051040
200/  041505  051117  020104  044523  042532  044440  020116  042504
220/  044506  042516  043040  046111  000105  032050  020060  042522
240/  052521  051505  020124  047506  020122  046102  041517  020113
260/  040514  043522  051105  052040  040510  020116  032466  031465
300/  000065  032051  020061  042504  044506  042516  043040  046111
320/  020105  052101  042524  050115  042524  020104  047117  047440
340/  042520  020116  047125  052111  021400  032463  040440  052124
360/  046505  052120  052040  020117  052517  050124  052125  052040
400/  020117  042522  042101  047440  046116  020131  044506  042514
420/  017000  030063  047040  020117  047522  046517  043040  051117
440/  041040  043125  042506  051522  025000  031064  046440  046505
460/  051117  020131  053117  051105  046106  053517  041440  046517
500/  044520  044514  043516  047440  045102  041505  020124  044524
520/  042515  043040  051117  040515  000124  032056  020066  047111
540/  044506  044516  042524  043040  051117  040515  020124  047514
560/  050117  025400  031464  051440  047131  040524  020130  051105
600/  047522  020122  047111  047440  045102  041505  020124  044524
620/  042515  043040  051117  040515  000124  032061  020071  047105
640/  043104  046111  020105  047117  051040  047101  047504  020115
660/  044506  042514  030000  034064  052440  044516  020124  046101
700/  042522  042101  020131  050117  047105  000000  020060  047516
720/  026516  047506  052122  040522  020116  051105  047522  020122
740/  040503  046114  005000  000000  011746  000401  005046  016504
760/  000002  012746  071030  012746  137661  024646  016446  000002
```

```
BLOCK NUMBER 00122
000/  011446 003534 006316 116666 000001 000014 112766 000200
020/  000001 006016 012746 002363 012746 040065 016646 000006
040/  016646 000006 012746 002363 012746 040065 012604 004437
060/  113356 122172 113326 106712 122220 122220 113162 122146
100/  122160 122160 122160 113162 113326 113162 113326 113162
120/  113326 113162 113326 122204 112700 122232 113162 113326
140/  122244 113162 122244 012600 012601 012702 122324 000402
160/  010146 010046 014246 014246 000134 012666 000012 012666
200/  000012 000134 005046 156616 000006 162716 000200 000134
220/  016646 000002 016646 000002 000134 012746 071030 012746
240/  040061 000134 105366 000005 002405 012746 055731 012746
260/  037736 000134 012600 012601 005726 000207 062706 000016
300/  104717 000773 037632 014525 037714 120036 040052 125332
320/  040400 000000 016504 000002 011400 003004 020027 141660
340/  101145 000403 020027 041660 101137 006300 020027 063000
360/  103527 005746 005046 012746 040200 016446 000002 011446
400/  016446 000002 011446 012604 004437 122502 113162 112550
420/  122514 112700 122502 106712 113356 122522 113162 113326
440/  106712 113326 113326 106712 122462 113326 122470 113162
460/  122616 062716 100200 000134 016646 000002 016646 000002
500/  000134 012746 125073 012746 040270 000134 011666 000012
520/  000134 006116 006100 162716 000400 101430 006000 006016
540/  011600 016601 000002 012746 036602 012746 141100 010146
560/  010046 012746 071571 012746 042426 012746 056133 012746
600/  041560 010146 010046 010146 010046 000134 022626 012600
620/  012601 012604 000304 105004 006204 060400 100405 000207
640/  005001 012700 040200 000405 104712 000401 104713 005000
660/  005001 000207 005702 003403 022702 000143 002001 104724
700/  004767 000056 011601 120221 001412 020100 000240 103773
720/  011601 105721 001404 020100 000240 103773 104725 110241
740/  016300 000006 162601 001404 062700 000034 005301 001374
760/  000207 011646 016300 000004 010066 000002 062700 000007

BLOCK NUMBER 00123
000/  000207 010546 010446 010146 010046 010246 005004 162702
020/  000012 100402 005204 000773 062702 000012 005704 001003
040/  060204 012702 177742 062704 000036 010446 006304 006304
060/  062604 006304 006304 006304 100363 010005 062705 000006
100/  011502 001021 010425 012701 123740 005711 001404 021116
120/  001402 022121 000772 014102 012725 024256 010425 012715
140/  014474 162705 000006 005710 100402 052710 000400 016300
160/  000020 010046 005001 005201 102452 006000 103774 110165
200/  000013 105365 000013 000261 006100 005301 001375 010063
220/  000020 004767 001150 016304 000120 010501 005737 000030
240/  001420 013705 000046 062705 010000 020527 123532 101411
260/  012705 123736 012700 000103 014546 005300 001375 004716
300/  000403 005005 004767 000220 006304 000164 123320 104737
320/  104733 104734 104735 000443 005726 116102 000012 001001
340/  005202 110261 000012 000302 010261 177776 016361 000014
360/  177774 006302 060263 000014 127327 000120 000024 001003
400/  052761 020000 177772 127327 000120 000003 001003 052761
420/  002000 177772 026363 000012 000014 101010 104736 012663
440/  000020 052761 000200 177772 105061 000012 012602 012600
460/  005060 000030 032710 000030 001404 032710 000020 001406
500/  000403 032710 002200 001402 052710 000040 052710 004000
520/  012601 012604 012605 000207 104346 005046 010100 010446
540/  104342 103004 010211 010446 104342 103463 016300 000010
560/  001406 010046 012700 000004 104353 005063 000010 012402
600/  122702 000004 001443 012402 005714 001013 160263 000012
620/  026363 000012 000014 101433 010100 016346 000012 104343
640/  103430 010604 005046 012700 000400 032761 000400 177772
660/  001004 016146 000022 012700 001000 010146 156100 000013
700/  010046 010600 104375 010406 103403 005216 005216 005216
720/  005216 104347 012604 005705 001001 000207 004636 100040
740/  000005 046600 000006 063320 000010 063200 000011 100040
760/  000007 075250 000001 015270 000000 010546 010446 010246
```

BLOCK NUMBER 00124
```
000/ 016703 175742 004767 176654 010063 000024 032710 004000
020/ 001547 105710 100560 004767 167514 032714 001000 001440
040/ 016464 000030 000026 001434 016402 000002 012705 000400
060/ 005022 005305 001375 032714 000400 001007 026464 000026
100/ 000032 101016 004767 170414 000771 012763 124134 000160
120/ 010446 010663 000144 004767 170372 000775 124136 012604
140/ 004767 000232 016405 000004 006305 016402 000002 032714
160/ 000001 001402 162702 001000 010246 010200 060500 012022
200/ 020063 000014 103774 160563 000014 012700 003000 032714
220/ 000004 001402 012700 001400 116401 000021 150100 104374
240/ 005000 000261 006100 005301 100375 040063 000020 012700
260/ 000016 005024 005300 001375 005063 000162 005063 000160
300/ 016304 000004 020463 000002 103012 112402 001773 004767
320/ 176342 021660 000002 103366 160560 000002 000763 005726
340/ 016300 000004 012602 122002 001376 105040 005063 000024
360/ 012604 012605 000207 010004 012746 177777 000730 104240
400/ 104241 104242 104243 104244 104245 104246 104247 104250
420/ 104251 104252 104253 104254 104255 104256 104257 000207
440/ 040440 046114 053517 042105 052040 020117 042502 051040
460/ 041505 044505 042526 020104 051106 046517 046040 044523
500/ 035040 005015 042011 052101 020101 051515 055111 027505
520/ 033061 034063 027464 005015 006503 041412 046040 043517
540/ 041511 046101 052440 044516 020124 047516 020123 047506
560/ 020122 047503 051516 046117 020105 047111 052520 026124
600/ 047440 052125 052520 020124 047101 020104 050114 035040
620/ 005015 042011 052101 020101 044514 027516 027465 005015
640/ 042011 052101 020104 047514 052125 033457 006457 004412
660/ 040504 040524 046040 050114 033057 006457 041412 005015
700/ 006503 041412 005015 041503 041503 006503 041412 041503
720/ 041503 025052 006452 041412 041503 041503 005015 020103
740/ 052515 052123 041040 020105 047504 042516 040440 020124
760/ 042502 044507 047116 047111 020107 040505 044103 051440
```

Appendix 2

AN AUTOMATED METHOD AND APPARATUS FOR
CLASSIFICATION OF CELLS WITH APPLICATION TO
THE DIAGNOSIS OF ANEMIA

BLOCK NUMBER 00000
```
000/ 000002 000000 000006 000000 000012 000000 000016 000000
020/ 000022 000000 000026 000000 000032 000000 000036 000000
040/ 000042 000000 000046 000000 000052 000000 000056 000000
060/ 000062 000000 000066 000000 000072 000000 000076 000000
100/ 000102 000000 000106 000000 000112 000000 000116 000000
120/ 000122 000000 000126 000000 000132 000000 000136 000000
140/ 000142 000000 000146 000000 000152 000000 000156 000000
160/ 000162 000000 000166 000000 000172 000000 000176 000000
200/ 000202 000000 000206 000000 000212 000000 000216 000000
220/ 000222 000000 000226 000000 000232 000000 000236 000000
240/ 000242 000000 000246 000000 000252 000000 000256 000000
260/ 000262 000000 000266 000000 000272 000000 000276 000000
300/ 000302 000000 000306 000000 000312 000000 000316 000000
320/ 000322 000000 000326 000000 000332 000000 000336 000000
340/ 000342 000000 000346 000000 000352 000000 000356 000000
360/ 176377 000000 000000 100007 000374 000000 000000 000000
400/ 000000 000000 000000 000000 000000 000000 000000 000000
420/ 000000 000000 000000 000000 000000 000000 000000 000000
440/ 000000 000000 000000 000000 000000 000000 000000 000000
460/ 000000 000000 000000 000000 000000 000000 000000 000000
500/ 000000 000000 000000 000000 000000 000000 000000 000000
520/ 000000 000000 000000 000000 000000 000000 000000 000000
540/ 000000 000000 000000 000000 000000 000000 000000 000000
560/ 000000 000000 000000 000000 000000 000000 000000 000000
600/ 000000 000000 000000 000000 000000 000000 000000 000000
620/ 000000 000000 000000 000000 000000 000000 000000 000000
640/ 000000 000000 000000 000000 000000 000000 000000 000000
660/ 000000 000000 000000 000000 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000
```

```
                                                                BLOCK
000/  000002 000000 000006 000000 000012 000000 000016 000000 NUMBER
020/  000022 000000 000026 000000 000032 000000 000036 000000  00
040/  000042 000000 000046 000000 000052 000000 000056 000000
060/  000062 000000 000066 000000 000072 000000 000076 000000
100/  000102 000000 000106 000000 000112 000000 000116 000000
120/  000122 000000 000126 000000 000132 000000 000136 000000
140/  000142 000000 000146 000000 000152 000000 000156 000000
160/  000162 000000 000166 000000 000172 000000 000176 000000
200/  000202 000000 000206 000000 000212 000000 000216 000000
220/  000222 000000 000226 000000 000232 000000 000236 000000
240/  000242 000000 000246 000000 000252 000000 000256 000000
260/  000262 000000 000266 000000 000272 000000 000276 000000
300/  000302 000000 000306 000000 000312 000000 000316 000000
320/  000322 000000 000326 000000 000332 000000 000336 000000
340/  000342 000000 000346 000000 000352 000000 000356 000000
360/  176377 000000 000000 100007 000374 000000 000000 000000
400/  000000 000000 000000 000000 000000 000000 000000 000000
420/  000000 000000 000000 000000 000000 000000 000000 000000
440/  000000 000000 000000 000000 000000 000000 000000 000000
460/  000000 000000 000000 000000 000000 000000 000000 000000
500/  000000 000000 000000 000000 000000 000000 000000 000000
520/  000000 000000 000000 000000 000000 000000 000000 000000
540/  000000 000000 000000 000000 000000 000000 000000 000000
560/  000000 000000 000000 000000 000000 000000 000000 000000
600/  000000 000000 000000 000000 000000 000000 000000 000000
620/  000000 000000 000000 000000 000000 000000 000000 000000
640/  000000 000000 000000 000000 000000 000000 000000 000000
660/  000000 000000 000000 000000 000000 000000 000000 000000
700/  000000 000000 000000 000000 000000 000000 000000 000000
720/  000000 000000 000000 000000 000000 000000 000000 000000
740/  000000 000000 000000 000000 000000 000000 000000 000000
760/  000000 000000 000000 000000 000000 000000 000000 000000

BLOCK NUMBER 00001
000/  012706 001000 004567 104152 004567 065430 000401 005652
020/  004567 064670 000401 003366 022767 000001 002330 001416
040/  022767 000002 002320 001401 000757 012700 000011 012701
060/  003370 012702 003412 012122 077002 000436 004567 065344
100/  000401 006310 004567 064740 000401 003412 012700 000004
120/  012701 006260 012703 006270 012167 000006 004567 065304
140/  000401 000000 012702 000002 012367 000006 004567 064670
160/  000401 000000 077207 077020 016700 002230 016701 002226
200/  070100 010167 002232 016700 002212 006200 010067 002214
220/  016700 002202 006200 010067 002204 016700 002156 016701
240/  002154 070100 010167 004260 004567 102742 000404 003412
260/  005534 005535 005532 022767 000001 004236 001002 000167
300/  004250 022767 000002 004222 001002 000167 004272 004567
320/  065064 000402 004504 003442 005067 013276 005067 013274
340/  005067 013272 016701 012640 012700 015060 005020 077102
360/  016701 012624 012700 014700 005020 077102 016701 012610
400/  012700 014734 005020 077102 016701 012574 012700 014770
420/  005020 077102 016701 012560 012700 015024 005020 077102
440/  005067 011622 005067 011620 005067 011626 005067 003026
460/  005067 004042 005267 004036 026767 004032 002002 001054
500/  005067 004022 004567 064770 000405 015712 003414 003416
520/  003420 003422 012700 015712 066700 003774 020037 170002
540/  001361 004567 077534 000404 005530 015712 004510 004512
560/  004567 077602 000405 004510 004512 004502 005512 005524
600/  005367 003706 004567 064434 000403 005512 007317 004500
620/  004567 064620 000401 007253 005267 011432 004567 064404
640/  000403 013266 006713 004500 005002 004567 064622 000405
660/  015712 003424 003426 003430 003432 005202 010267 012724
700/  004567 064340 000403 014624 006734 004500 004567 064524
720/  000401 006676 012700 015712 066700 001504 020037 170002
740/  001344 016703 001532 005004 005267 002532 020367 002526
760/  001067 005067 002520 004567 077310 000404 003440 015712
```

```
BLOCK NUMBER 00002
000/  004510  004512  004567  077356  000405  004510  004512  004502
020/  005512  005524  016701  003462  005301  016700  001440  060300
040/  020100  003401  005204  006303  160300  020100  002001  005204
060/  010167  012540  004567  064154  000403  014624  007173  004500
100/  004567  064340  000401  007125  005704  001412  004567  064324
120/  000401  007204  000000  006203  005303  010367  002350  000644
140/  004567  101712  000404  003412  005536  005542  005532  022767
160/  000001  003346  001002  000167  003360  022767  000002  003332
200/  001002  000167  003402  012767  003502  002106  012767  004324
220/  002222  012767  000001  011056  000167  005350  004567  101616
240/  000404  003412  005537  005535  005532  022767  000001  003252
260/  001002  000167  003264  022767  000002  003236  001002  000167
300/  003306  026727  002014  003502  001003  005067  002130  000406
320/  016700  001776  162700  003502  010067  002112  004567  102562
340/  000402  004502  004446  005767  002074  001405  004567  102542
360/  000402  004446  003502  016700  001020  004567  102574  000402
400/  005550  005532  005767  003122  001023  142767  000200  003130
420/  126767  003124  003117  001417  126767  003114  003111  001431
440/  126767  003104  003100  001002  000167  000442  000167  003072
460/  077034  000167  003122  004567  101664  000404  015712  003424
500/  003426  005532  005767  003022  001402  000167  004612  000167
520/  000374  004567  063660  000402  004450  016700  000674
540/  010067  000304  010067  000304  162700  000002  010067  000074
560/  016700  000652  162700  000002  010067  000140  012702  004450
600/  012267  001642  016703  000624  016704  000622  012201  005301
620/  006301  006301  006301  062701  004324  012100  005300  010067
640/  000132  010067  000162  162100  005400  020027  000000  003415
660/  010067  011740  004567  063354  000403  014624  007001  004500
700/  004567  063540  000401  006753  000000  012100  005300  010067
720/  000064  010067  000076  162100  005400  020027  000000  003415
740/  010067  011660  004567  063274  000403  014624  007066  004500
760/  004567  063460  000401  007040  000000  022703  000000  002402

BLOCK NUMBER 00003
000/  010367  000024  022704  000000  002402  010467  000006  016701
020/  000402  070127  000000  062701  000000  062701  015712  012700
040/  055714  112120  077302  012703  000000  062701  000000  077407
060/  004567  101272  000404  055714  003434  003436  005532  005767
100/  002430  001402  000167  004220  005367  001332  001233  016700
120/  000270  004567  102044  000402  005550  005532  005767  002372
140/  001015  142767  000200  002400  126767  002374  002362  001417
160/  126767  002364  002353  001405  000167  002356  077026  000167
200/  002406  004567  063236  000401  006632  000167  176246  004567
220/  063222  000401  006654  000167  007234  004567  100620  000404
240/  003412  005543  005544  005532  022767  000001  002254  001002
260/  000167  002266  022767  000002  002240  000167  000167  002310
300/  020227  003502  001003  005067  001134  000406  016722  007762
320/  162702  003502  010267  001116  004567  101566  000402  004502
340/  004446  005767  001100  001405  004567  101546  000402  004446
360/  003502  000167  175662  017000  023420  000200  000060  000276
400/  000315  000200  000200  000276  000067  040265  002201  000534
420/  026000  124000  133605  157012  173777  161055  154377  001777
440/  173404  151035  154377  103777  173400  145012  173777  146055
460/  142377  001777  173407  137035  141377  145377  000001  000054
500/  000012  000207  005267  177670  026767  177676  177662  002003
520/  016767  177654  177664  000207  005367  177644  026767  177650
540/  177636  003403  016767  177630  000456  005000  172000  117205
560/  103777  054000  000001  000054  102770  004567  002442  000404
600/  005067  000072  013567  000070  013567  000066  013567  000064
620/  004567  000516  000402  103074  103076  004567  000504  000402
640/  000703  022000  017000  040206  041206  140206  036025  014206
660/  073572  125011  001001  040001  041206  176606  006035  000000
700/  073400  177000  022404  000001  000054  103104  004567  002326
720/  000405  013500  070035  010067  000124  010167  000122  004567
740/  000406  000402  103246  103250  163501  005600  163500  010067
760/  000100  000414  026000  065000  073606  037020  073400  167011
```

```
BLOCK NUMBER 00004
000/  001000 125001 126206 140206 123025 014206 141172 001025
020/  030000 175024 101777 140176 121025 010206 073572 115011
040/  000001 000034 103220 000504 000402 103246 103250 016775
060/  000014 000000 000167 002230 041710 000000 000747 026000
100/  127000 073606 066011 002404 073401 121027 033400 116012
120/  073400 120011 001000 054001 055207 140207 052025 010207
140/  073572 107027 033400 104012 115000 000001 000054 103324
160/  004567 000210 000402 103534 103536 075000 016767 000172
200/  000164 016767 000162 000154 004567 000346 000402 103534
220/  103536 016775 000144 000611 026000 175000 001206 173400
240/  055035 056000 173400 051035 052000 140000 002345 010000
260/  073572 044027 033400 041012 073400 043011 001000 054001
300/  055207 134207 000001 000054 103440 162700 000004 075030
320/  012767 000012 000056 005067 000050 004567 000054 000402
340/  103530 103532 162700 000004 075020 004567 000222 000402
360/  000615 014000 043000 056207 057207 176607 010035 001000
400/  073400 163000 132403 100500 046004 000001 000054 103540
420/  004567 001672 000402 005775 000000 001003 005775 000002
440/  001460 005001 017502 000000 017503 000002 005702 100006
460/  005102 005103 062703 000576 026000 103000 000607 000026
500/  000001 000002 000036 114025 000400 100040 004000 113404
520/  000566 102000 141012 100065 175000 000003 004341 141001
540/  000065 037777 000001 000054 103654 001404 073227 177777
560/  005204 000771 060400 042702 000200 072027 000007 074002
600/  005701 001402 052702 100000 010275 000000 010375 000002
620/  000716 005000 151000 073607 062000 137003 000001 000054
640/  103726 004567 001504 000402 005775 000000 001003 005775
660/  000002 001440 005001 017502 000000 017503 000002 005702
700/  100003 042702 100000 005201 000500 026000 176000 100207
720/  140020 077505 001200 141100 100125 013400 174564 140377
740/  114345 100000 140566 002413 041003 041412 141412 000545
760/  041000 136413 076420 000001 000020 104042 000000 010375

BLOCK NUMBER 00005
000/  000002 000167 001416 000656 026000 026000 073610 167011
020/  002002 040001 000037 073400 001035 004000 073400 010011
040/  001002 104001 000210 073400 027011 001002 105001 103210
060/  173610 031413 000001 000054 104122 000062 001010 142767
100/  000200 000056 126775 000052 000004 001403 000406 077026
120/  000411 005075 000006 000167 001310 012775 000001 000006
140/  000451 012000 074000 073610 137000 176402 001025 003000
160/  073400 132000 066402 000001 000010 104210 000001 000746
200/  026000 106000 073610 107011 002002 040001 000037 073400
220/  157011 001001 165001 163210 173610 041013 004000 173402
240/  100305 037000 176400 035255 001000 055400 000001 000054
260/  104262 001403 000416 077021 000421 016567 000004 000010
300/  004567 000614 000402 104350 000000 005075 000006 000167
320/  001150 012775 000001 000006 000574 012000 154000 073610
340/  057000 176402 001025 003000 073400 052000 146402 000001
360/  000010 104350 000001 000606 026000 166000 073610 027011
400/  002002 073401 142023 073400 001237 012400 073401 002237
420/  010000 036401 003012 140000 172025 173611 053035 171167
440/  144000 037213 000001 000054 104422 001430 004567 000546
460/  000402 105006 105010 005767 000346 001010 142767 000200
500/  000334 126720 000330 001001 000757 005300 005367 000312
520/  000452 026000 034000 165611 176402 004025 051106 042115
540/  043514 040520 052102 051516 073400 004567 060666 000401
560/  005564 000000 020040 020040 025040 045040 047125 020113
600/  051105 047522 006522 000012 004567 060630 000401 005622
620/  000000 020040 020040 025040 052040 046511 026505 052517
640/  020124 051105 047522 006522 000012 020040 020040 042504
660/  040506 046125 020124 047514 050117 052040 046511 020105
700/  020075 030061 030060 006460 020012 020040 042040 043105
720/  052501 052114 054040 054454 042040 046511 047105 044523
740/  047117 020123 043117 046040 053517 053440 047111 047504
760/  020127 020075 031061 026070 032040 006470 020012 020040
```

```
BLOCK NUMBER 00006
000/ 042040 043105 052501 052114 046040 053517 053440 047111
020/ 047504 020127 043117 051506 052105 020123 020075 034461
040/ 026060 031040 032460 005015 020040 020040 042504 040506
060/ 046125 020124 026130 020131 044504 042515 051516 047511
100/ 051516 047440 020106 044520 052103 051125 020105 020075
120/ 031061 026070 030440 034062 005015 020040 020040 042504
140/ 040506 046125 020124 044520 052103 051125 020105 044527
160/ 042116 053517 047440 043106 042523 051524 036440 030440
200/ 030071 020054 032465 005015 020040 020040 043111 040440
220/ 054516 041440 040510 043516 026105 052040 050131 020105
240/ 027131 042440 051514 026105 047040 020056 037055 000040
260/ 006340 006416 006475 006550 003414 003416 003420 003422
300/ 003424 003426 003430 003432 020040 020040 042440 052116
320/ 051105 046040 047517 020120 044524 042515 035040 000040
340/ 020040 020040 042440 052116 051105 046040 053517 053440
360/ 047111 047504 020127 044504 042515 051516 047511 051516
400/ 024040 044443 020130 044443 024531 035040 000040 020040
420/ 020040 042440 052116 051105 046040 053517 053440 047111
440/ 047504 020127 043117 051506 052105 020123 021450 047511
460/ 030506 021440 047511 031106 020051 020072 020000 020040
500/ 020040 047105 042524 020122 044520 052103 051125 020105
520/ 044504 042515 051516 047511 051516 024040 044443 020130
540/ 044443 024531 035040 000040 020040 020040 042440 052116
560/ 051105 050040 041511 052524 042522 053440 047111 047504
600/ 020127 043117 051506 052105 020123 021450 043117 020061
620/ 044443 043117 024462 035040 000040 020040 020040 043440
640/ 051040 041505 044505 042526 006504 000012 020040 020040
660/ 046040 051040 041505 044505 042526 006504 000012 020040
700/ 020040 050040 041511 052524 042522 010440 062716 000002
720/ 020346 044504 044507 044524 042532 020104 000000 001000
740/ 000000 052040 046511 051505 005015 020000 020040 020040
760/ 026530 044504 020115 043117 041440 046105 020114 051511

BLOCK NUMBER 00007
000/ 000040 023000 005400 006401 020012 020040 020040 047503
020/ 052116 047111 042525 041040 020131 050047 006447 000012
040/ 020040 020040 054440 042055 046511 047440 020106 042503
060/ 046114 044440 020123 046000 047000 000000 005015 020040
100/ 020040 041440 047117 044524 052516 020105 054502 023440
120/ 023520 005015 020000 020040 020040 044520 052103 051125
140/ 020105 040502 045503 051107 052517 042116 043440 042522
160/ 026531 042514 042526 020114 051511 000040 000212 000000
200/ 006616 000012 020040 020040 025040 040440 045104 051525
220/ 020124 044526 042504 027117 041440 047117 044524 052516
240/ 020105 054502 023440 023520 005015 020000 020040 020040
260/ 047514 020127 044527 042116 053517 041040 041501 043513
300/ 047522 047125 020104 042514 042526 020114 051511 000040
320/ 000000 000322 006400 000012 016700 176176 005001 006200
340/ 103402 005201 000774 006301 016167 007370 000006 004567
360/ 057062 000401 000000 000000 007376 007446 007522 020040
400/ 020040 020052 044520 020103 051124 047101 046523 051511
420/ 044523 047117 052040 046511 026505 052517 020124 051105
440/ 047522 006522 000012 020040 020040 020052 044520 020103
460/ 051124 047101 046523 051511 044523 047117 045040 047125
500/ 020113 042515 051523 043501 020105 051105 047522 006522
520/ 000012 020040 020040 020052 044520 020103 051124 047101
540/ 046523 051511 044523 047117 044440 051516 043125 044506
560/ 044503 047105 020124 050123 041501 020105 051105 047522
600/ 006522 000012 016767 003476 003472 016767 173634 003470
620/ 004567 056764 000405 015712 003440 013310 013304 005532
640/ 022767 000001 175664 001002 000167 172360 005267 003410
660/ 012700 013232 012701 000016 012720 177777 077103 012767
700/ 177777 003374 012767 177777 004674 012767 177777 004670
720/ 005067 003346 005067 003344 005067 003342 004567 056756
740/ 000413 015712 003424 003426 013304 013310 013312 013314
760/ 014134 013306 004500 005532 022767 000001 175534 001002
```

BLOCK NUMBER 00010
```
000/ 000167 005270 022767 000002 175520 001456 004567 071566
020/ 000420 013304 003424 003426 013314 014134 014136 014140
040/ 014142 014144 014154 014146 014150 014152 014156 013236
060/ 005532 022767 000001 175442 001002 000167 005262 022767
100/ 000000 004032 001421 022767 000000 004026 001415 016701
120/ 173302 005301 020167 004010 001407 016701 173270 005301
140/ 020167 004000 001401 000404 005367 003114 000167 177424
160/ 026767 003770 173300 002770 004567 073064 000405 014150
200/ 014146 014154 014160 013234 016701 003742 070127 000144
220/ 005000 071067 003732 010067 003006 005002 026767 002774
240/ 173202 002012 026767 002766 173174 002006 026767 002760
260/ 173166 002002 005202 000407 026767 003660 173172 002403
300/ 005267 002776 000721 004567 057276 000415 013304 003424
320/ 003426 015712 013314 014134 013310 013232 013242 013272
340/ 004500 014206 005532 022767 000001 175156 001002 000167
360/ 005054 016700 002644 070067 173104 160167 002644 005667
400/ 002670 160067 002664 022702 000001 001434 026767 002616
420/ 173024 002414 026767 002610 173016 002404 012704 000005
440/ 000167 001602 012704 000006 000167 001572 026767 002560
460/ 172766 002404 012704 000007 000167 001552 012704 000010
500/ 000167 001542 004567 070072 000415 015712 003424 003426
520/ 014136 014140 014212 014142 014144 014356 014522 014524
540/ 014526 014530 000433 005003 016700 003752 012701 014212
560/ 112102 042702 177400 060203 077005 016700 003732 012701
600/ 014356 112102 042702 177400 060203 077005 005002 016700
620/ 003704 066700 003702 071200 010267 002422 004567 070336
640/ 000402 014526 014212 004567 070112 000407 014526 014212
660/ 014626 014532 014556 014602 014606 004567 070300 000402
700/ 014530 014356 004567 070054 000407 014530 014356 014626
720/ 014544 014570 014604 014610 022767 000003 003644 001057
740/ 012700 014556 011001 066001 000010 006201 010102 166702
760/ 002326 006202 006202 160201 026001 000002 002023 026001
```

BLOCK NUMBER 00011
```
000/ 000006 002020 016002 000002 066002 000006 006202 166002
020/ 000004 005402 010267 002220 020267 172440 002402 000167
040/ 001036 000415 004567 067714 000407 014526 014212 004502
060/ 014532 014556 014602 014612 066767 003516 003510 022767
100/ 000003 003500 001060 012700 014570 011001 066001 000010
120/ 006201 010102 166702 002160 006202 006202 160201 026001
140/ 000002 002024 026001 000006 002021 016002 000002 066002
160/ 000006 006202 166002 000004 005402 010267 002052 020267
200/ 172272 002402 000167 000670 000167 000674 004567 067544
220/ 000407 014530 014356 004502 014544 014570 014604 014614
240/ 066767 003350 003342 022767 000001 003326 001006 012700
260/ 014556 011060 000004 011060 000002 022767 000001 003304
300/ 001006 012700 014570 011060 000004 011060 000002 012700
320/ 000002 016001 014556 066001 014570 006201 010167 003256
340/ 012700 000004 016702 003206 066002 014556 066702 003210
360/ 066002 014570 006202 006202 010267 003224 160102 010267
400/ 001650 016700 003212 166700 172064 010067 001640 010067
420/ 003200 004567 071460 000405 013232 014622 013242 013272
440/ 013260 026727 001604 000010 002406 026767 001602 172004
460/ 003402 000167 000106 026767 001540 171746 002004 012704
500/ 000004 000167 000540 004567 071260 000404 013232 013272
520/ 013242 013254 026767 001524 171730 002404 012704 000004
540/ 000167 000502 026767 001462 171704 002004 012704 000002
560/ 000167 000462 012704 000003 000167 000452 026767 001432
600/ 171670 002002 000167 000300 016700 001436 006200 066700
620/ 002774 010067 001462 004567 066652 000406 015712 014522
640/ 013310 014532 013304 005532 022767 000001 173654 001002
660/ 000167 003640 004567 055026 000413 015712 003424 003426
700/ 013304 013310 013312 013314 014134 013306 014206 005532
720/ 022767 000001 173604 001002 000167 003540 022767 000002
740/ 173570 001002 000167 003660 004567 067632 000420 013304
760/ 003424 003426 013314 014134 014162 014164 014166 014170
```

```
BLOCK NUMBER 00012
000/  013244 014172 014174 014176 014200 014204 005532 022767
020/  000001 173506 001002 000167 003326 005767 001206 001004
040/  012767 000310 001200 000410 004567 071204 000405 014174
060/  014172 013244 014202 013246 026767 001152 171356 002404
100/  012704 000011 000167 000136 016700 001156 016701 001122
120/  073027 177776 020167 171330 002024 026767 001074 171302
140/  002004 012704 000012 000167 000074 026767 001054 171276
160/  002004 012704 000013 000167 000054 012704 000014 000167
200/  000044 026767 001024 171232 002004 012704 000015 000167
220/  000024 026767 001004 171226 002404 012704 000016 000167
240/  000004 012704 000001 016767 002334 001006 016767 002330
260/  001002 010467 001012 020427 000001 001013 022767 177777
300/  000754 001407 005267 002326 066767 000742 002316 005567
320/  002310 005304 006304 005264 015060 066764 000674 015024
340/  005564 014770 066764 000672 014734 005564 014700 066764
360/  000710 014700 022767 177777 000662 001007 004567 070372
400/  000404 013232 013272 013242 013254 016700 171704 012701
420/  013232 012702 000024 012120 077202 010067 171664 016700
440/  172002 012701 014136 012702 000004 012120 077202 010067
460/  171762 000167 175116 004567 053752 000401 013146 005004
500/  012702 003502 022704 000034 001002 000167 170514 005764
520/  015060 001002 000167 000406 005704 001011 016700 002072
540/  016701 002070 071067 002066 010064 015240 000402 005064
560/  015240 016400 014770 016401 015024 071064 015060 010067
600/  002060 005067 002052 004567 070730 000402 014660 014662
620/  012700 014654 075020 004567 071076 000402 014660 014662
640/  016764 002016 015114 016467 014700 002014 016467 014734
660/  002010 004567 070654 000402 014670 014672 012700 014664
700/  075030 011060 000004 016060 000002 000006 005010 016460
720/  015060 000002 004567 070612 000402 014670 014672 075030
740/  004567 070764 000402 014674 014676 016764 001720 015150
760/  016700 001712 070027 000144 071064 015114 010064 015204

BLOCK NUMBER 00013
000/  010403 006203 005203 012700 014640 010320 016420 015060
020/  016420 015114 016420 015150 016420 015204 016420 015240
040/  012701 000006 012700 014640 012022 077102 012701 000005
060/  005704 001002 012701 000006 012700 014640 012067 001524
100/  004567 053140 000403 014624 013220 004500 004567 053324
120/  000401 013220 077115 004567 053312 000401 013227 062704
140/  000002 000167 177336 005015 020040 041440 040514 051523
160/  041440 046105 051514 020040 041515 020101 020040 041515
200/  020110 046440 044103 020104 020040 041515 006524 000012
220/  002424 002426 000543 006400 000012 000400 143004 000424
240/  040006 000407 055010 002011 072040 144410 000440 142044
260/  000424 012046 000405 013050 032005 000001 000034 000003
300/  007030 012314 013134 013136 013140 000620 013144 013154
320/  013146 013150 013152 000620 027000 002000 000400 146004
340/  000424 056006 000426 057010 000426 060012 000426 061014
360/  000426 062016 000426 066020 000426 063022 000426 064024
400/  000426 065026 013426 000001 000056 000003 007054 013156
420/  012236 004532 022767 000001 175442 001002 000167 005262
440/  022767 000000 004032 001421 022767 000000 004026 001415
460/  016701 173302 000530 011000 002000 000400 067004 000426
500/  117006 000424 055010 035411 000001 000056 000003 007122
520/  005301 020167 004010 001407 016701 173270 005301 020167
540/  004000 001401 000404 005367 003114 000167 177424 026767
560/  003770 173300 002770 000500 027000 001400 074000 073416
600/  000011 002400 064001 063026 066026 070026 116026 140424
620/  161035 053407 062160 000000 033412 155162 033407 003020
640/  091006 173412 003455 000001 000040 000004 003004 062332
660/  012072 005001 013150 006001 013146 007001 013154 010001
700/  013160 011001 012234 000510 027000 001400 117000 176016
720/  101005 005366 173404 173055 076005 003366 173404 170055
740/  073005 001366 101004 003412 173401 130055 075007 001766
760/  133405 177012 145005 000001 000040 000003 007304 000721
```

```
BLOCK NUMBER 00014
000/ 004567 000000 000415 012304 002424 002426 014712 012314
020/ 013134 012310 012232 000737 026000 002000 002000 044410
040/ 024571 000426 142014 000424 012016 000405 013020 000405
060/ 145022 000431 146024 000424 056026 000426 144030 000424
100/ 115032 053424 000001 000056 000003 007334 012242 012272
120/ 003500 013206 004532 022767 000001 175156 001002 000167
140/ 005054 016700 002644 070067 173104 160167 002644 005667
160/ 002670 000776 015000 002000 000400 121004 000424 135006
200/ 000424 040010 000407 177777 000016 055014 165011 000001
220/ 000056 000003 007402 160067 002664 022702 000001 001434
240/ 026767 002616 173024 002414 026767 002610 173016 002404
260/ 012704 000005 000167 001602 012704 000006 000635 027000
300/ 001400 024000 073417 075000 173403 070055 173005 002365
320/ 142005 003425 073400 065000 142003 004025 073400 061000
340/ 073403 000011 006400 145001 012031 005405 000001 000024
360/ 000004 021004 063136 035101 023001 014712 024001 002424
400/ 000466 016000 001400 047000 013017 057005 060026 105026
420/ 061026 062026 167026 051026 052027 053027 123427 000001
440/ 000056 000004 002001 002426 003001 013136 004001 013140
460/ 005001 013212 006001 013142 007001 013144 010001 013356
500/ 011001 013522 012001 013524 013001 013526 000545 027000
520/ 001400 061000 054017 015427 001401 140012 165035 140407
540/ 105025 041026 141224 000105 101777 002540 140176 155035
560/ 140407 167025 041026 141224 000105 145777 000001 000022
600/ 000004 002001 013530 010001 013212 021001 013356 000635
620/ 027000 001400 104000 000003 000012 001176 140012 142035
640/ 140007 141155 100007 133562 011020 073405 037165 141217
660/ 053001 105027 042621 020000 003400 053001 151027 000001
700/ 000036 000004 015004 074327 077141 017001 013526 020001
720/ 013212 022004 062716 004101 024001 013526 000412 020000
740/ 001400 127000 105017 113026 055027 067027 101027 103027
760/ 073427 000011 001000 054001 167027 073426 030011 000001

BLOCK NUMBER 00015
000/ 000054 000004 002001 013212 003001 013626 004001 013532
020/ 005001 013556 006001 013602 007001 013606 011004 074327
040/ 077141 013001 013530 014001 013356 000463 027000 001400
060/ 143000 000017 003400 054001 167027 113026 062027 074027
100/ 102027 104027 173427 001445 122000 027407 140002 067025
120/ 000427 000422 004154 100400 021414 000001 000054 000004
140/ 002004 062716 004101 004001 013530 005001 013356 006001
160/ 013636 007001 013544 010001 013570 011001 013604 012001
200/ 013610 020001 013556 000730 027000 001400 166000 041017
220/ 141020 153355 101004 101014 100414 000740 001054 011400
240/ 000404 003054 010000 001004 001034 001000 003154 101000
260/ 001014 002354 155000 000001 000056 000003 004567 051144
300/ 000401 015314 005367 175760 000167 164720 020040 020040
320/ 025040 046440 051117 020105 044124 047101 032040 030060
340/ 041440 040510 047111 041440 042117 051505 005015 040400
360/ 004567 051060 000401 015400 005367 175674 000167 164634
400/ 020040 020040 025040 041440 040510 047111 041440 042117
420/ 030105 040526 052514 020105 020076 006467 000012 004567
440/ 051002 000401 015456 005367 175616 000167 164556 020040
460/ 020040 025040 046440 051117 020105 044124 047101 034440
500/ 041040 052517 042116 051101 020131 047520 047111 051524
520/ 005015 000000 004567 050714 000401 015544 005367 175530
540/ 000167 164470 020040 020040 025040 050040 046101 047514
560/ 020122 047520 047111 020124 047516 020124 047105 047503
600/ 047125 042524 042522 020104 042502 047506 042522 053040
620/ 046101 042514 006531 000012 004567 050610 000401 015650
640/ 005367 175424 000167 164364 020040 020040 025040 050040
660/ 046101 047514 020122 051511 040440 051440 047111 046107
700/ 020105 047520 047111 006524 000012 017001 013614 000622
720/ 027000 001400 125000 153020 003006 140002 067025 030027
740/ 002022 030000 001022 173400 000445 142000 003006 140002
760/ 074025 030027 002022 030000 001022 140000 115025 000001
```

```
BLOCK NUMBER 00016
000/  000016 000004 005001 013556 017001 013570 000657 027000
020/  001400 150000 001020 000400 067034 000427 074154 100427
040/  073414 127020 140006 002025 141000 103035 001006 067154
060/  141027 104155 001006 074154 101027 003414 000001 000026
100/  000004 004001 013556 006001 013570 017001 013556 023001
120/  013570 000541 027000 001400 173000 101020 133414 112020
140/  041006 133740 124020 140003 105035 140006 032355 033764
160/  120020 033403 100020 073406 000011 002400 115001 111024
200/  067427 000001 000024 000004 021004 023356 143300 023001
220/  012232 024001 013622 000600 027000 001400 016000 121021
240/  135024 130024 153424 102055 004003 003000 173405 101055
260/  002003 001364 073407 043000 173400 060055 163003 002363
300/  142004 002025 007400 000001 000022 000004 002001 012242
320/  003001 012272 004001 012260 000614 027000 001400 041000
340/  073421 060000 073401 000011 002000 115001 135024 121024
360/  126024 173424 052055 154003 002363 142005 002025 073400
400/  041000 173401 031055 166403 000034 000004 000004 005004
420/  023356 143160 007001 012232 010001 012272 011001 012242
440/  012001 012254 000515 027000 001400 064000 142021 002363
460/  142004 001025 073400 031000 142001 001425 073400 025000
500/  173401 015055 134003 001363 073404 140000 140000 017035
520/  100003 160014 000001 000056 000003 010616 066700 002774
540/  010067 001462 004567 000000 000406 014712 013522 012310
560/  013532 012304 004532 022767 000001 173654 001002 000167
600/  003640 000510 023000 002000 002000 115016 020567 000424
620/  145022 000431 051024 000427 144026 000424 055030 000427
640/  142032 000424 055034 015411 000001 000036 000003 010664
660/  004567 000000 000413 014712 002424 002426 012304 012310
700/  012312 012314 013134 000622 026000 002000 002000 000406
720/  110424 000472 145012 000431 012014 000405 013016 000405
740/  142020 000424 144022 000424 145024 000424 146026 000424
760/  056030 055026 000001 000056 000003 010712 012306 013206

BLOCK NUMBER 00017
000/  004532 022767 000001 173604 001002 000167 003340 022767
020/  000002 173570 001002 000167 003660 004567 000000 000420
040/  012304 000771 016000 002000 000400 143004 000424 103006
060/  000426 055010 002011 072044 144410 000440 142050 061424
100/  000001 000034 000003 010760 002424 002426 012314 013134
120/  013162 013164 013166 013170 012244 013172 000745 027000
140/  002000 000400 012004 000405 013006 000405 146010 000424
160/  056012 000426 071014 000426 072016 000426 073020 000426
200/  074022 000426 122024 000424 075026 043426 000001 000056
220/  000003 011004 013174 013176 013200 013204 004532 022767
240/  000001 173506 001002 000167 003326 005767 001206 001004
260/  012767 000310 001200 000410 004567 000737 015000 002000
300/  000400 076004 000426 077006 000426 100010 000426 102012
320/  000426 055014 175411 000001 000056 000003 011052 000000
340/  000405 013174 013172 012244 013202 012246 026767 001152
360/  171356 002404 012704 000011 000167 000136 016700 001156
400/  016701 001122 000661 020000 002000 002000 155004 035144
420/  000424 076010 000426 075012 000426 122014 000424 101016
440/  000426 123020 155024 000001 000056 000003 011120 073027
460/  177776 020167 171330 002024 026767 001074 171302 002004
500/  012704 000012 000167 000074 026767 001054 171276 002004
520/  012704 000013 000707 027000 001400 073000 073422 026000
540/  142000 006025 073400 022000 173400 012055 115002 002362
560/  142004 006425 073400 012000 173400 002055 113002 002362
600/  142005 050025 000001 000056 000003 011234 000016 000167
620/  000004 012704 000001 016767 002334 001006 016767 002330
640/  001002 010467 001012 020427 000001 001013 022767 177777
660/  000754 000454 027000 001400 141000 003422 133403 153012
700/  173404 161155 147001 073404 144013 142004 142012 132014
720/  030012 172030 136155 012001 072030 174013 172027 135155
740/  353001 000001 000022 000004 015001 014060 020001 014024
760/  022001 013770 000405 027000 001400 164000 156022 072027
```

```
BLOCK NUMBER 00020
000/ 140013 172027 144155 140001 173427 177445 131377 003401
020/ 073402 000011 002000 115001 135024 121024 126024 140024
040/ 142035 124763 000001 000050 000004 002001 013734 004001
060/ 013700 007001 013700 015004 023356 143160 017001 012232
100/ 020001 012272 021001 012242 022001 012254 000463 027000
120/ 001400 007000 140423 115025 141024 012025 050000 101024
140/ 033576 132020 140363 001035 140764 057025 141026 002025
160/ 050000 101024 033576 171020 073763 166400 000001 000016
200/ 000004 003001 012232 015001 013136 000651 027000 001400
220/ 032000 047023 073772 000011 000400 063001 002024 141012
240/ 041025 142005 016045 001000 073402 046000 172361 030013
260/ 001030 073402 003000 142001 141013 000001 000030 000004
300/ 004004 026476 123521 006001 012146 011001 002502 020001
320/ 014060 000452 027000 001400 055000 004423 140002 035035
340/ 140404 034035 033404 033162 032004 120020 001030 032001
360/ 120012 000030 174035 000427 012035 032030 030162 033430
400/ 117020 000001 000032 000004 012001 014240 015001 014240
420/ 017001 013770 021001 014024 023001 014060 000525 027000
440/ 001400 100000 030023 033404 025012 073404 000011 001000
460/ 130001 131027 140027 126025 010027 073572 000011 001000
500/ 130001 131027 172027 007035 046004 144430 000001 000052
520/ 000004 006004 035204 023557 010001 013660 011001 013662
540/ 013001 013654 016004 023557 035204 020001 013660 021001
560/ 013662 024001 014114 000412 027000 001400 123000 033423
600/ 140035 006027 033404 156035 004027 073404 000011 001000
620/ 134001 135027 140027 132025 014027 030172 002022 030000
640/ 001034 003000 114000 000001 000040 000004 003001 013700
660/ 006001 013734 011004 035204 023557 013001 013670 014001
700/ 013672 016001 013664 000733 027000 001400 146000 004023
720/ 030012 030035 001030 073400 000011 001000 134001 135027
740/ 014027 073572 000011 001000 136001 137027 172027 150035
760/ 064003 140030 022435 000001 000052 000004 004001 014060

BLOCK NUMBER 00021
000/ 007004 035204 023557 011001 013670 012001 013672 015004
020/ 023557 035204 017001 013674 020001 013676 023001 014150
040/ 000521 027000 001400 171000 145023 013403 062160 032000
060/ 046162 032030 102020 001430 101421 101414 140012 120025
100/ 150027 010020 030035 010030 046035 010030 064035 154030
120/ 000001 000036 000004 006001 014114 010001 014204 015001
140/ 013640 020001 014060 022001 014114 024001 014150 000522
160/ 027000 001400 014000 010024 102035 010030 120035 140430
200/ 003025 140000 120025 011027 041024 140576 002425 142000
220/ 001013 140402 003025 140000 120025 033427 042424 000001
240/ 000026 000004 003001 014204 005001 014240 011001 013640
260/ 023001 013640 000727 027000 001400 037000 052024 073403
300/ 000011 001400 112001 110027 040024 073407 000011 000400
320/ 110001 046424 073576 000011 000400 113401 142024 001145
340/ 073400 045400 000001 000054 000004 004003 035204 004473
360/ 006001 013624 007001 012230 010001 003500 012004 026476
400/ 123521 014001 012220 017004 026476 123521 021001 012227
420/ 000563 027000 001400 062000 157024 006776 020012 020040
440/ 046103 051501 020123 042503 046114 020123 046440 040503
460/ 020040 046440 044103 020040 041515 042110 020040 172440
500/ 000001 000016 000003 012212 041515 006524 000012 000525
520/ 005000 002000 004000 113000 037424 000001 000014 000000
540/ 012226 006400 000012 000457 005000 002000 004000 145000
560/ 005424 000001 000012 000003 012312 000620 000603 005000
600/ 002000 004000 103000 046426 000001 000014 000003 013206
620/ 177777 000016 000510 005000 002000 004000 113000 036027
640/ 000001 000014 000003 013626 000003 000012 000466 005000
660/ 002000 004000 126000 023027 000001 000014 000003 013654
700/ 037165 141217 000451 005000 002000 004000 132000 017027
720/ 000001 000014 000003 013664 042621 020000 000457 005000
740/ 002000 004000 136000 012430 000001 000056 000003 014274
760/ 001567 000000 000401 014314 005367 175760 000167 164720
```

```
BLOCK NUMBER 00022
000/ 020040 020040 025040 046440 051117 020105 044124 047101
020/ 032040 030060 041440 000771 010000 002000 002000 037006
040/ 050455 000647 146012 107430 000001 000025 000003 014342
060/ 040510 047111 041440 042117 051505 005015 024000 000001
100/ 000012 000004 000010 014360 000741 027000 001400 170000
120/ 073430 000011 000400 000001 173431 136012 073773 116000
140/ 020351 020040 020040 020052 044103 044501 020116 047503
160/ 042504 053040 046101 113525 000001 000020 000004 003004
200/ 026476 123521 005001 014400 000532 027000 001400 013000
220/ 042431 037040 033440 005015 073400 000011 000400 027001
240/ 173431 107012 073773 067000 020351 020040 020040 020052
260/ 047515 042522 052040 112110 000001 000020 000004 007004
300/ 026476 123521 011001 014456 000434 017400 001400 036000
320/ 040431 020116 020071 047502 047125 040504 054522 050040
340/ 044517 052116 006523 000012 000410 005000 002000 004000
360/ 052000 076031 000001 000056 000003 014524 004567 000000
400/ 000401 014544 005367 175530 000167 164470 020040 020040
420/ 025040 050040 046101 047514 020122 047520 047111 020124
440/ 047516 000533 010000 002000 002000 037006 050455 000647
460/ 062012 173031 000001 000056 000003 014572 020124 047105
500/ 047503 047125 042524 042522 020104 042502 047506 042522
520/ 053040 046101 042514 006531 000012 004567 000000 000401
540/ 014650 000561 010000 002000 002000 037044 050455 000647
560/ 124050 073031 000001 000056 000003 014640 005367 175424
600/ 000167 164364 020040 020040 025040 050040 046101 047514
620/ 020122 051511 040440 051440 047111 046107 020105 047520
640/ 047111 000651 006000 001400 143000 052031 005015 123000
660/ 000001 000006 000006 000363 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000

BLOCK NUMBER 00023
000/ 000001 000054 001000 012706 001000 004567 104152 004567
020/ 065430 000401 005652 004567 064670 000401 003366 022767
040/ 000001 002330 001416 022767 000002 002320 000455 026000
060/ 023000 000402 167403 140001 004425 140400 174025 141006
100/ 005025 051007 001024 017176 073401 162011 000552 144001
120/ 073414 160011 000551 005001 114007 000001 000054 001114
140/ 012700 000004 012701 006260 012703 006270 012167 000006
160/ 004567 065304 000401 000000 012702 000002 012367 000006
200/ 004567 064670 000401 000660 026000 071000 000002 103400
220/ 010176 140176 114035 140404 113035 040004 073560 115020
240/ 140004 105035 100004 033414 106020 140004 101035 100004
260/ 033414 001020 000000 000054 001230 002204 016700 002156
300/ 016701 002154 070100 010167 004260 004567 102742 000404
320/ 003412 005534 005535 005532 022767 000001 004236 001002
340/ 000455 026000 137000 073402 124000 173410 001045 111000
360/ 001010 073402 135000 073410 032011 001152 042001 021011
400/ 033407 137012 033426 136012 033426 135012 023426 000001
420/ 000054 001344 016701 012640 012700 015060 005020 077102
440/ 016701 012624 012700 014700 005020 077102 016701 012610
460/ 012700 014734 005020 077102 016701 000525 026000 005000
500/ 076003 140025 174025 010031 041012 140576 070035 140025
520/ 012025 010032 041012 033576 111012 033423 110012 033423
540/ 113012 033423 013012 022006 000001 000054 001460 005067
560/ 004042 005267 004036 026767 004032 002002 001054 005067
600/ 004022 004567 064770 000405 015712 003414 003416 003420
620/ 003422 012700 000600 025000 053000 145003 140033 176155
640/ 017407 001040 170760 073402 056011 002177 054001 145013
660/ 044033 045011 073411 101011 002577 044001 045011 146011
700/ 000001 000052 001572 004502 005512 005524 005367 003706
720/ 004567 064434 000403 005512 007317 004500 004567 064620
740/ 000401 007253 005267 011432 004567 000545 020000 117000
760/ 002003 001551 133001 145426 040015 001011 073412 111011
```

BLOCK NUMBER 00024
```
000/ 002551 145001 012033 013007 014007 013407 000001 000054
020/ 001670 003432 005202 010267 012724 004567 064340 000403
040/ 014624 006734 004500 004567 064524 000401 006676 012700
060/ 015712 066700 001504 020037 000631 026000 157000 001003
100/ 162360 141402 055035 002003 133412 055012 173405 053040
120/ 033405 033402 050012 073405 144011 002176 020001 145007
140/ 044033 045011 171411 000001 000054 002004 004567 077356
160/ 000405 004510 004512 004502 005512 005524 016701 003462
200/ 005301 016700 001440 060300 020100 003401 005204 006303
220/ 160300 000717 026000 025000 040004 000440 102004 073412
240/ 060020 073425 066011 001550 112001 075431 040016 073411
260/ 160011 000550 052401 142016 005013 073403 152011 015150
300/ 000001 000054 002120 000401 007204 000000 006203 005303
320/ 010367 002350 000644 004567 101712 000404 003412 005536
340/ 005542 005532 022767 000001 003346 001002 000714 026000
360/ 073000 073404 170000 173406 001045 155000 001006 073402
400/ 001000 173407 041025 043007 173404 152025 111010 173404
420/ 000425 027000 073422 164000 113412 000001 000054 002234
440/ 004567 101616 000404 003412 005537 005535 005532 022767
460/ 000001 003252 001002 000167 003264 022767 000002 003236
500/ 001002 000167 003306 000512 026000 141000 153404 006055
520/ 041004 001407 033402 054012 003004 140001 177035 140003
540/ 041345 033407 045020 073404 071011 001205 041001 023011
560/ 173411 130013 000001 000054 002350 002074 001405 004567
600/ 102542 000402 004446 003502 016700 001020 004567 102574
620/ 000402 005550 005532 005767 003122 001023 142767 000200
640/ 000707 026000 007000 054005 173406 052255 047406 007406
660/ 173403 046255 044406 014406 173403 042255 040006 001006
700/ 073402 021000 073401 035000 016006 073576 001000 000001
720/ 000054 002464 003122 004567 101664 000404 015712 003424
740/ 003426 005532 005767 003022 001402 000167 004612 000167
760/ 000374 004567 063660 000402 004476 000607 026000 055000
```

BLOCK NUMBER 00025
```
000/ 024005 140011 136035 033401 142020 033400 142020 140000
020/ 001345 033400 036020 140000 125035 140001 001345 033400
040/ 060020 141000 024025 105411 000001 000054 002600 012267
060/ 001642 016703 000624 016704 000622 012201 005301 006301
100/ 006301 006301 062701 004324 012100 005300 010067 000132
120/ 010067 000162 000664 026000 123000 040005 000344 013413
140/ 000040 006400 033407 160020 073423 166011 001546 112001
160/ 000431 040016 073411 060011 000547 165401 000015 040000
200/ 002024 000001 000054 002714 005300 010067 000064 010067
220/ 000076 162100 005400 020027 000000 003415 010067 011660
240/ 004567 063274 000403 014624 007066 004500 004567 000524
260/ 026000 171000 030005 000547 020001 000016 141400 000045
300/ 001000 173405 012020 142000 000045 001000 033405 003021
320/ 140400 001035 053401 000160 140400 177545 000001 000054
340/ 003030 000000 062701 015712 012700 055714 112120 077302
360/ 012703 000000 062701 000000 077407 004567 101272 000404
400/ 055714 003434 003436 005532 000561 026000 037000 173406
420/ 014013 001005 073403 110000 173410 155012 115402 140002
440/ 134035 073400 022011 001204 064001 055013 173413 175013
460/ 006404 173402 077705 000001 000054 003144 000200 002400
500/ 126767 002374 002362 001417 126767 002364 002353 001405
520/ 000167 002356 077026 000167 002406 004567 063236 000401
540/ 006632 000771 026000 105000 073406 123000 073774 111011
560/ 000546 126001 073415 116000 073416 110011 002201 005001
600/ 061407 062013 055013 173413 000445 126000 001004 016002
620/ 000001 000054 003260 000167 002266 022767 000002 002240
640/ 001002 000167 002310 020227 003502 001003 005067 001134
660/ 000406 016722 007762 162702 003502 010267 000621 023000
700/ 153000 047006 073402 073011 001203 041001 023011 173411
720/ 040013 002402 073403 063011 001203 023001 041011 073407
740/ 171000 061773 000001 000030 003370 023420 000200 000060
760/ 000276 000315 000200 000200 000276 000067 000602 004000
```

```
BLOCK NUMBER 00026
000/ 040000 005007 123000 000001 000016 004476 000026 000001
020/ 000002 000036 000563 004000 044000 000011 122401 000001
040/ 000022 005534 051106 042115 043514 040520 052102 051516
060/ 000402 026000 065000 073413 133011 000541 072001 000013
100/ 020000 020040 020040 020052 052512 045516 042440 051122
120/ 051117 005015 073400 114011 000541 111001 045413 000001
140/ 000054 005620 000000 020040 020040 025040 052040 046511
160/ 026505 052517 020124 051105 047522 006522 000012 020040
200/ 020040 042504 040506 046125 020124 000624 026000 133000
220/ 046013 047517 020120 044524 042515 036440 030440 030060
240/ 030060 005015 020040 020040 042504 040506 046125 020124
260/ 026130 020131 044504 104115 000001 000054 005734 047105
300/ 044523 047117 020123 043117 046040 053517 053440 047111
320/ 047504 020127 020075 031061 026070 032040 006470 020012
340/ 020040 042040 000543 026000 001000 042414 040506 046125
360/ 020124 047514 020127 044527 042116 053517 047440 043106
400/ 042523 051524 036440 030440 030071 020054 030062 006465
420/ 127412 000001 000054 006050 020040 020040 042504 040506
440/ 046125 020124 026130 020131 044504 042515 051516 047511
460/ 051516 047440 020106 044520 052103 051125 020105 000763
500/ 026000 047000 036414 030440 034062 020054 031061 006470
520/ 020012 020040 042040 043105 052501 052114 050040 041511
540/ 052524 042522 053440 047111 047504 145127 000001 000054
560/ 006164 047440 043106 042523 051524 036440 030440 030071
600/ 020054 032465 005015 020040 020040 043111 040440 054516
620/ 041440 040510 043516 026105 000454 026000 115000 020014
640/ 054524 042520 054440 020056 046105 042523 020054 027116
660/ 026440 020076 160000 007014 036415 064015 006015 007007
700/ 010007 011007 045007 000001 000054 006300 003424 003426
720/ 003430 003432 020040 020040 042440 052116 051105 046040
740/ 047517 020120 044524 042515 035040 000040 020040 020040
760/ 042440 000551 026000 163000 047014 042524 020122 047514

BLOCK NUMBER 00027
000/ 020127 044527 042116 053517 042040 046511 047105 044523
020/ 047117 020123 021450 054111 021440 054511 020051 010472
040/ 000001 000054 006414 000040 020040 020040 042440 052116
060/ 051105 046040 053517 053440 047111 047504 020127 043117
100/ 051506 052105 020123 021450 047511 030506 000676 026000
120/ 031000 020015 044443 043117 024462 035040 000040 020040
140/ 020040 042440 052116 051105 050040 041511 052524 042522
160/ 042040 046511 047105 044523 146117 000001 000054 006530
200/ 051516 024040 044443 020130 044443 024531 035040 000040
220/ 020040 020040 042440 052116 051105 050040 041511 052524
240/ 042522 053440 047111 000721 026000 077000 042015 053517
260/ 047440 043106 042523 051524 024040 047443 030506 021440
300/ 047511 031106 020051 020072 020000 020040 020040 020107
320/ 042522 016103 000001 000054 006644 044505 042526 006504
340/ 000012 020040 020040 046040 051040 041505 044505 042526
360/ 006504 000012 020040 020040 050040 041511 052524 042522
400/ 000570 003400 145000 020015 000401 010470 150400 020015
420/ 044504 044507 044524 042532 020104 000463 022400 161000
440/ 020015 044524 042515 006523 000012 020040 020040 054040
460/ 042055 046511 047440 020106 042503 046114 044440 020123
500/ 000542 026000 003400 006416 020012 020040 020040 047503
520/ 052116 047111 042525 041040 020131 050047 006447 000012
540/ 020040 020040 054440 042055 046511 047440 056506 000001
560/ 000017 007055 041440 046105 020114 051511 114440 000001
600/ 000054 007074 005015 020040 020040 041440 047117 044524
620/ 052516 020105 054502 023440 023520 005015 020000 020040
640/ 020040 044520 052103 051125 020105 000401 017400 061000
660/ 041016 041501 043513 047522 047125 020104 051107 054505
700/ 046055 053105 046105 044440 020123 000670 026000 100400
720/ 006416 000012 020040 020040 025040 040440 045104 051525
740/ 020124 044526 042504 027117 041440 047117 044524 052516
760/ 020105 054502 023440 156120 000001 000054 007247 006447
```

```
BLOCK NUMBER 00030
000/  000012 020040 020040 046040 053517 053440 047111 047504
020/  020127 040502 045503 051107 052517 042116 046040 053105
040/  046105 044440 000525 004000 146400 051416 124440 000001
060/  000053 007325 005015 140000 077035 000774 100012 001014
100/  100607 176012 140401 073414 174034 003016 073400 031011
120/  000536 000001 000000 177000 050416 000001 000054 007372
140/  007446 007522 020040 020040 020052 044520 020103 051124
160/  047101 046523 051511 044523 047117 052040 046511 026505
200/  052517 020124 051105 000632 026000 020000 051017 051117
220/  005015 020000 020040 025040 050040 041511 052040 040522
240/  051516 044515 051523 047511 020116 052512 045516 046440
260/  051505 075123 000001 000054 007506 043501 020105 051105
300/  047522 006522 000012 020040 020052 044520 020103
320/  051124 047101 046523 051511 044523 047117 044440 051516
340/  000566 026000 066000 052417 043106 041511 042511 052116
360/  051440 040520 042503 042440 051122 051117 005015 173400
400/  037035 035007 173407 116035 034367 073407 067011 000001
420/  000054 007622 056764 000405 015712 003440 013310 013304
440/  005532 022767 000001 175664 001002 000167 172360 005267
460/  003410 012700 013232 012701 000016 000516 026000 134000
500/  150017 177425 041777 173576 177425 176377 173406 177425
520/  136377 173411 177425 134377 033411 163012 033406 162012
540/  033406 161012 073406 140411 000001 000032 007736 056756
560/  000413 015712 003424 003426 013304 013310 013312 013314
600/  014134 000626 026000 171000 143017 040026 055011 173413
620/  000445 056000 001373 073402 134000 173412 001045 050000
640/  027373 073403 073011 010163 142001 012026 013007 070407
660/  000001 000032 010030 013314 014134 014136 014140 014142
700/  014144 014154 014146 014150 014152 000577 026000 026000
720/  067020 117030 055026 173413 000445 021000 001373 073402
740/  131000 173412 000045 015000 010410 173403 000045 013000
760/  006410 140403 141035 052766 000001 000054 010122 005301

BLOCK NUMBER 00031
000/  020167 004010 001407 016701 173270 005301 020167 004000
020/  001401 000404 005367 003114 000167 177424 026767 003770
040/  173300 002770 000503 026000 074000 073420 032011 002566
060/  064001 063030 066030 070030 116030 140426 161035 053407
100/  062160 000000 033412 155162 033407 003020 001006 173412
120/  053055 000001 000054 010236 002774 173202 002012 026767
140/  002766 173174 002006 026767 002760 173166 002002 005202
160/  000407 026767 003660 173172 002403 005267 002776 000715
200/  017000 142000 150420 073401 137011 006536 142001 012026
220/  013007 145007 146033 056026 144030 115026 133026 000001
240/  000054 010334 013242 013272 004500 014206 005532 022767
260/  000001 175156 001002 000167 005054 016700 002644 070067
300/  173104 160167 002644 005667 002670 000767 026000 001000
320/  033421 132340 141005 000445 016000 173403 107055 012005
340/  006366 173405 104055 007005 002366 142005 002425 073400
360/  101000 142003 003025 120000 000001 000054 010450 000167
400/  001572 026767 002560 172766 002404 012704 000007 000167
420/  001552 012704 000010 000167 001542 004567 070072 000415
440/  015712 003424 000540 015000 047000 013021 057007 060030
460/  105030 061030 062030 167030 051030 052031 053031 113031
500/  000001 000054 010542 014530 000433 005003 016700 003752
520/  012701 014212 112102 042702 177400 060203 077005 016700
540/  003732 012701 014356 112102 042702 177400 000710 026000
560/  104000 101421 002540 001176 140012 142035 140007 141155
600/  100007 133562 011020 073405 157011 001160 053001 105031
620/  073430 045011 003560 053001 143431 000001 000036 010656
640/  014212 014626 014532 014556 014602 014606 004567 070300
660/  000402 014530 014356 004567 000763 026000 143000 026021
700/  003560 054001 167031 113030 062031 074031 102031 104031
720/  173431 001445 122000 027407 140002 067025 000431 000422
740/  004154 100400 075014 000001 000054 010754 010102 166702
760/  002326 006202 006202 160201 026001 000002 002023 026001
```

```
BLOCK NUMBER 00032
000/  000006 002020 016002 000002 066002 000006 006202 166002
020/  000004 000735 026000 011000 001022 133413 110020 133404
040/  020040 001365 073405 017000 006402 073401 146011 003557
060/  053001 105031 041030 055011 067031 101031 105031 054031
100/  000001 000054 011070 066767 003516 003510 022767 000003
120/  003500 001060 012700 014570 011001 066001 000010 006201
140/  010102 166702 002160 006202 006202 160201 000574 026000
160/  057000 000422 001054 012000 000404 003054 010400 001004
200/  001034 001000 003154 101000 001014 002354 001000 133413
220/  025020 133404 135040 001364 031005 000001 000054 011204
240/  000167 000670 000167 000674 004567 067544 000407 014530
260/  014356 004502 014544 014570 014604 014614 066767 003350
300/  003342 022767 000001 000425 026000 125000 153022 003006
320/  140002 067025 030031 002022 030000 001022 173400 000445
340/  142002 003006 140002 074025 030031 002022 030000 001022
360/  140000 114425 000001 000054 011320 000002 016001 014556
400/  066001 014570 006201 010167 003256 012700 000004 016702
420/  003206 066002 014556 066702 003210 066002 014570 006202
440/  000402 026000 173000 101022 133414 112020 041006 133740
460/  124020 140003 105035 140006 032355 033764 120020 033403
500/  100020 073406 030011 002563 115001 111026 145431 000001
520/  000054 011434 013242 013272 013260 026727 001604 000010
540/  002406 026767 001602 172004 003402 000167 000106 026767
560/  001540 171746 002004 012704 000004 000414 026000 041000
600/  073423 060000 073401 130011 002162 115001 135026 121026
620/  126026 173426 052055 154003 002363 142005 002025 073400
640/  041000 173401 031055 143003 000001 000054 011550 171704
660/  002004 012704 000002 000167 000462 012704 000003 000167
700/  000452 026767 001432 171670 002002 000167 000300 016700
720/  001436 006200 000743 026000 107000 140023 176155 033405
740/  031020 073403 125011 003155 145001 051033 144031 055026
760/  142031 055026 173413 000445 126000 001367 073402 120000

BLOCK NUMBER 00033
000/  024007 000001 000034 011664 004567 055026 000413 015712
020/  003424 003426 013304 013310 013312 013314 014134 000425
040/  026000 145000 143023 103026 055030 173413 000445 102000
060/  001367 073402 160000 173406 001045 074000 001367 073402
100/  130000 073407 115011 010157 142001 165426 000001 000032
120/  011760 003424 003426 013314 014134 014162 014164 014166
140/  014170 013244 014172 000724 026000 002000 076024 077030
160/  100030 102030 055030 173413 000445 043000 001367 073402
200/  153000 173406 103013 002002 173402 144025 100000 004002
220/  073401 154011 000001 000054 012052 071204 000405 014174
240/  014172 013244 014202 013246 026767 001152 171356 002404
260/  012704 000011 000167 000136 016700 001156 016701 001122
300/  000664 026000 050000 013424 177166 073777 154040 012362
320/  173404 036055 141002 002362 142004 005025 073400 036000
340/  173400 026055 137002 002362 142004 005425 145000 000001
360/  000054 012166 000167 000054 012704 000014 000167 000044
400/  026767 001024 171232 002004 012704 000015 000167 000024
420/  026767 001004 171226 002404 012704 000523 026000 116000
440/  007024 073400 002000 142000 000425 173400 156035 003004
460/  173402 154035 001004 033402 005021 013402 000441 005400
500/  173402 177445 166377 027401 000001 000054 012302 001407
520/  005267 002326 066767 000742 002316 005567 002310 005304
540/  006304 005264 015060 066764 000674 015024 005564 014770
560/  066764 000672 000523 026000 164000 156024 072031 140013
600/  172031 144155 140001 173431 177445 131377 003401 073402
620/  175011 002160 115001 135026 121026 126026 140026 142035
640/  032363 000001 000054 012416 012701 013232 012702 000024
660/  012120 077202 010067 171664 016700 172002 012701 014136
700/  012702 000004 012120 077202 010067 171762 000167 000754
720/  026000 032000 047025 073772 165011 000527 063001 002026
740/  141012 041025 142007 016045 001000 073402 046000 172361
760/  030013 001032 073402 003000 142001 077013 000001 000054
```

```
BLOCK NUMBER 00034
000/  012532 001011 016700 002072 016701 002070 071067 002066
020/  010064 015240 000402 005064 015240 016400 014770 016401
040/  015024 071064 015060 010067 000627 026000 100000 030025
060/  033404 025012 073404 154011 001161 130001 131031 140031
100/  126025 010031 073572 037011 001162 130001 131031 172031
120/  007035 046004 143432 000001 000054 012646 016467 014700
140/  002014 016467 014734 002010 004567 070654 000402 014670
160/  014672 012700 014664 075030 011060 000004 016060 000002
200/  000006 000564 026000 146000 004025 030012 030035 001032
220/  073400 105011 001161 134001 135031 014031 073572 172011
240/  001161 136001 137031 172031 150035 064003 140032 136035
260/  000001 000054 012762 001712 070027 000144 071064 015114
300/  010064 015204 010403 006203 005203 012700 014640 010320
320/  016420 015060 016420 015114 016420 015150 000717 026000
340/  014000 010026 102035 010032 120035 140432 003025 140000
360/  120025 011031 041024 140576 002425 142000 001013 140402
400/  003025 140000 120025 033431 040024 000001 000054 013076
420/  001524 004567 053140 000403 014624 013220 004500 004567
440/  053324 000401 013220 077115 004567 053312 000401 013227
460/  062704 000002 000167 000504 026000 062000 157026 006776
500/  020012 020040 046103 051501 020123 042503 046114 020123
520/  046440 040503 020040 046440 044103 020040 041515 042110
540/  020040 174040 000001 000014 013212 041515 006524 000012
560/  000530 005000 113000 000026 005015 031000 000001 000010
600/  013312 000620 000606 005000 103000 177430 007377 045400
620/  000001 000012 014626 000003 000012 000471 005000 126000
640/  072431 107476 026302 000001 000012 014664 042621 020000
660/  000462 026000 136000 073432 062011 000522 146001 173432
700/  170012 073773 150000 020351 020040 020040 020052 047515
720/  042522 052040 040510 020116 030064 020060 042103 000001
740/  000023 015342 040510 047111 041440 042117 051505 005015
760/  025400 000001 000054 015360 004567 051060 000401 015400

BLOCK NUMBER 00035
000/  005367 175674 000167 164634 020040 020040 025040 041440
020/  040510 047111 041440 042117 020105 040526 052514 000426
040/  026000 013000 042433 037040 033440 005015 073400 001011
060/  000522 027001 173433 107012 073773 067000 020351 020040
100/  020040 020052 047515 042522 052040 040510 000001 000035
120/  015474 047101 034440 041040 052517 042116 051101 020131
140/  047520 047111 051524 005015 005400 000001 000054 015524
160/  004567 050714 000401 015544 005367 175530 000167 164470
200/  020040 020040 025040 050040 046101 047514 020122 047520
220/  047111 020124 047516 000477 026000 075000 052033 042440
240/  041516 052517 052116 051105 042105 041040 043105 051117
260/  020105 040526 046114 054505 005015 073400 104011 000521
300/  124001 114433 000001 000054 015640 005367 175424 000167
320/  164364 020040 020040 025040 050040 046101 047514 020122
340/  051511 040440 051440 047111 046107 020105 047520 047111
360/  000454 005000 143000 052033 005015 124400 000001 000054
400/  065714 004567 017520 000401 105737 177560 100375 113701
420/  177562 042701 177600 022701 000015 001401 010102 105737
440/  177564 100375 110137 177566 000400 026000 171000 140553
460/  006445 166400 157402 072213 176777 157600 005225 073000
500/  141377 047045 005000 141003 054445 001400 036403 000012
520/  003400 176401 057025 000001 000026 066030 000001 000000
540/  000403 012775 000002 000000 000167 017424 000642 026000
560/  024000 073554 172011 000436 140401 114025 001154 157412
600/  070213 176777 140200 071227 140377 100105 157777 072213
620/  176777 017600 073220 013777 067040 000001 000054 066116
640/  000060 002410 020027 000071 003005 005202 162700 000060
660/  010021 000751 005702 001001 000746 020027 000015 001006
700/  105737 177564 100375 000630 025000 072000 157554 005225
720/  073000 140777 114025 041554 113424 000440 002400 141003
740/  153412 005160 041400 102144 176576 000020 073400 122000
760/  002436 000001 000054 066244 004567 017170 000403 012703
```

BLOCK NUMBER 00036
```
000/ 000005 016502 000002 112712 000040 062702 000006 005004
020/ 005775 000004 100004 112767 000001 000015 000403 000603
040/ 026000 145000 173554 100225 002400 040000 000037 001000
060/ 000001 102013 000412 000020 013412 005162 140400 030125
100/ 061000 144220 141576 002025 145000 015245 000001 000034
120/ 066360 000060 001003 112722 000040 077306 005704 001402
140/ 112742 000055 000167 017066 000504 022000 003000 073555
160/ 013011 001036 040001 000037 040400 001035 157400 104213
200/ 176773 150600 105227 003373 073576 014000 065036 000001
220/ 000042 066444 004567 016770 000401 011500 105710 001406
240/ 105737 177564 100375 112037 177566 000770 000167 016774
260/ 000773 026000 040000 073555 156011 002435 157401 101025
300/ 040155 017400 041012 173400 040025 133000 073602 124025
320/ 141202 002025 140400 102025 040155 000027 155413 000001
340/ 000044 066546 110021 077204 016767 000030 101232 016767
360/ 000020 101222 012767 000101 101204 000001 000167 016672
400/ 000002 000501 026000 104000 073555 112011 002435 076401
420/ 001057 003000 013400 041005 041423 001037 101400 073540
440/ 002037 005000 042000 003037 142000 102012 013540 140245
460/ 000001 000046 066656 000000 103407 160204 010475 000006
500/ 005075 000010 000167 016574 020304 001364 012775 000001
520/ 000010 000167 016556 000442 026000 147000 073555 047011
540/ 005435 041001 040025 033427 035020 033400 133020 033400
560/ 152020 033400 063020 140001 033412 117020 033400 136020
600/ 033400 131420 000001 000054 066764 000340 005200 005200
620/ 010067 000240 010067 000276 013501 005301 010167 000322
640/ 013503 005303 060302 005000 010301 071027 000000 010003
660/ 000526 026000 015000 040156 140420 073420 140027 073400
700/ 164027 041400 073425 007025 033401 150012 073400 020025
720/ 156401 003413 173600 101225 123400 173400 102425 000001
740/ 000054 067100 000001 000372 000406 112767 000207 000231
760/ 012767 000000 000354 012567 000336 005067 000330 012737
```

BLOCK NUMBER 00037
```
000/ 000435 067436 012737 000431 067346 000773 026000 063000
020/ 002156 133412 114020 173400 004025 132000 073400 010020
040/ 001401 173401 004025 124000 007400 067235 177557 007401
060/ 073235 177557 141001 130745 000001 000054 067214 000000
100/ 005200 005301 000434 162702 000000 005301 000430 162702
120/ 000000 005300 005301 000423 005302 005300 000420 062702
140/ 000000 005300 000764 026000 131000 100556 005412 141001
160/ 000145 100400 003412 141001 000145 100000 100412 001012
200/ 101001 100012 140012 023413 140405 022413 140005 000045
220/ 035400 000001 000054 067330 002442 022701 000000 002437
240/ 121227 000000 000434 005204 042704 177770 110423 005304
260/ 042704 177770 020167 000216 003402 010167 000210 000711
300/ 026000 177000 113556 000012 113400 000040 012000 002003
320/ 077235 153557 000012 131400 173402 000525 015000 005400
340/ 102001 000412 102001 142012 174105 041777 000001 000054
360/ 067444 005327 000000 001255 052767 000002 000002 012737
400/ 000000 000000 016737 177706 000000 022727 000000 000001
420/ 001411 005267 000076 016701 000705 026000 045000 035157
440/ 053400 000160 100400 057412 000020 073400 161000 173433
460/ 102025 137012 173777 102025 100012 173777 004025 135000
500/ 154377 001401 105010 000001 000034 067560 010414 014424
520/ 021035 007005 013016 017426 002437 003405 000407 001401
540/ 002403 000713 026000 104000 073557 112011 006433 036401
560/ 014012 173400 004425 135000 176400 001012 073400 001037
600/ 152000 073400 001037 177000 136400 001012 073400 003437
620/ 000001 000054 067656 000002 000330 017567 000002 000370
640/ 005275 000002 017567 000002 000316 017567 000002 000356
660/ 005375 000002 012767 000024 000250 012767 000672 026000
700/ 152000 012157 151000 173400 012025 030000 173401 012025
720/ 076000 073401 006037 050000 040001 000037 140000 040012
740/ 003155 141000 124035 141401 106425 000001 000054 067772
760/ 003720 005022 005303 001375 005775 000024 100004 112767
```

```
BLOCK NUMBER 00040
000/ 000203 000457 000403 112767 000206 000447 005775 000026
020/ 100004 016767 000602 000525 026000 020000 066160 001401
040/ 173401 074035 062001 141001 060035 073401 055021 040401
060/ 004035 042400 005037 101400 141420 001145 145000 000045
100/ 005000 030003 000001 000054 070106 011204 020023 001411
120/ 005304 001374 021227 000000 002402 000167 000444 010013
140/ 005212 005305 001454 112104 116417 070630 000777 005200
160/ 000534 026000 066000 144560 000245 173000 161403 140001
200/ 000345 141000 000345 141000 007055 001001 133603 004020
220/ 154401 140001 000345 172400 140001 000345 171400 000001
240/ 000054 070222 000762 005300 022705 000001 001717 122711
260/ 000004 001736 000713 062700 000000 062702 000000 000706
300/ 062700 000000 000772 062700 000000 000740 026000 134000
320/ 173560 142401 150035 041000 100421 140424 000045 022400
340/ 140403 000445 017400 140403 100012 002020 001412 033412
360/ 133024 101400 140412 016440 000001 000054 070336 003011
400/ 022067 000254 101005 014067 000246 010004 062700 000002
420/ 000764 022704 000000 001403 011214 016712 000222 005301
440/ 022701 000000 000414 026000 002000 001561 141003 001145
460/ 161000 142401 000145 153000 002001 033412 076012 033400
500/ 075012 033400 071012 142400 065035 040000 000421 140424
520/ 075045 000001 000054 070452 000000 001433 011002 012003
540/ 005203 005301 001403 121327 000000 000771 160203 112204
560/ 042704 177400 060467 000112 005567 000110 005267 000456
600/ 026000 050000 040161 141400 172412 140402 000045 000400
620/ 164003 142401 000145 160000 142401 022035 176400 023035
640/ 007000 176400 021035 010000 176400 073035 000001 000034
660/ 070566 000036 000022 000167 014676 016705 000012 012775
700/ 000001 000030 000167 014660 000447 014000 111000 000161
720/ 000000 000000 000000 007405 012422 021035 122045 072161
740/ 041571 000001 000054 100504 004567 004730 000406 005075
760/ 000012 017567 000004 000024 017501 000002 005301 016502

BLOCK NUMBER 00041
000/ 000006 061201 016203 000002 161203 122127 000000 000461
020/ 017000 065000 003201 142203 176576 000425 005000 073400
040/ 142000 040411 076743 004020 073400 135000 153411 000001
060/ 000054 100602 004567 004632 000415 017500 000014 067500
100/ 000016 006200 017501 000002 070100 010100 067500 000006
120/ 061500 010075 000022 016501 000012 000552 026000 124000
140/ 041201 004037 041000 003357 101000 136412 013020 010400
160/ 101224 040576 006037 076400 001160 040000 040420 003037
200/ 040400 004157 100400 120014 000001 000054 100716 060100
220/ 061500 010075 000024 016501 000020 017502 000016 167502
240/ 000014 005202 010275 000030 111021 067500 000002 077204
260/ 000167 004510 000467 026000 172000 073601 024011 003411
300/ 036401 006012 073400 066023 040000 140027 073412 063023
320/ 040400 073425 066027 031400 041407 041025 073425 016023
340/ 066000 000001 000054 101032 005035 012704 000001 122111
360/ 101005 005204 005300 001373 005304 005200 005767 000112
400/ 001431 005237 000000 010423 005112 114112 062702 000703
420/ 026000 040000 001202 100400 173412 032012 102000 140012
440/ 012412 044403 175644 173606 023013 003400 011403 005021
460/ 045012 141230 001145 100400 157412 110401 000001 000034
500/ 101146 005235 004567 000022 000402 000000 000000 162705
520/ 000016 000705 000167 004300 000402 026000 077000 073602
540/ 117011 001010 040401 040027 140425 001012 141222 000105
560/ 101777 001020 141222 000105 002377 000634 142000 000105
600/ 001777 101541 147414 000001 000044 101244 060203 006203
620/ 110320 005301 001361 111004 042704 177400 060403 006203
640/ 060304 006204 110410 000167 004172 000516 026000 141000
660/ 073602 055011 002010 040001 040427 041025 041427 011423
700/ 141012 176412 162402 041013 141027 041412 002025 042012
720/ 001324 000441 102203 113020 000001 000024 101350 006304
740/ 060304 005214 005300 001366 000167 004106 000560 026000
760/ 173000 073602 023011 002410 073401 046023 040000 140027
```

```
BLOCK NUMBER 00042
000/  073412  043023  040400  041025  022027  041407  073425  015023
020/  016400  142012  000425  044400  116044  000001  000054  101434
040/  003005  005204  005300  001373  005304  005200  005702  001415
060/  005237  000000  010423  005302  005204  005300  001416  022111
100/  002373  005702  001402  000537  017000  041000  011603  166021
120/  073401  010011  001000  000001  000000  142400  005345  152400
140/  073401  161000  107007  000001  000054  101532  004567  003702
160/  000402  013501  012500  005301  005002  010203  011002  066003
200/  000002  006203  060203  006203  005301  001366  026003
220/  060310  000663  006000  100000  104203  073414  133000  024007
240/  000001  000054  101606  004567  003626  000420  005075  000036
260/  017501  000000  005301  005000  071075  000002  010167  000762
300/  016767  000756  000756  016767  000752  000740  000405  026000
320/  126000  033603  163020  173401  161035  161001  173401  157035
340/  151001  033401  155012  033401  157012  033401  156012  033401
360/  155012  033401  140012  000401  051412  000001  000054  101722
400/  005002  017503  000010  117567  000006  000712  016500  000006
420/  010567  000644  112004  020427  000010  002402  000167  000604
440/  116417  102602  000777  000403  026000  174000  133603  117012
460/  140401  107155  173401  123011  034001  133401  114012  140401
500/  100155  141001  173412  113011  173401  147011  027001  133401
520/  103012  124401  000001  000054  102036  004767  000704  000451
540/  005267  000576  166701  000542  005202  004767  000614  004767
560/  000660  000437  005267  000536  166701  000516  004767  000572
600/  000557  026000  042000  014204  133401  054012  140401  040355
620/  141001  173412  065011  173401  075011  007001  133401  043012
640/  173401  070011  004401  133401  037012  140401  073555  000001
660/  000054  102152  000442  005202  004767  000470  004767  000534
700/  020327  000001  003003  116705  000450  000401  111005  160504
720/  005704  100002  062704  000010  022704  000753  026000  110000
740/  001204  004400  142003  001445  003000  141403  141412  001013
760/  073403  041000  001777  133401  163012  173400  142401  155035

BLOCK NUMBER 00043
000/  176400  156035  016000  171400  000001  000054  102266  016775
020/  000330  000012  016775  000324  000014  016775  000320  000016
040/  016775  000314  000020  006202  060201  010175  000022  016703
060/  000300  066703  000727  026000  156000  143204  176400  012020
100/  141400  136035  141400  136155  176400  013020  000400  001012
120/  173412  127355  121000  173400  125355  122000  173400  114013
140/  145000  000001  000054  102402  100004  005467  000222  012701
160/  000002  005767  000222  100004  005467  000214  012702  000002
200/  005067  000202  004567  001100  000402  102640  102642  000611
220/  026000  024000  140205  116025  010205  073572  123011  001002
240/  120001  121205  173605  057055  062000  011400  173403  053055
260/  056000  003400  100405  076412  014020  020400  000001  000054
300/  102516  016775  000110  000032  000416  062702  000002  010275
320/  000030  016775  000100  000032  000406  012775  000000  000030
340/  012775  000000  000032  000167  000437  016000  072000  143205
360/  142405  010035  176400  000425  017000  174000  000001  010407
400/  020026  030447  023466  000001  000012  102634  040265  002201
420/  000532  026000  125000  133605  157012  173777  161055  154377
440/  003777  173404  151035  154377  173400  154012  173777
460/  146055  142377  001777  173407  137035  141377  144377  000001
500/  000054  102720  000207  005267  177670  026767  177676  177662
520/  002003  016767  177654  177664  000207  005367  177644  026767
540/  177650  177636  003403  016767  177630  000454  005000  173000
560/  117205  103777  053000  000001  000054  102772  004567  002442
600/  000404  005067  000072  013567  013567  000066  013567
620/  000064  004567  000516  000402  103076  103100  004567  000504
640/  000402  000675  022000  020000  041206  042206  140206  037025
660/  014206  073572  125011  001001  041001  042206  176606  006035
700/  000000  073400  177000  014404  000001  000054  103106  004567
720/  002326  000405  013500  070035  010067  000124  010167  000122
740/  004567  000406  000402  103250  103252  163501  005600  163500
760/  010067  000100  000406  026000  066000  073606  037020  073400
```

```
BLOCK NUMBER 00044
000/ 167011 001000 126001 127206 140206 124025 014206 141172
020/ 001025 030000 175024 101777 140176 122025 010206 073572
040/ 110011 000001 000034 103222 000504 000402 103250 103252
060/ 016775 000014 000000 000167 002230 041710 000000 000741
100/ 026000 130000 073606 066011 002404 073401 121027 033400
120/ 116012 073400 120011 001000 055001 056207 140207 053025
140/ 010207 073572 107027 033400 104012 111000 000001 000054
160/ 103326 004567 000210 000402 103536 103540 075000 016767
200/ 000172 000164 016767 000162 000154 004567 000346 000402
220/ 103536 103540 016775 000144 000577 026000 176000 001206
240/ 173400 055035 056000 173400 051035 052000 140000 002345
260/ 010000 073572 044027 033400 041012 073400 043011 001000
300/ 055001 056207 131207 000001 000054 103442 162700 000004
320/ 075030 012767 000012 000056 005067 000050 004567 000054
340/ 000402 103532 103534 162700 000004 075000 004567 000222
360/ 000402 000607 014000 044000 057207 060207 176607 010035
400/ 001000 073400 163000 132403 100500 043004 000001 000054
420/ 103542 004567 001672 000402 005775 000000 001003 005775
440/ 000002 001460 005001 017502 000000 017503 000002 005702
460/ 100006 005102 005103 062703 000574 026000 104000 000607
500/ 041000 100413 002012 140012 114025 113400 100040 004000
520/ 113404 000566 102000 141012 100065 175000 000003 004341
540/ 141001 000065 036777 000001 000054 103656 001404 073227
560/ 177777 005204 000771 060400 042702 000200 072027 000007
600/ 074002 005701 001402 052702 100000 010275 000000 010375
620/ 000002 000714 005000 152000 073607 062000 136003 000001
640/ 000054 103730 004567 001504 000402 005775 000000 001003
660/ 005775 000002 001440 005001 017502 000000 017503 000002
700/ 005702 100003 042702 100000 005201 000476 026000 177000
720/ 100207 140020 077505 001200 141100 100125 013400 174564
740/ 140377 114345 100000 140566 002413 041003 041412 141412
760/ 000545 041000 136413 075420 000001 000020 104044 000000

BLOCK NUMBER 00045
000/ 010375 000002 000167 001416 000654 026000 027000 073610
020/ 167011 002002 040001 000037 073400 001035 004000 073400
040/ 010011 001002 105001 000210 073400 027011 001002 106001
060/ 104210 173610 025413 000001 000054 104124 000062 001010
100/ 142767 000200 000056 126775 000052 000004 001403 000406
120/ 077026 000411 005075 000006 000167 001310 012775 000001
140/ 000006 000447 012000 075000 073610 137000 176402 001025
160/ 003000 073400 132000 065402 000001 000010 104212 000001
200/ 000744 026000 107000 073610 107011 002002 040001 000037
220/ 073400 157011 001001 166001 164210 173610 041013 004000
240/ 173402 100305 037000 176400 035255 001000 052400 000001
260/ 000054 104264 001403 000416 077021 000421 016567 000004
300/ 000010 004567 000614 000402 104352 000000 005075 000006
320/ 000167 001150 012775 000001 000006 000570 012000 155000
340/ 073610 057000 176402 001025 003000 073400 052000 145402
360/ 000001 000010 104352 000001 000604 026000 167000 073610
400/ 027011 002002 073401 142023 073400 001237 012400 073401
420/ 002237 010000 036401 003012 140000 173025 173611 052035
440/ 171167 144000 036213 000001 000054 104424 001430 004567
460/ 000546 000402 105010 105012 005767 000346 001010 142767
500/ 000200 000334 126720 000330 001001 000757 005300 005367
520/ 000312 000444 026000 035000 165611 176402 004025 003000
540/ 073400 173000 173401 002425 135000 073400 001011 001001
560/ 003001 010212 140212 175025 173611 134011 073400 105011
600/ 000001 000054 104540 000436 000402 105010 105012 005767
620/ 000236 001025 142767 000200 000224 126767 000220 000203
640/ 001423 126767 000210 000174 001405 012775 000614 026000
660/ 103000 001211 003000 073400 127000 176401 002025 003000
700/ 073400 122000 176401 000425 003000 073400 115000 001001
720/ 001412 141012 064735 141400 071335 000001 000054 104654
740/ 000146 070302 010367 000130 004567 000232 000402 105014
760/ 000000 005067 000114 016700 177766 005001 112001 060167
```

```
BLOCK NUMBER 00046
000/  000100  005367  000072  000643  026000  151000  174611  173402
020/  033235  027400  173400  000425  023000  073400  067011  001000
040/  003001  004612  140212  177425  173611  022011  073400  043000
060/  051001  056120  000001  000021  104770  000111  050122  043400
100/  051105  042120  010000  000001  000011  105020  050124  062523
120/  000001  000054  105026  105710  001417  004567  000142  000402
140/  105010  105012  005767  177742  001010  142767  000200  177730
160/  126720  177724  001010  000757  000207  005726  000421  016000
200/  036000  176612  000425  003000  073400  173000  153000  176413
220/  001025  003000  073400  165000  035400  000001  000046  105122
240/  004567  000312  000402  017501  000000  016500  000002  105737
260/  175614  100375  112037  175616  005301  001371  000167  000312
300/  000500  026000  071000  173612  105227  123373  102400  173400
320/  001025  010001  073400  116011  001000  157401  002025  140213
340/  017400  141012  173400  105227  104373  033400  050412  000001
360/  000054  105230  000176  012767  000005  000174  012767  023420
400/  000164  042737  000100  175610  052737  000100  175610  022767
420/  000001  000140  001420  005367  000134  000444  026000  137000
440/  173612  000045  053000  173000  173402  000045  050000  010000
460/  173403  010025  043047  173400  042012  166000  176401  040235
500/  000000  036400  001012  142000  000054  105344  012767
520/  113767  177646  000167  000116  042737  000100  175610  012775
540/  000001  000002  012767  113767  177620  000167  000070  042737
560/  000100  175610  000646  012000  005000  173613  105227  007373
600/  173400  000425  001000  001000  022000  000001  000054  105440
620/  010446  010346  010246  010146  010046  010504  016605  000012
640/  022524  001001  000114  000167  000020  000205  012600  012601
660/  012602  012603  012604  000721  005000  043000  102613  102425
700/  002400  000001  000030  105512  010544  005046  010616  062716
720/  000002  012746  001777  000004  000777  000626  026000  000000
740/  001000  000000  003000  000000  005000  000000  007000  000000
760/  011000  000000  013000  000000  015000  000000  017000  000000

BLOCK NUMBER 00047
000/  021000  000000  023000  005400  000001  000054  000046  000000
020/  000052  000000  000056  000000  000062  000000  000066  000000
040/  000072  000000  000076  000000  000102  000000  000106  000000
060/  000112  000000  000643  026000  046000  047000  000000  051000
100/  000000  053000  000000  055000  000000  057000  000000  061000
120/  000000  063000  000000  065000  000000  067000  000000  071000
140/  143400  000001  000054  000162  000000  000166  000000  000172
160/  000000  000176  000000  000202  000000  000206  000000  000212
200/  000000  000216  000000  000222  000000  000226  000000  000653
220/  026000  114000  115000  000000  117000  000000  121000  000000
240/  123000  000000  125000  000000  127000  000000  131000  000000
260/  133000  000000  135000  000000  137000  101400  000001  000054
300/  000276  000000  000302  000000  000306  000000  000312  000000
320/  000316  000000  000322  000000  000326  000000  000332  000000
340/  000336  000000  000342  000000  000663  021000  162000  163000
360/  000000  165000  000000  167000  000000  171000  000000  173000
400/  000000  175000  000000  177000  000000  055400  000001  000006
420/  001000  000367  000000  000000  000000  000000  000000  000000
440/  000000  000000  000000  000000  000000  000000  000000  000000
460/  000000  000000  000000  000000  000000  000000  000000  000000
500/  000000  000000  000000  000000  000000  000000  000000  000000
520/  000000  000000  000000  000000  000000  000000  000000  000000
540/  000000  000000  000000  000000  000000  000000  000000  000000
560/  000000  000000  000000  000000  000000  000000  000000  000000
600/  000000  000000  000000  000000  000000  000000  000000  000000
620/  000000  000000  000000  000000  000000  000000  000000  000000
640/  000000  000000  000000  000000  000000  000000  000000  000000
660/  000000  000000  000000  000000  000000  000000  000000  000000
700/  000000  000000  000000  000000  000000  000000  000000  000000
720/  000000  000000  000000  000000  000000  000000  000000  000000
740/  000000  000000  000000  000000  000000  000000  000000  000000
760/  000000  000000  000000  000000  000000  000000  000000  000000
```

```
BLOCK NUMBER 00050
000/ 052122 030455 020061 044514 045516 020040 020040 030126
020/ 026464 032060 020101 020040 046040 040517 020104 040515
040/ 020120 005015 046123 053101 020105 046056 040504 020040
060/ 020040 020040 020040 020040 020040 020040 032062 045055
100/ 047101 033455 006470 005012 042523 052103 047511 020116
120/ 042101 051104 020040 020040 044523 042532 020040 020040
140/ 047105 051124 020131 020040 042101 051104 020040 020040
160/ 047105 051124 020131 020040 042101 051104 020040 020040
200/ 047105 051124 020131 020040 042101 051104 005015 005015
220/ 020056 041101 027123 030011 030060 030060 004464 030060
240/ 030061 030060 051411 052105 031460 004440 030060 030060
260/ 030060 006411 004412 030060 030061 030060 030011 032066
300/ 030467 004464 041122 030103 020063 030011 030460 030060
320/ 004460 005015 030011 032466 030467 004464 030060 030460
340/ 032063 042411 044103 047117 004531 033060 033465 032061
360/ 006411 004412 033060 030066 030065 030011 030060 033461
400/ 004464 047503 030103 020063 030011 033066 032460 004460
420/ 005015 030011 033066 032062 004464 030060 030460 031064
440/ 044411 052116 051501 004503 033060 031066 032064 006411
460/ 004412 033060 032066 033060 030011 030060 031460 004466
500/ 042507 040504 031460 030011 033066 030064 004466 005015
520/ 030011 033066 032064 004464 030060 030060 032063 043411
540/ 053111 030132 004463 033060 032066 032064 006411 004412
560/ 033060 032466 030060 030011 030060 030461 004460 044504
600/ 050107 041511 030011 033066 030065 004460 005015 030011
620/ 033066 030466 004460 030060 030460 033060 051411 040503
640/ 031516 004440 033060 033066 030061 006411 004412 033060
660/ 033466 033061 030011 030060 033466 004462 044103 044501
700/ 031516 030011 033066 030467 004466 005015 030011 033466
720/ 030466 004460 030460 033060 032067 051411 044520 052503
740/ 004463 033060 033067 030061 006411 004412 030061 032460
760/ 032060 030011 030060 033460 004466 000000 000000 000000

BLOCK NUMBER 00051
000/ 042523 041522 031510 030411 030060 030065 004464 005015
020/ 030411 030060 030066 004462 030060 030460 031066 050011
040/ 043117 046111 004463 030061 033060 031060 006411 004412
060/ 030061 033460 032066 030011 030060 030462 004462 045520
100/ 040526 031514 030411 030060 033067 004464 005015 030411
120/ 030460 033461 004466 030060 030460 032060 051411 047515
140/ 044124 004463 030061 030461 033067 006411 004412 030061
160/ 031461 031060 030011 030060 033060 004464 044510 052123
200/ 020061 030411 030460 030063 004462 005015 030411 030460
220/ 033063 004466 030060 030460 032064 050011 053113 046101
240/ 004461 030061 031461 033066 006411 004412 030061 032461
260/ 031063 030011 030060 032460 004464 046523 052117 030510
300/ 030411 030460 031465 004462 005015 030411 030460 030066
320/ 004466 030060 030461 032066 040411 042116 044505 004463
340/ 030061 033061 033060 006411 004412 030061 033462 031067
360/ 030011 030060 030461 004464 044506 030506 020060 030411
400/ 031060 033467 004462 005015 030411 031460 030061 004466
420/ 030060 030460 031065 043011 043111 031061 004440 030061
440/ 030463 033060 006411 004412 030061 031063 030066 030011
460/ 030060 033062 004462 042520 041522 051111 030411 031460
500/ 033062 004460 005015 030411 031460 032065 004462 030060
520/ 030460 033066 044411 052116 046106 004517 030061 032463
540/ 031064 006411 004412 030061 033463 030063 030011 030060
560/ 031061 004466 046106 044517 052116 030411 031460 031467
600/ 004460 005015 030411 032060 032460 004466 030060 030460
620/ 033463 051411 030127 020063 004440 030061 030064 033065
640/ 006411 004412 030061 031064 033061 030011 030060 031461
660/ 004467 051527 031460 020040 030411 032060 030462 004466
700/ 005015 030411 032060 032463 004466 030060 032460 032064
720/ 054011 044515 030124 004463 030061 031464 033065 006411
740/ 004412 030061 030465 031062 030011 030060 032060 004460
760/ 044507 030126 020063 000011 000000 000000 000000 000000
```

```
BLOCK NUMBER 00052
000/ 030061 030465 031062 006411 004412 030061 030465 031066
020/ 030011 030060 032462 004465 042522 030123 020063 030411
040/ 032460 033061 004462 052107 030124 020063 030411 032460
060/ 033461 004462 042507 030124 020063 030411 032460 030062
100/ 004460 005015 030411 032460 032064 004460 030060 030060
120/ 031065 051411 053101 042522 004507 030061 032065 030064
140/ 051011 051505 042522 004507 030061 032065 032067 006411
160/ 004412 030061 032465 031061 030011 030060 031060 004462
200/ 040502 041504 046101 030411 032460 030465 004462 005015
220/ 052012 040522 051516 042506 020122 042101 051104 051505
240/ 020123 020075 030060 030061 030060 006411 044012 043511
260/ 020110 044514 044515 020124 020075 030061 032465 032063
300/ 000014 000000 000000 000000 000000 000000 000000 000000
320/ 000000 000000 000000 000000 000000 000000 000000 000000
340/ 000000 000000 000000 000000 000000 000000 000000 000000
360/ 000000 000000 000000 000000 000000 000000 000000 000000
400/ 000000 000000 000000 000000 000000 000000 000000 000000
420/ 000000 000000 000000 000000 000000 000000 000000 000000
440/ 000000 000000 000000 000000 000000 000000 000000 000000
460/ 000000 000000 000000 000000 000000 000000 000000 000000
500/ 000000 000000 000000 000000 000000 000000 000000 000000
520/ 000000 000000 000000 000000 000000 000000 000000 000000
540/ 000000 000000 000000 000000 000000 000000 000000 000000
560/ 000000 000000 000000 000000 000000 000000 000000 000000
600/ 000000 000000 000000 000000 000000 000000 000000 000000
620/ 000000 000000 000000 000000 000000 000000 000000 000000
640/ 000000 000000 000000 000000 000000 000000 000000 000000
660/ 000000 000000 000000 000000 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000

BLOCK NUMBER 00053
000/ 000001 000056 000001 070323 140250 000000 000000 127401
020/ 007624 000410 000000 004164 020311 002100 000000 012001
040/ 035221 002100 000000 012433 140250 002100 000000 000440
060/ 027000 000400 067400 065432 040145 000004 140000 004437
100/ 040140 000004 167000 070046 040306 000004 167000 140046
120/ 040306 000004 067400 102047 040072 000004 121400 000001
140/ 000056 000001 026214 005421 002100 000000 026476 123521
160/ 002100 000000 026476 140250 002100 000000 027364 140250
200/ 002100 000000 031573 100730 002100 000000 000741 027000
220/ 000400 102000 035472 040011 000004 102000 067472 040047
240/ 000004 155000 035144 040024 000004 147000 037545 040010
260/ 000004 147000 040545 040010 000004 122000 000001 000056
300/ 000001 063136 035101 002100 000000 070533 140250 002100
320/ 000000 073471 056250 002100 000000 073632 012041 002100
340/ 000000 073634 140250 002100 000000 000624 027000 000400
360/ 153400 060570 040176 000004 044400 024571 040026 000004
400/ 073000 040172 040316 000004 153000 040222 040316 000004
420/ 010400 150630 040201 000004 157000 000001 000036 000001
440/ 000000 000000 000450 064714 070323 140250 002150 000000
460/ 000000 000000 001450 000000 000500 003000 001000 173400
500/ 000001 000016 000004 000007 000000 000000 000000 000746
520/ 027000 001400 000000 143000 000025 073400 000011 073400
540/ 000011 000400 125001 073411 000011 000400 173001 173404
560/ 000445 154000 007004 173403 001045 150000 143400 000001
600/ 000044 000004 003001 000000 005004 070533 140250 007004
620/ 026476 123521 011001 004652 013004 017700 060011 015001
640/ 002366 000734 027000 001400 023000 000400 167403 140001
660/ 004425 140400 174025 141004 005025 051005 001024 017176
700/ 073401 000011 000400 144001 073412 000011 000400 005001
720/ 032005 000001 000042 000004 007001 002370 011001 002412
740/ 016004 026476 123521 020001 005310 022004 012433 140250
760/ 024001 002412 000476 027000 001400 046000 140000 002025
```

```
BLOCK NUMBER 00054
000/  140400 130025 141412 134025 073412 003024 073400 000011
020/  000400 000001 141000 001025 173400 003024 073400 000011
040/  000400 000001 000001 000032 000004 005001 005260 007001
060/  005270 013004 026476 123521 023004 012433 140250 000414
100/  027000 001400 071000 000000 103400 010176 140176 114035
120/  140404 113035 040004 073560 115020 140004 105035 100004
140/  033414 106020 140004 101035 100004 033414 177420 000001
160/  000056 000003 000230 002204 016700 002156 016701 002154
200/  070100 010167 004260 004567 000000 000404 002412 004534
220/  004535 004532 022767 000001 004236 001002 000631 016000
240/  002000 002000 153026 040222 000716 005032 000405 056034
260/  000411 056436 000411 055040 115011 000001 000056 000003
300/  000276 000167 004250 022767 000002 004222 001002 000167
320/  004272 004567 000000 000402 003504 002442 005067 013276
340/  005067 013274 005067 013272 000706 012000 002000 002000
360/  106026 010454 000413 042032 000407 021034 047405 000001
400/  000056 000003 000344 016701 012640 012700 014060 005020
420/  077102 016701 012624 012700 013700 005020 077102 016701
440/  012610 012700 013734 005020 077102 016701 000530 011000
460/  002000 000400 030012 000430 140026 000427 156042 111027
500/  000001 000056 000003 000412 012574 012700 013770 005020
520/  077102 016701 012560 012700 014024 005020 077102 005067
540/  011622 005067 011620 005067 011626 005067 003026 000445
560/  007000 002000 000400 174010 000427 012024 112030 000001
600/  000056 000003 000460 005067 004042 005267 004036 026767
620/  004032 002002 001054 005067 004022 004567 000000 000405
640/  014712 002414 002416 002420 002422 012700 000750 020000
660/  002000 002000 067432 065432 000545 145036 000431 006040
700/  000405 007042 000405 010044 000405 011046 101005 000001
720/  000054 000003 000526 014712 066700 003774 020037 170002
740/  001361 004567 000000 000404 004530 014712 003510 003512
760/  004567 000000 000405 003510 003512 000663 027000 002000

BLOCK NUMBER 00055
000/  000400 145004 002031 075422 154063 000601 054026 000411
020/  145030 000431 044032 000407 045034 002007 147040 037545
040/  000410 044044 000407 045046 171007 000001 000054 000003
060/  000572 003502 004512 004524 005367 003706 004567 000000
100/  000403 004512 006317 003500 004567 000000 000401 006253
120/  005267 011432 004567 000756 027000 002000 000400 041004
140/  000407 045006 000411 052010 002011 102020 035472 000411
160/  045024 000411 147426 000414 040030 002007 037034 050455
200/  000647 125440 112014 000001 000042 000003 000636 000000
220/  000403 012266 005713 003500 005002 004567 000000 000405
240/  014712 002424 002426 002430 000612 027000 002000 002000
260/  102004 035472 000411 133010 000424 145412 000413 040014
300/  002007 067422 065432 000545 145026 000431 012030 000405
320/  013032 000405 014034 130005 000001 000056 000003 000670
340/  002432 005202 010267 012724 004567 000000 000403 013624
360/  005734 003500 004567 000000 000401 005676 012700 014712
400/  066700 001504 020037 000647 025000 002000 000400 015004
420/  002005 102016 035472 000411 112022 000427 156024 000413
440/  040026 002007 037032 050455 000647 137036 000413 145042
460/  011031 000001 000056 000003 000736 170002 001344 016703
500/  001532 005004 005267 002532 020367 002526 001067 005067
520/  002520 004567 000000 000404 002440 014712 003510 003512
540/  000476 016000 002000 002000 075436 154063 000601 020042
560/  000405 145044 000431 044046 000407 045050 073007 000001
600/  000056 000003 001004 004567 000000 000405 003510 003512
620/  003502 004512 004524 016701 003462 005301 016700 001440
640/  060300 020100 003401 005204 006303 160300 000502 020000
660/  002000 002000 147006 037545 000410 044012 000407 045014
700/  000407 041016 000407 045020 000411 052022 071411 000001
720/  000056 000003 001052 020100 002001 005204 010167 012540
740/  004567 000000 000403 013624 006173 003500 004567 000000
760/  000401 006125 005704 001412 004567 000000 000567 024000
```

```
BLOCK NUMBER 00056
000/  002000 002000 102020 035472 000411 112024 000427 075426
020/  000414 040030 002007 037034 050455 000647 052440 002014
040/  037050 050455 065647 000001 000056 000003 001120 000401
060/  006204 000000 006203 005303 010367 002350 000644 004567
100/  000000 000404 002412 004536 004542 004532 022767 000001
120/  003346 001002 000440 020000 002000 000400 102006 002014
140/  073026 040172 000716 005032 000405 057034 000411 061036
160/  000411 055040 070011 000001 000056 000003 001166 000167
200/  003360 022767 000002 003332 001002 000167 003402 012767
220/  002502 002106 012767 003324 002222 012767 000001 011056
240/  000167 005350 000630 007000 002000 000400 041026 000405
260/  152034 114006 000001 000056 000003 001234 004567 000000
300/  000404 002412 004537 004535 004532 022767 000001 003252
320/  001002 000167 003264 022767 000002 003236 001002 000167
340/  003306 000540 016000 002000 002000 073006 040172 000716
360/  005012 000405 057414 000411 056416 000411 055020 057411
400/  000001 000056 000003 001302 026727 002014 002502 001003
420/  005067 002130 000406 016700 001776 162700 002502 010067
440/  002112 004567 000000 000402 003502 003446 005767 000654
460/  016000 002000 000400 041010 000405 041030 002005 037040
500/  124055 000700 041044 000407 023046 073007 000001 000056
520/  000003 001350 002074 001405 004567 000000 000402 003446
540/  002502 016700 001020 004567 000000 000402 004550 004532
560/  005767 003122 001023 142767 000200 000664 021000 002000
600/  002000 037012 124055 000700 023016 000407 041020 002005
620/  172030 124056 000700 064034 000411 055036 127011 000001
640/  000056 000003 001416 003130 126767 003124 003117 001417
660/  126767 003114 003111 001431 126767 003104 003100 001002
700/  000167 000442 000167 003072 077034 000167 000777 027000
720/  001400 032000 051003 073406 000011 002000 145001 012031
740/  013005 055005 173411 011013 001006 073403 105000 073411
760/  176000 073400 000011 001000 037001 156007 000001 000046

BLOCK NUMBER 00057
000/  000004 004004 114021 100721 006001 014712 007001 002424
020/  010001 002426 011001 004532 022004 026214 005421 024001
040/  003476 000652 027000 001400 055000 024003 140007 136035
060/  033401 142020 033400 142020 140000 001345 033400 036020
100/  140000 125035 140001 001345 033400 060020 141000 024025
120/  106007 000001 000016 000004 002001 003450 024001 003450
140/  000541 027000 001400 100000 133403 121024 141403 112035
160/  142001 111035 100401 140424 140412 140414 140414 140414
200/  152145 040006 140024 033412 055020 033400 071020 131400
220/  000001 000012 000004 016001 003324 000772 027000 001400
240/  123000 040003 000344 013413 000040 006400 033407 160020
260/  073423 000011 001400 112001 000427 040014 073407 000011
300/  000400 165401 000013 040000 021024 000001 000042 000004
320/  012004 035204 004473 014001 013624 015001 006001 016001
340/  003500 020004 026476 123521 022001 005753 000715 027000
360/  001400 146000 140003 033412 032020 033400 037020 040000
400/  000344 013413 000004 006400 033407 130020 073423 000011
420/  001400 112001 033027 040014 073407 074411 000001 000030
440/  000004 017004 035204 004473 021001 013624 022001 006066
460/  023001 003500 000434 027000 001400 171000 000003 000400
500/  020001 000014 141400 000045 001000 173405 012020 142000
520/  000045 001000 033405 003021 140400 001035 053401 000160
540/  140400 112545 000001 000020 000004 002004 026476 123521
560/  004001 006040 000513 027000 001400 014000 000004 140400
600/  145145 140031 146025 050131 141224 141576 000025 140400
620/  000145 003400 073577 000011 002000 146001 016131 017005
640/  055005 133011 000001 000044 000004 004001 014712 006001
660/  054714 017004 114021 100721 021001 054714 022001 002434
700/  023001 002436 024001 004532 000470 027000 001400 037000
720/  173404 014013 001005 073403 110000 173410 155012 115402
740/  140002 134035 073400 000011 001000 064001 055011 173411
760/  175013 006404 173402 024305 000001 000024 000004 015004
```

```
BLOCK NUMBER 00060
000/  027364 140250 017001 004550 020001 004532 000453 027000
020/  001400 062000 100004 000000 173405 176255 171004 007404
040/  173403 172255 165404 002404 073403 167000 013004 073576
060/  003000 073405 000011 000400 115001 176013 000001 000020
100/  000004 022004 026476 123521 024001 005632 000622 027000
120/  001400 105000 073404 123000 073774 000011 000400 126001
140/  073413 116000 073416 000011 002000 005001 061405 062011
160/  055011 173411 000445 126000 001004 026002 000001 000046
200/  000004 005004 026476 123521 007001 005654 013004 075166
220/  147100 015001 002412 016001 004543 017001 004544 020001
240/  004532 000703 027000 001400 130000 073404 133000 173404
260/  001045 120000 001004 073402 144000 113404 041040 001405
300/  033402 056012 003002 151001 171035 141017 041345 133405
320/  111020 000001 000016 000004 013001 002502 023001 002502
340/  000441 024000 001400 153000 047004 073402 000011 001000
360/  041001 023007 173407 040013 002402 073403 000011 001000
400/  023001 041007 073405 131000 045373 000001 000046 000004
420/  004004 026476 140250 006001 003502 007001 003446 014004
440/  026476 140250 016001 003446 017001 002502 000010 002370
460/  000701 015000 001400 174000 010004 100047 030000 137000
500/  146400 100000 100000 137000 033400 077400 000001 000012
520/  000004 000010 002500 000644 005000 001400 040000 005005
540/  121400 000001 000012 000004 000010 003476 000644 010000
560/  001400 037000 013007 000400 000011 017000 070000 000001
600/  000012 000004 000010 003510 000632 005000 001400 044000
620/  000007 121001 000001 000012 000004 000010 004534 000604
640/  012000 001400 056000 043011 046522 046104 050107 041101
660/  047124 177523 000001 000012 000004 000010 004552 000566
700/  027000 001400 065000 073411 000011 000400 072001 000011
720/  020000 020040 020040 020052 052512 045516 042440 051122
740/  051117 005015 073400 000011 000400 111001 056011 000001
760/  000032 000004 003004 026476 123521 005001 004564 022004

BLOCK NUMBER 00061
000/  026476 123521 024001 004622 000635 027000 001400 110000
020/  000011 020000 020040 020040 020052 044524 042515 047455
040/  052125 042440 051122 051117 005015 020000 020040 042040
060/  043105 052501 052114 110440 000001 000056 000003 004666
100/  047514 050117 052040 046511 020105 020075 030061 030060
120/  006460 020012 020040 042040 043105 052501 052114 054040
140/  054454 042040 046511 000605 027000 001400 156000 042411
160/  051516 047511 051516 047440 020106 047514 020127 044527
200/  042116 053517 036440 030440 034062 020054 034064 005015
220/  020040 020040 060104 000001 000056 000003 005002 043105
240/  052501 052114 046040 053517 053440 047111 047504 020127
260/  043117 051506 052105 020123 020075 034461 026060 031040
300/  032460 005015 000654 027000 001400 024000 020012 020040
320/  042040 043105 052501 052114 054040 054454 042040 046511
340/  047105 044523 047117 020123 043117 050040 041511 052524
360/  042522 170040 000001 000056 000003 005116 020075 031061
400/  026070 030440 034062 005015 020040 020040 042504 040506
420/  046125 020124 044520 052103 051125 020105 044527 042116
440/  053517 000707 027000 001400 072000 020012 043117 051506
460/  052105 020123 020075 034461 026060 032440 006465 020012
500/  020040 044440 020106 047101 020131 044103 047101 042507
520/  024454 000001 000056 000003 005232 052040 050131 020105
540/  027131 042440 051514 026105 047040 020056 037055 000040
560/  005340 005416 005475 005550 002414 002416 002420 002422
600/  000527 023000 002000 000400 160032 000412 007034 000413
620/  036436 000413 064040 000413 006042 000405 007044 000405
640/  010046 000405 011050 133405 000001 000056 000003 005300
660/  002424 002426 002430 002432 020040 020040 042440 052116
700/  051105 046040 047517 020120 044524 042515 035040 000040
720/  020040 020040 042440 000556 013000 002000 000400 012004
740/  000405 013006 000405 014010 000405 015012 052405 000001
760/  000056 000003 005346 052116 051105 046040 053517 053440
```

```
BLOCK NUMBER 00062
000/  047111 047504 020127 044504 042515 051516 047511 051516
020/  024040 044443 020130 044443 024531 035040 000416 027000
040/  001400 006000 020013 020000 020040 020040 047105 042524
060/  020122 047514 020127 044527 042116 053517 047440 043106
100/  042523 051524 024040 044443 043117 135461 000001 000056
120/  000003 005462 021440 047511 031106 020051 020072 020066
140/  020040 020040 047105 042524 020122 044520 052103 051125
160/  020105 044504 042515 051516 047511 000711 027000 001400
200/  054000 047013 020123 021450 054111 021440 054511 020051
220/  020072 020000 020040 020040 047105 042524 020122 044520
240/  052103 051125 020105 044527 147116 000001 000056 000003
260/  005576 047504 020127 043117 051506 052105 020123 021450
300/  043117 020061 044443 043117 024462 035040 000040 020040
320/  020040 043440 051040 041505 000431 027000 001400 122000
340/  042413 053111 042105 005015 020000 020040 020040 020114
360/  042522 042503 053111 042105 005015 020000 020040 020040
400/  044520 052103 051125 072505 000001 000011 000003 005712
420/  177040 000001 000012 000004 000010 005721 000415 011400
440/  001400 150400 020013 044504 044507 044524 042532 020104
460/  000460 005000 002000 004000 161000 176013 000001 000047
500/  000003 005742 052040 046511 051505 005015 020000 020040
520/  020040 026530 044504 020115 043117 041440 046105 020114
540/  051511 057440 000001 000004 000010 006007 000726 000000
560/  027000 001400 000003 400 006414 020012 020040 020040 047503
600/  052116 047111 042525 041040 020131 050047 006447 000012
620/  020040 020040 054440 042055 046511 047440 055106 000001
640/  000021 000003 006055 041440 046105 020114 051511 113040
660/  000001 000012 000004 000010 006074 000641 027000 001400
700/  036000 006414 020012 020040 020040 047503 052116 047111
720/  042525 041040 020131 050047 006447 000012 020040 020040
740/  050040 041511 052524 042522 177040 000001 000041 000003
760/  006142 040502 045503 051107 052517 042116 043440 042522

BLOCK NUMBER 00063
000/  026531 042514 042526 020114 051511 132440 000001 000012
020/  000004 000010 006201 000534 027000 001400 100400 006414
040/  000012 020040 020040 025040 040440 045104 051525 020124
060/  044526 042504 027117 041440 047117 044524 052516 020105
100/  054502 023440 154520 000001 000056 000003 006247 006447
120/  000012 020040 020040 046040 053517 053440 047111 047504
140/  020127 040502 045503 051107 052517 042116 046040 053105
160/  046105 044440 000522 005000 001400 146400 051414 123040
200/  000001 000012 000004 000010 006325 000410 026400 001400
220/  152400 006414 000012 016700 176176 005001 006200 103402
240/  005201 000774 006301 016167 006370 000006 004567 000000
260/  000401 000000 000000 006376 000742 012000 002000 000400
300/  174031 002014 037037 050455 000647 177047 010414 000001
320/  000056 000003 006372 006446 006522 020040 020040 020052
340/  044520 020103 051124 047101 046523 051511 044523 047117
360/  052040 046511 026505 052517 020124 051105 000633 007000
400/  002000 000400 023004 000415 051006 047415 000001 000056
420/  000003 006440 047522 006522 000012 020040 020040 020052
440/  044520 020103 051124 047101 046523 051511 044523 047117
460/  045040 047125 020113 042515 051523 000567 027000 001400
500/  043000 040415 042507 042440 051122 051117 005015 020000
520/  020040 025040 050040 041511 052040 040522 051516 044515
540/  051523 047511 020116 047111 071523 000001 000056 000003
560/  006554 043125 044506 044503 047105 020124 050123 041501
600/  020105 051105 047522 006522 000012 016767 003476 003472
620/  016767 173634 003470 004567 000553 027000 001400 111000
640/  000015 002400 145001 020031 144005 142024 055024 173411
660/  000445 132000 001373 073402 170000 133764 004012 140007
700/  115025 140424 007025 124000 000001 000044 000004 002004
720/  073471 056250 004001 014712 005001 002440 006001 012310
740/  007001 012304 010001 004532 022001 012232 000750 027000
760/  001400 134000 150015 177425 041777 173576 177425 176377
```

BLOCK NUMBER 00064
```
000/ 173406 177425 136377 173411 177425 134377 033411 163012
020/ 033406 162012 033406 161012 073406 137011 000001 000034
040/ 000003 006736 000000 000413 014712 002424 002426 012304
060/ 012310 012312 012314 013134 000756 026000 002000 002000
100/ 000404 110424 000472 145010 000431 012012 000405 013014
120/ 000405 142016 000424 144020 000424 145022 000424 146024
140/ 000424 056026 066026 000001 000056 000003 006762 012306
160/ 003500 004532 022767 000001 175534 001002 000167 005270
200/ 022767 000002 175520 001456 004567 000000 000420 012304
220/ 002424 002426 000543 022000 002000 000400 143004 000424
240/ 040006 000407 055010 002011 072040 144410 000440 142044
260/ 000424 012046 000405 013050 032005 000001 000034 000003
300/ 007030 012314 013134 013136 013140 013142 013144 013154
320/ 013146 013150 013152 000620 027000 002000 000400 146004
340/ 000424 056006 000426 057010 000426 060012 000426 061014
360/ 000426 062016 000426 066020 000426 063022 000426 064024
400/ 000426 065026 013426 000001 000056 000003 007054 013156
420/ 012236 004532 022767 000001 175442 001002 000167 005262
440/ 022767 000000 004032 001421 022767 000000 004026 001415
460/ 016701 173302 000530 011000 002000 000400 067004 000426
500/ 117006 000424 055010 035411 000001 000056 000003 007122
520/ 005301 020167 004010 001407 016701 173270 005301 020167
540/ 004000 001401 000404 005367 003114 000167 177424 026767
560/ 003770 173300 002770 000500 027000 001400 074000 073416
600/ 000011 002400 064001 063026 066026 070026 116026 140424
620/ 161035 053407 062160 000000 033412 155162 033407 003020
640/ 001006 173412 003455 000001 000040 000004 003004 062332
660/ 012072 005001 013150 006001 013146 007001 013154 010001
700/ 013160 011001 012234 000510 027000 001400 117000 176016
720/ 101005 005366 173404 173055 076005 003366 173404 170055
740/ 073005 001366 101004 003412 173401 130055 075007 001766
760/ 133405 177012 145005 000001 000040 000003 007304 000721
```

BLOCK NUMBER 00065
```
000/ 004567 000000 000415 012304 002424 002426 014712 012314
020/ 013134 012310 012232 000737 026000 002000 002000 044410
040/ 024571 000426 142014 000424 012016 000405 013020 000405
060/ 145022 000431 146024 000424 056026 000426 144030 000424
100/ 115032 053424 000001 000056 000003 007334 012242 012272
120/ 003500 013206 004532 022767 000001 175156 001002 000167
140/ 005054 016700 002644 070067 173104 160167 002644 005667
160/ 002670 000776 015000 002000 000400 121004 000424 135006
200/ 000424 040010 000407 103012 000426 055014 165011 000001
220/ 000056 000003 007402 160067 002664 022702 000001 001434
240/ 026767 002616 173024 002414 022610 026767 012610 173016 002404
260/ 012704 000005 000167 001602 012704 000006 000635 027000
300/ 001400 024000 073417 075000 173403 070055 173005 002365
320/ 142005 003425 073400 065000 142003 004025 073400 061000
340/ 073403 000011 006400 145001 012031 005405 000001 000024
360/ 000004 021004 063136 035101 023001 014712 024001 002424
400/ 000466 016000 001400 047000 013017 057005 060026 105026
420/ 061026 062026 167026 051026 052027 053027 123427 000001
440/ 000056 000004 002001 002426 003001 013136 004001 013140
460/ 005001 013212 006001 013142 007001 013144 010001 013356
500/ 011001 013522 012001 013524 013001 013526 000545 027000
520/ 001400 061000 054017 015427 001401 140012 165035 140407
540/ 105025 041026 141224 000105 101777 002540 140176 155035
560/ 140407 167025 041026 141224 000105 145777 000001 000022
600/ 000004 002001 013530 010001 013212 021001 013356 000635
620/ 027000 001400 104000 101417 002540 001176 140012 142035
640/ 140007 141155 100007 133562 011020 073405 000011 001000
660/ 053001 105027 073426 000011 003400 053001 151027 000001
700/ 000036 000004 015004 074327 077141 017001 004567 017520
720/ 000401 105737 177560 100375 113701 177562 042701 177600
740/ 022701 000015 001401 010102 105737 177564 100375 110137
760/ 177566 022701 000015 001355 105737 177564 100375 112737
```

```
BLOCK NUMBER 00066
000/  000012  177566  022702  000116  001412  022702  000131  001403
020/  005075  000000  000407  012775  000001  000000  000403  012775
040/  000002  000000  000167  017424  004567  017364  000401  012701
060/  066230  005002  105737  177560  100375  113700  177562  042700
100/  177600  105737  177564  100375  110037  177566  020027  000060
120/  002410  020027  000071  003005  005202  162700  000060  010021
140/  000751  005702  001001  000746  020027  000015  001006  105737
160/  177564  100375  112737  000012  177566  012701  066230  012103
200/  020227  001405  005302  070327  000012  062103  077204
220/  010375  000000  000167  017244  100414  000740  001054  011400
240/  000404  003054  004567  017170  000403  012703  000005  016502
260/  000002  112712  000040  062702  000006  005004  005775  000004
300/  100004  112767  000001  000015  000403  112767  000200  000005
320/  017500  000000  000402  005400  005204  010001  005000  071027
340/  000012  052701  000060  110142  077310  012703  000004  122712
360/  000060  001003  112722  000040  077306  005704  001402  112742
400/  000055  000167  017066  004567  017026  000402  017500  000000
420/  016501  000002  105737  175610  100375  113721  175612  077006
440/  000167  017030  004567  016770  000401  011500  105710  001406
460/  105737  177564  100375  112037  177566  000770  000167  016774
500/  004567  016734  000405  012737  066602  000100  005037  000102
520/  012767  000100  101266  012567  101250  012702  000004  012701
540/  066604  013500  005400  110021  077204  016767  000030  101232
560/  016767  000020  101222  012767  000101  101204  000001  000167
600/  016672  000002  136000  073401  004567  016624  000405  027575
620/  000002  000006  002427  011502  017503  000002  060203  017567
640/  000004  000012  017504  000006  005304  060204  122427  000000
660/  103407  160204  010475  000006  005075  000010  000167  016574
700/  020304  001364  012775  000001  000010  000167  016556  004567
720/  016516  000413  012502  013500  010067  000072  010067  000266
740/  010067  000324  010067  000546  005300  010067  000236  010067
760/  000274  010067  000340  005200  005200  010067  000240  010067

BLOCK NUMBER 00067
000/  000276  013501  005301  010167  000322  013503  005303  060302
020/  005000  010301  071027  000000  010003  010100  010301  013567
040/  000300  013567  000350  012503  012567  000416  005067  000320
060/  012567  000440  005735  100007  112767  000202  000247  012767
100/  000001  000372  000406  112767  000207  000231  012767  000000
120/  000354  012567  000336  005067  000330  012737  000435  067436
140/  012737  000431  067346  005004  010267  000230  012767  000010
160/  000264  010167  000420  000403  012767  000010  000250  116417
200/  067556  000777  116417  067566  000777  162702  000000  005200
220/  005301  000434  162702  000000  005301  000430  162702  000000
240/  005300  005301  000423  005302  005300  000420  062702  000000
260/  005300  005201  000413  062702  000000  005201  000407  062702
300/  000000  005200  005201  000402  005202  005200  005700  002447
320/  005701  002445  022700  000000  002442  022701  000000  002437
340/  121227  000000  000434  005204  042704  177770  110423  005304
360/  042704  177770  020167  000216  003402  010167  000210  005227
400/  000000  020227  000000  001424  116404  067576  005327  000000
420/  001263  052767  000001  000032  000413  005204  000401  005204
440/  042704  177770  005327  000000  001255  052767  000002  000002
460/  012737  000000  000000  016737  177706  000000  022727  000000
500/  000001  001411  005267  000076  016701  000072  070127  000000
520/  005201  010137  000000  000167  015742  012767  005204  177676
540/  012767  005204  177600  012767  000010  177672  000730  004003
560/  010414  014424  021035  007005  013016  017426  002437  003405
600/  000407  001401  002403  002000  004567  015624  000415  005075
620/  000030  012767  000011  000272  005375  000002  017567  000002
640/  000324  017567  000002  000376  005275  000002  017567  000002
660/  000330  017567  000002  000370  005275  000002  017567  000002
700/  000316  017567  000002  000356  005375  000002  012767  000024
720/  000250  012767  000024  000322  012767  000024  000460  012767
740/  000024  000574  017567  000014  000520  017500  000000  005300
760/  066500  000006  016702  000650  012703  003720  005022  005303
```

```
BLOCK NUMBER 00070
000/ 001375 005775 000024 100004 112767 000203 000457 000403
020/ 112767 000206 000447 005775 000026 100004 016767 000602
040/ 000554 000403 016767 000570 000544 016702 000540 010567
060/ 000532 016501 000010 017505 000012 010203 062703 000002
100/ 022712 000000 001412 011204 020023 001411 005304 001374
120/ 021227 000000 002402 000167 000444 010013 005212 005305
140/ 001454 112104 116417 070630 000777 005200 122711 000000
160/ 001766 000743 162700 000000 162702 000000 026702 000416
200/ 101402 010267 000410 000731 162700 000000 000765 162700
220/ 000000 000762 005300 022705 000001 001717 122711 000004
240/ 001736 000713 062700 000000 062702 000000 000706 062700
260/ 000000 000772 062700 000000 000767 016705 000320 010502
300/ 012201 022701 000000 001445 022701 000001 001437 005301
320/ 010200 005004 005003 012067 000266 005203 020301 003011
340/ 022067 000254 101005 014067 000246 010004 062700 000002
360/ 000764 022704 000000 001403 011214 016712 000222 005301
400/ 022701 000000 001403 062702 000002 000742 062705 000000
420/ 000726 005004 005067 000174 005067 000172 005067 000162
440/ 016705 000152 010500 012001 022701 000000 001433 011002
460/ 012203 005203 005301 001403 121327 000000 000771 160203
500/ 112204 042704 177400 060467 000112 005567 000110 005267
520/ 000100 005303 001365 022701 000000 001401 000750 062705
540/ 000000 000740 016705 000044 016775 000046 000016 016775
560/ 000042 000020 016775 000036 000022 000167 014676 016705
600/ 000012 012775 000001 000030 000167 014660 006411 043012
620/ 047514 000000 000000 000000 002400 011017 016425 022442
640/ 070644 074564 030061 004440 005015 041505 047510 054516
660/ 006411 042012 043511 044520 004503 005015 047503 030103
700/ 020063 006411 041412 040510 047111 004463 005015 047101
720/ 042504 031511 006411 005012 051124 047101 043123 051105
740/ 040440 042104 042522 051523 036440 030040 030460 030060
760/ 004460 005015 044510 044107 046040 046511 052111 036440

BLOCK NUMBER 00071
000/ 033060 033465 031061 000014 000000 000000 000000 000000
020/ 000000 000000 000000 000000 000000 000000 000000 000000
040/ 000000 000000 000000 000000 000000 000000 000000 000000
060/ 000000 000000 000000 000000 000000 000000 000000 000000
100/ 000000 000000 000000 000000 000000 000000 000000 000000
120/ 000000 000000 000000 000000 000000 000000 000000 000000
140/ 000000 000000 000000 000000 000000 000000 000000 000000
160/ 000000 000000 000000 000000 000000 000000 000000 000000
200/ 000000 000000 000000 000000 000000 000000 000000 000000
220/ 000000 000000 000000 000000 000000 000000 000000 000000
240/ 000000 000000 000000 000000 000000 000000 000000 000000
260/ 000000 000000 000000 000000 000000 000000 000000 000000
300/ 000000 000000 000000 000000 000000 000000 000000 000000
320/ 000000 000000 000000 000000 000000 000000 000000 000000
340/ 000000 000000 000000 000000 000000 000000 000000 000000
360/ 000000 000000 000000 000000 000000 000000 000000 000000
400/ 000000 000000 000000 000000 000000 000000 000000 000000
420/ 000000 000000 000000 000000 000000 000000 000000 000000
440/ 000000 000000 000000 000000 000000 000000 000000 000000
460/ 000000 000000 000000 000000 000000 000000 000000 000000
500/ 000000 000000 000000 000000 000000 000000 000000 000000
520/ 000000 000000 000000 000000 000000 000000 000000 000000
540/ 000000 000000 000000 000000 000000 000000 000000 000000
560/ 000000 000000 000000 000000 000000 000000 000000 000000
600/ 000000 000000 000000 000000 000000 000000 000000 000000
620/ 000000 000000 000000 000000 000000 000000 000000 000000
640/ 000000 000000 000000 000000 000000 000000 000000 000000
660/ 000000 000000 000000 000000 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000
```

```
BLOCK NUMBER 00072
000/  052122  030455  020061  044514  045516  020040  020040  030126
020/  026464  032060  020101  020040  046040  040517  020104  040515
040/  020120  005015  041122  030103  020063  046056  040504  020040
060/  020040  020040  020040  020040  020040  020040  032062  045055
100/  047101  033455  006470  005012  042523  052103  047511  020116
120/  042101  051104  020040  020040  044523  042532  020040  020040
140/  047105  051124  020131  020040  042101  051104  020040  020040
160/  047105  051124  020131  020040  042101  051104  020040  020040
200/  047105  051124  020131  020040  042101  051104  005015  005015
220/  020056  041101  027123  030011  030060  030060  004460  030060
240/  030061  030060  051411  052105  031460  004440  030060  030060
260/  030060  006411  004412  030060  030061  030060  030011  032066
300/  030467  004462  041122  030103  020063  030011  030460  030060
320/  004460  005015  030011  032466  030467  004462  030060  030460
340/  032063  042411  044103  047117  004531  033060  033465  031061
360/  006411  004412  033060  030066  033464  030011  030060  033461
400/  004464  047503  030103  020063  030011  033066  032060  004466
420/  005015  030011  033066  032062  004462  030060  030460  031064
440/  044411  052116  051501  004503  033060  031066  031064  006411
460/  004412  033060  032066  032060  030011  030060  031460  004466
500/  042507  040504  031460  030011  033066  030064  004464  005015
520/  030011  033066  032064  004462  030060  030060  032063  043411
540/  053111  030132  004463  033060  032066  031064  006411  004412
560/  033060  032066  033067  030011  030060  030461  004460  044504
600/  050107  041511  030011  033066  033464  004466  005015  030011
620/  033066  030066  004466  030060  030460  033060  051411  040503
640/  031516  004440  033060  033066  033060  006411  004412  033060
660/  033466  032061  030011  030060  033466  004462  044103  044501
700/  031516  030011  033066  030467  004466  005015  030011  033466
720/  030066  004466  030460  033066  032067  051411  044520  052503
740/  004463  033060  033067  033060  006411  004412  030061  032460
760/  031060  030011  030060  033460  004466  000000  000000  000000

BLOCK NUMBER 00073
000/  042523  041522  031510  030411  030060  030065  004462  005015
020/  030411  030060  030066  004460  030060  030460  031066  050011
040/  043117  046111  004463  030061  033060  030060  006411  004412
060/  030061  033460  031066  030011  030060  030462  004462  045520
100/  040526  031514  030411  030060  033067  004462  005015  030411
120/  030460  033461  004464  030060  030460  032060  051411  047515
140/  044124  004463  030061  030461  032067  006411  004412  030061
160/  031461  030060  030011  030060  033060  004464  044510  052123
200/  020061  030411  030460  030063  004460  005015  030411  030460
220/  033063  004464  030060  030460  032064  050011  053113  046101
240/  004461  030061  031461  032066  006411  004412  030061  032461
260/  030063  030011  030060  032460  004464  046523  052117  030510
300/  030411  030460  031465  004460  005015  030411  030460  030066
320/  004464  030060  030461  032066  040411  042116  044505  004463
340/  030061  033061  032060  006411  004412  030061  033462  030067
360/  030011  030060  030461  004464  044506  030506  020060  030411
400/  031060  033467  004460  005015  030411  031460  030061  004464
420/  030060  030460  031065  043111  031061  004440  030061
440/  030463  032060  006411  004412  030061  031063  033065  030011
460/  030060  033062  004462  042520  041522  051111  030411  031460
500/  032462  004466  005015  030411  031460  032065  004460  030060
520/  030460  033066  044411  052116  046106  004517  030061  032463
540/  030064  006411  004412  030061  033463  033062  030011  030060
560/  031061  004466  046106  044517  052116  030411  031460  031067
600/  004466  005015  030411  032060  032460  004464  030060  030460
620/  033463  051411  030127  020063  004440  030061  030064  032065
640/  006411  004412  030061  031064  032061  030011  030060  031461
660/  004467  051527  031460  020040  030411  032060  030462  004464
700/  005015  030411  032060  032463  004464  030060  032460  032064
720/  054011  044515  030124  004463  030061  031464  032065  006411
740/  004412  030061  030465  030062  030011  030060  032060  004460
760/  044507  030126  020063  000011  000000  000000  000000  000000
```

BLOCK NUMBER 00074
000/ 030061 030465 030062 006411 004412 030061 030465 030066
020/ 030011 030060 032462 004465 042522 030123 020063 030411
040/ 032460 033061 004460 052107 030124 020063 030411 032460
060/ 033461 004460 042507 030124 020063 030411 032460 033461
100/ 004466 005015 030411 032460 031464 004466 030060 030060
120/ 031065 051411 053101 042522 004507 030061 032065 033063
140/ 051011 051505 042522 004507 030061 032065 031067 006411
160/ 004412 030061 032465 030061 030011 030060 031060 004462
200/ 040502 041504 046101 030411 032460 030465 004460 005015
220/ 052012 040522 051516 042506 020122 042101 051104 051505
240/ 020123 020075 030060 030061 030060 006411 044012 043511
260/ 020110 044514 044515 020124 020075 030061 032465 031063
300/ 000014 000000 000000 000000 000000 000000 000000 000000
320/ 000000 000000 000000 000000 000000 000000 000000 000000
340/ 000000 000000 000000 000000 000000 000000 000000 000000
360/ 000000 000000 000000 000000 000000 000000 000000 000000
400/ 000000 000000 000000 000000 000000 000000 000000 000000
420/ 000000 000000 000000 000000 000000 000000 000000 000000
440/ 000000 000000 000000 000000 000000 000000 000000 000000
460/ 000000 000000 000000 000000 000000 000000 000000 000000
500/ 000000 000000 000000 000000 000000 000000 000000 000000
520/ 000000 000000 000000 000000 000000 000000 000000 000000
540/ 000000 000000 000000 000000 000000 000000 000000 000000
560/ 000000 000000 000000 000000 000000 000000 000000 000000
600/ 000000 000000 000000 000000 000000 000000 000000 000000
620/ 000000 000000 000000 000000 000000 000000 000000 000000
640/ 000000 000000 000000 000000 000000 000000 000000 000000
660/ 000000 000000 000000 000000 000000 000000 000000 000000
700/ 000000 000000 000000 000000 000000 000000 000000 000000
720/ 000000 000000 000000 000000 000000 000000 000000 000000
740/ 000000 000000 000000 000000 000000 000000 000000 000000
760/ 000000 000000 000000 000000 000000 000000 000000 000000

BLOCK NUMBER 00075
000/ 002551 145001 012033 013007 014007 013407 000001 000054
020/ 001670 003432 005202 010267 012724 004567 064340 000403
040/ 014624 006734 004500 004567 064524 000401 006676 012700
060/ 015712 066700 001504 020037 000631 026000 157000 001003
100/ 162360 141402 055035 002003 133412 055012 173405 053040
120/ 033405 033402 050012 073405 144011 002176 020001 145007
140/ 044033 045011 171411 000001 000054 002004 004567 077354
160/ 000405 004510 004512 004502 005512 005524 016701 003462
200/ 005301 016700 001440 060300 020100 003401 005204 006303
220/ 160300 000717 026000 025000 040004 000440 102004 073412
240/ 060020 073425 066011 001550 112001 075431 040016 073411
260/ 160011 000550 052401 142016 005013 073403 152011 015150
300/ 000001 000054 002120 000401 007204 000000 006203 005303
320/ 010367 002350 000644 004567 101712 000404 003412 005536
340/ 005542 005532 022767 000001 003346 001002 000714 026000
360/ 073000 073404 170000 173406 001045 155000 001006 073402
400/ 001000 173407 041025 043007 173404 152025 111010 173404
420/ 000425 027000 073422 164000 113412 000001 000054 002234
440/ 004567 101616 000404 003412 005537 005535 005532 022767
460/ 000001 003252 001002 000167 003264 022767 000002 003236
500/ 001002 000167 003306 000512 026000 141000 153404 006055
520/ 041004 001407 033402 054012 003004 140001 177035 140003
540/ 041345 033407 045020 073404 071011 001205 041001 023011
560/ 173411 130013 000001 000054 002350 002074 001405 004567
600/ 102542 000402 004446 003502 016700 001020 004567 102574
620/ 000402 005550 005532 005767 003122 001023 142767 000200
640/ 000707 026000 007000 054005 173406 052255 047406 007406
660/ 173403 046255 044406 014406 173403 042255 040006 001006
700/ 073402 021000 073401 035000 016006 073576 001000 000001
720/ 000054 002464 003122 004567 101664 000404 015712 003424
740/ 003426 005532 005767 003022 001402 000167 004612 000167
760/ 000374 004567 063660 000402 004476 000607 026000 055000

```
BLOCK NUMBER 00076
000/  024005 140011 136035 033401 142020 033400 142020 140000
020/  001345 033400 036020 140000 125035 140001 001345 033400
040/  060020 141000 024025 105411 000000 000054 002600 012267
060/  001642 016703 000624 016704 000622 012201 005301 006301
100/  006301 006301 062701 004324 012100 005300 010067 000132
120/  010067 000162 000664 026000 123000 040005 000344 013413
140/  000040 006400 033407 160020 073423 166011 001546 112001
160/  000431 040016 073411 060011 000547 165401 000015 040000
200/  002024 000001 000054 002714 005300 010067 000064 010067
220/  000076 162100 005400 020027 000000 003415 010067 011660
240/  004567 063274 000403 014624 007066 004500 004567 000524
260/  026000 171000 030005 000547 020001 000016 141400 000045
300/  001000 173405 012020 142000 000045 001000 033405 003021
320/  140400 001035 053401 000160 140400 177545 000001 000054
340/  003030 000000 062701 015712 012700 055714 112120 077302
360/  012703 000000 062701 000000 077407 004567 101272 000404
400/  055714 003434 003436 005532 000561 026000 037000 173406
420/  014013 001005 073403 110000 173410 155012 115402 140002
440/  134035 073400 022011 001204 064001 055013 173413 175013
460/  006404 173402 077705 000001 000054 003144 000200 002400
500/  126767 002374 002362 001417 126767 002364 002353 001405
520/  000167 002356 077026 000167 002640 004567 063236 000401
540/  006632 000771 026000 105000 073406 123000 073774 111011
560/  000546 126001 073415 116000 073416 110011 002201 005001
600/  061407 062013 055013 173413 000445 126000 001004 016002
620/  000001 000054 003260 000167 002266 022767 000002 002240
640/  001002 000167 002310 020227 003502 001003 005067 001134
660/  000406 016722 007762 162702 003502 010267 000621 023000
700/  153000 047006 073402 073011 001203 041001 023011 173411
720/  040013 002402 073403 063011 001203 023001 041011 073407
740/  131000 061773 000001 000030 003370 023420 000200 000060
760/  000276 000315 000200 000200 000276 000067 000602 004000

BLOCK NUMBER 00077
000/  040000 005007 123000 000001 000016 004476 000026 000001
020/  000002 000036 000563 004000 044000 000011 122401 000001
040/  000022 005534 051106 042115 043514 040520 052102 051516
060/  000402 026000 065000 073413 133011 000541 072001 000013
100/  020000 020040 020040 020052 052512 045516 042440 051122
120/  051117 005015 073400 114011 000541 111001 045413 000001
140/  000054 005620 000000 020040 020040 025040 052040 046511
160/  026505 052517 020124 051105 047522 006522 000012 020040
200/  020040 042504 040506 046125 020124 000624 026000 133000
220/  046013 047517 020120 044524 042515 036440 030440 030060
240/  030060 005015 020040 020040 042504 040506 046125 020124
260/  026130 020131 044504 104115 000001 000054 005734 047105
300/  044523 047117 020123 043117 046040 053517 053440 047111
320/  047504 020127 020075 031061 026070 032040 006470 020012
340/  020040 042040 000543 026000 001000 042414 040506 046125
360/  020124 047514 020127 044527 042116 053517 047440 043106
400/  042523 051524 036440 030440 030071 020054 030062 006465
420/  127412 000001 000054 006050 020040 020040 042504 040506
440/  046125 020124 026130 020131 044504 042515 051516 047511
460/  051516 047440 020106 044520 052103 051125 020105 000763
500/  026000 047000 036414 030440 034062 020054 031061 006470
520/  020012 020040 042040 043105 052501 052114 050040 041511
540/  052524 042522 053440 047111 047504 145127 000001 000054
560/  006164 047440 043106 042523 051524 036440 030440 030071
600/  020054 032465 005015 020040 020040 043111 040440 054516
620/  041440 040510 043516 026105 000454 115000 020014
640/  054524 042520 054440 020056 046105 042523 020054 027116
660/  026440 020076 160000 007014 036415 064015 006015 007007
700/  010007 011007 045007 000001 000054 006300 003424 003426
720/  003430 003432 020040 020040 042440 052116 051105 046040
740/  047517 020120 044524 042515 035040 000040 020040 020040
760/  042440 000551 026000 163000 047014 042524 020122 047514
```

```
BLOCK NUMBER 00100
000/ 020127 044527 042116 053517 042040 046511 047105 044523
020/ 047117 020123 021450 054111 021440 054511 020051 010472
040/ 000001 000054 006414 000040 020040 020040 042440 052116
060/ 051105 046040 053517 053440 047111 047504 020127 043117
100/ 051506 052105 020123 021450 047511 030506 000676 026000
120/ 031000 020015 044443 043117 024462 035040 000040 020040
140/ 020040 042440 052116 051105 050040 041511 052524 042522
160/ 042040 046511 047105 044523 146117 000001 000054 006530
200/ 051516 024040 044443 020130 044443 024531 035040 000040
220/ 020040 020040 042440 052116 051105 050040 041511 052524
240/ 042522 053440 047111 000721 026000 077000 042015 053517
260/ 047440 043106 042523 051524 024040 047443 030506 021440
300/ 047511 031106 020051 020072 020000 020040 020040 020107
320/ 042522 016103 000001 000054 006644 044505 042526 006504
340/ 000012 020040 020040 046040 051040 041505 044505 042526
360/ 006504 000012 020040 020040 050040 041511 052524 042522
400/ 000570 003400 145000 020015 000401 010400 150400 020015
420/ 044504 044507 044524 042532 020104 000463 022400 161000
440/ 020015 044524 042515 006523 000012 020040 020040 054040
460/ 042055 046511 047440 020106 042503 046114 044440 020123
500/ 000542 026000 004567 004730 000406 005075 000012 017567
520/ 000004 000024 017501 000002 005301 016502 000006 061201
540/ 016203 000002 161203 122127 000000 101406 077304 012775
560/ 000001 000012 000167 004704 161501 010175 000010 000167
600/ 004672 004567 004632 000415 017500 000014 067500 000016
620/ 006200 017501 000002 070100 010100 067500 000006 061500
640/ 010075 000022 016501 000012 017502 000010 167502 000006
660/ 005202 010275 000026 112021 077202 017501 000014 070175
700/ 000002 010100 017501 000006 067501 000010 006201 060100
720/ 061500 010075 000024 016501 000020 017502 000016 167502
740/ 000014 005202 010275 000030 111021 067500 000002 077204
760/ 000167 004510 004567 004450 000407 005075 000014 011567

BLOCK NUMBER 00101
000/ 000154 013500 005300 011567 000146 012501 013567 000154
020/ 003463 012503 012502 011567 000034 005035 012704 000001
040/ 122111 101005 005204 005300 001373 005304 005200 005767
060/ 000112 001431 005237 000000 010423 005012 114112 062702
100/ 000002 005201 005367 000064 005204 005300 001425 122111
120/ 103373 005767 000046 001407 010423 005012 114112 062702
140/ 000002 005201 000737 005235 004567 000022 000402 000000
160/ 000000 162705 000016 000705 000167 004300 046511 004567
200/ 004236 000402 013501 012500 005301 111002 042702 177400
220/ 010203 111002 042702 177400 116004 000001 042704 177400
240/ 060403 006203 060203 006203 110320 005301 001361 111004
260/ 042704 177400 060403 006203 060304 006204 110410 000167
300/ 004172 004567 004132 000404 013500 012501 013502 011503
320/ 005023 005302 001375 005745 013502 005302 012503 005004
340/ 152104 020402 101401 010204 006304 060304 005214 005300
360/ 001366 000167 004106 004567 004046 000405 011567 000114
400/ 013500 005300 011567 000106 012501 013502 003444 012503
420/ 011567 000032 005035 012704 000001 022111 003005 005204
440/ 005300 001373 005304 005200 005702 001415 005237 000000
460/ 010423 005302 005204 005300 001416 022111 002373 005702
500/ 001402 010423 000754 004567 000020 000402 000000 000000
520/ 162705 000012 000725 000167 003742 004567 003702 000402
540/ 013501 012500 005301 005002 010203 011002 066003 000002
560/ 006203 060203 006203 010320 005301 001366 006203 060310
600/ 006210 000167 003666 004567 003626 000420 005075 000036
620/ 017501 000000 005301 005000 071075 000002 010167 000762
640/ 016767 000756 000756 016767 000752 000740 010067 000746
660/ 016767 000742 000742 016767 000736 000722 005067 000732
700/ 005067 000736 005067 000734 005067 000732 005067 000700
720/ 005001 005002 017503 000010 117567 000006 000712 016500
740/ 000006 010567 000644 112004 020427 000010 002402 000167
760/ 000604 116417 102602 000777 005267 000636 066701 000616
```

BLOCK NUMBER 00102
```
000/ 004767 000646 000470 005267 000630 066701 000600 005302
020/ 004767 000626 004767 000716 000456 005267 000606 004767
040/ 000704 000451 005267 000576 166701 000542 005202 004767
060/ 000614 004767 000660 000437 005267 000536 166701 000516
100/ 004767 000572 000430 005267 000530 166701 000500 005302
120/ 004767 000552 004767 000572 000416 005267 000506 004767
140/ 000560 000411 005267 000476 066701 000442 005202 004767
160/ 000470 004767 000534 020327 000001 003003 116705 000450
200/ 000401 111005 160504 005704 100002 062704 000010 022704
220/ 000002 001411 022704 000003 001406 005303 005703 001402
240/ 000167 177502 000403 005267 000346 000767 016705 000332
260/ 016775 000334 000034 016775 000330 000012 016775 000324
300/ 000014 016775 000320 000016 016775 000314 000020 006202
320/ 060201 010175 000022 016703 000300 066703 000306 010375
340/ 000024 016703 000274 066703 000274 010375 000026 005001
360/ 005002 166767 000256 000242 166767 000252 000244 005767
400/ 000230 100004 005467 000222 012701 000002 005767 000222
420/ 100004 005467 000214 012702 000002 005067 000202 004567
440/ 001100 000402 102640 102642 012700 102634 075020 004567
460/ 001246 000402 102640 102642 026767 000136 000144 001423
500/ 026767 000126 000134 002407 005201 010175 000030 016775
520/ 000110 000032 000416 062702 000002 010275 000030 016775
540/ 000100 000032 000406 012775 000000 000030 012775 000000
560/ 000032 000167 002706 016705 000020 012775 000001 000036
600/ 000770 003400 013021 023440 033061 001160 053001 105031
620/ 073430 045011 003560 053001 143431 000001 040265 002201
640/ 014212 014626 014532 014556 014602 005267 177736 026767
660/ 177742 177730 002003 016767 177722 177730 000207 005367
700/ 177712 026767 177714 177704 003403 016767 177676 177702
720/ 000207 005267 177670 026767 177676 177662 002003 016767
740/ 177654 177664 000207 005367 177644 026767 177650 177636
760/ 003403 016767 177630 177636 000207 004567 002442 000404
```

BLOCK NUMBER 00103
```
000/ 005067 000072 013567 000070 013567 000066 013567 000064
020/ 004567 000516 000402 103076 103100 004567 000504 000402
040/ 103102 103104 012700 103076 075030 004567 000652 000402
060/ 103102 103104 016775 000014 000000 000167 002376 054031
100/ 000001 000054 011070 004567 002326 000405 013500 070035
120/ 010067 000124 010167 000122 004567 000406 000402 103250
140/ 103252 163501 005600 163500 010067 000100 010167 000076
160/ 004567 000356 000402 103254 103256 012700 103250 075030
200/ 012702 000002 012060 177772 077203 012700 103244 075020
220/ 004567 000504 000402 103250 103252 016775 000014 000000
240/ 000167 002230 041710 000000 004567 067544 000407 014530
260/ 004567 002154 000405 013567 000242 005067 000234 004567
300/ 000240 000402 103532 103534 012700 103526 075020 013567
320/ 000216 005067 000210 004567 000210 000402 103536 103540
340/ 075000 016767 000172 000164 016767 000162 000154 004567
360/ 000346 000402 103536 103540 016775 000144 000002 016767
400/ 000132 000134 016767 000122 000124 162700 000004 075020
420/ 013567 000110 005067 000102 004567 000106 000402 103532
440/ 103534 162700 000004 075030 012767 000012 000056 005067
460/ 000050 004567 000054 000402 103532 103534 162700 000004
500/ 075020 004567 000222 000402 103536 103540 016775 000020
520/ 000002 000167 001746 040265 002201 026727 001604 000010
540/ 002406 004567 001672 000402 005775 000000 001003 005775
560/ 000002 001460 005001 017502 000000 017503 000002 005702
600/ 100006 005102 005103 062703 000001 005502 005201 005004
620/ 012700 000230 020227 000200 002010 073227 000001 005204
640/ 032702 000200 001772 160400 000410 032702 177400 001404
660/ 073227 177777 005204 000771 060400 042702 000200 072027
700/ 000007 074002 005701 001402 052702 100000 010275 000000
720/ 010375 000002 000167 001544 004567 001504 000402 005775
740/ 000000 001003 005775 000002 001440 005001 017502 000000
760/ 017503 000002 005702 100003 042702 100000 005201 010200
```

```
BLOCK NUMBER 00104
000/ 042700 100177 040002 052702 000200 072027 177771 162700
020/ 000230 073200 005701 001405 005102 005103 062703 000001
040/ 005502 010275 000000 010375 000002 000167 001416 004567
060/ 001356 000404 017500 000000 016567 000002 000010 004567
100/ 001020 000402 104212 000000 004567 001056 000402 104214
120/ 104210 005767 000062 001010 142767 000200 000056 126775
140/ 000052 000004 001403 000406 077026 000411 005075 000006
160/ 000167 001310 012775 000001 000006 000167 001276 012775
200/ 000002 000006 000167 001264 173402 000001 100000 004567
220/ 001216 000404 017500 000000 004567 000736 000402 104354
240/ 104350 005767 000102 001010 142767 000200 000076 126775
260/ 000072 000002 001403 000416 077021 000421 016567 000004
300/ 000010 004567 000614 000402 104352 000000 005075 000006
320/ 000167 001150 012775 000001 000006 000167 001136 012775
340/ 000002 000006 000167 001124 142004 000001 145000 004567
360/ 001056 000404 011567 000304 117567 000002 000425 117567
400/ 000004 000420 005075 000006 012700 104766 016767 073524
420/ 000362 105710 001430 004567 000546 000402 105010 105012
440/ 005767 000346 001010 142767 000200 000334 126720 000330
460/ 001001 000757 005300 005367 000312 001353 012775 000010
500/ 000006 000167 000766 012767 000005 000272 004567 000402
520/ 000402 105006 105020 012700 104772 004767 000270 004567
540/ 000436 000402 105010 105012 005767 000236 001025 142767
560/ 000200 000224 126767 000220 000203 001423 126767 000210
600/ 000174 001405 012775 000002 000006 000167 000656 012775
620/ 000004 000006 000167 000644 012775 000001 000006 000167
640/ 000632 005002 005003 156702 000151 156703 000146 070302
660/ 010367 000130 004567 000232 000402 105014 000000 005067
700/ 000114 016700 177766 005001 112001 060167 000100 005367
720/ 000072 001371 116767 000066 000057 012767 000001 000046
740/ 004567 000156 000402 105006 105011 012700 104777 004767
760/ 000044 000167 000506 050122 000111 050122 043400 051105

BLOCK NUMBER 00105
000/ 042120 001000 016700 002072 016701 002070 071067 002066
020/ 050124 015123 000402 105710 001417 004567 000142 000402
040/ 105010 105012 005767 177742 001010 142767 000200 177730
060/ 126720 177724 001010 000757 000207 005726 012775 000001
100/ 000006 000167 000366 005726 012775 000002 000006 000167
120/ 000352 004567 000312 000402 017501 000000 016500 000002
140/ 105737 175614 100375 112037 175616 005301 001371 000167
160/ 000312 113767 175612 000246 000205 012767 000402 000020
200/ 004567 000234 000402 012737 105404 000300 005037 000302
220/ 113767 175612 000210 005067 000176 012767 000005 000174
240/ 012767 023420 000164 042737 000100 175610 052737 000100
260/ 175610 022767 000001 000140 001420 005367 000134 022767
300/ 000000 000126 001366 022767 000000 000120 001420 012767
320/ 023420 000106 005367 000104 000754 116775 000100 000000
340/ 005075 000002 012767 113767 177646 000167 000116 042737
360/ 000100 175610 012775 000001 000002 012767 113767 177620
400/ 000167 000070 042737 000100 175610 113767 175612 000016
420/ 012767 000001 000002 000002 014624 013220 004500 004567
440/ 010446 010346 010246 010146 010046 010504 016605 000012
460/ 022524 001001 000114 000167 000020 000205 012600 012601
500/ 012602 012603 012604 012605 000205 010546 005046 010616
520/ 062716 000002 012746 001777 000004 000777 041515 042110
540/ 020040 174040 000001 000014 013212 041515 006524 000012
560/ 000530 005000 113000 000026 005015 031000 000001 000010
600/ 013312 000620 000606 005000 103000 177430 007377 045400
620/ 000001 000012 014626 000003 000012 000471 005000 126000
640/ 072431 107476 026302 000001 000012 014664 042621 020000
660/ 000462 026000 136000 073432 062011 000522 146001 173432
700/ 170012 073773 150000 020351 020040 020040 020052 047515
720/ 042522 052040 040510 020116 030064 020060 042103 000001
740/ 000023 015342 040510 047111 041440 042117 051505 005015
760/ 025400 000001 000054 015360 004567 051060 000401 015400
```

What is claimed is:

1. A method of automatically analyzing red blood cells in a sample of a patient's blood for an anemia or other red blood cell disorder comprising the steps of:

examining the red blood cells in patient's blood sample, measuring characteristics of blood cells and classifying normal and abnormal cells into a plurality of mutually exclusive subpopulations, determining parameters for the red blood cells in respective ones of said subpopulations, and comparing parameters of respective ones of the patient's red blood cell subpopulations with predetermined reference characteristic values of red blood cell subpopulations from a person having a known kind of anemia or other red blood cell disorder, and reporting the results of the comparison to provide an indication of a specific anemia or red blood cell disorder or the lack thereof.

2. A method in accordance with claim 1 in which the step of classifying the red blood cells includes the step of classifying spherocytic cells, target cells and elongated cells into different subpopulations and in which the comparing step comprises a comparison of at least one parameter for each of the spherocytic, target and elongated cell subpopulations to a predetermined reference characteristic value for similar cell subpopulations of persons having recognized kinds of anemias.

3. A method in accordance with claim 1 in which the classifying step comprises separating biconcave red blood cells having a substantially round exterior and a central pallor of a predetermined configuration into a cell subpopulation constituting the major subpopulation of cells.

4. A method in accordance with claim 3 in which the determining step includes generating parameters indicating the variation of cell size and of cell hemoglobin for said subpopulation of cells having the biconcave cells.

5. A method in accordance with claim 4 including the steps of generating a mean cell size parameter, generating a mean cell hemoglobin parameter, and generating first and second eigen parameters for said subpopulation of cells having biconcave cells therein.

6. A method in accordance with claim 1 in which the step of determining predetermined parameters includes generating a parameter of dispersion of distribution of cells in at least one subpopulation and determining a parameter with respect to variation in size of central pallors for the red blood cells.

7. A method in accordance with claim 6 in which the step of generating parameters for the subpopulations comprises generating a mean cell hemoglobin parameter, a mean cell size parameter, and the number of cells in the subpopulation relative to the total number of cell parameters.

8. A method in accordance with claim 7 in which the step of generating parameters comprises generating a skewness parameter for said subpopulation having said biconcave cells therein.

9. A method in accordance with claim 1 in which the determining step comprises generating a plurality of parameters to define a patient's blood and in which the resemblance of the patient's blood to reference characteristic values for a specific anemia or blood cell disorder, if any, is reported.

10. A method in accordance with claim 1 in which the determining step comprises generating multivariate distributions of the cells in said subpopulations in accordance with the variables of cell size, cell hemoglobin content, and central pallor, and the comparing step comprises comparing descriptors of these distributions to predetermined distribution descriptors for recognized kinds of anemias.

11. A method in accordance with claim 1 in which the reporting step comprises reporting for said cell subpopulation having normal cells therein values of the mean cell size, the mean cell hemoglobin, and the amount of bivariate dispersion thereof.

12. A method in accordance with claim 11 in which the reporting step comprises reporting out the mean cell size and mean cell hemoglobin for the abnormal cell subpopulations of spherocytic cells, elongated cells, irregular cells and target cells, and further comprises reporting out the relationship of the patient's blood sample to known anemias including the iron deficient anemia, chronic disease anemia, B-thalassemia, megaloblastic, hemoglobin SS, hemoglobin SC, and spherocytic anemia.

13. A method of automatically analyzing red blood cells in a sample of a patient's blood comprising the steps of:

examining the red blood cells in a patient's blood sample, measuring characteristics of the red blood cells, determining parameters of the dispersion of the distribution of the measured characteristics of said red blood cells, and reporting on said parameters to provide a description of the blood.

14. A method of automatically analyzing red blood cells in accordance with claim 13 in which the step of examining the red blood cells includes the step of segregating individual red blood cells into mutually exclusive subpopulations and in which the step of reporting on said parameters includes the step of reporting the parameters of dispersion of distribution of one of said subpopulations of red blood cells.

15. A method in accordance with claim 13 including the further step of comparing the parameters of the dispersion of distribution of the patient's blood to reference characteristic values for a specific anemia or blood disorder and reporting the results of said comparison.

16. A method in accordance with claim 13 in which the step of determining said parameters includes the step of determining the skewness of said distribution with respect to a measured characteristic and in which said reporting on said parameters includes reporting an indication of said skewness.

17. A method in accordance with claim 13 in which the step of measuring cell characteristics includes the steps of measuring red cell size and red cell hemoglobin and in which the determining step includes determining the parameters of dispersion of distribution of the red blood cells with respect to red blood cell size and hemoglobin content.

18. A method in accordance with claim 13 in which the step of measuring of characteristics includes the step of measuring the size of the central pallors of red blood cells and in which the determining of parameters step includes determining the dispersion of distribution with respect to central pallor size.

19. A method in accordance with claim 18 in which the step of determining the parameters of dispersion of distribution with respect to central pallor size includes the step of determining the standard deviation thereof.

20. A method of automatically analyzing red blood cells in a sample of a patient's blood for an anemia or blood cell disorder, said method comprising the steps of:
  examining the red blood cells in a patient's blood sample,
  measuring characteristics of the red blood cells,
  generating a plurality of measured properties from said measured characteristics to define a patient's blood,
  comparing the resemblance of the patient's blood to reference characteristic values for a specific anemia or blood cell disorder, and reporting with respect to the results of said comparison.

21. A method in accordance with claim 20 in which the step of examining the red blood cells includes the step of segregating individual blood cells into mutually exclusive subpopulations and in which the step of generating a plurality of measured properties includes the generating of parameters for at least one of said subpopulations.

22. A method in accordance with claim 20 in which the step of generating a plurality of measured properties includes the step of determining parameters of disperion of the distribution of the measured characteristics for said red blood cells, and in which the patient's dispersion of distribution is compared to reference characteristic values for a specific anemia or blood disorder.

23. A method in accordance with claim 20 in which the step of measuring characteristics of the red blood cells includes the step of measuring the size of the central pallors of red blood cells and in which the step of generating a plurality of measured properties includes the step of determining the dispersion of distribution with respect to central pallor size.

24. A method in accordance with claim 20 in which the step of generating a plurality of measured properties includes the steps of determining the dispersion of distribution with respect to a measured characteristic of the red blood cells and includes the step of determining the skewness of said distribution.

25. A method in accordance with claim 20 in which the step of measuring cell characteristics includes the step of measuring cell size and cell hemoglobin content and in which the generating of a plurality of measured properties step includes generating parameters of dispersion of distribution of the red blood cells with respect to cell size and hemoglobin content.

26. A method of automatically analyzing red blood cells in a sample of a patient's blood comprising the steps of:
  examining the red blood cells in a patient's blood sample;
  measuring characteristics of the red blood cells;
  classifying the cells into a plurality of mutually exclusive subpopulations including a normal and abnormal subpopulation;
  determining subpopulation parameters including the dispersion of the distribution of at least one of said subpopulations;
  and reporting on the results of the dispersion of distribution as a description of the blood.

27. A method in accordance with claim 26 including the step of comparing the parameters of the dispersion of distribution of said subpopulation of the patient's blood to reference characteristic values for a specific anemia or blood disorder;
  and reporting the results of said comparison.

28. A method in accordance with claim 26 in which the step of determining said parameters includes the step of determining the skewness of the distribution with respect to a measured characteristic for all of the red blood cells;
  and in which a reporting is made of the indication of said skewness.

29. A method in accordance with claim 26 in which the step of measuring of the characteristics of the red blood cells includes a measuring of the cell size and hemoglobin content;
  and in which a report is made of the dispersion of the distribution with respect to cell size and hemoglobin content.

30. A method in accordance with claim 26 in which the step of measuring characteristics of the red blood cells includes the step of measuring the size of the central pallors of red blood cells;
  and in which a report is made of the dispersion of distribution of the pallor size for the said red blood cells.

31. A method of automatically and rapidly analyzing cells on a support, said method comprising the steps of:
  producing an optical image on an imaging means of a field of the cells on the support;
  converting the image into a point by point distribution representative of the image;
  converting each point into a digital signal;
  controlling said imaging means by a first processing means so that a plurality of fields may be imaged on said imaging means;
  analyzing the digital signals of each field of the cells imaged by a second processing means and measuring characteristics of the digitized signals for predetermined red blood cell characteristics;
  and reporting parameters relating to the measured characteristics of the cells analyzed.

32. A method of automatically and rapidly analyzing cells on a slide comprising the steps of:
  producing a first optical image on an imaging means of a field of the cells on the slide;
  converting the image into a point by point distribution representative of the image;
  converting each point into a digital signal with a digitizing means;
  controlling said imaging means by a first processing means so that an additional field may be imaged;
  analyzing the digital signals of each field of the cells imaged by a second processing means for a plurality of cell features;
  synchronizing the first processing means with the digitizing means so that the first processing means may cause an additional field to be imaged after the first image is digitized.

33. A method of analyzing with apparatus including an optical imaging means controlled by a first processing means and at least one additional processing means for measuring cell characteristics, said method comprising the steps of:
  producing a first optical image on said imaging means and digitizing said image to produce digital signals under the control of said first processing means,
  measuring characteristics of the cells from the digitized image signals in one of said additional processing means and analyzing the measured characteristics while said first processing means is controlling the imaging means and producing another image for cell measuring and analyzing,
  transferring information concerning said analyzed and measured characteristic from one of said additional processing means to said first processing means for storing therein, and controlling the imaging means by said first processing means to transfer digitized image signals to one of said additional processing means.

34. A method in accordance with claim 33 in which a plurality of additional processing means are provided and including the step of transferring digital signal images to a second one of said additional processing means while a first one of said additional processing means is still measuring and analyzing characteristics from a previous image so that a plurality of images may be in process simultaneously.

35. A method of automatically testing blood for abnormalities by analyzing red blood cells having quantifiable features in a blood specimen, said method comprising the steps of identifying at least one subpopulation of the red blood cells in said specimen, determining a distribution of the red blood cells for said subpopulation with respect to a plurality of the quantifiable features of the red blood cells; and reporting parameters relating to said distribution to provide an indication of a blood abnormality or a lack thereof.

36. A method in accordance with claim 35 in which the step of determining a distribution comprises a determining of cell size and cell hemoglobin and the distribution is a bivariate distribution with respect to the two quantifiable features of cell size and cell hemoglobin.

37. A method for automatically testing blood for abnormalities by analyzing red blood cells having quantifiable features in a blood specimen, said method comprising the steps of identifying at least one subpopulation of the red blood cells, determining a distribution of the red blood cells of said subpopulation with respect to a plurality of the quantifiable features of the red blood cells including the size of the red blood cells and the hemoglobin content of the red blood cells, and reporting parameters relating to said distribution including the mean cell size, mean cell hemoglobin content, and the dispersion of the distribution relative to the size and hemoglobin content of the red blood cells.

38. A method for automatically classifying blood and its relationship to recognized categories of anemia wherein a sample of red blood cells having quantifiable features is analyzed, said method comprising the steps of: identifying at least one defined subpopulation of red blood cells, determining the proportion of said subpopulation in said sample, and comparing said proportion to the proportion of a similarly defined subpopulation in a sample from a recognized category of anemic red blood cells.

39. The method of claim 38 further comprising determining a distribution of the red blood cells of said subpopulation with respect to a plurality of the quantifiable features of the red blood cells and comparing parameters relating to the distribution of the subpopulation to the parameters of the distribution of the similarly defined subpopulation in the sample of anemic red blood cells with respect to the same plurality of quantifiable features.

40. A method for automatically classifying blood and its relationship to recognized categories of anemias wherein a sample of red blood cells having quantifiable features is analyzed, said method comprising the steps of identifying at least one defined subpopulation of red blood cells, determining a distribution of the red blood cells of the subpopulation with respect to a plurality of the quantifiable features of the red blood cells and comparing parameters of the distribution to the parameters of a distribution of a similarly defined subpopulation in a sample from a recognized category of anemic red blood cells.

41. A method for automatically classifying blood and its relationship to recognized categories of anemias wherein a sample of red blood cells having quantifiable features is analyzed, said method comprising determining the average of a plurality of said quantifiable features including the pallor size from said sample and comparing said averages to averages of the same quantifiable features of a sample from a recognized category of anemic red blood cells.

42. The method of claim 41 further comprising the step of determining a distribution of the red blood cells of the sample with respect to at least one of the quantifiable features, determining parameters relating to said distribution and comparing said parameters to the parameters of the distribution of a sample from a recognized category of anemic red blood cells.

43. A method for automatically identifying target cells in a sample of red blood cells comprising:
determining a first cross-sectional profile of a red blood cell and determining a second cross-sectional profile in a direction substantially transverse to said first profile, each of said profiles relating to the thickness of the red blood cell at points along each cross section and defining relative maxima and minima; and
detecting the existence of three relative maxima and two relative minima on either profile.

44. The method of claim 43 including the further step of comparing the two relative minima detected to a predetermined value.

45. The method of claim 44 in which said step of comparing comprises comparing the two detected minima to a predetermined value which is one half the average of the first and third relative maxima.

46. The method of claim 43 including the step of comparing the second relative maxima to a predetermined value.

47. The method of claim 43 wherein the step of determining each profile includes measuring the hemoglobin density along each respective cross section.

48. A method for determining a parameter relating to the size of the central pallor of a round red blood cell comprising:
determining a first cross-sectional profile of the red blood cell and determining a second cross-sectional profile substantially transverse to said first profile, each of said profiles relating to the thickness or density of the red blood cell at points along each cross section and defining relative maxima of the profiles;
determining the volume of a cylinder defined by the average of said maxima and the area of said round red blood cell; and
determining a volume relating to the volume occupied by the red blood cell, and determining a parameter defined by the difference between the volume of said cylinder and the volume relating to the volume of the red blood cell.

49. The method of claim 48 wherein the determining of said profile relating to the thickness of the red blood cell at points along each cross section includes measuring the hemoglobin density at said points along each cross section and the determining of said volume relating to the volume occupied by the red blood cell includes determining the aggregate hemoglobin density of the red blood cell.

50. A method of automatically analyzing red blood cells in a sample of a patient's blood comprising the steps of:
examining the red blood cells in patient's blood sample, measuring a plurality of characteristics of each of the red blood cells, determining parameters of the multivariate dispersion of the distribution of the measured plurality of characteristics for said red blood cells,
and reporting on said parameters to provide a description of the blood.

51. An apparatus for automatically analyzing red blood cells in a sample of a patient's blood for an anemia or other red blood cell disorder comprising:
means for examining the red blood cells in patient's blood sample, means for measuring characteristics of blood cells and for classifying normal and abnormal cells into a plurality of mutually exclusive subpopulations, means for determining parameters for the red blood cells in respective ones of said subpopulations, and means comparing parameters of respective ones of the patient's red blood cell subpopulations with predetermined reference characteristic values of red blood cell subpopulations from a person having a known kind of anemia or other red blood cell disorder,
and means for reporting the results of the comparison to provide an indication of a specific anemia or red blood cell disorder or the lack thereof.

52. An apparatus in accordance with claim 51 in which said classifying means comprises means for separating biconcave red blood cells having a substantially round exterior and a central pallor of a predetermined configuration into a cell subpopulatfion constituting the major subpopulation of cells.

53. An apparatus in accordance with claim 52 in which said determining means includes means for generating parameters indicating the variation of cell size and of cell hemoglobin for said subpopulation of cells having the biconcave cells.

54. An apparatus in accordance with claim 53 including means for generating a mean cell size parameter, means for generating a mean cell hemoglobin parameter, and means for generating first and second eigen parameters for said subpopulation of cells having biconcave cells therein.

55. An apparatus in accordance with claim 51 in which said means for determining parameters generates a parameter of dispersion of distribution of cells in at least one subpopulation and determines a parameter with respect to variation in size of central pallors for the red blood cells.

56. An apparatus in accordance with claim 55 in which said means for determining parameters for the subpopulations generates a mean cell hemoglobin parameter, a mean cell size parameter, and the number of cells in the subpopulation relative to the total number of cell parameters.

57. An apparatus in accordance with claim 56 in which said means for determining parameters generates a skewness parameter for said subpopulation having said biconcave cells therein.

58. An apparatus in accordance with claim 51 in which said determining means comprises means for generating a plurality of parameters to define a patient's blood and in which the resemblance of the patient's blood to reference characteristic values for a specific anemia or blood cell disorder, if any, is reported.

59. An apparatus in accordance with claim 51 in which said determining means comprises means for generating multivariate distributions of the cells in said subpopulations in accordance with the variables of cell size, cell hemoglobin content, and central pallor, and said comparing means compares descriptors of these distributions to predetermined distribution descriptors for recognized kinds of anemias.

60. An apparatus in accordance with claim 58 in which said means for reporting reports for said cell subpopulation having normal cells therein values of the mean cell size, the mean cell hemoglobin, and the amount of bivariate dispersion thereof.

61. An apparatus in accordance with claim 60 in which said reporting means reports out the mean cell size and mean cell hemoglobin for the abnormal cell subpopulations of spherocytic cells, elongated cells, irregular cells and target cells, and further comprises means for reporting out the relationship of the patient's blood sample to known anemias including the iron deficient anemia, chronic disease anemia, B-thalassemia, megaloblastic, hemoglobin SS, hemoglobin SC, and spherocytic anemia.

62. An apparatus for automatically analyzing red blood cells in a sample of a patient's blood comprising
means for examining the red blood cells in a patient's blood sample, means for measuring characteristics of the red blood cells, means for determining parameters of the dispersion of the distribution of the measured characteristics of said red blood cells,
and means for reporting on said parameters to provide a description of the blood.

63. An apparatus for automatically analyzing red blood cells in accordance with claim 62 in which said means for examining the red blood cells includes means for segregating individual red blood cells into mutually exclusive subpopulations and said means for reporting on said parameters reports the parameters of dispersion of distribution of one of said subpopulations of red blood cells.

64. An apparatus in accordance with claim 62 including means for comparing the parameters of the dispersion of distribution of the patient's blood to reference characteristic values for a specific anemia or blood disorder and for reporting the results of said comparison.

65. An apparatus in accordance with claim 62 in which said means for determining said parameters determines the skewness of said distribution with respect to a measured characteristic and in which said means for reporting on said parameters reports an indication of said skewness.

66. An apparatus in accordance with claim 62 in which said means for measuring cell characteristics includes means for measuring red cell size and red cell hemoglobin and in which said determining means includes means for determining the parameters of dispersion of distribution of the red blood cells with respect to red blood cell size and hemoglobin content.

67. An apparatus in accordance with claim 62 in which said means for measuring characteristics measures the size of the central pallors of red blood cells and in which said means for determining parameters determines the dispersion of distribution with respect to central pallor size.

68. An apparatus in accordance with claim 67 in which said means for determining the parameters of dispersion of distribution with respect to central pallor size determines the standard deviation thereof.

69. An apparatus for automatically analyzing red blood cells in a sample of a patient's blood for an anemia or blood cell disorder, said apparatus comprising:
means for examining the red blood cells in a patient's blood sample,
means for measuring characteristics of the red blood cells,
means for generating a plurality of measured properties from said measured characteristics to define a patient's blood,
means for comparing the resemblance of the patient's blood to reference characteristic values for a specific anemia or blood cell disorder, and means for reporting with respect to the results of said comparison.

70. An apparatus in accordance with claim 69 in which said means for examining the red blood cells includes means for segregating individual blood cells into mutually exclusive subpopulations and in which said means for generating a plurality of measured properties generates parameters for at least one of said subpopulations.

71. An apparatus in accordance with claim 69 in which said means for generating a plurality of measured properties includes means for determining parameters of dispersion of the distribution of the measured characteristics for said red blood cells, and in which said comparing means compares the patient's dispersion of distribution to reference characteristic values for a specific anemia or blood disorder.

72. An apparatus in accordance with claim 69 in which said means for measuring characteristics of the red blood cells measures the size of the central pallors of red blood cells and in which said means for generating a plurality of measured properties includes means for determining the dispersion of distribution with respect to central pallor size.

73. An apparatus in accordance with claim 69 in which said means for generating a plurality of measured properties includes means for determining the dispersion of distribution with respect to a measured characteristic of the red blood cells and for determining the skewness of said distribution.

74. An apparatus in accordance with claim 69 in which said means for measuring cell characteristics measures cell size cell hemoglobin content and in which said means for generating a plurality of measured properties generates parameters of dispersion of distribution of the red blood cells with respect to cell size and hemoglobin content.

75. An apparatus for automatically analyzing red blood cells in a sample of a patient's blood comprising:
means for examining the red blood cells in a patient's blood sample;
means for measuring characteristics of the red blood cells;
means for classifying the cells into a plurality of mutually exclusive subpopulations including a normal and abnormal subpopulation;
means for determining subpopulation parameters including the dispersion of the distribution of at least one of said subpopulations;
and means for reporting on the results of the dispersion of distribution as a description of the blood.

76. An apparatus in accordance with claim 75 including means for comparing the parameters of the dispersion of distribution of said subpopulation of the patient's blood to reference characteristic values for a specific anemia or blood disorder;
and said means for reporting reports of said comparison.

77. An apparatus in accordance with claim 75 in which said means for determining said parameters determines the skewness of the distribution with respect to a measured characteristic for all of the red blood cells;
and in which said reporting means reports the indication of said skewness.

78. An apparatus in accordance with claim 75 in which said means for measuring of the characteristics of the red blood cells measures the cell size and hemoglobin content; and said reporting means reports the dispersion of the distribution with respect to cell size and hemoglobin content.

79. An apparatus in accordance with claim 75 in which said means for measuring characteristics of the red blood cells measures the size of the central pallors of red blood cells;
and in which said reporting means reports the dispersion of distribution of the pallor size for the said red blood cells.

80. An apparatus for automatically and rapidly analyzing cells on a support, said apparatus comprising:
a plurality of processing means;
means for producing an optical image on an imaging means of a field of the cells on the support;
means for converting the image into a point by point distribution representative of the image;
means for converting each point into a digital signal;
means for controlling said imaging means by a first of said processing means so that a plurality of fields may be imaged on said imaging means;
means for analyzing the digital signals of each field of the cells imaged by a second one of said processing means and for measuring characteristics of the digitized signals for predetermined red blood cell characteristics;
and means for reporting parameters relating to the measured characteristics of the cells analyzed.

81. An apparatus for automatically and rapidly analyzing cells on a slide comprising:
a plurality of processing means;
means for producing a first optical image on an imaging means of a field of the cells on the slide;
means for converting the image into a point by point distribution representative of the image;
a digitizing means for converting each point into a digital signal;
means for controlling said imaging means by a first one of said processing means so that an additional field may be imaged;
means for analyzing the digital signals of each field of the cells imaged by a second one of said processing means for a plurality of cell features;
means for synchronizing the first processing means with said digitizing means so that said first processing means may cause an additional field to be imaged after the first image is digitized.

82. An apparatus for automatically and rapidly analyzing red blood cells comprising:
a first processing means and at least one additional processing means,
an optical imaging means for producing a first optical image, said first processing means digitizing said image to produce digital signals under the control of said first processing means,
means for measuring characteristics of the red blood cells from the digitized image signals in said additional processing means and for analyzing the measured characteristics while said first processing means is controlling the imaging means and producing another image for cell measuring and analyzing,
means for transferring information concerning said analyzed and measured characteristics from additional processing means to said first processing means for storing therein,
and means for controlling the imaging means by said first processing means to transfer digitized image signals to one of said additional processing means.

83. An apparatus in accordance with claim 82 in which said transferring means transfers digital signal images to a second one of said additional processing means while a first one of said additional processing means is still measuring and analyzing characteristics from a previous image so that a plurality of images may be in process simultaneously.

84. An apparatus for automatically testing blood for abnormalities by analyzing red blood cells having quantifiable features in a blood specimen, said apparatus comprising:
means for identifying at least one subpopulation of the red blood cells in said specimen;
means for determining a distribution of the red blood cells for said subpopulation with respect to a plurality of the quantifiable features of the red blood cells; and
means for reporting parameters relating to said distribution to provide an indication of a blood abnormality or a lack thereof.

85. An apparatus in accordance with claim 84 in which said means for determining a distribution determines cell size and cell hemoglobin and the distribution is a bivariate distribution with respect to the two quantifiable features of cell size and cell hemoglobin.

86. An apparatus for automatically testing blood for abnormalities by analyzing red blood cells having quantifiable features in a blood specimen, said apparatus comprising:
means for identifying at least one subpopulation of the red blood cells;
means for determining a distribution of the red blood cells of said subpopulation with respect to a plurality of the quantifiable features of the red blood cells including the size of the red blood cells and the hemoglobin content of the red blood cells; and
means for reporting parameters relating to said distribution including the mean cell size, mean cell hemoglobin content, and the dispersion of the distribution relative to the size and hemoglobin content of the red blood cells.

87. An apparatus for automatically classifying blood and its relationship to recognized categories of anemia wherein a sample of red blood cells having quantifiable features is analyzed, said apparatus comprising:
means for identifying at least one defined subpopulation of red blood cells;
means for determining the proportion of said subpopulation in said sample; and
means for comparing said proportion to the proportion of a similarly defined subpopulation in a sample from a recognized category of anemic red blood cells.

88. The apparatus of claim 87 in which said means for determining determines a distribution of the red blood cells of said subpopulation with respect to a plurality of the quantifiable features of the red blood cells and said means for comparing compares parameters relating to the distribution of the subpopulation to the parameters of the distribution of the similarly defined subpopulation in the sample of anemic red blood cells with respect to the same plurality of quantifiable features.

89. An apparatus for automatically classifying blood and its relationship to recognized categories of anemias wherein a sample of red blood cells having quantifiable features is analyzed, said apparatus comprising:
a means for identifying at least one defined subpopulation of red blood cells; p1 means for determining a distribution of the red blood cells of the subpopulation with respect to a plurality of the quantifiable features of the red blood cells; and
means for comparing parameters of the distribution to the parameters of a distribution of a similarly defined subpopulation in a sample from a recognized category of anemic red blood cells.

90. An apparatus for automatically classifying blood and its relationship to recognized categories of anemias wherein a sample of red blood cells having quantifiable features is analyzed, said apparatus comprising:
means for determining the average of a plurality of said quantifiable features including the pallor size from said sample; and
means for comparing said averages to the averages of the same quantifiable features of a sample from a recognized category of anemic red blood cells.

91. The apparatus of claim 90 in which said means for determining determines a distribution of the red blood cells of the sample with respect to at least one of the quantifiable features and determines parameters relating to said distribution and, said comparing means comparing said parameters to the parameters of the distribution of a sample from a recognized category of anemic red blood cells.

92. An apparatus for automatically identifying target cells in a sample of red blood cells comprising:
means for determining a first cross-sectional profile of a red blood cell and for determining a second cross-sectional profile in a direction substantially transverse to said first profile, each of said profiles relating to the thickness of the red blood cell at points along each cross section and defining relative maxima and minima; and
means for detecting the existence of three relative maxima and two relative minima on either profile.

93. The apparatus of claim 92 including means for comparing the two relative minima detected to a predetermined value.

94. The apparatus of claim 92 in which said means for comparing uses a predetermined value which is one half the average of the first and third relative maxima.

95. The apparatus of claim 92 in which said comparing means compares the second relative maxima to a predetermined value.

96. The apparatus of claim 92 wherein said means for determining each profile measures the hemoglobin density along each respective cross section.

97. An apparatus for determining a parameter relating to the size of the central pallor of a round red blood cell comprising:
   means for determining a first cross-sectional profile of the red blood cell and for determining a second cross-sectional profile substantially transverse to said first profile, each of said profiles relating to the thickness or density of the red blood cell at points along each cross section and defining relative maxima of the profiles;
   means for determining the volume of a cylinder defined by the average of said maxima and the area of said round red blood cell; and
   means for determining a volume relating to the volume occupied by the red blood cell, and means for determining a parameter defined by the difference between the volume of said cylinder and the volume relating to the volume of the red blood cell.

98. The apparatus of claim 97 wherein said means for determining said profile measures the hemoglobin density at said points along each cross section and said means for determining of said volume relating to the volume occupied by the red blood cell determines the aggregate hemoglobin density of the red blood cell.

99. An apparatus for automatically analyzing red blood cells in a sample of a patient's blood comprising:
   means for examining the red blood cells in patient's blood sample;
   means for measuring a plurality of characteristics of each of the red blood cells;
   means for determining parameters of the multivariate dispersion of the distribution of the measured plurality of characteristics for said red blood cells; and
   means for reporting on said parameters to provide a description of the blood.

* * * * *

UNITED STATES PATENT AND TRADEMARK OFFICE
CERTIFICATE OF CORRECTION

PATENT NO. : 4,199,748
DATED : April 22, 1980
INVENTOR(S) : JAMES W. BACUS

It is certified that error appears in the above—identified patent and that said Letters Patent is hereby corrected as shown below:

```
Column 5, line 12,  change "normal" to --novel--.
Column 5, line 40,  change "accomulating" to --accumulating--.
Column 5, line 50,  change "sset" to --set--.
Column 6, line 67,  "body" should be --blood--.
Column 8, line 49,  "of" second occurrence should be --and--.
Column 8, line 53,  "subpowlation" should be --subpopulations--.
Column 11, line 27, "describe" should be --described--.
Column 17, line 58, "forward" should be --forwarded--.
Column 19, line 44, "heigh" should be --height--.
Column 22, line 59, "266" should be --268--.
 Column 22, line 59, after "subsection" insert --268 which takes
    the square root of the output provided by the logic
    subsection--.
Column 194, line 15, "58" should be --51--.
Column 195, line 54, after "size" insert --and--.
Column 198, line 25, delete "pl".
```

Signed and Sealed this

Fourth Day of May 1982

[SEAL]

Attest:

Attesting Officer

GERALD J. MOSSINGHOFF

Commissioner of Patents and Trademarks